US011273066B2

(12) United States Patent
Janzen et al.

(10) Patent No.: US 11,273,066 B2
(45) Date of Patent: Mar. 15, 2022

(54) THORACOLUMBAR TRANSLATOR AND ASSOCIATED METHODS

(71) Applicant: ScoliWRx Inc., Campbell, CA (US)

(72) Inventors: Matthew I. Janzen, Campbell, CA (US); Michael E. Janzen, Campbell, CA (US)

(73) Assignee: ScoliWRx Inc., Campbell, CA (US)

( * ) Notice: Subject to any disclaimer, the term of this patent is extended or adjusted under 35 U.S.C. 154(b) by 407 days.

(21) Appl. No.: 16/104,729

(22) Filed: Aug. 17, 2018

(65) Prior Publication Data

US 2019/0053934 A1 Feb. 21, 2019

Related U.S. Application Data

(60) Provisional application No. 62/547,713, filed on Aug. 18, 2017.

(51) Int. Cl.
*A61F 5/02* (2006.01)
*A61H 1/00* (2006.01)
(Continued)

(52) U.S. Cl.
CPC .............. *A61F 5/024* (2013.01); *A61H 1/008* (2013.01); *A61H 1/0292* (2013.01); *A61F 5/32* (2013.01);
(Continued)

(58) Field of Classification Search
CPC .. A61F 5/024; A61F 5/032; A61F 5/02; A61F 5/04; A61F 5/042; A61H 1/008;
(Continued)

(56) References Cited

U.S. PATENT DOCUMENTS 164,706 A 6/1875 Allen
3,465,750 A * 9/1969 Albert ................... A63B 21/04
601/122

(Continued)

FOREIGN PATENT DOCUMENTS

JP 2014-158540 A2 9/2014
JP 2014158540 A * 9/2014

OTHER PUBLICATIONS

Kieu, Translation of JP2014158540A (Year: 2014).*
PCT/US18/46988, International Search Report, dated Oct. 31, 2018, 3 pages.

*Primary Examiner* — Alireza Nia
*Assistant Examiner* — Daniel A Miller
(74) *Attorney, Agent, or Firm* — Penilla IP, APC

(57) ABSTRACT

A frame includes a front segment extending across an anterior side of a human and a back segment extending across a posterior side of the human in a fixed spatial relationship. A clamp bar extends between the front segment and the back segment to interface with a first lateral side of the human at a location between an ilium bone structure and a thoracic cage of the human. A lateral restraint is positioned between the front segment and the back segment and is configured to interface with a second lateral side of the human over an engagement area corresponding to a portion of the thoracic cage of the human. A downward treatment force is applied to the frame at a location opposite the clamp bar from the lateral restraint. The human works to laterally translate their spinal column toward the lateral restraint to maintain the frame in a near-level orientation.

22 Claims, 82 Drawing Sheets

(51) Int. Cl.
*A61H 1/02* (2006.01)
*A61F 5/32* (2006.01)

(52) U.S. Cl.
CPC .............. *A61H 2001/0207* (2013.01); *A61H 2201/0157* (2013.01); *A61H 2201/0192* (2013.01); *A61H 2201/1261* (2013.01); *A61H 2201/163* (2013.01); *A61H 2201/1616* (2013.01); *A61H 2201/1659* (2013.01); *A61H 2203/0406* (2013.01); *A61H 2205/081* (2013.01)

(58) Field of Classification Search
CPC ...... A61H 1/0292; A61H 1/02; A61H 1/0218; A61H 2001/0207; A61H 2201/0157; A61H 2201/0192; A61H 2201/1261; A61H 2201/1616; A61H 2201/163; A61H 2201/1659; A61H 2203/0406; A61H 2203/0475; A61H 2205/081; A61H 39/04; A61H 7/007; A61H 2201/1646; A61H 2201/1614; A61H 2201/1652; A61H 2201/1609; A61H 2201/1623; A61H 2201/5023; A61H 2201/0134; A63B 23/00; A63B 23/02; A63B 23/0238; A63B 2203/006; A63B 2208/0238; A63B 2225/09; A63B 2203/0437
USPC ...................................................... 602/16, 19
See application file for complete search history.

(56) References Cited

U.S. PATENT DOCUMENTS

| | | | | |
|---|---|---|---|---|
| 3,596,655 | A * | 8/1971 | Corcoran | A61H 1/0218 |
| | | | | 602/32 |
| 10,568,797 | B1 * | 2/2020 | Janzen | A61H 1/0292 |
| 2007/0149359 | A1 * | 6/2007 | Rahman | A61C 19/04 |
| | | | | 482/4 |
| 2010/0069806 | A1 * | 3/2010 | Jinright | A61F 5/026 |
| | | | | 602/19 |
| 2012/0150085 | A1 * | 6/2012 | Kayser | A61F 5/026 |
| | | | | 602/19 |
| 2015/0328035 | A1 * | 11/2015 | Idowu | A61F 5/03 |
| | | | | 602/19 |
| 2017/0216077 | A1 * | 8/2017 | Chahrour | A61F 5/028 |
| 2019/0254907 | A1 * | 8/2019 | Miller | A61H 39/04 |
| 2020/0121542 | A1 * | 4/2020 | Janzen | A61H 1/0292 |

\* cited by examiner

| Curve Type | Proximal Thoracic | Main Thoracic | Thoracolumbar/ Lumbar | Description |
|---|---|---|---|---|
| 1 | Nonstructural | Structural [1] | Nonstructural | Main Thoracic (MT) |
| 2 | Structural [2] | Structural [1] | Nonstructural | Double Thoracic (DT) |
| 3 | Nonstructural | Structural [1] | Structural [2] | Double Major (DM) |
| 4 | Structural [2] | Structural [3] | Structural [3] | Triple Major (TM) |
| 5 | Nonstructural | Nonstructural | Structural [1] | Thoracolumbar/Lumbar (TL/L) |
| 6 | Nonstructural | Structural [2] | Structural [1] | Thoracolumbar/Lumbar-Main Thoracic (TL/L-MT) |

[1] Major Curve: Largest Cobb measurement, always structural.   [2] Minor Curve: Remaining structural curves.
[3] Type 4 - MT or TL/L can be the major curve.

Structural Criteria (Minor Curves)
Proximal Thoracic: Side Bending Cobb ≥ 25°; T2-T5 Kyphosis ≥ +20°
Main Thoracic: Side Bending Cobb ≥ 25°; T10-L2 Kyphosis ≥ +20°
Thoracolumbar/Lumbar: Side Bending Cobb ≥ 25°; T10-L2 Kyphosis ≥ +20°

Location of Apex (SRS Definition)
Thoracic Curve: T2 to T11/12 Disc
Thoracolumbar Curve: T12/L1
Lumbar Curve: L1/2 Disc to L4

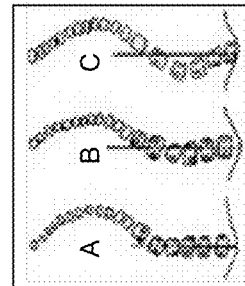

Modifiers

| Lumbar Coronal Modifier | Center Sacral Vertical Line to Lumbar Apex |
|---|---|
| A | Between Pedicles |
| B | Touches Apical Body(ies) |
| C | Completely Medial |

| Thoracic Sagittal Profile T5-T12 | |
|---|---|
| Modifier | Cobb Angle |
| "-" (Hypo) | < 10° |
| "N" (Normal) | 10° - 40° |
| "+" (Hyper) | > 40° |

Curve Classification = Curve Type (1-6) + Lumbar Coronal Modifer (A, B, C) + Thoracic Sagittal Profile Modifier (-, N, +)

FIG. 1V

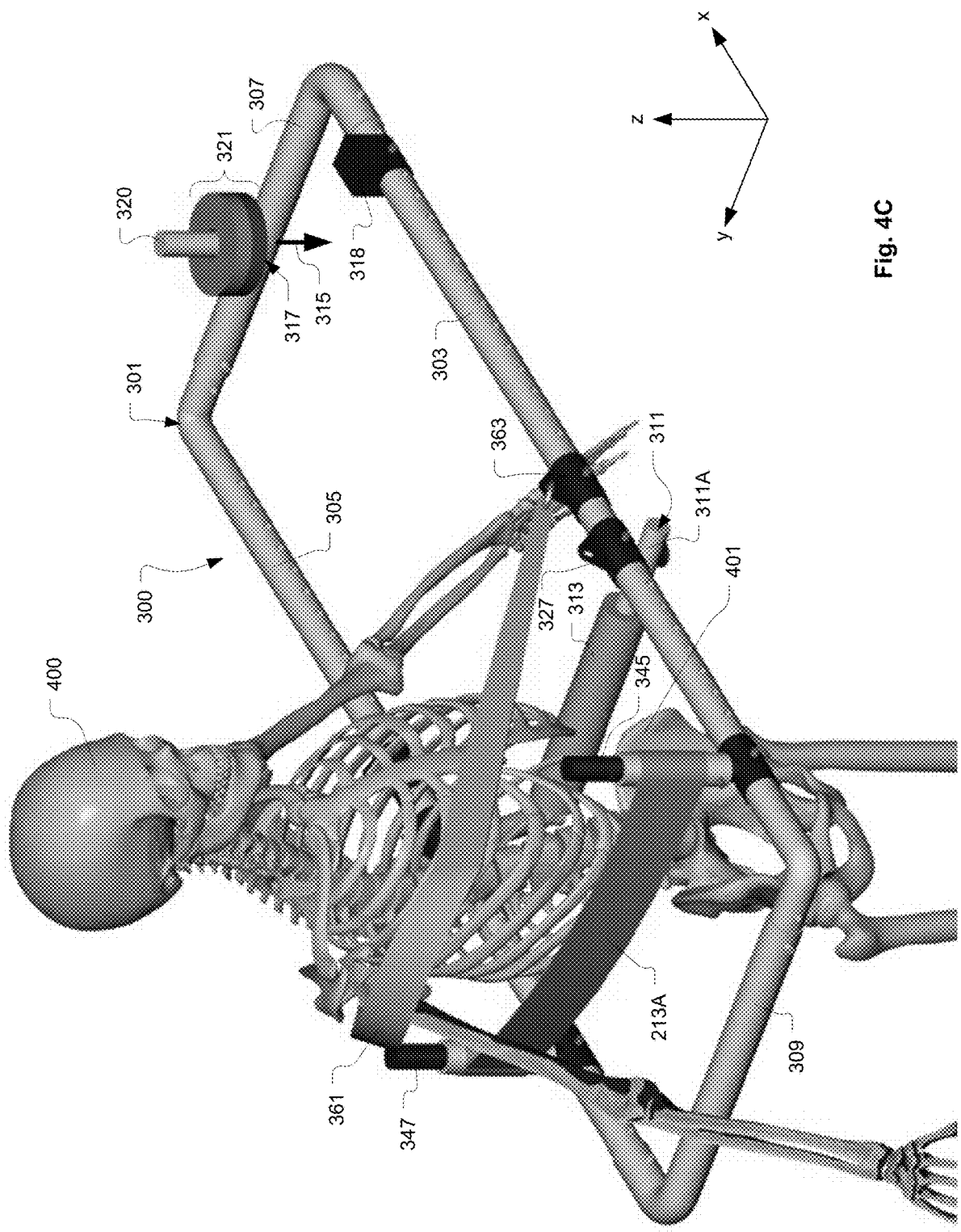

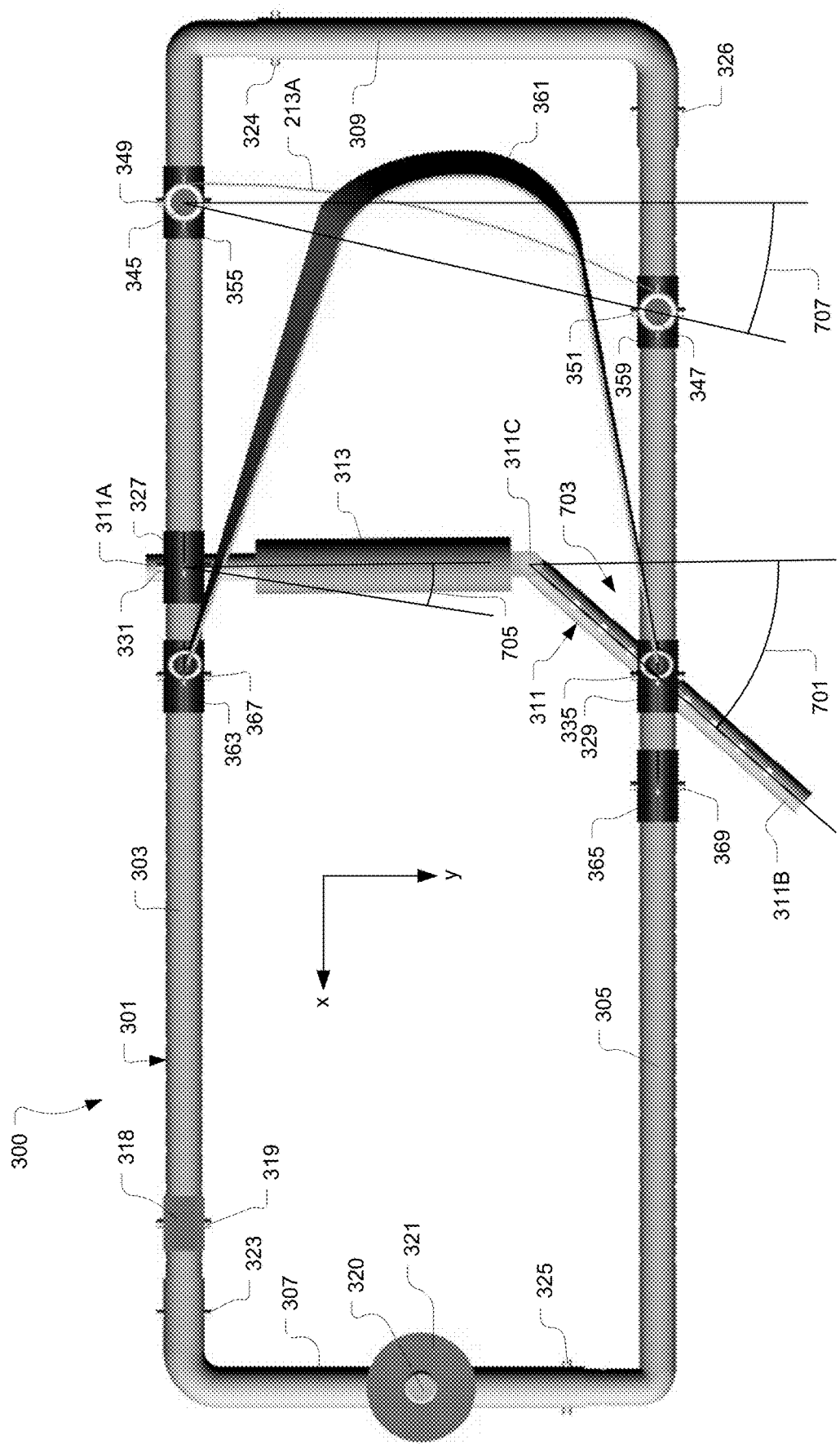

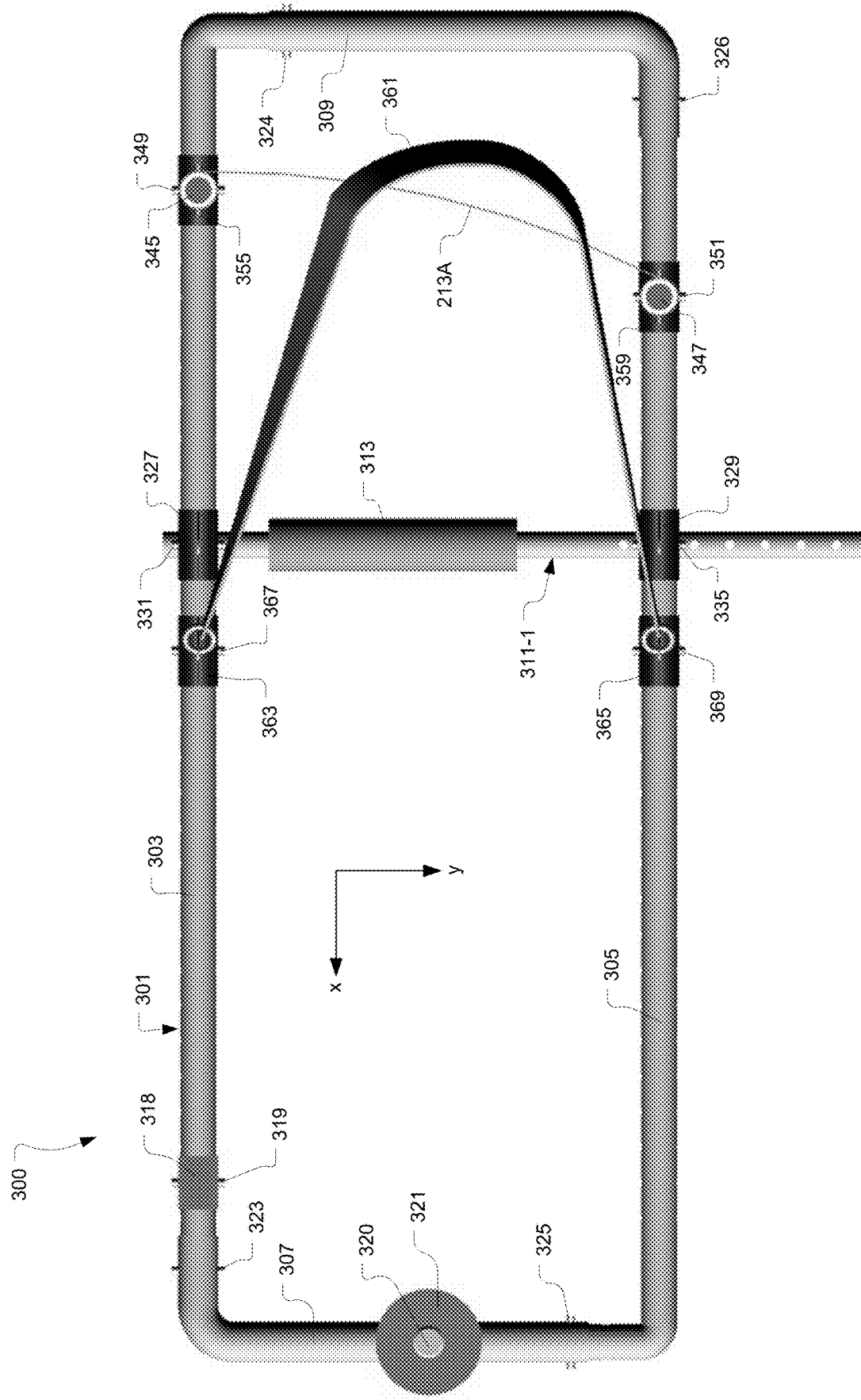

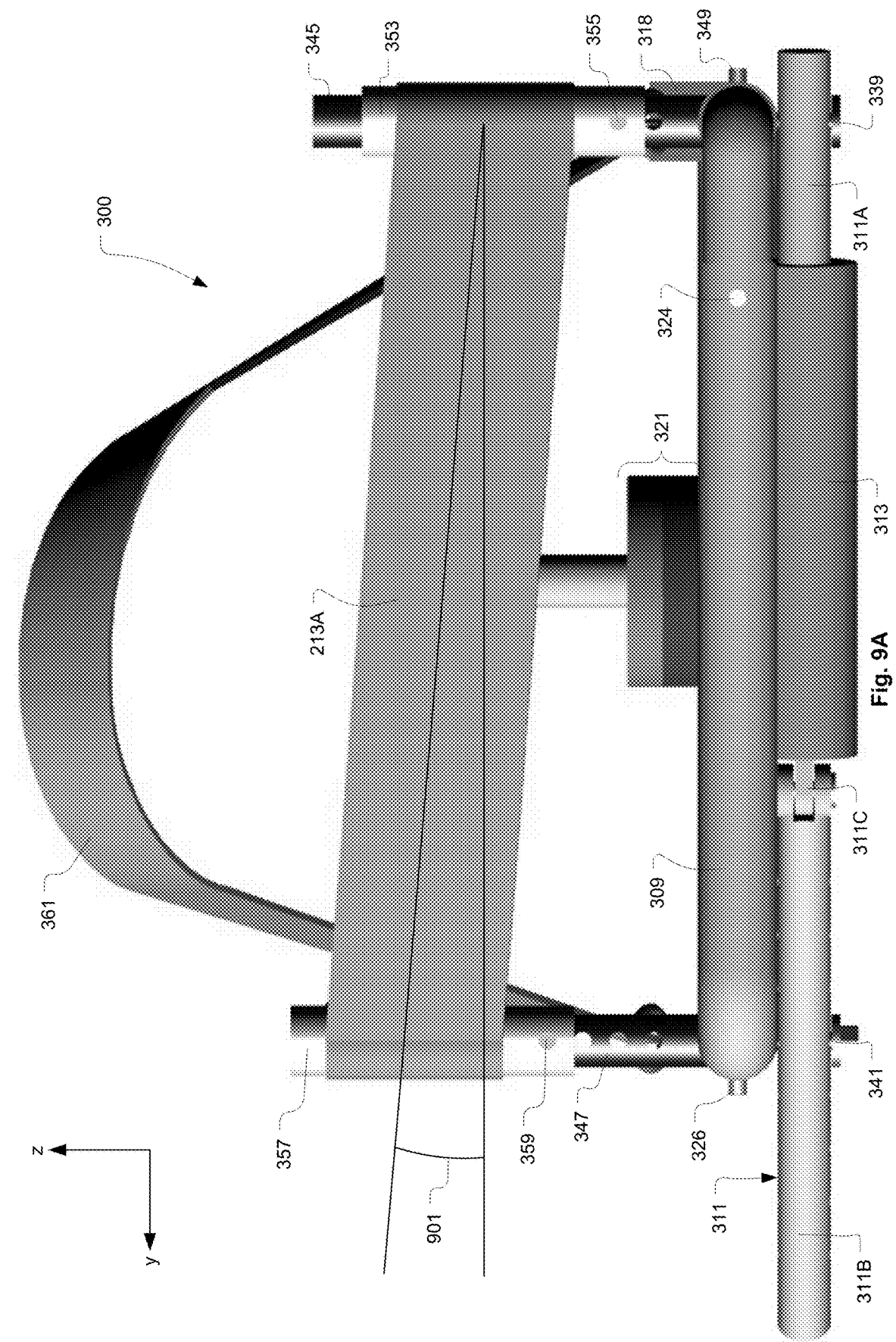

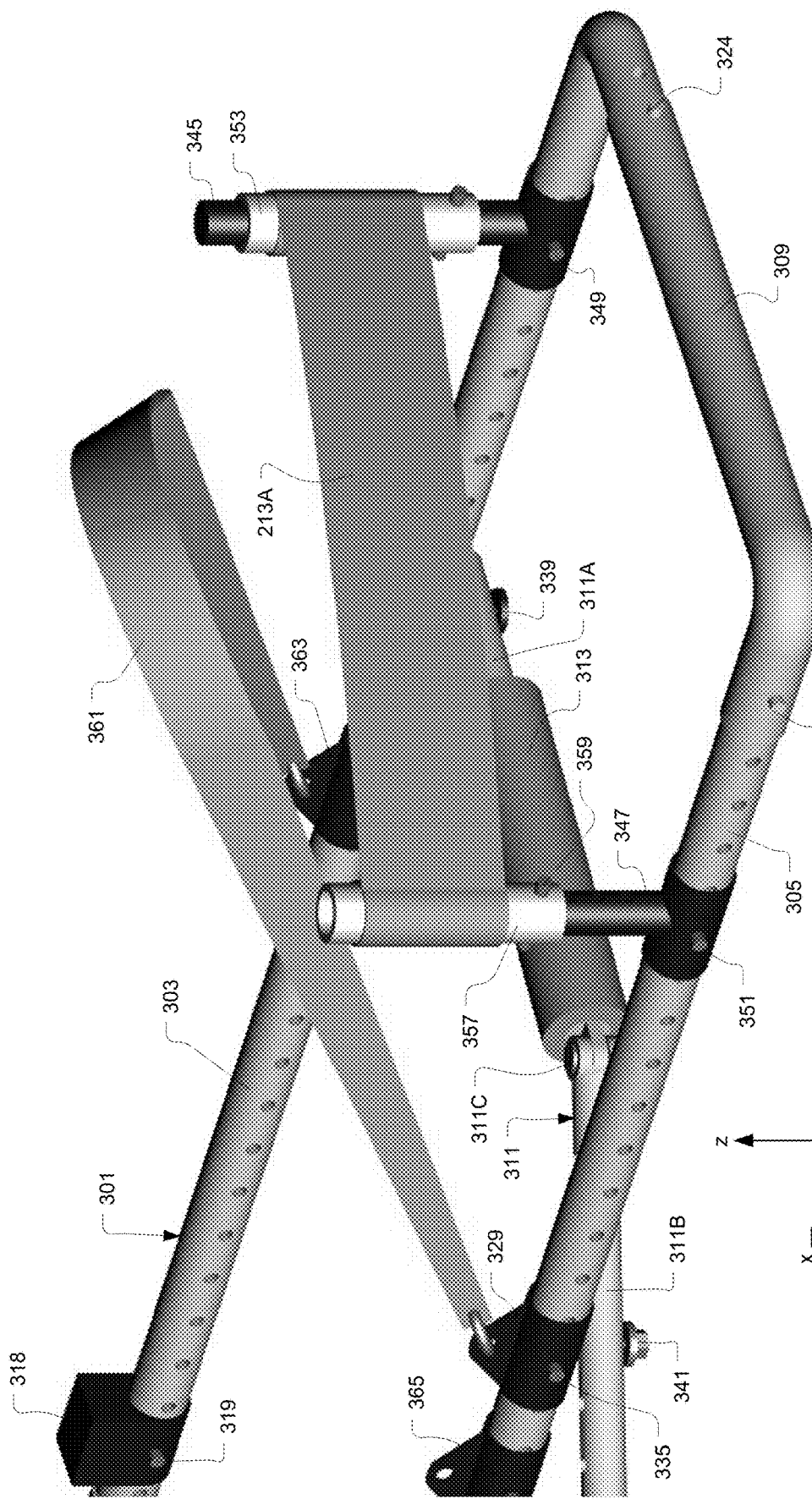

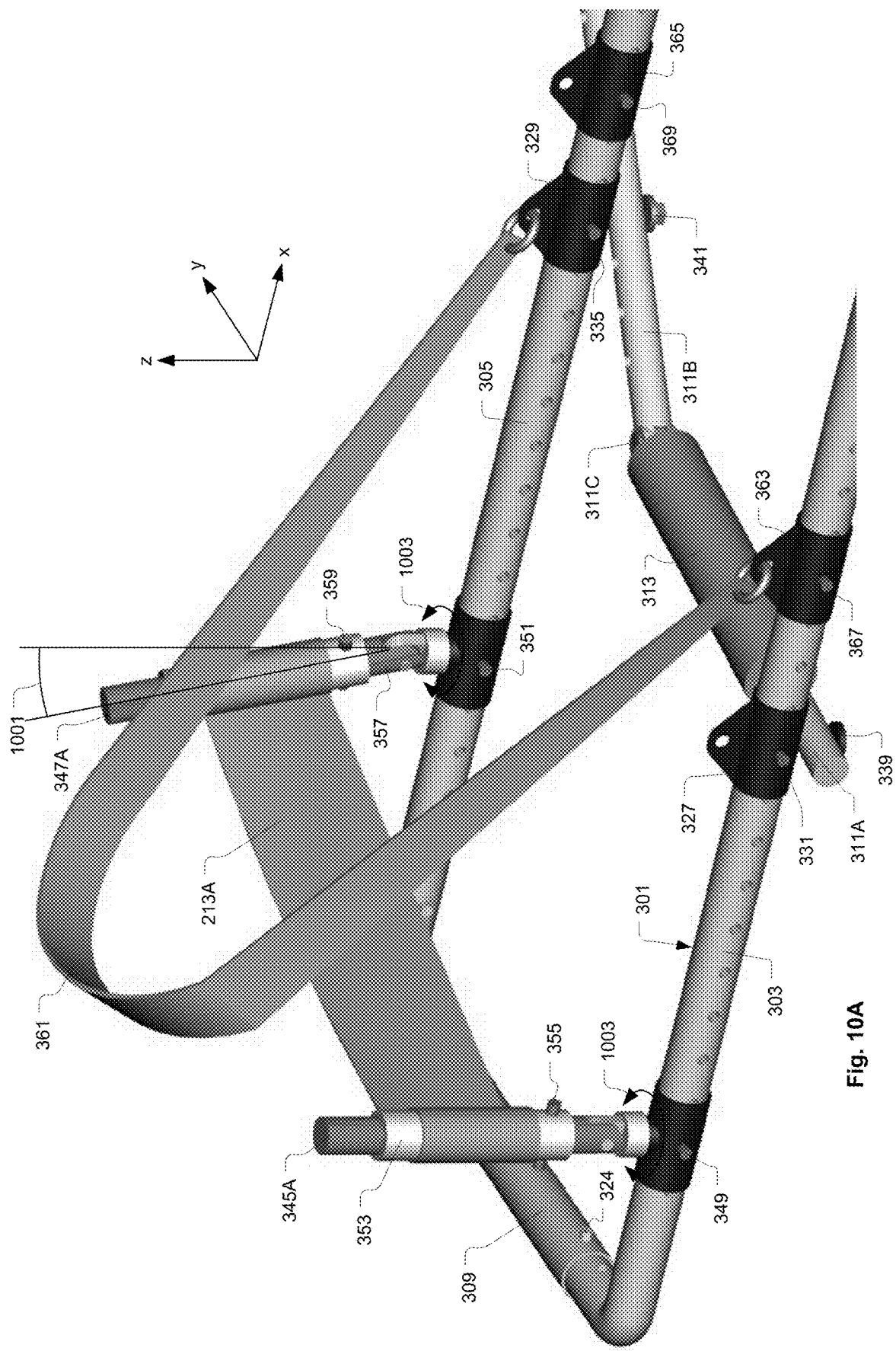

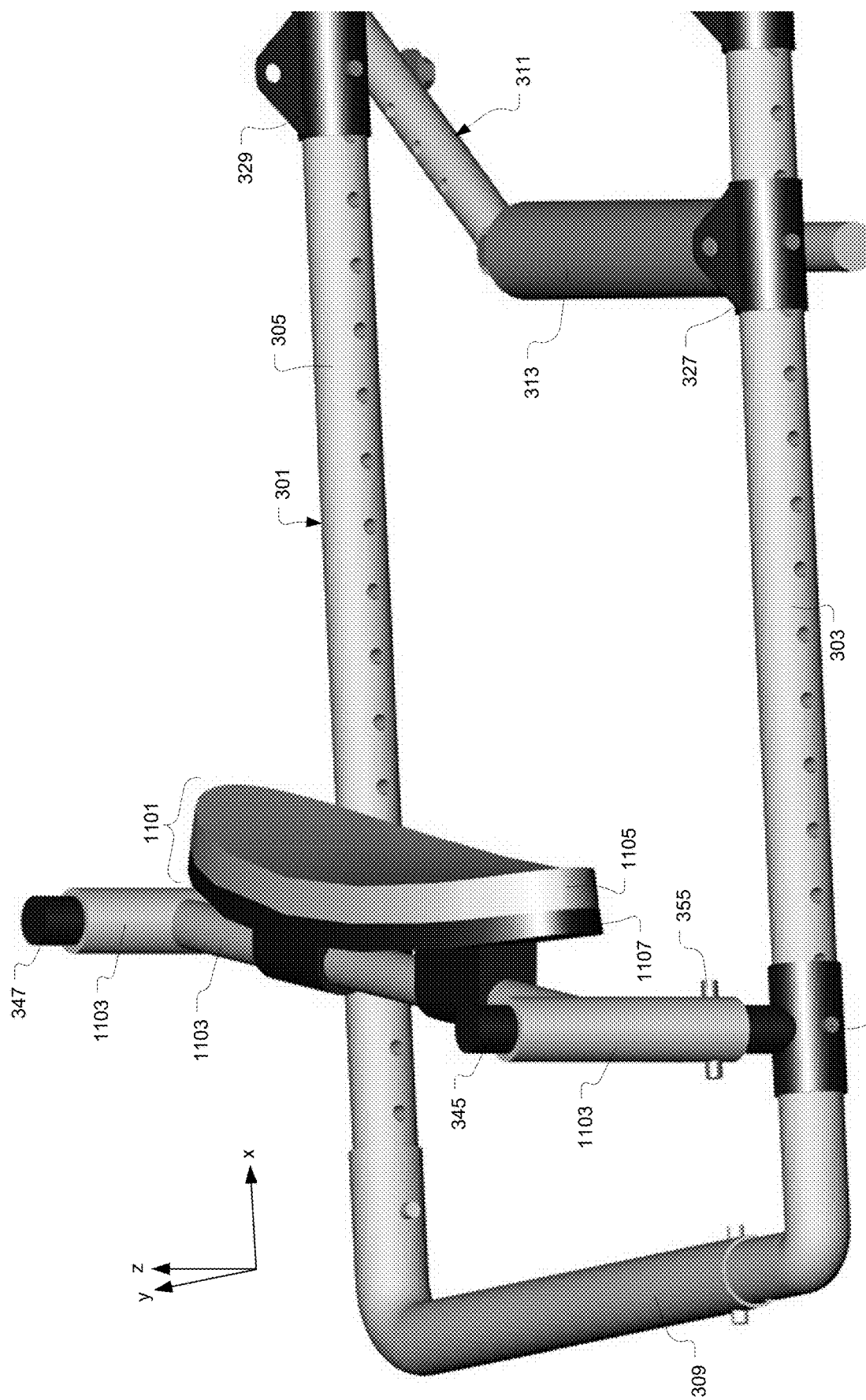

THORACOLUMBAR TRANSLATOR AND ASSOCIATED METHODS

CLAIM OF PRIORITY

This application claims priority under 35 U.S.C. 119(e) to U.S. Provisional Patent Application No. 62/547,713, filed Aug. 18, 2017, the disclosure of which is incorporated herein by reference in its entirety for all purposes.

BACKGROUND

1. Field of the Invention

The present invention relates to treatment of human scoliosis.

2. Description of the Related Art

FIG. 1A shows an anterior view of a normal human spinal column. The anterior view is toward the front of the person. A cervical region 101 of the spinal column includes seven cervical vertebrae C1-C7. The first cervical vertebra C1 is referred to as the Atlas vertebra. The second cervical vertebra C2 is referred to as the Axis vertebra. A thoracic region 103 of the spinal column is located below the cervical region 101. The thoracic region 103 includes twelve thoracic vertebrae T1-T12. A lumbar region 105 is located below the thoracic region 103. The lumbar region 105 of the spinal column includes five lumbar vertebrae L1-L5. A sacrum region 107 is located below the lumbar region 105. And, a coccyx (tailbone) region 109 is located below the sacrum region 107. FIG. 1B shows a posterior view of the normal human spinal column. The posterior view is toward the back of the person. FIG. 1C shows a left lateral view of the normal human spinal column. The lateral view is toward the left side of the person.

While each of the first cervical vertebra C1 and the second cervical vertebra C2 is uniquely configured, the cervical vertebrae C3-C7 have a similar structure to one another and include essentially the same structural elements. Therefore, to describe the structure of the cervical vertebrae C3-C7, attention is drawn to the fourth cervical vertebra C4 and the seventh cervical vertebra C7. FIG. 1D shows a superior view of the fourth cervical vertebra C4. The superior view is a view from above looking down. FIG. 1E shows an inferior view of the fourth cervical vertebra C4. The inferior view is a view from below looking up. The fourth cervical vertebra C4 includes a body structure 111. A right transverse process 112R extends laterally away from the body structure 111 toward the right side of the person. And, a left transverse process 112L extends laterally away from the body structure 111 toward the left side of the person. The right transverse process 112R includes a right anterior tubercle 121R and a right posterior tubercle 122R between which pass a spinal nerve. The left transverse process 112L includes a left anterior tubercle 121L and a left posterior tubercle 122L between which pass a spinal nerve. The right transverse process 112R includes a right transverse foramen 113R. The left transverse process 112L includes a left transverse foramen 113L. Each of the right and left transverse foramen 113R, 113L give passage to vertebral arteries and veins, and to a plexus of sympathetic nerves. A right pedicle 114R extends from the body structure 111 to a right inferior articular process 115R. A left pedicle 114L extends from the body structure 111 to a left inferior articular process 115L. A right lamina 116R extends from the right inferior articular process 115R to a spinous process 117. A left lamina 116L extends from the left inferior articular process 115L to the spinous process 117. The spinous process 117 extends toward the back of the person in a direction generally away from the body structure 111. Collectively, the body structure 111, the right inferior articular process 115R, the right lamina 116R, the left inferior articular process 115L, the left lamina 116L, and the spinous process 117 circumscribe a vertebral foramen (vertebral canal) 118, which is a passage through which the spinal cord passes through the vertebra. The fourth cervical vertebra C4 also includes several facets corresponding to joints between adjacent vertebrae. These facets include a right superior articular facet 119R and a left superior articular facet 119L which respectively form joints with respective inferior articular facets of the third cervical vertebra C3. Also, a right inferior articular facet 120R and a left inferior articular facet 120L respectively form joints with respective superior articular facets of the fifth cervical vertebra C5.

FIG. 1F shows a superior view of the seventh cervical vertebra C7. FIG. 1G shows an inferior view of the seventh cervical vertebra C7. Although the seventh cervical vertebra C7 is shaped differently from the fourth cervical vertebra C4, they include essentially the same elements. The seventh cervical vertebra C7 includes the body structure 111, with the right transverse process 112R extending laterally away from the body structure 111 toward the right side of the person, and with the left transverse process 112L extending laterally away from the body structure 111 toward the left side of the person. The right transverse process 112R includes the right anterior tubercle 121R and the right posterior tubercle 122R between which pass the spinal nerve. The left transverse process 112L includes the left anterior tubercle 121L and the left posterior tubercle 122L between which pass the spinal nerve. The right transverse process 112R includes the right transverse foramen 113R. The left transverse process 112L includes the left transverse foramen 113L. Each of the right and left transverse foramen 113R, 113L give passage to vertebral arteries and veins, and to a plexus of sympathetic nerves. The right pedicle 114R extends from the body structure 111 to the right inferior articular process 115R. The left pedicle 114L extends from the body structure 111 to the left inferior articular process 115L. The right lamina 116R extends from the right inferior articular process 115R to the spinous process 117. The left lamina 116L extends from the left inferior articular process 115L to the spinous process 117. And, the spinous process 117 extends toward the back of the person in a direction generally away from the body structure 111. Collectively, the body structure 111, the right inferior articular process 115R, the right lamina 116R, the left inferior articular process 115L, the left lamina 116L, and the spinous process 117 circumscribe the vertebral foramen (vertebral canal) 118, through which the spinal cord passes. The seventh cervical vertebra C7 also includes the right superior articular facet 119R and the left superior articular facet 119L which form joints with respective inferior articular facets of the sixth cervical vertebra C6. Also, the right inferior articular facet 120R and the left inferior articular facet 120L form joints with respective superior articular facets of the first thoracic vertebra T1.

FIG. 1H shows a superior view of the fifth thoracic vertebra T5, which has a structure typical of thoracic vertebrae T1-T11. FIG. 1I shows an inferior view of the fifth thoracic vertebra T5. The thoracic vertebrae includes a body structure 131. A right pedicle 132R extends from the body structure 131 to connect with a right transverse process 133R. A right lamina 134R extends from the right transverse process 133R to connect with a spinous process 135. Similarly, a left pedicle 132L extends from the body structure 131 to connect with a left transverse process 133L. And, a left lamina 134L extends from the left transverse process 133L to connect with the spinous process 135. Collectively, the body structure 131, right and left pedicles 132R, 132L, right and left transverse processes 133R, 133L, right and left lamina 134R, 134L, and spinous process 135 circumscribe a vertebral foramen (vertebral canal) 136, which is a passage through which the spinal cord passes through the vertebra. A right superior articular facet 137R and a left superior articular facet 137L form joints with a right inferior articular facet 138R and a left inferior articular facet 138L, respectively, of the vertebra above.

Each of thoracic vertebrae T1-T9 has a right costal facet 139R, a right superior costal demifacet 140R, and a right inferior costal demifacet 141R for forming joints with ribs. Each of thoracic vertebrae T1-T9 has a left costal facet 139L, a left superior costal demifacet 140L, and a left inferior costal demifacet 141L for forming joints with ribs. Specifically, each of ribs one through nine has a tubercle that interfaces and articulates with the costal facet 139R/139L of its numerically corresponding vertebra to form the costo-transverse joint. And, each of ribs one through nine has two articular facets that respectively interface and articulate with the superior costal demifacet 140R/140L of its numerically corresponding vertebra and with the inferior costal demifacet 141R/141L of the vertebra above to form the costo-vertebral joint.

The twelfth thoracic vertebra T12 provides a transition from the thoracic region 103 to the lumbar region 105 and correspondingly has a somewhat unique configuration to relative to thoracic vertebrae T1-T11. FIG. 1J shows a superior view of the twelfth thoracic vertebra T12. FIG. 1K shows an inferior view of the twelfth thoracic vertebra T12. On the superior portion of the twelfth thoracic vertebra T12, the features are similar to those of thoracic vertebrae T1-T11. The twelfth thoracic vertebra T12 includes: the body structure 131, the right pedicle 132R extending from the body structure 131 to connect with the right transverse process 133R, the right lamina 134R extending from the right transverse process 133R to connect with the spinous process 135, the left pedicle 132L extending from the body structure 131 to connect with the left transverse process 133L, and the left lamina 134L extending from the left transverse process 133L to connect with the spinous process 135. Collectively, the body structure 131, right and left pedicles 132R, 132L, right and left transverse processes 133R, 133L, right and left lamina 134R, 134L, and spinous process 135 circumscribe the vertebral foramen (vertebral canal) 136, which provides passage for the spinal cord. The twelfth thoracic vertebra T12 also includes the right superior articular facet 137R and a left superior articular facet 137L to form joints with the right inferior articular facet 138R and a left inferior articular facet 138L of the eleventh thoracic vertebra T11. The right inferior articular facet 138R and the left inferior articular facet 138L of the twelfth thoracic vertebra T12 are uniquely configured to interface with respective superior articular facets of the first lumbar vertebra L1. The twelfth thoracic vertebra T12 also has a right costal facet 143R and a left costal facet 143L to which the twelfth ribs connect.

FIG. 1L shows a superior view of the third lumbar vertebra L3, which is representative of the other lumbar vertebrae L1-L2 and L4-L5. FIG. 1M shows a superior view of the third lumbar vertebra L3. The lumbar vertebrae includes a body structure 151. A right pedicle 152R extends from the body structure 151 to connect with a right transverse process 153R. A right lamina 154R extends from the right transverse process 153R to connect with a spinous process 155. Similarly, a left pedicle 152L extends from the body structure 151 to connect with a left transverse process 153L. And, a left lamina 154L extends from the left transverse process 153L to connect with the spinous process 155. Collectively, the body structure 151, right and left pedicles 152R, 152L, right and left transverse processes 153R, 153L, right and left lamina 154R, 154L, and spinous process 155 circumscribe a vertebral foramen (vertebral canal) 156, through which the spinal cord passes. A right superior articular facet 157R and a left superior articular facet 157L form joints with a right inferior articular facet 158R and a left inferior articular facet 158L, respectively, of the vertebra above.

The twelve thoracic vertebrae T1-T12 that make up the thoracic region 103 of the spinal column are configured to connect with and support the rib cage (thoracic cage). FIG. 1N shows a right lateral view of the spinal column with the thoracic cage 160 shown attached to the thoracic vertebrae T1-T12. FIG. 1O shows a right lateral section view of the thoracic cage attached the thoracic vertebrae T1-T12. FIG. 1P shows an anterior view of the thoracic cage connected to the thoracic vertebrae T1-T12. FIG. 1Q shows a posterior view of the thoracic cage connected to the thoracic vertebrae T1-T12. The thoracic cage includes twelve right side ribs R1R, R2R, R3R, R4R, R5R, R6R, R7R, R8R, R9R, R10R, R11R, and R12R, and twelve left side ribs R1L, R2L, R3L, R4L, R5L, R6L, R7L, R8L, R9L, R10L, R11L, and R12L. Ribs one through seven, R1R-R7R and R1L-R7L, attach independently to the sternum 161 through costal cartilages C1R-C7R and C1L-C7L, respectively. Ribs eight through ten, R8R-R10R and R8L-R10L, attach to respective costal cartilages C8R-C10R and C8L-C10L, each of which attaches to its superior costal cartilage. Specifically, costal cartilages C8R and C8L attach to costal cartilages C7R and C7L, respectively, with costal cartilages C7R and C7L attaching to the sternum 161. And, costal cartilages C9R and C9L attach to costal cartilages C8R and C8L, respectively. And, costal cartilages C10R and C10L attach to costal cartilages C9R and C9L, respectively.

Ribs eleven and twelve, R11R-R12R and R11L-R12L, do not have an anterior attachment and terminate in the abdominal musculature and are thus referred to as floating ribs. Each rib has facet(s) for connecting to the thoracic vertebral column. Each of the first ribs R1R and R1L has one facet for articulation with the first thoracic vertebra T1. The posterior end of each of the second through tenth ribs, R2R-R10R and R2L-R10L, has an inferior articular facet for connection to its numerically corresponding thoracic vertebra and a superior articular facet for connection to the thoracic vertebra above its numerically corresponding thoracic vertebra. Also, each of the second through tenth ribs, R2R-R10R and R2L-R10L, has a tubercle that includes an articular portion for articulation with the costal facet of the transverse process of its numerically corresponding thoracic vertebra. Each of the eleventh and twelfth ribs R11R, R11L, R12R, R12L has one facet at its posterior end for articulation with its numerically corresponding thoracic vertebra.

FIG. 1R shows a superior view of an interface between thoracic vertebra T6 and each of ribs R6R and R6L. The posterior end of the rib R6R has its inferior articular facet connected to the superior costal demifacet 140R of thoracic vertebra T6 to form part of the costovertebral joint at that location. Similarly, the posterior end of the rib R6L has its inferior articular facet connected to the superior costal demifacet 140L of thoracic vertebra T6 to form part of the costovertebral joint at that location. Also, rib R6R has a tubercle that includes an articular portion for articulation with the costal facet 139R of the transverse process 133R of the thoracic vertebra T6. Similarly, rib R6L has a tubercle that includes an articular portion for articulation with the costal facet 139L of the transverse process 133L of the thoracic vertebra T6. FIG. 1S shows an isometric view of the interface between the sixth thoracic vertebra T6 and the seventh thoracic vertebra T7, including the ribs R7R and R7L. FIG. 1S shows the posterior end of the rib R7L having its superior articular facet connected to the inferior costal demifacet 141L of thoracic vertebra T6, and having its inferior articular facet connected to the superior costal demifacet 140L of thoracic vertebra T7 (hidden from view in FIG. 1S), to form the costovertebral joint at that location. Also, FIG. 1S shows the tubercle 171 of the rib R7L that includes the articular portion for articulation with the costal facet 139L of the transverse process 133L of the thoracic vertebra T7.

When viewed posteriorly, the spinal column should follow a straight line extending vertically upward from the vertical centerline of the sacrum 107, which is referred to as the sacral vertical line. However, a person can be afflicted with a condition known as scoliosis in which a three-dimensional torsional deformity manifests in the spine and trunk of the person. With scoliosis, the spinal column assumes (develops into) a configuration having one or more lateral curves (side-to-side curves) relative to the sagittal plane that divides the human body into left and right halves. Also, scoliosis often includes rotation of vertebrae in a direction transverse direction relative to the vertebral foramen. FIG. 1T shows diagrams from a posterior perspective of the human spinal column having a normal configuration 173, a scoliotic configuration 175 exhibiting a generalized "C-shaped" curvature, and a scoliotic configuration 177 exhibiting a generalized "S-shaped" curvature. The "C-shaped" curvature of the scoliotic configuration 175 includes a single curve 179 relative to the sacral vertical line 172. The "S-shaped" curvature of the scoliotic configuration 177 includes an upper curve 181 relative to the sacral vertical line 172 and a lower curve 183 relative to the sacral vertical line 172. It should be understood that the "C-shaped" curvature of the scoliotic configuration 175 and the "S-shaped" curvature of the scoliotic configuration 177 are simplified representations of the actual scoliotic condition provided for purposes of description. In reality, actual scoliotic configurations of the human spinal column can include more than two curves and can include substantial vertebral rotations that "twist" the thoracic cage causing noticeable physical deformities and in some cases significant pain and suffering.

Additionally, scoliosis is not to be confused with the normal coronal curvature (front-to-back curvature) of the spinal column relative to the coronal plane that divides the human body into anterior and posterior halves. FIG. 1U shows diagrams from a right-lateral perspective of the human spinal column having a normal coronal configuration 185, a kyphosis coronal configuration 186, and a lordosis coronal configuration 187. The normal coronal configuration 185 includes a cervical coronal curvature 188 along the cervical region 101, a thoracic coronal curvature 189 along the thoracic region 103, and a lumbar coronal curvature 190 along the lumbar region 105. In the kyphosis coronal configuration 186, the thoracic coronal curvature 189 is greater than normal, which can manifest as a persistent downward bend or hunch in the human's posture. In the lordosis coronal configuration 187, the lumbar coronal curvature 190 is greater than normal, which can manifest as backward lean in the human's posture. Scoliotic configurations of the human spinal column may contribute to or worsen the kyphosis coronal configuration 186 and/or the lordosis coronal configuration 187 when present.

About 10% of adolescents have some amount of scoliosis. And, about 1% of adolescents have scoliotic curvatures that require significant medical attention. However, as the 10% of the adolescents that have some amount of scoliosis reach older age, the effects of their scoliosis can become more significant, and possibly lead to struggles with pain and other forms of spinal degeneration. Four out of five cases of scoliosis are considered idiopathic, which means that the cause of scoliosis in those cases is unknown. Also, a person with scoliosis can be otherwise healthy.

Idiopathic scoliosis can be typed according to age of onset. For infantile idiopathic scoliosis, scoliotic spinal curvature appears before age three. For juvenile idiopathic scoliosis, scoliotic spinal curvature appears between ages three and ten. For adolescent idiopathic scoliosis (AIS), scoliotic spinal curvature appears between ages ten and thirteen, near the beginning of puberty. Except for the age of onset, AIS and juvenile idiopathic scoliosis can be considered essentially equivalent to each other. AIS is the most common type of scoliosis. For adult idiopathic scoliosis, scoliotic spinal curvature appears after physical maturation is complete.

Scoliosis can cause noticeable asymmetry in the human torso region. In some cases, a person having scoliosis may appear to be standing with one shoulder higher than the other, or with a tilt in their waistline. In some cases, a shoulder blade of a person having scoliosis may appear more prominent than the other shoulder blade due to transverse rotation of the spinal column. Scoliotic curvatures tend to increase more rapidly near the adolescent growth spurt. Also, scoliosis that begins at an earlier age is more likely to progress to a significant condition as compared with scoliosis that begins later in puberty.

Although idiopathic scoliosis is considered to have an unknown cause, some theories exist as to the root cause. A theory that a tight spinal cord could be the cause of adolescent scoliosis was first proposed by a neuroradiologist named Dr. Roth in 1968. The theory was further expounded upon by Dr. Porter in 2001, and has become known as the Roth-Porter Hypothesis. To understand how a tight spinal cord can cause scoliosis, Roth and Porter used the analogy of a string that runs through the middle of a spring. The spring represents the spinal bones, and the string represents the spinal cord. As the string is pulled tight, the spring coils down into a scoliotic shape. Most commonly, nerve tension will be due to a problem called "Uncoupled Neuro-Osseous Development," which means that the bones are growing faster than the nerves, creating a spinal cord or meningeal tension. This relatively short spinal cord results in a tugging force on the posterior parts of the vertebral column, causing the column to compress down. Just like tension on a string will cause the spring to coil down, so tension on the spinal cord will cause the spine to coil down. This coiled-down scoliotic position actually relieves the tension on a tight spinal cord. Under the Roth-Porter Hypothesis, scoliosis is an adaptive position in response to nerve tension.

With the Roth-Porter Hypothesis in mind, a nerve tension scoliosis case is a situation where there is either a tight, inelastic, or tethered spinal cord. The nerve root or meninges create the main driving force causing the spine to coil down into scoliosis. Nerve tension is likely the most common root cause of scoliosis. If a scoliosis is progressing rapidly, and has been diagnosed as "idiopathic," the scoliosis likely has a nerve tension root cause. Examples of nerve tension pathologies that can cause scoliosis include: tumors or cysts, intraspinal anomalies, tethered cord syndrome, and uncoupled neuro-osseous development. Tumors or cysts can bind the meninges or cord and cause a tension on the nerves, leading to scoliosis. Tumors or cysts can also cause neuromuscular dysfunction. With intraspinal anomalies, the spinal cord or nerves develop embryologically in a way such that one side or one part of the cord is pulled tight at birth. Even though the problem happens at birth, it may not appear until the child begins to have growth spurts. Tethered cord syndrome is a condition that exists from birth and causes the entire spinal cord to be pulled noticeably lower towards the sacrum, placing tension on the spinal cord. Uncoupled neuro-osseous development means that the spinal cord (neuro) is not growing as fast or as long as the bones of the spine (osseous). Some physicians believe that uncoupled neuro-osseous development is likely to become recognized as the most common cause of adolescent scoliosis.

Beyond idiopathic scoliosis, causes are known for some types of scoliosis, including congenital scoliosis, neuromuscular scoliosis, and degenerative scoliosis. Congenital scoliosis is caused by congenital abnormal formation of the bones of the spine and is often associated with other organ defects. Neuromuscular scoliosis is caused by loss of control of the nerves and/or muscles that support the spinal column. Some causes of neuromuscular scoliosis include cerebral palsy, poliomyelitis, muscular dystrophy, severe chiari and syringomyelia, and functional neurologic deficits. Degenerative scoliosis is caused by degeneration of intervertebral discs and/or arthritis in vertebral joints.

In some cases, there may be structural or biomechanical root causes of scoliosis. "Structural" root causes may refer to bones that are asymmetric or incorrectly shaped. For example, a half-formed vertebra at birth, known as a hemivertebra, may also create a scoliosis. Another example of structural-biomechanical scoliosis is when one leg grows a little longer than the other, causing the sacrum to not be level. The sacrum is the base of the spine, so when the sacrum tilts, the spine tilts, and there can be a mild (and sometimes moderate) scoliosis as a result. "Structural causes" may also apply to ligament damage from trauma or from degeneration of discs. If key stabilizing ligaments of the spine are damaged or torn, the vertebra may tilt in response, creating a scoliotic curve. Structural or biomechanical conditions that lead to scoliosis are common and usually cause mild to moderate non-progressive scoliosis.

In the case of scoliosis caused by neuro-muscular pathology, there is a breakdown in either the body's control system (the brain) or the nerves that connect the brain to the muscles, or the muscles themselves cannot work correctly. For example, in cerebral palsy, there is a lack of proper central nervous system control within the brain. In poliomyelitis, the peripheral nerves that carry signals from the brain to the muscles are damaged. In muscular dystrophy, there is weakness of the muscles, rendering the muscles unable to support a straight spine. Neuro-muscular pathology cases tend to be more aggressive. Progression of the scoliosis, i.e., the tendency for the curve to grow large, is often quite high for neuro-muscular pathology cases.

Whatever the root cause of a scoliosis, it will usually begin as a small, flexible scoliosis. At this stage, the spine is still capable of going through its normal range of motion (more or less). In a small, flexible, or "functional" scoliosis, lateral bending X-rays would show an easy correction of the curve when bending the spine sideways to the left and right. As a scoliosis grows, increasing distortion occurs in the soft tissues of the spine, which leads to loss of normal range of motion. When normal range of motion is lost, severe stiffness can set in.

As a scoliotic curve size increases, the ability to exercise the spine throughout its full range of motion is lost. As a result, the scoliosis becomes rigid and stiff primarily due to changes in soft tissue. Secondary stiffness comes from small changes in the shapes of the bones. "Structural scoliosis" is a term applied when the scoliotic curve has become stiff, inflexible, and rigid. Calling a scoliosis "structural" does not mean the curve was caused by a structural asymmetry, such as a wedge-shaped vertebra. It may be more accurate to simply call the scoliosis "rigid" instead of "structural." Some physicians prefer to use the term "structural" in order to divide scoliosis into two categories: 1) functional (flexible) scoliosis, and 2) structural (rigid) scoliosis. This may be considered a false dichotomy, as most scoliotic curves have both some functional and some structural qualities. Also, using the term "structural" for a scoliotic curve that is rigid creates the false impression that the curve is being caused by bones that are "structurally" misshaped. In truth, most larger, rigid scoliotic curves have relatively minimal distortion in the bones. Additionally, the term "structural" is often used to communicate to the person that nothing at this point could straighten their spine, except surgery. However, this is not always true.

In child and adolescent scoliosis, a small flexible scoliotic curve can quickly become a large, stiff, and rigid. During growth of the spinal bones, the tightness of the spinal cord causes the vertebra to "coil down" like a spring that has a tight string run through it, such as according to the Roth-Porter Hypothesis. The spine is now constantly postured in a scoliotic pattern, unable to straighten even when the person tries to bend out of it. This means that the ligaments, muscles, and discs are no longer being exercised through their normal range of motion. Failure to move muscles and joints always results in stiff "contractures" of the joints. These "contractured" joints are so stiff, that it can feel like bone running into bone, when in reality, it is really just soft tissue that has become stiff, shortened, and tough. This is good and bad news. Good news because soft tissue contractures can be loosened up with proper mobilization. Bad news, because it is a difficult and arduous process to loosen up contractured soft tissue around the joints.

A typical progression of AIS begins with an early stage flexible and functional scoliosis. Then, the scoliotic curve size progresses, which lead to a loss of range of motion of the spinal column. This loss of range of motion in turn leads to joint contractures of within the spinal column. With the joint contractures, the scoliotic portions of spinal column are no longer being exercised, which causes stiffer, rigid, "structural" scoliosis. Ultimately, the bones of the spine can change shape in response to the mechanical stresses placed on them by the scoliosis, causing wedge-shaped vertebra, asymmetric pedicles, and thoracic cage deformity.

Early stage spinal bone changes in a small scoliosis have been observed. These early stage changes are most noticeable in the front part of the thoracic vertebral bodies. It has been observed that the front part of the vertebral body can grow taller than what is normal. This is called Relative Anterior Spinal Overgrowth (RASO). In other words, with RASO, the front of the vertebra is growing taller than it should. This can lead to a lordosis condition in which there is a loss of the normal thoracic coronal curvature. The existence of RASO and a loss of the normal thoracic coronal curvature is most likely in response to nerve tension. Nerve tension will cause the thoracic region of the spine to flatten out its normally curved shape (see the normal thoracic coronal curvature 189 of FIG. 1U). The loss of thoracic coronal curvature, or "flat back," is a position that relieves tension on the spinal cord. The "flat back" posture is an early adaptive position in response to a tight spinal cord. It is suspected that nerve tension occurs first, followed by the "flat back" in response to the nerve tension.

As a scoliotic curve becomes larger, the thoracic cage distorts to adapt to the growing scoliosis. Also, a scoliotic curve becomes larger, the pedicles of the spine may grow asymmetric in length and thickness. Further, a scoliotic curve becomes larger, the normally rectangular vertebra may develop a slight rhomboid-wedge shape at the apex of the scoliotic curve.

A system for classifying AIS has been developed by Lawrence G. Lenke, MD, and was published in the "Journal of Bone and Joint Surgery" in 2001. This system is commonly referred to as the "Lenke Classification System for AIS." FIG. 1V shows a chart of the Lenke Classification System for AIS. FIG. 1W shows a chart of scoliotic spinal diagrams corresponding to scoliosis curve classifications within the Lenke Classification System for AIS. To use the Lenke Classification System for AIS, it is necessary to measure the Cobb angle(s) of the scoliotic curve(s) along the spinal column. FIG. 1X shows a diagram illustrating how to measure the Cobb angle of scoliotic curve. In the example of FIG. 1X, the scoliotic curve extends from vertebra V2 to vertebra V8, with the apex of the curve occurring at vertebra V5. The most significantly angled vertebra within the curve above the apex is vertebra V3. The most significantly angled vertebra within the curve below the apex is vertebra V7. To measure the Cobb angle, an upper line is drawn parallel to the upper border of the most significantly angled vertebra within the curve above the apex. Therefore, in the example of FIG. 1X, an upper line 191 is drawn parallel to the upper border of vertebra V3. Further, a lower line is drawn parallel to the lower border of the most significantly angled vertebra within the curve below the apex. In the example of FIG. 1X, a lower line 192 is drawn parallel to the lower border of vertebra V7. A upper perpendicular line is drawn to extend downward in a direction perpendicular to the upper line that is drawn parallel to the upper border of the most significantly angled vertebra within the curve above the apex. In the example of FIG. 1X, an upper perpendicular line 193 is drawn to extend downward in a direction perpendicular to the upper line 191. A lower perpendicular line is drawn to extend upward in a direction perpendicular to the lower line that is drawn parallel to the lower border of the most significantly angled vertebra within the curve below the apex. In the example of FIG. 1X, an lower perpendicular line 194 is drawn to extend upward in a direction perpendicular to the lower line 192. The angle formed between the upper perpendicular line and the lower perpendicular line at their point of crossing is the Cobb angle, or the angle of curvature of the scoliotic curve.

Given the foregoing, it is of interest to determine new and effective ways for mitigating and reversing scoliosis, and particularly AIS, for the benefit of humanity. It is within this context that the present invention arises.

SUMMARY

In an example embodiment, an apparatus is disclosed for treatment of human scoliosis. The apparatus includes a front segment of a frame configured to extend across an anterior side of a human when the human is present within the apparatus. The apparatus also includes a back segment of the frame configured to extend across a posterior side of the human when the human is present within the apparatus. The back segment has a fixed spatial relationship with respect to the front segment. The apparatus also includes a clamp bar configured to extend between the front segment and the back segment. The clamp bar is configured to extend across a first lateral side of the human when the human is present within the apparatus. The clamp bar is configured to interface with the first lateral side of the human at a location between an ilium bone structure of the human and a thoracic cage of the human when the human is present within the apparatus. The apparatus also includes a lateral restraint positioned between the front segment and the back segment and rigidly connected to both the front segment and the back segment. The lateral restraint is configured to interface with a second lateral side of the human over an engagement area corresponding to a portion of the thoracic cage of the human when the human is present within the apparatus. The apparatus also includes a weight receiver connected to apply a downward treatment force to both the front segment and the back segment at a position opposite the clamp bar from the lateral restraint. The lateral restraint is configured to receive a lateral translation force generated by the human to maintain a near-level orientation of the front segment and the back segment when the downward treatment force is applied from the weight receiver.

In an example embodiment, an apparatus is disclosed for treatment of human scoliosis. The apparatus includes a frame that includes a front segment, a back segment, a first side segment, and a second side segment. Each of the first side segment and the second side segment extend between and rigidly connect to the front segment and the back segment. The apparatus also includes a clamp bar extending between and connected to the front segment and the back segment. A downward lever arm portion of the frame includes the first side segment, and a portion of the front segment extending between the clamp bar and the first side segment, and a portion of the back segment extending between the clamp bar and the first side segment. An upward lever arm portion of the frame includes the second side segment, and a portion of the front segment extending between the clamp bar and the second side segment, and a portion of the back segment extending between the clamp bar and the second side segment. The apparatus also includes a lateral restraint attached to the upward lever arm portion of the frame. The lateral restraint is positioned at a vertical location above the frame. The apparatus also includes a treatment weight receiver attached to the downward lever arm portion of the frame. A region between the clamp bar and the lateral restraint and between the front segment and the back segment is configured for occupancy by a human. The clamp bar is configured to interface with a first lateral side of the human at a location between an ilium bone structure of the human and a thoracic cage of the human when the human is present within the region. The lateral restraint is configured to interface with a second lateral side of the human over an engagement area corresponding to a portion of the thoracic cage of the human when the human is present within the region.

In an example embodiment, a method is disclosed for treatment of human scoliosis. The method includes positioning a clamp bar to interface with the human at a location between an ilium bone structure of the human and the thoracic cage of the human on a first lateral side of the human. The method also includes positioning a lateral restraint over an engagement area corresponding to a portion of a thoracic cage of a human on a second lateral side of the human opposite from the first lateral side of the human. The lateral restraint is rigidly connected to a frame through a corresponding support structure. The clamp bar is rigidly connected to the frame. The method also includes applying a downward force to the frame at a location opposite the clamp bar from the lateral restraint. The method also includes directing the human to laterally translate their spinal column toward the lateral restraint so as to maintain the frame in a near-level orientation.

In an example embodiment, a treatment apparatus for scoliosis is disclosed. The treatment apparatus includes a frame. The treatment apparatus also includes an attachment section of the frame for coupling the treatment apparatus to a human. The treatment apparatus also includes an extension section of the frame. The extension section is a lateral continuation of the frame to a side of the attachment section. The treatment apparatus also includes a weight receiver coupled to an outer end of the extension section that is away from the attachment section.

In an example embodiment, an apparatus for scoliosis is disclosed. The apparatus includes a frame having a first side and a second side. The frame is configured to surround a mid-section of a human body. The apparatus also includes an attachment section of the frame. The attachment section has a clamp attachment for contacting a first lateral side of the human body and a lateral attachment for contacting the second lateral side of the human body. The lateral attachment is coupled to the second side of the frame. And, the clamp attachment is coupled to the frame proximate to the first lateral side of the human body. The apparatus also includes an extension section of the frame extending in a direction away from the clamp attachment and away from the first lateral side of the human body. The apparatus also includes a weight receiver coupled to the extension section of the frame. The weight receiver is configured to connect to one or more weight units for adding a weighted gravitational force to the extension section. The apparatus also includes a strap configured for connection to a first point of the frame and a second point of the frame. The strap is further configured to contact a side-shoulder of the second lateral side of the human body, when the apparatus is disposed on the human body for treatment. The clamp attachment is configured to press upon the first lateral side of the human body between a lower rib and above a hip bone. The lateral attachment is configured to press upon lower ribs of the second lateral side of the human body.

In an example embodiment, a treatment apparatus for scoliosis is disclosed. The treatment apparatus includes a frame having a front side, a back side, a left side, and a right side. The frame is configured to surround a mid-section of a human body. A front of the human body is oriented to face the front side of the frame when the frame is surrounding the mid-section. The treatment apparatus also includes an attachment section of the frame. The attachment section has a clamp attachment for contacting a first lateral side of the human body and a lateral attachment for contacting a second lateral side of the human body. The lateral attachment is coupled proximate to the right side of the frame. And, the clamp attachment is coupled to the frame proximate to the second lateral side of the human body, when present. The treatment apparatus also includes an extension section of the frame extending in a direction toward the left side of the frame and away from the first lateral side of the human body. The treatment apparatus also includes a weight receiver coupled proximate to the left side of the frame. The weight receiver is configured to hold one or more weights for increasing a gravitational force at the left side of the frame. The treatment apparatus also includes a strap configured for connection to a first point on the front side of the frame and to a second point on the back side of the frame. The strap has a side-shoulder section that is configured to contact a side-shoulder of the second lateral side of the human body, when the treatment apparatus is disposed on the human body for treatment. The clamp attachment is configured to press upon the first lateral side of the human body between a lower rib and above a hip bone. And, the lateral attachment is configured to press upon lower ribs of the second lateral side of the human body.

In an example embodiment, an apparatus for scoliosis is disclosed. The apparatus includes a frame having a first side and a second side. The frame is configured to surround a mid-section of a human body, when the apparatus is worn by the human body for treating scoliosis. The apparatus also includes an attachment section of the frame having a pad clamp attachment for contacting a first lateral side of the human body and a lateral attachment band for contacting a second lateral side of the human body. The lateral attachment band is coupled proximate to the second side of the frame. And, the pad clamp attachment is coupled to the frame proximate to the first lateral side of the human body. The apparatus also includes an extension section of the frame extending in a direction away from the pad clamp attachment and away from the first lateral side of the human body. The apparatus also includes a weight coupled to the extension section of the frame. The weight is configured to increase gravitational force at the extension section. The apparatus also includes a strap configured for connection to a first point of the frame and to a second point of the frame. The strap has a side-shoulder attachment for interfacing with a lower side shoulder at the second lateral side of the human body, when the apparatus is worn by the human body for treatment. The pad clamp attachment is configured to contact the first lateral side of the human body between a lower rib and above a hip bone. The lateral attachment band is configured to transfer a contact force to lower ribs of the human body at the second lateral side.

Other aspects and advantages of the invention will become more apparent from the following detailed description, taken in conjunction with the accompanying drawings, illustrating by way of example the present invention.

BRIEF DESCRIPTION OF THE DRAWINGS

FIG. 1O shows a right lateral section view of the thoracic cage attached the thoracic vertebrae T1-T12.

FIG. 1V shows a chart of the Lenke Classification System for AIS.

FIG. 4C shows the isometric view of the TLT apparatus of FIG. 3C with the human positioned within the TLT apparatus in the therapeutic position, in accordance with some embodiments of the present invention.

FIG. 4O shows the TLT apparatus 300A with the human 400 positioned therein for treatment, in accordance with some embodiments of the present invention.

FIG. 7 shows a top view of the TLT apparatus illustrating an angle of the second segment of the clamp bar in the x-y plane relative to the y-axis, in accordance with some embodiments of the present invention.

FIG. 8A shows the TLT apparatus with a clamp bar configured to have a substantially straight configuration, in accordance with some embodiments of the present invention.

FIG. 9A shows a view of the right end of the TLT apparatus with the lateral restraint band positioned at an angle relative to the frame, in accordance with some embodiments of the invention.

FIG. 9B shows an isometric view of the TLT apparatus as shown in FIG. 9A, in accordance with some embodiments of the invention.

FIG. 11C shows an example of the lateral restraint pad formed by multiple layers of material, in accordance with some embodiments of the present invention.

DETAILED DESCRIPTION

In the following description, numerous specific details are set forth in order to provide a thorough understanding of the present invention. It will be apparent, however, to one skilled in the art that the present invention may be practiced without some or all of these specific details. In other instances, well known process operations have not been described in detail in order not to unnecessarily obscure the present invention.

Figure 1A:
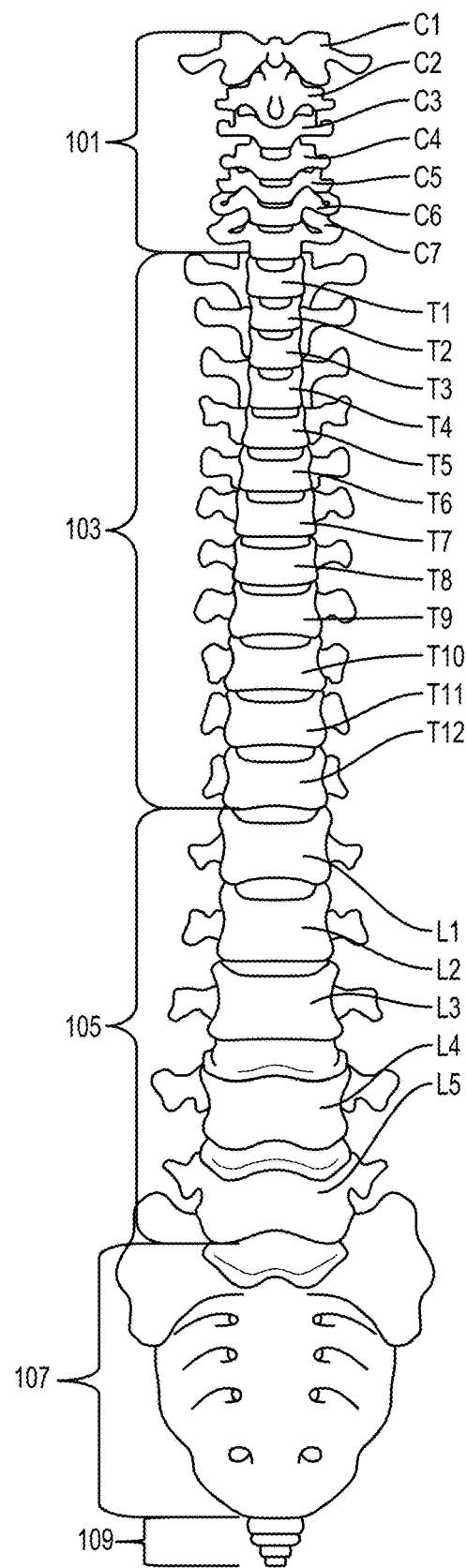
FIG. 1A shows an anterior view of a normal human spinal column.
Figure 1B:
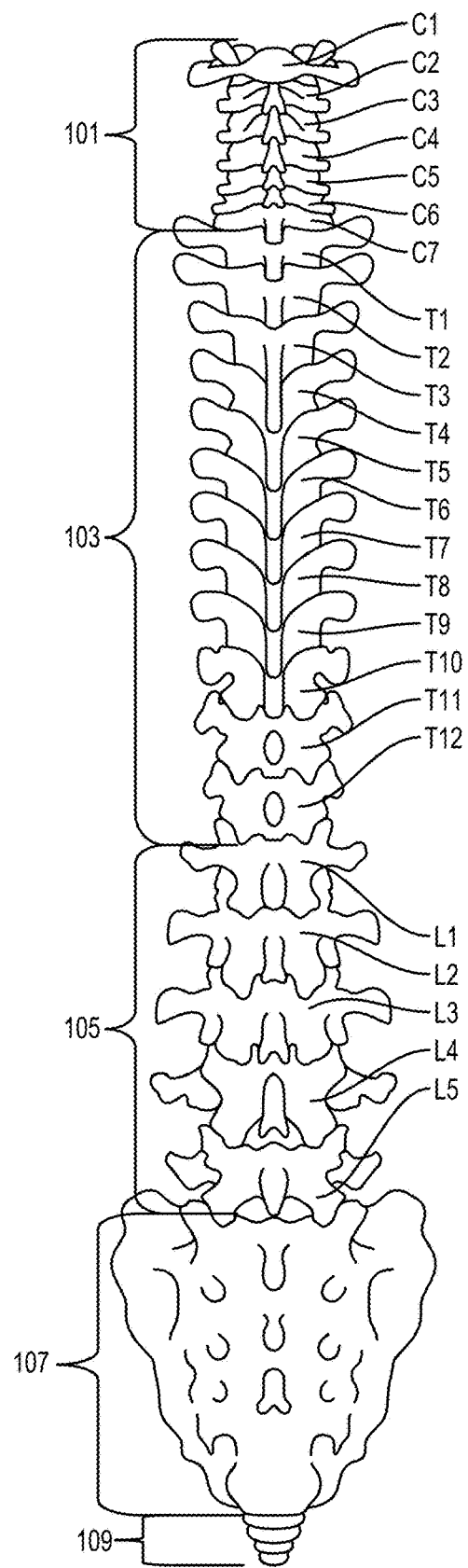
FIG. 1B shows a posterior view of the normal human spinal column.
Figure 1C:
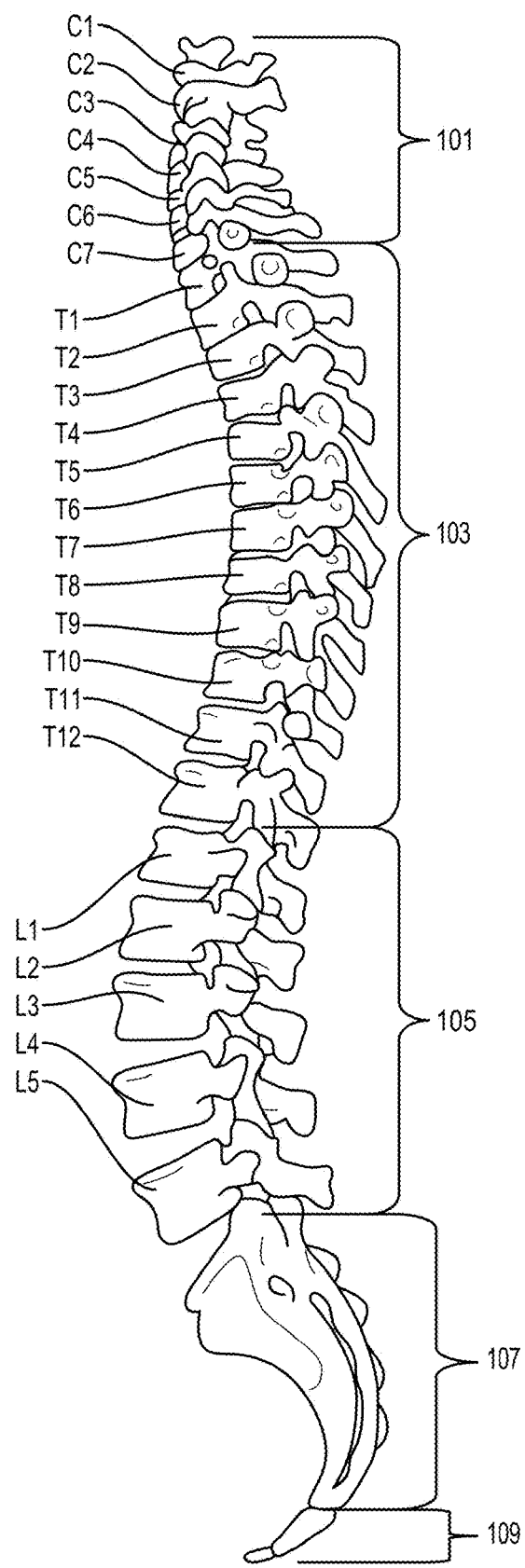
FIG. 1C shows a left lateral view of the normal human spinal column.
Figure 1D:
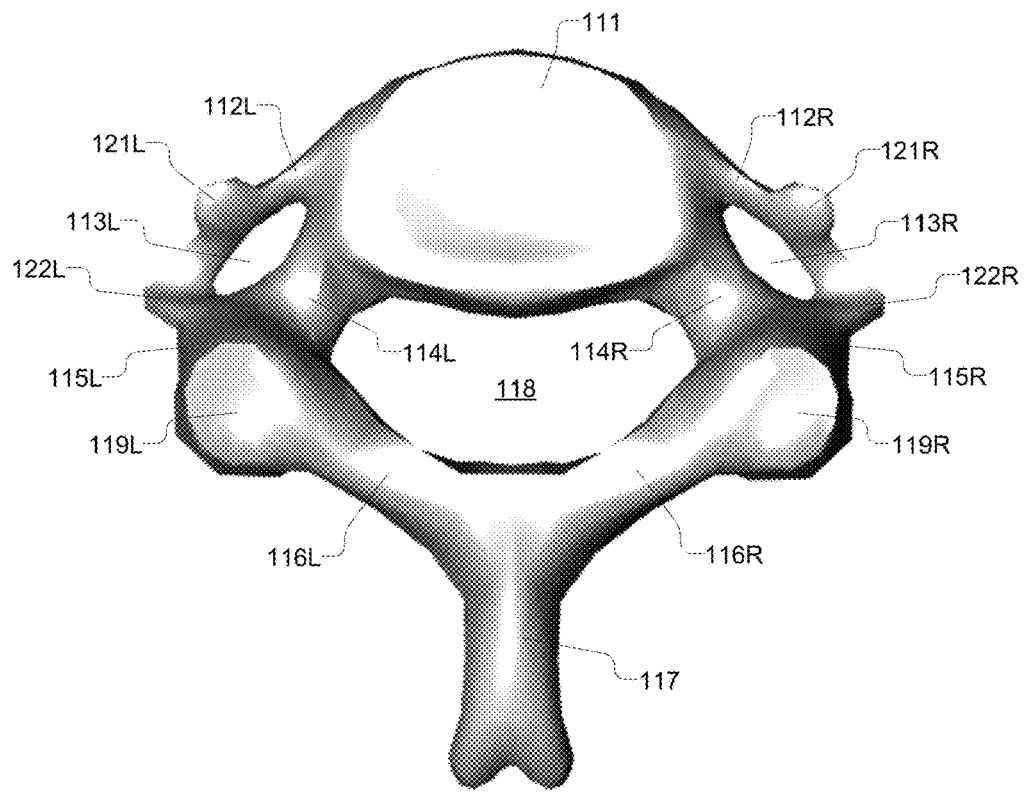
FIG. 1D shows a superior view of the fourth cervical vertebra C4.
Figure 1E:
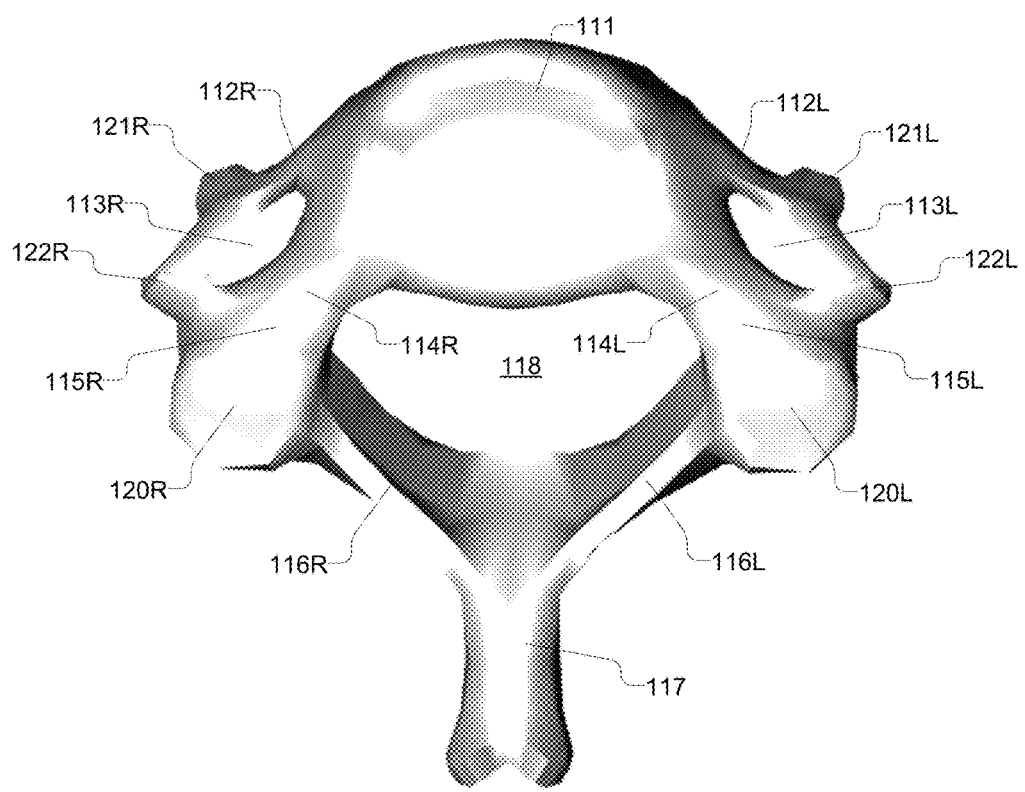
FIG. 1E shows an inferior view of the fourth cervical vertebra C4.
Figure 1F:
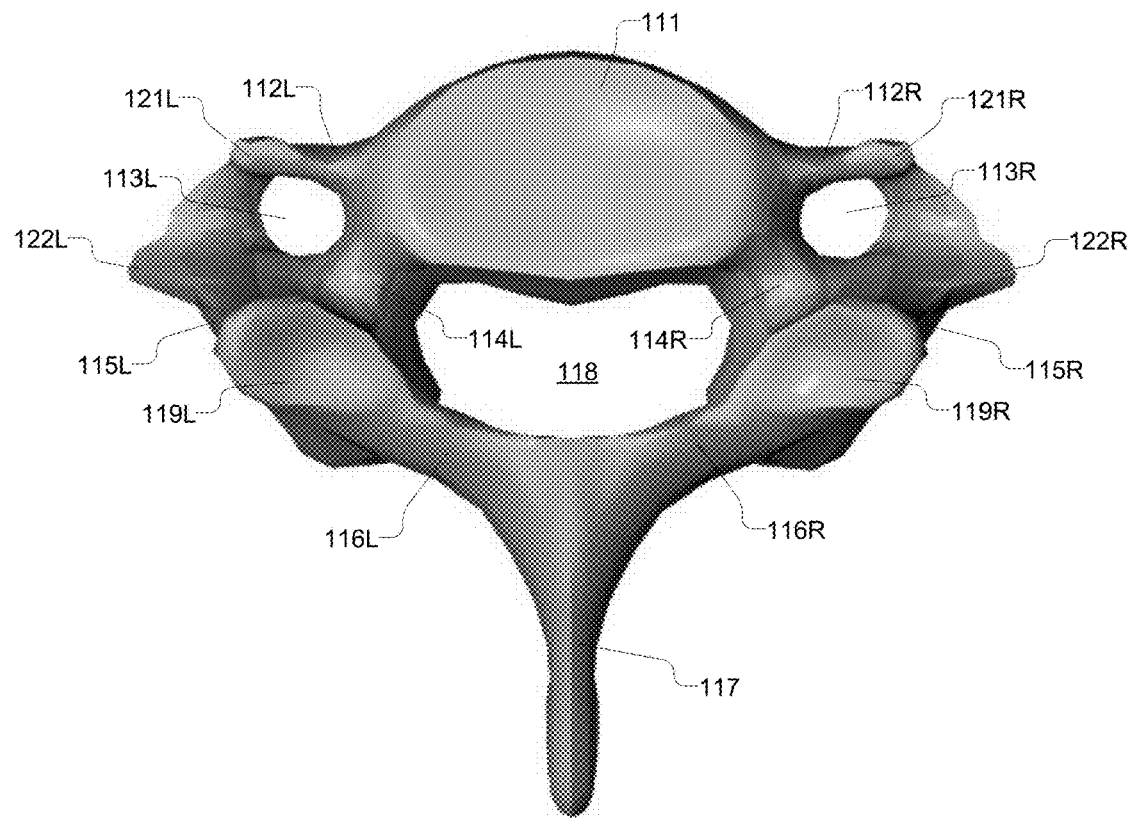
FIG. 1F shows a superior view of the seventh cervical vertebra C7.
Figure 1G:
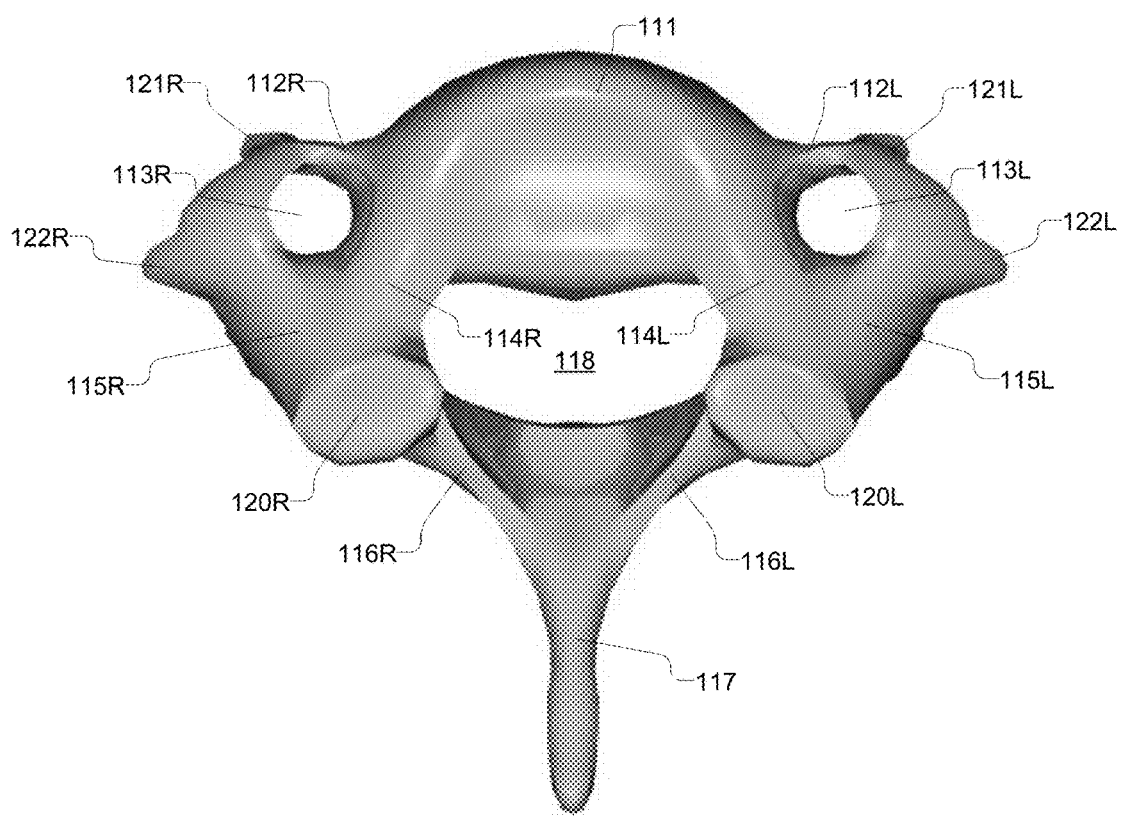
FIG. 1G shows an inferior view of the seventh cervical vertebra C7.
Figure 1H:
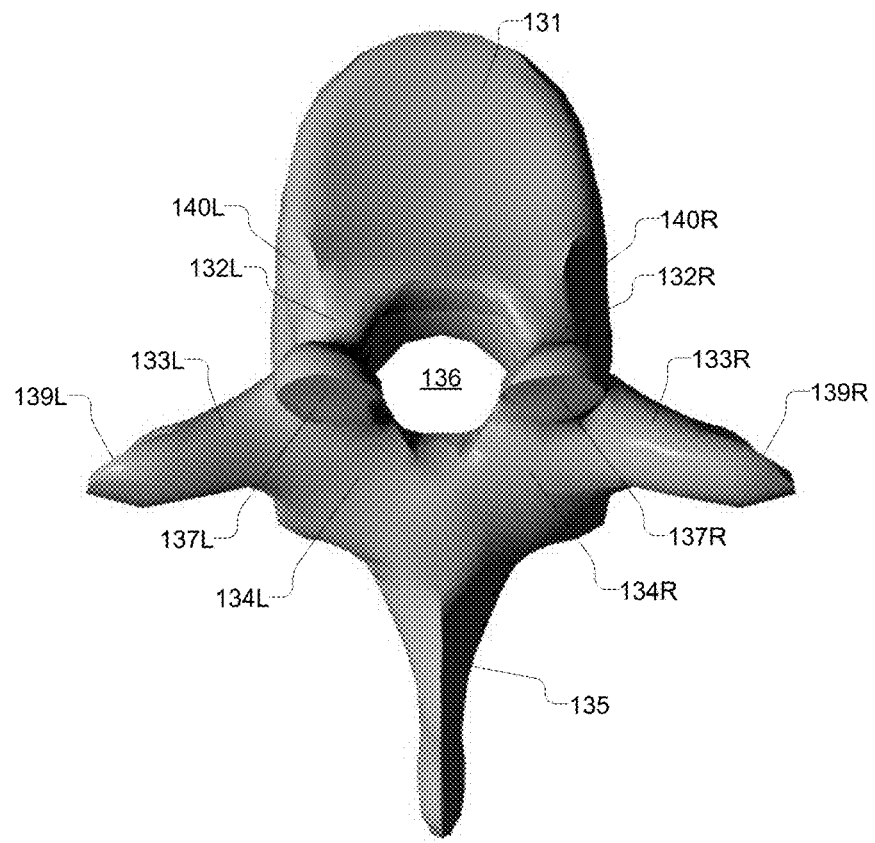
FIG. 1H shows a superior view of the fifth thoracic vertebra T5, which has a structure typical of thoracic vertebrae T1-T11.
Figure 1I:
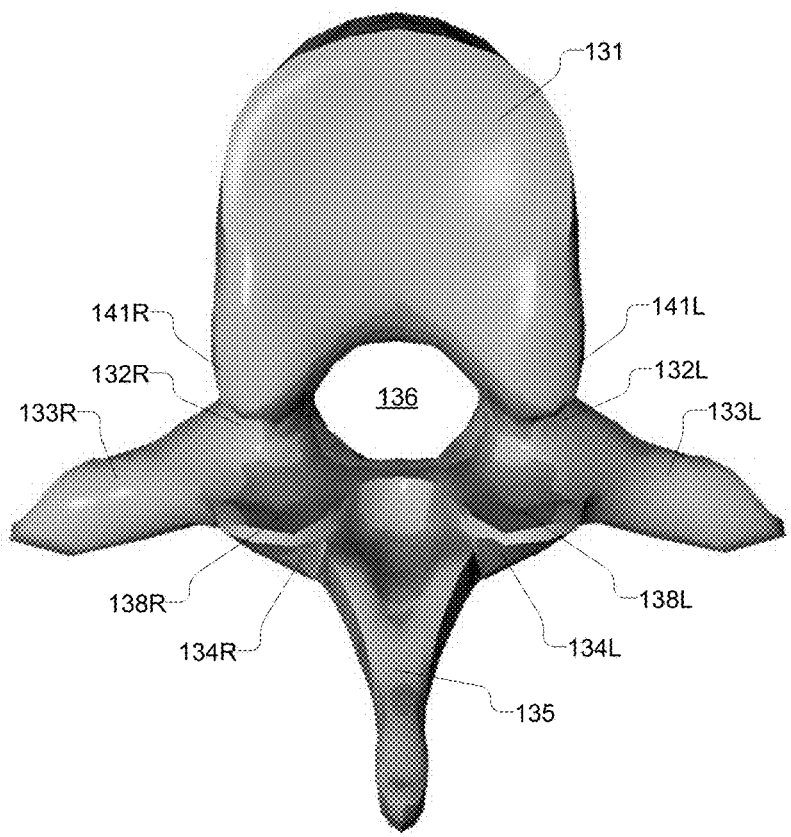
FIG. 1I shows an inferior view of the fifth thoracic vertebra T5.
Figure 1J:
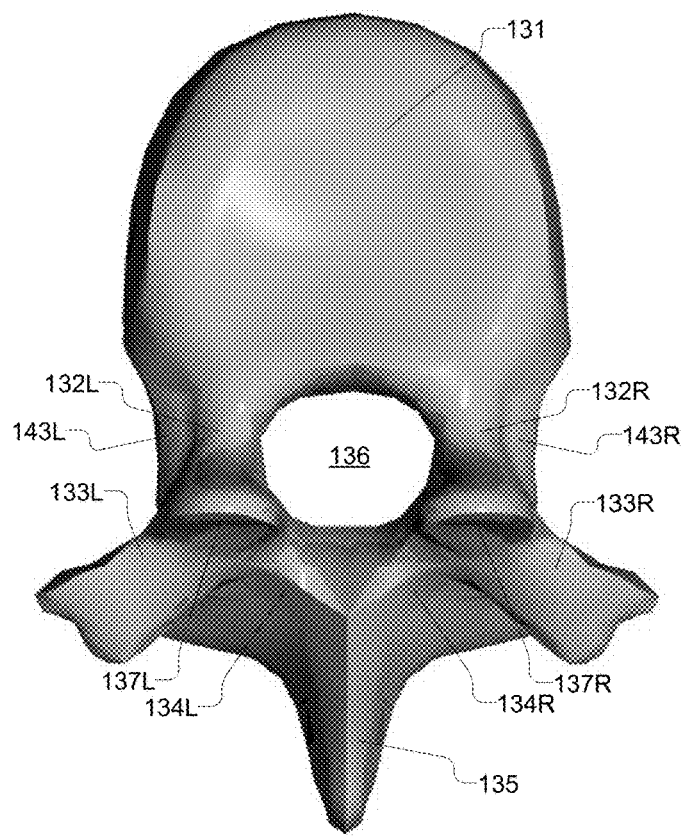
FIG. 1J shows a superior view of the twelfth thoracic vertebra T12.
Figure 1K:
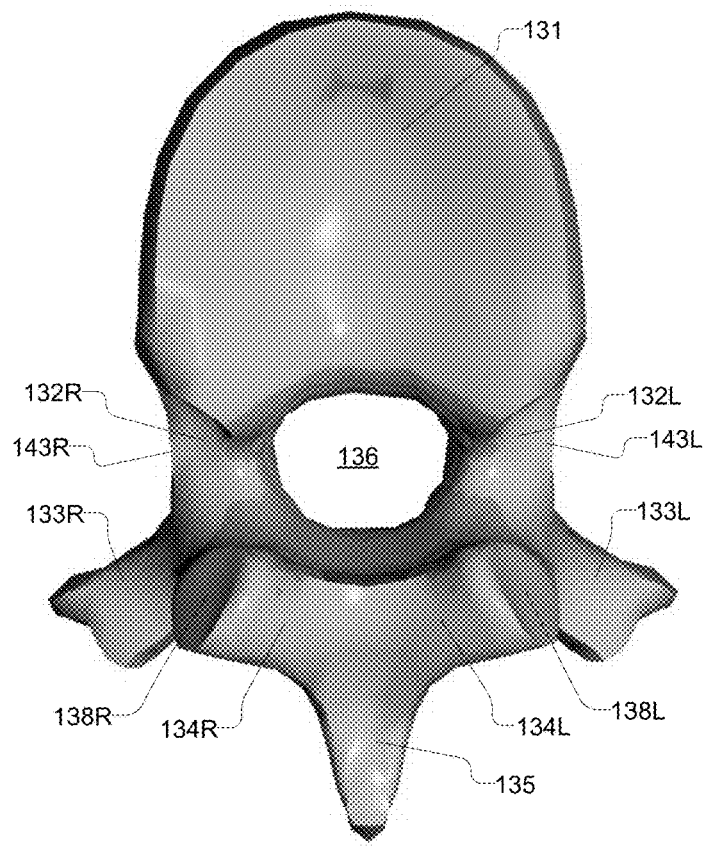
FIG. 1K shows an inferior view of the twelfth thoracic vertebra T12.
Figure 1L:
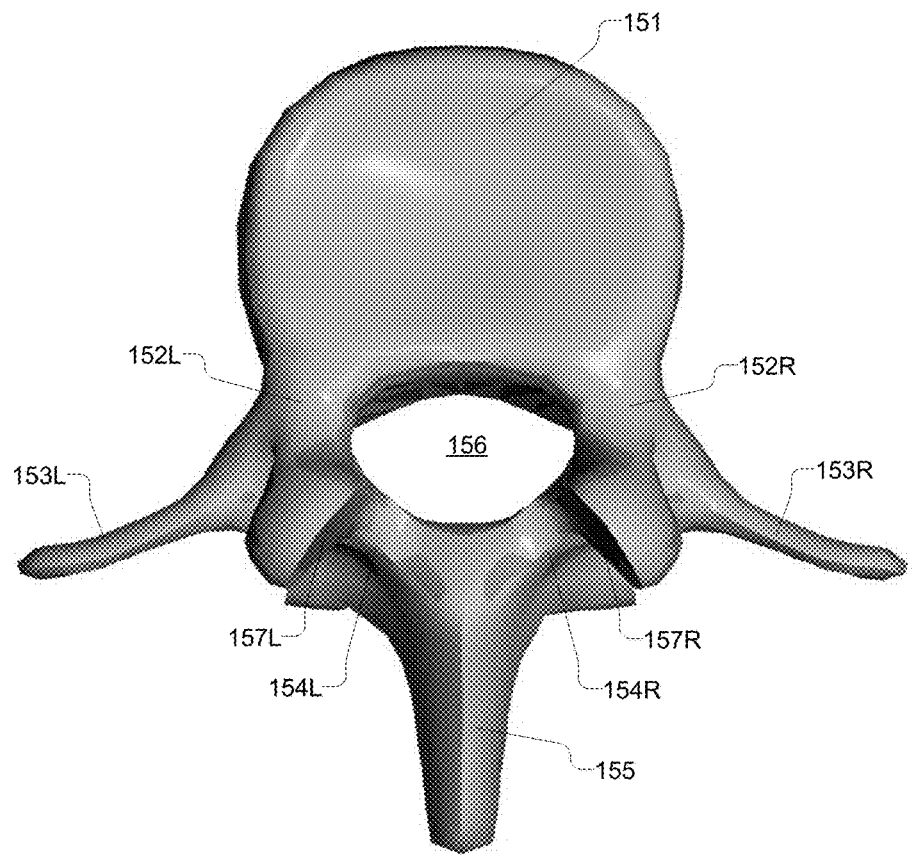
FIG. 1L shows a superior view of the third lumbar vertebra L3, which is representative of the other lumbar vertebrae L1-L2 and L4-L5.
Figure 1M:
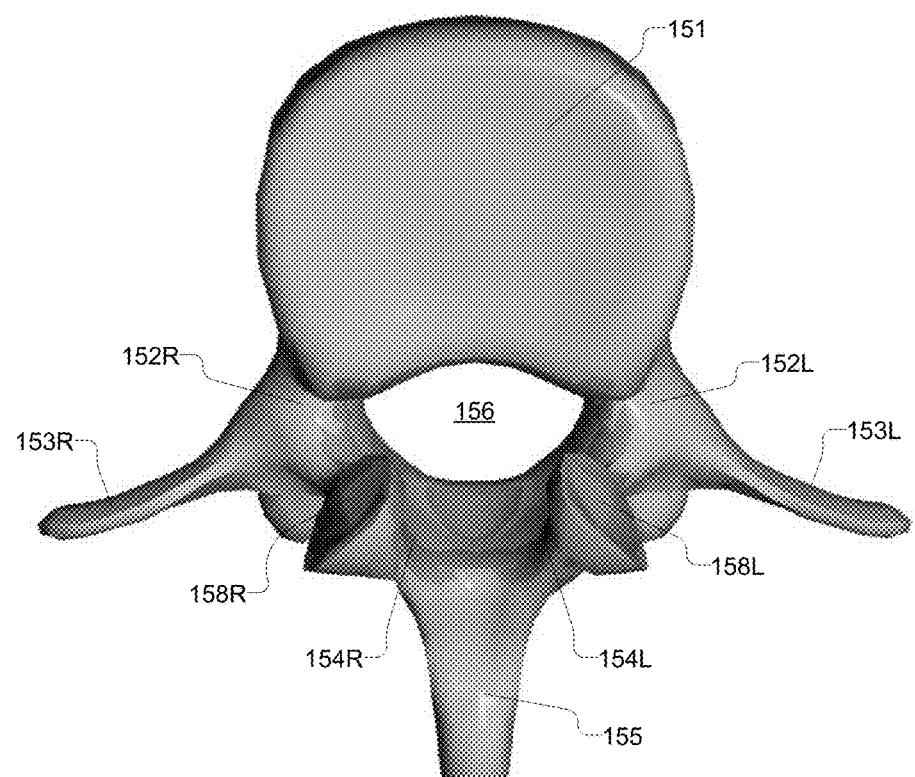
FIG. 1M shows a superior view of the third lumbar vertebra L3.
Figure 1N:
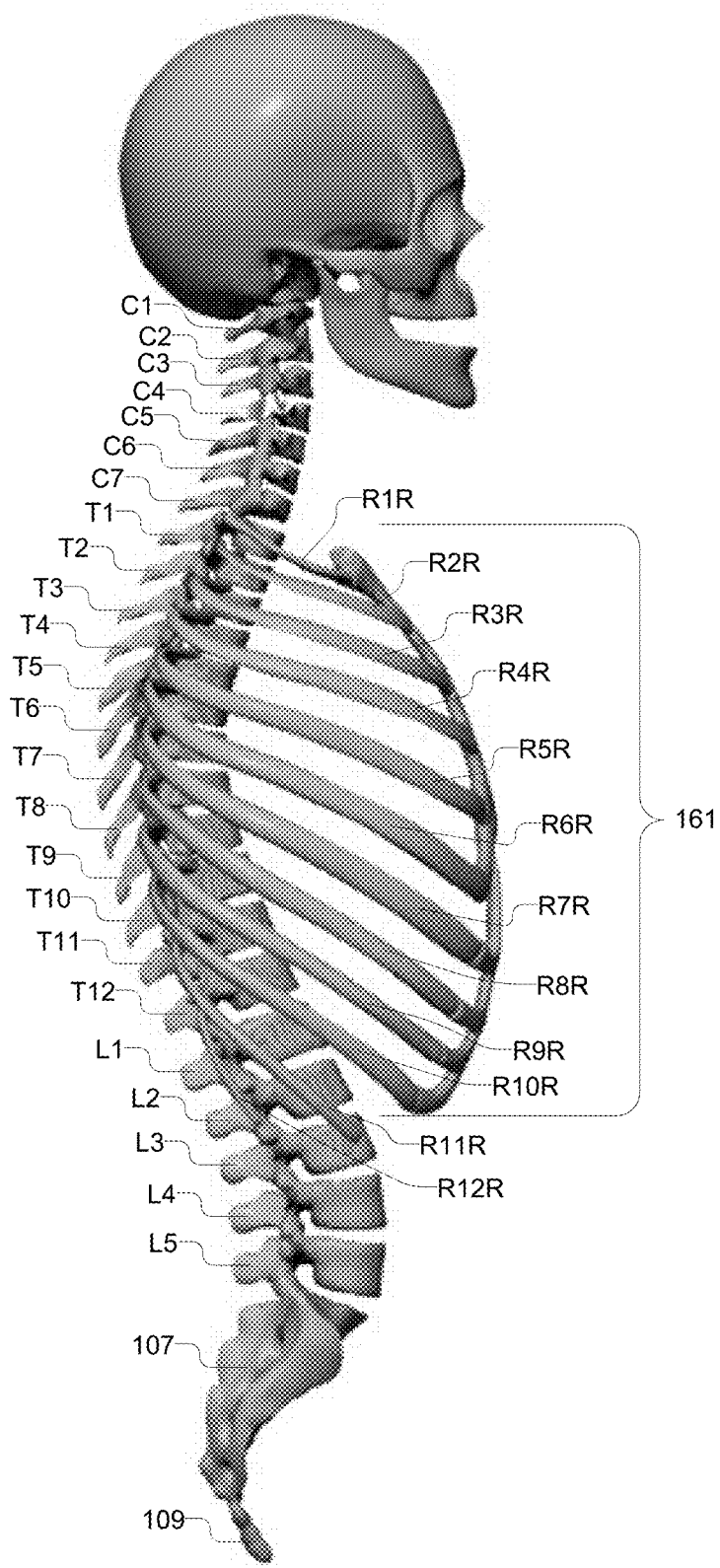
FIG. 1N shows a right lateral view of the spinal column with the thoracic cage 160 shown attached to the thoracic vertebrae T1-T12.
Figure 1P:
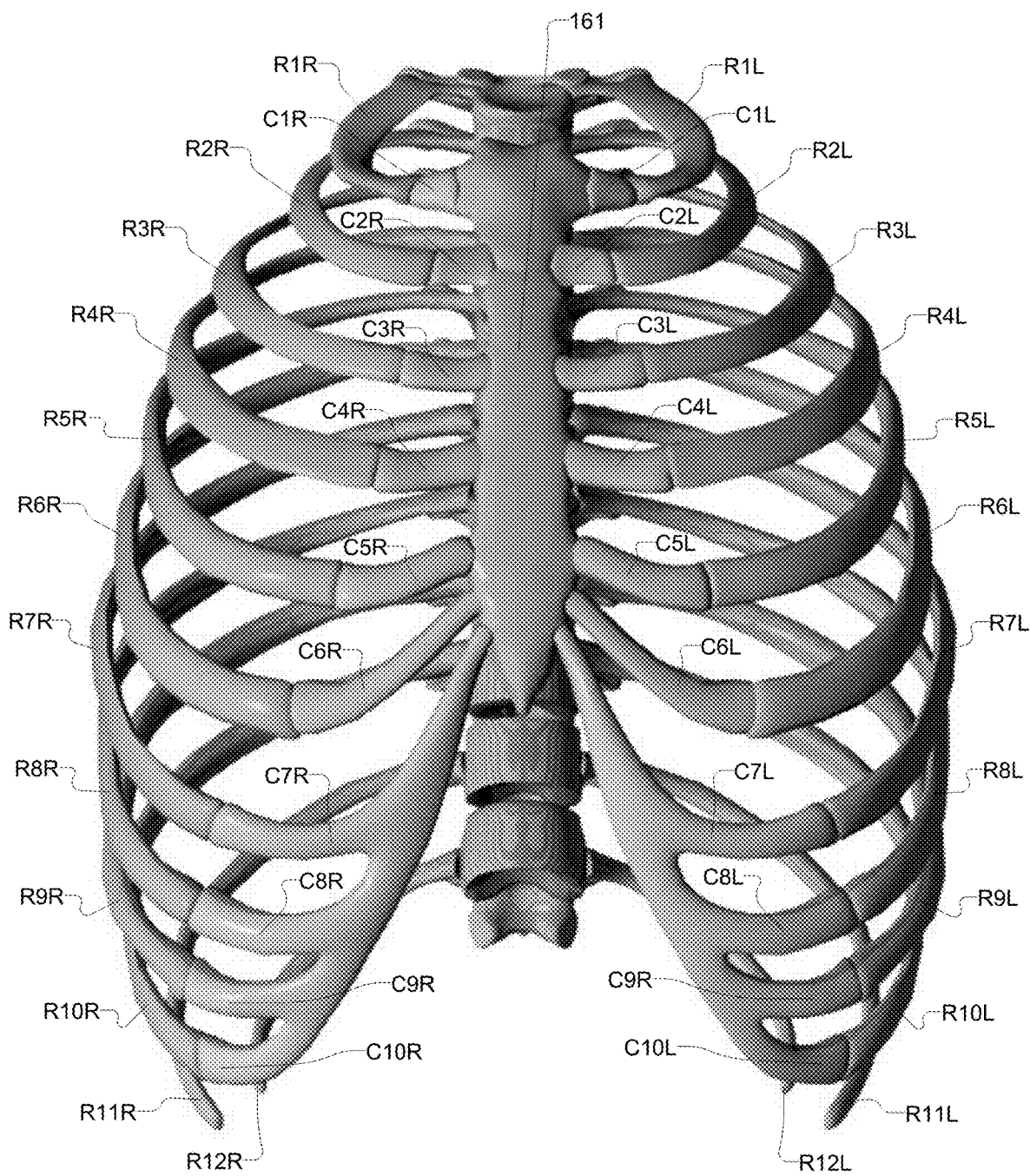
FIG. 1P shows an anterior view of the thoracic cage connected to the thoracic vertebrae T1-T12.
Figure 1Q:
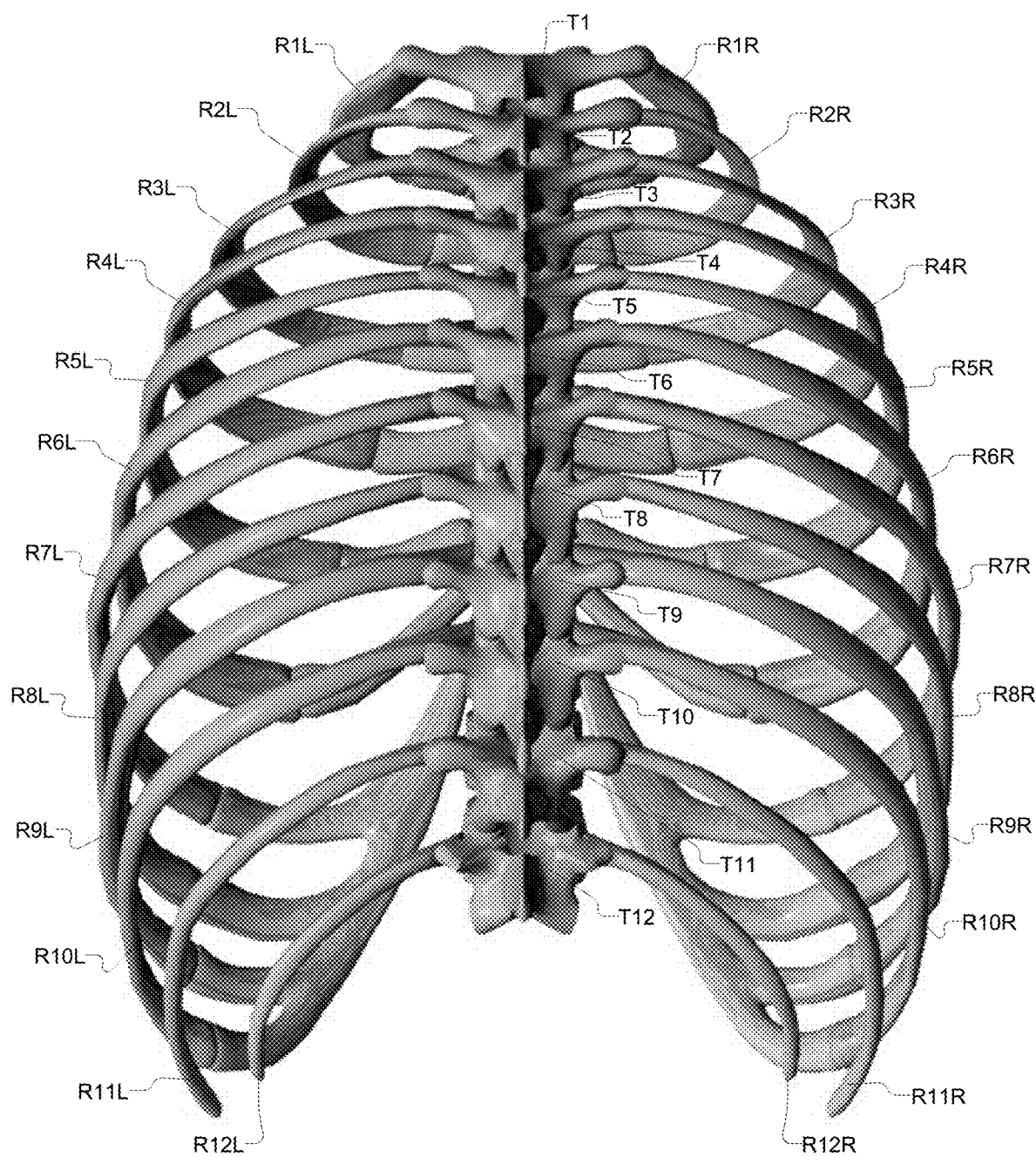
FIG. 1Q shows a posterior view of the thoracic cage connected to the thoracic vertebrae T1-T12.
Figure 1R:
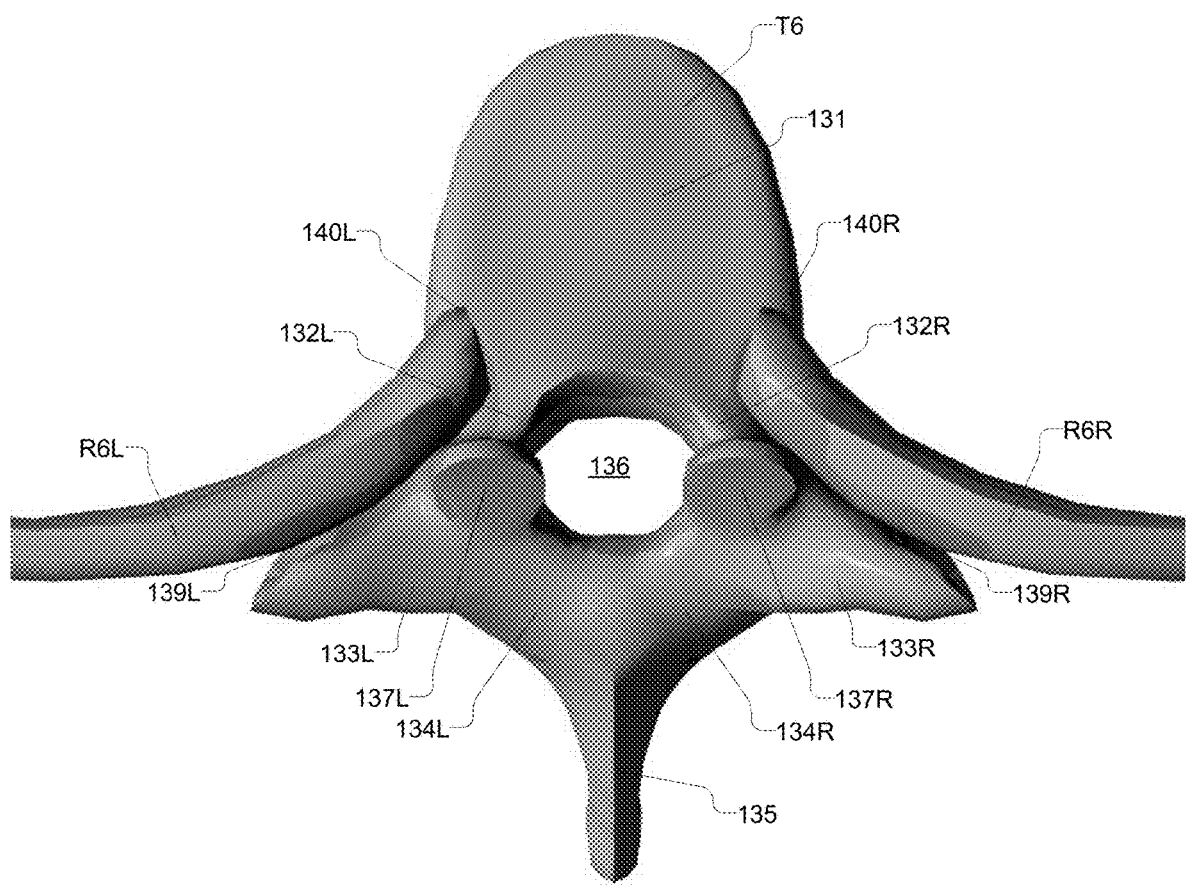
FIG. 1R shows a superior view of an interface between thoracic vertebra T6 and each of ribs R6R and R6L.
Figure 1S:
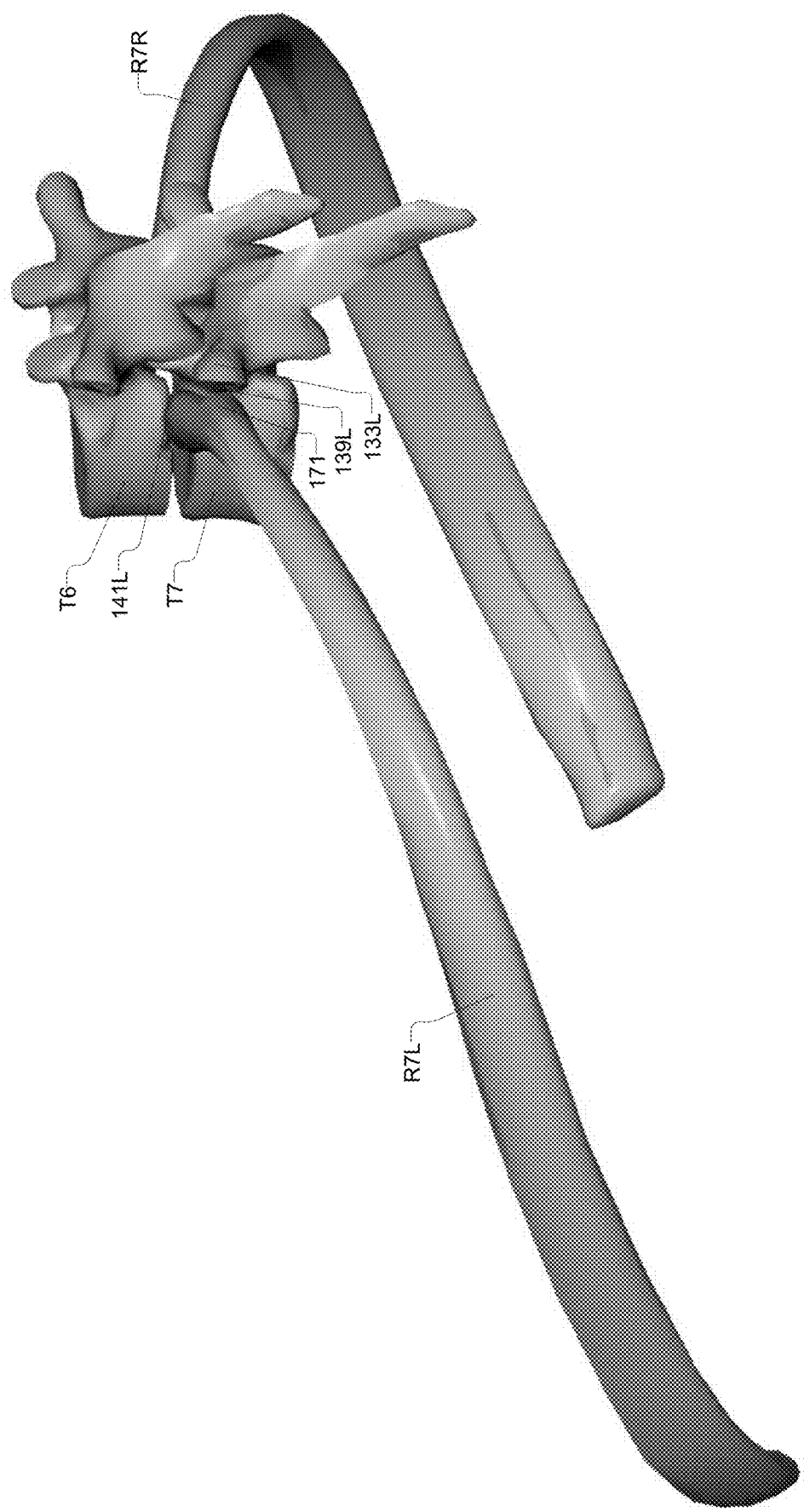
FIG. 1S shows an isometric view of the interface between the sixth thoracic vertebra T6 and the seventh thoracic vertebra T7, including the ribs R7R and R7L.
Figure 1T:
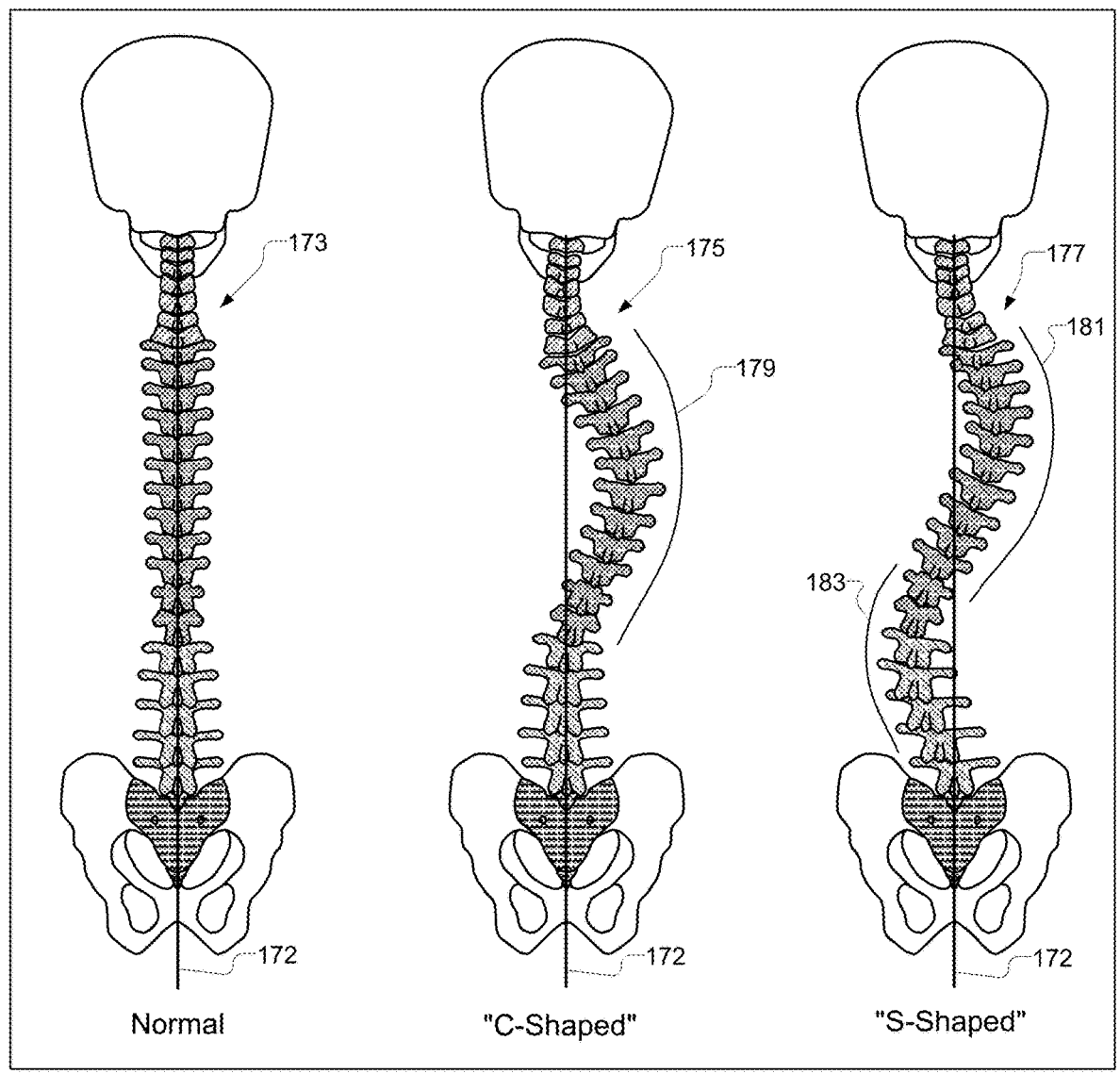
FIG. 1T shows diagrams from a posterior perspective of the human spinal column having a normal configuration, a scoliotic configuration exhibiting a generalized "C-shaped" curvature, and a scoliotic configuration exhibiting a generalized "S-shaped" curvature.
Figure 1U:
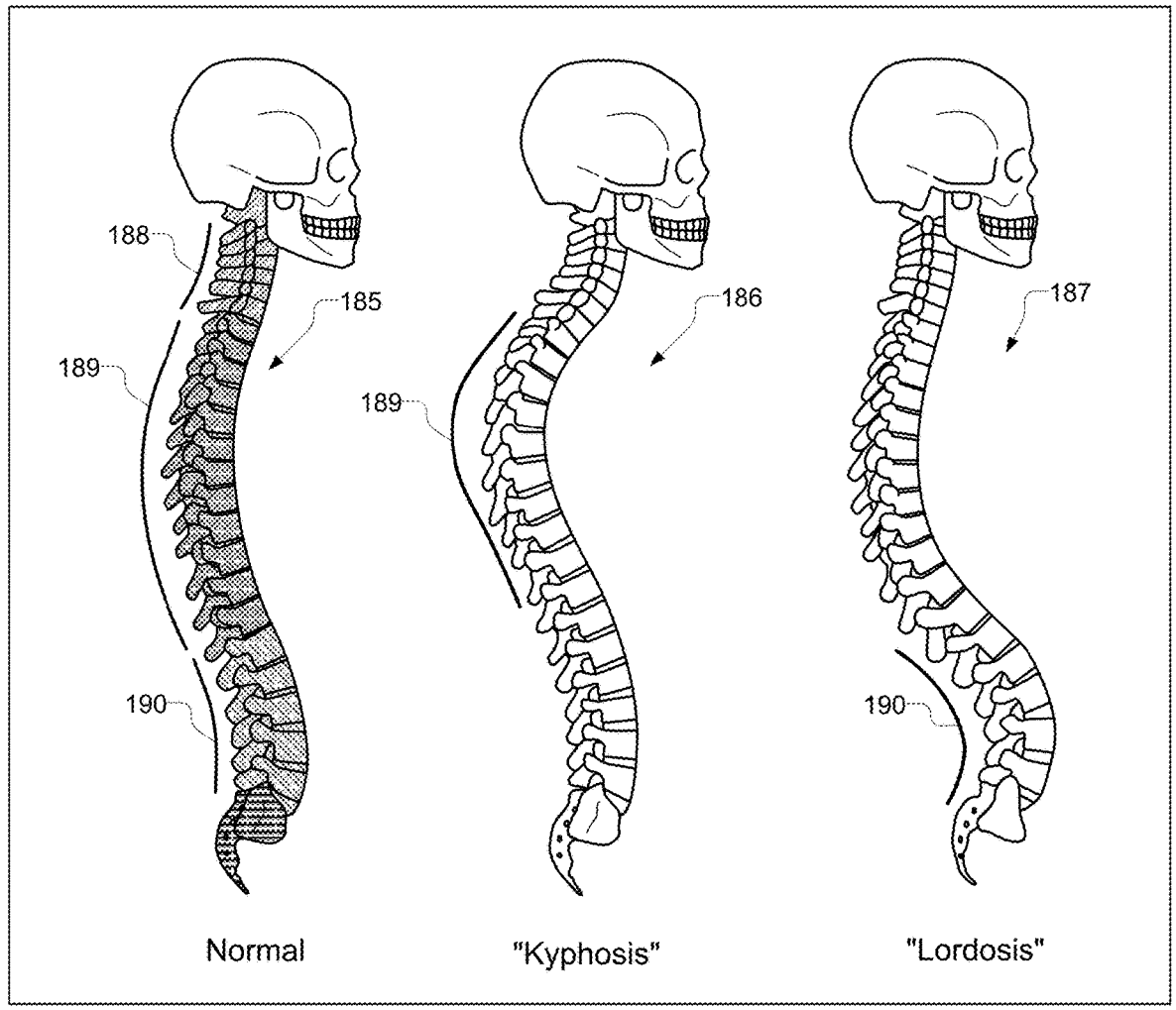
FIG. 1U shows diagrams from a right-lateral perspective of the human spinal column having a normal coronal configuration, a kyphosis coronal configuration, and a lordosis coronal configuration.
Figure 1W:
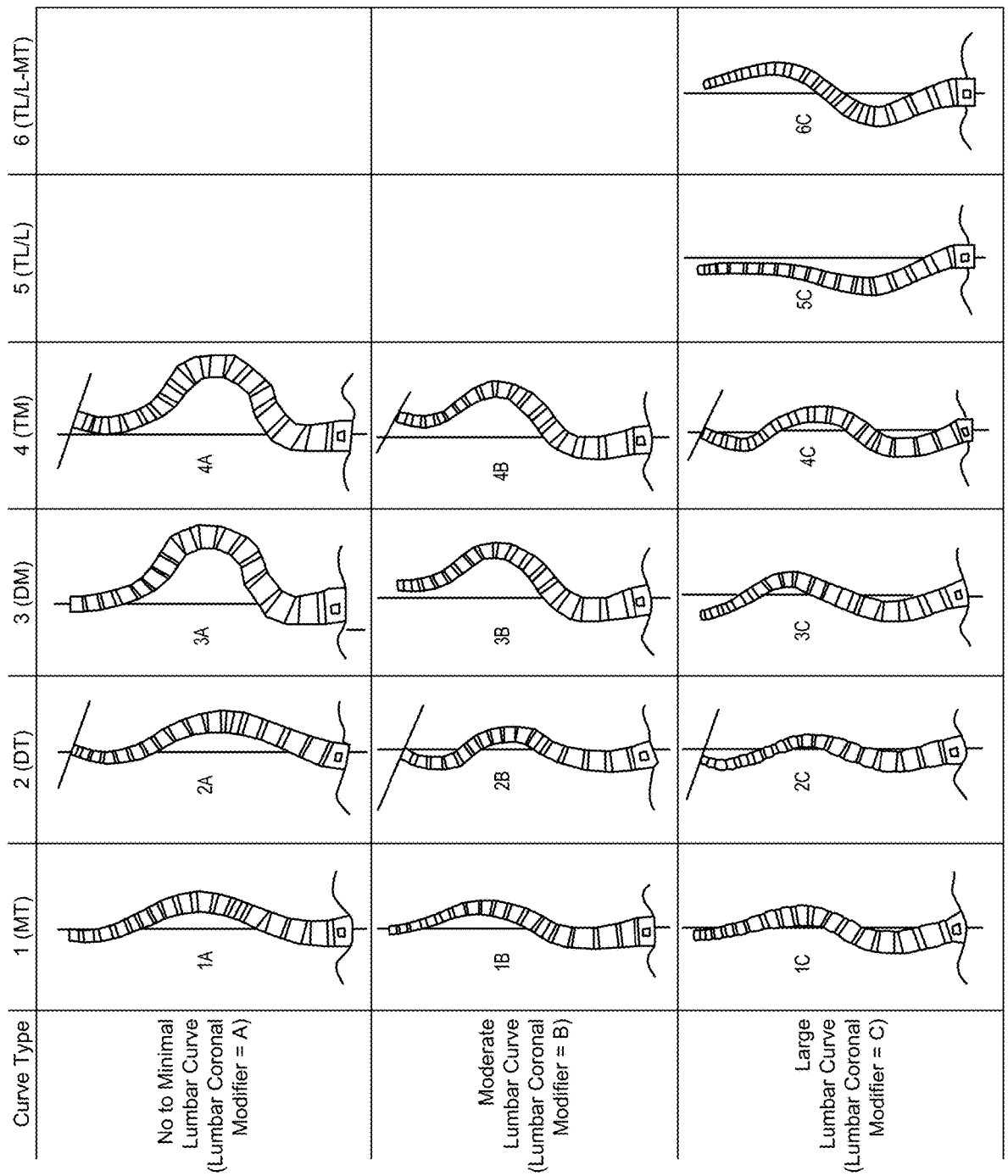
FIG. 1W shows a chart of scoliotic spinal diagrams corresponding to scoliosis curve classifications within the Lenke Classification System for AIS.
Figure 1X:
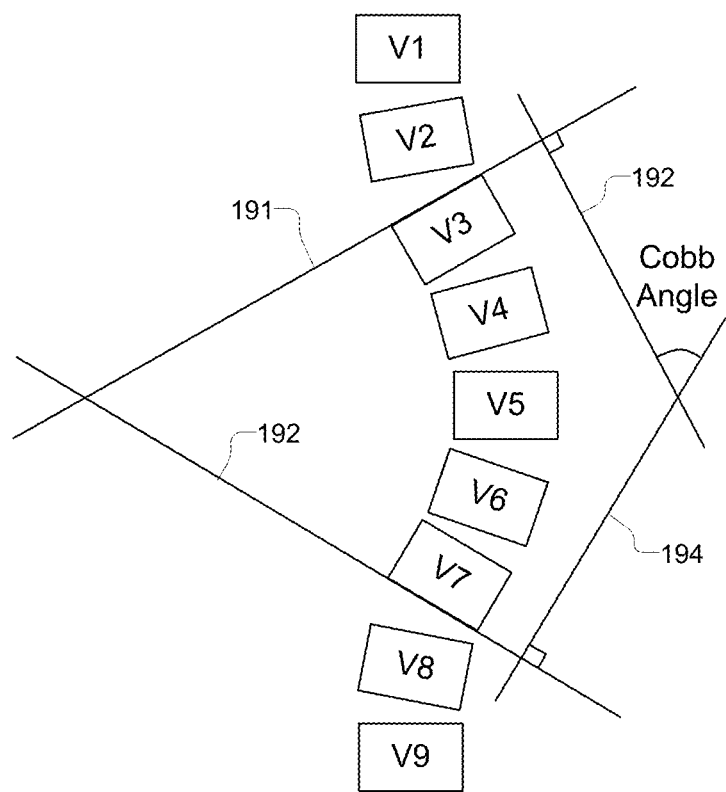
FIG. 1X shows a diagram illustrating how to measure the Cobb angle of scoliotic curve.
Figure 2:
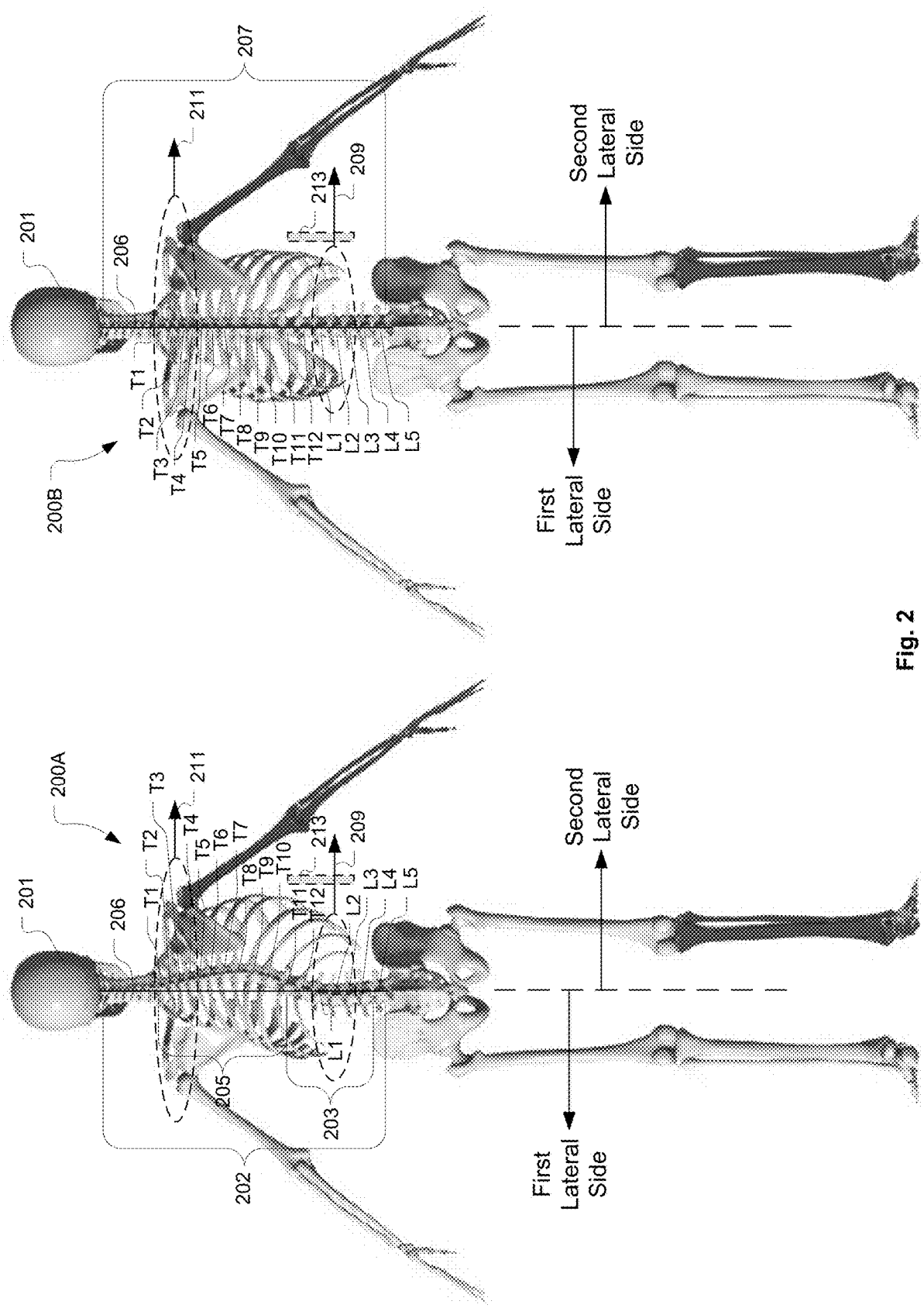
FIG. 2 shows a posterior view of a skeleton of a human exhibiting an example of a scoliotic spinal column that includes a lumbar curve and a thoracic curve relative to a sacral vertical line.

FIG. 2 shows a posterior view 200A of a skeleton of a human 201 exhibiting an example of a scoliotic spinal column 202 that includes a lumbar curve 203 and a thoracic curve 205 relative to a sacral vertical line 206. In the example of FIG. 2, the lumbar curve 203 extends from the T11 vertebra to the L5 vertebra with an apex between vertebrae L1 and L2. And, the thoracic curve 205 extends from the T1 vertebra to the T12 vertebra with an apex between T8 and T9. It should be understood that the scoliotic spinal column 202 of FIG. 2 is presented by way of example to facilitate description of the present invention and that the various apparatuses and methods disclosed herein can be used with equal effectiveness to also treat other scoliotic spinal column curvatures beyond the example scoliotic spinal column 202. For example, with reference to FIGS. 1V and 1W, it should be understood that the various apparatuses and methods disclosed herein are suited for treatment of scoliotic spinal column curvatures having a curve type of 1, 2, 3, 4, 5, or 6 with a lumbar coronal modifier of B or C, as classified by the Lenke Classification System for AIS. However, it should also be understood that the various apparatuses and methods disclosed herein may be used for other scoliotic curves, such as other curves shown in FIGS. 1V and 1W, when the physiology of the human subject permits and when the applied physics associated with the apparatuses and methods disclosed herein can provide benefit to the human subject.

FIG. 2 also shows a posterior view 200B of the human 201 having a normal, non-scoliotic spinal column 207 relative to the sacral vertical line 206. Various apparatuses and methods are disclosed herein to assist the human 201 in transitioning in a non-surgical manner from having a scoliotic spinal column, such as the example scoliotic spinal column 202, to having the normal, non-scoliotic spinal column 207. Each of the various apparatuses disclosed herein can be referred to as a "Thoracolumbar Translator" or "TLT."

Considering the posterior view 200B as shown in FIG. 2, it is of interest to have the human 201 work to laterally translate and hold the lower portion of their spinal column under their own neuro-muscular effort so as to straighten the lumbar curve 203. In this regard, the human 201 works to shift their lower torso in a lateral translational direction 209 so as to straighten the lumbar curve 203. However, for this to occur, it is necessary for the upper portion of the lumbar curve 203 to be held in a fixed position as the human 201 works to shift their lower torso in the lateral translational direction 209. More specifically, it is necessary to substantially limit lateral movement of the vertebrae of the lumbar curve 203 to a starting lateral position of the upper end of the lumbar curve 203, e.g., of the vertebra T10 in the example scoliotic spinal column 202 of FIG. 2, while the human 201 works to shift their lower torso in the lateral translational direction 209.

As described in detail below, the TLT apparatus disclosed herein is configured to provide a lateral restraint 213 that limits movement of the vertebrae of the lumbar curve 203 in the lateral translational direction 209 beyond the starting lateral position of the upper end of the lumbar curve 203 as the human 201 works to straighten the lumbar curve 203 through their own neuro-muscular effort. As the human 201 shifts their lower torso in the lateral translational direction 209, an exterior of the human 201 contacts the lateral restraint 213, which in turn causes transmission of force through a portion of the body and ribs of the human 201 that effectively engage with the lateral restraint 213. And, the forces transmitted through the ribs of the human 201 by the lateral restraint 213 serve to prevent lateral movement of the vertebrae to which those ribs are connected beyond what is necessary to achieve straightening of the lumbar curve 203. It should be understood and appreciated that through use of the TLT apparatus disclosed herein, the nerves and muscles of the human 201 can be trained and strengthened to resist a proclivity of their spinal column to assume the lumbar curve 203 configuration.

Additionally, for the example scoliotic spinal column 202 of FIG. 2, in conjunction with the human 201 working to straighten the lumbar curve 203 through their own neuro-muscular effort by laterally translating the lower portion of their torso, it is also of interest to have the human 201 work through their own neuro-muscular effort to straighten the thoracic curve 205. In this regard, the TLT apparatus disclosed herein also directs the human 201 to shift their upper torso in a translational direction 211 so as to straighten the thoracic curve 205, while the lateral restraint 213 of the TLT apparatus provides a rigid structure about which the thoracic curve 205 can be straightened. More specifically, the lateral restraint 213 of the TLT apparatus is configured to maintain a lateral position of the vertebra just below the apex of the thoracic curve 205, e.g., the vertebra T9 in the example scoliotic spinal column 202 of FIG. 2, which allows the human 201 to straighten their spinal column above the apex of the thoracic curve 205, i.e., above T9, as they move their upper torso in the translational direction 211.

Figure 3A:
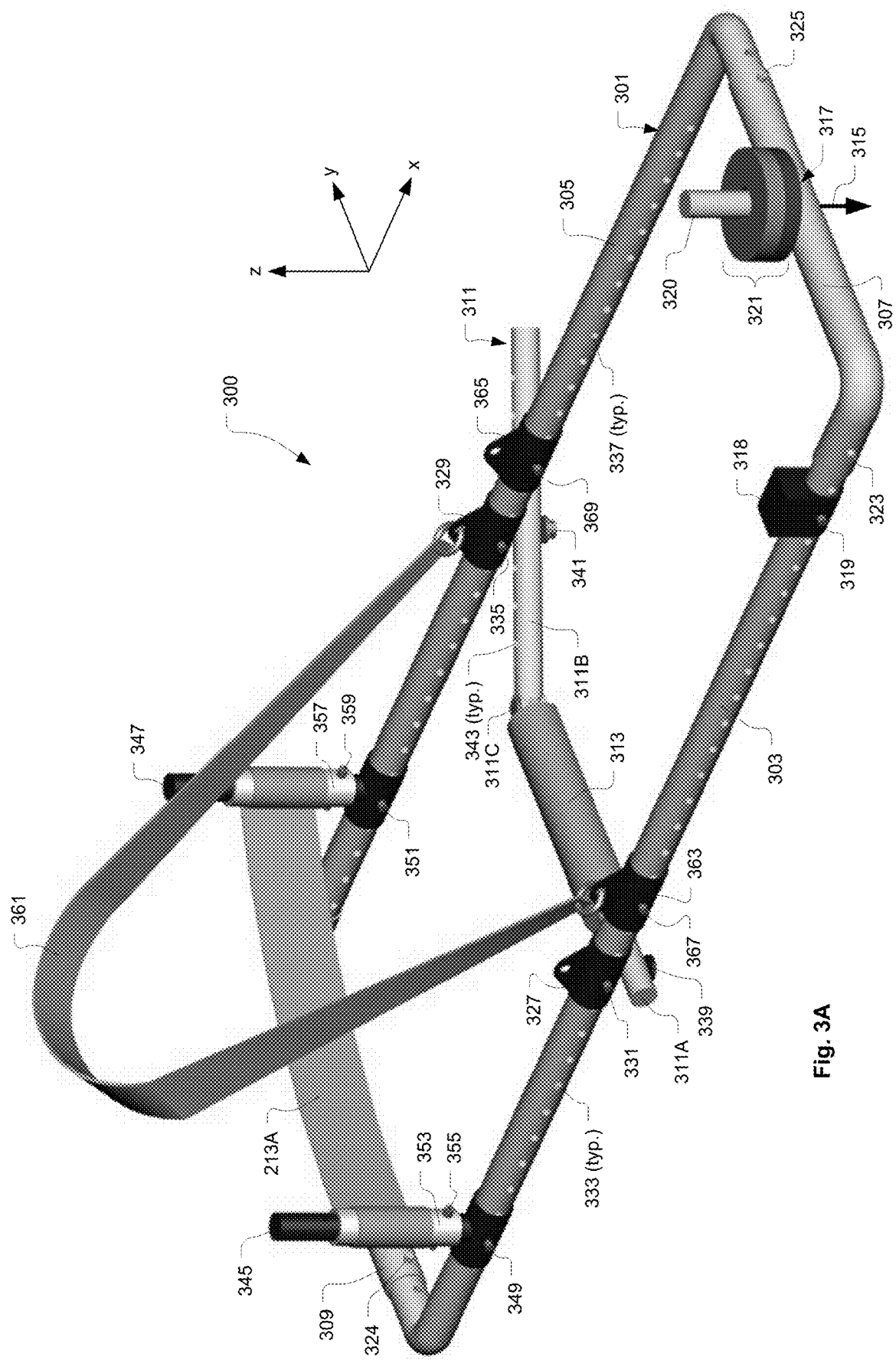
FIG. 3A shows an isometric view of a TLT apparatus for treatment of human scoliosis from a viewpoint looking down toward a front-left corner of the TLT apparatus, in accordance with some embodiments of the present invention.
Figure 3B:
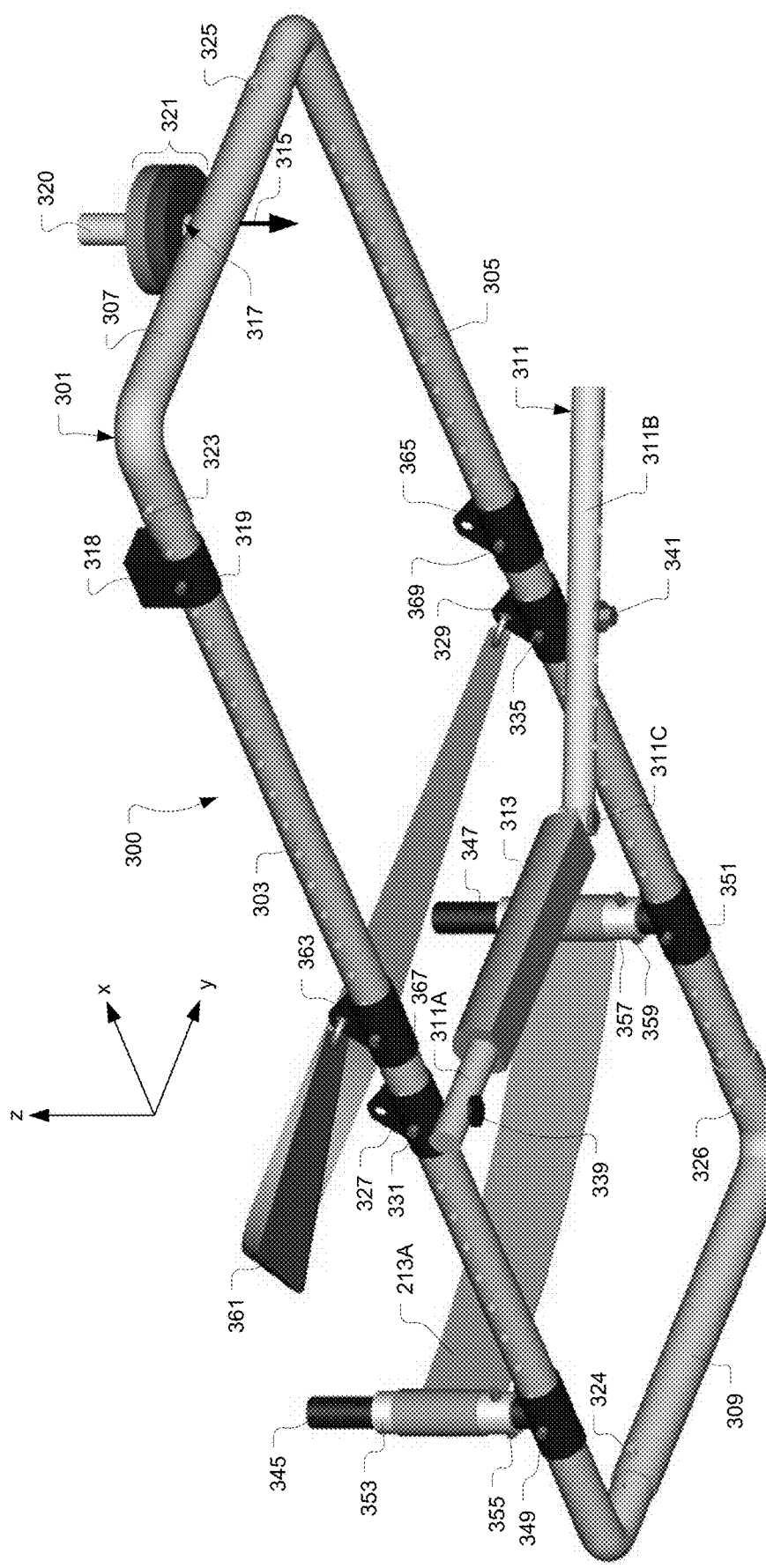
FIG. 3B shows an isometric view of the TLT apparatus from a viewpoint looking up toward the front-left corner of the TLT apparatus, in accordance with some embodiments of the present invention.
Figure 3C:
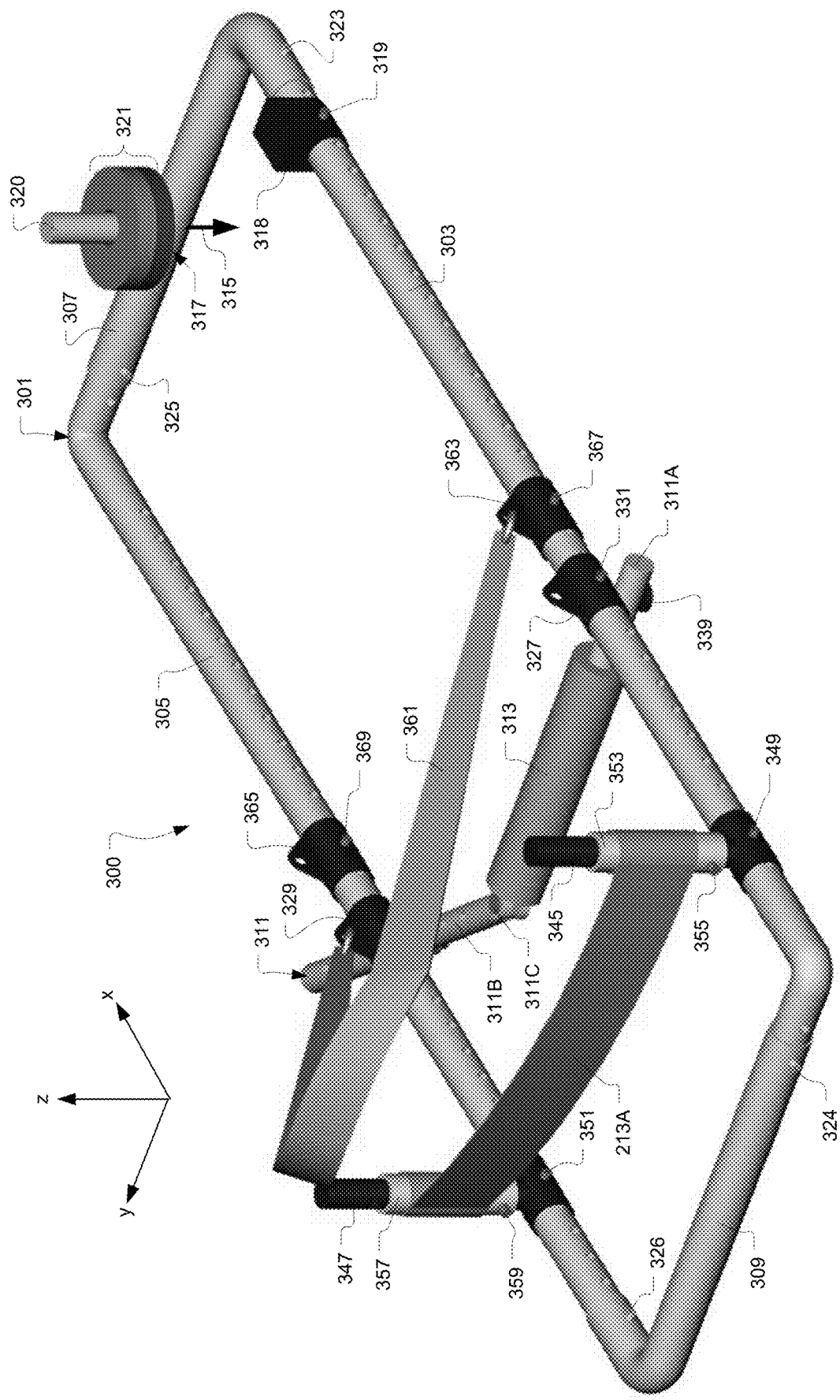
FIG. 3C shows an isometric view of the TLT apparatus from a viewpoint looking down toward the front-right corner of the TLT apparatus, in accordance with some embodiments of the present invention.
Figure 3D:
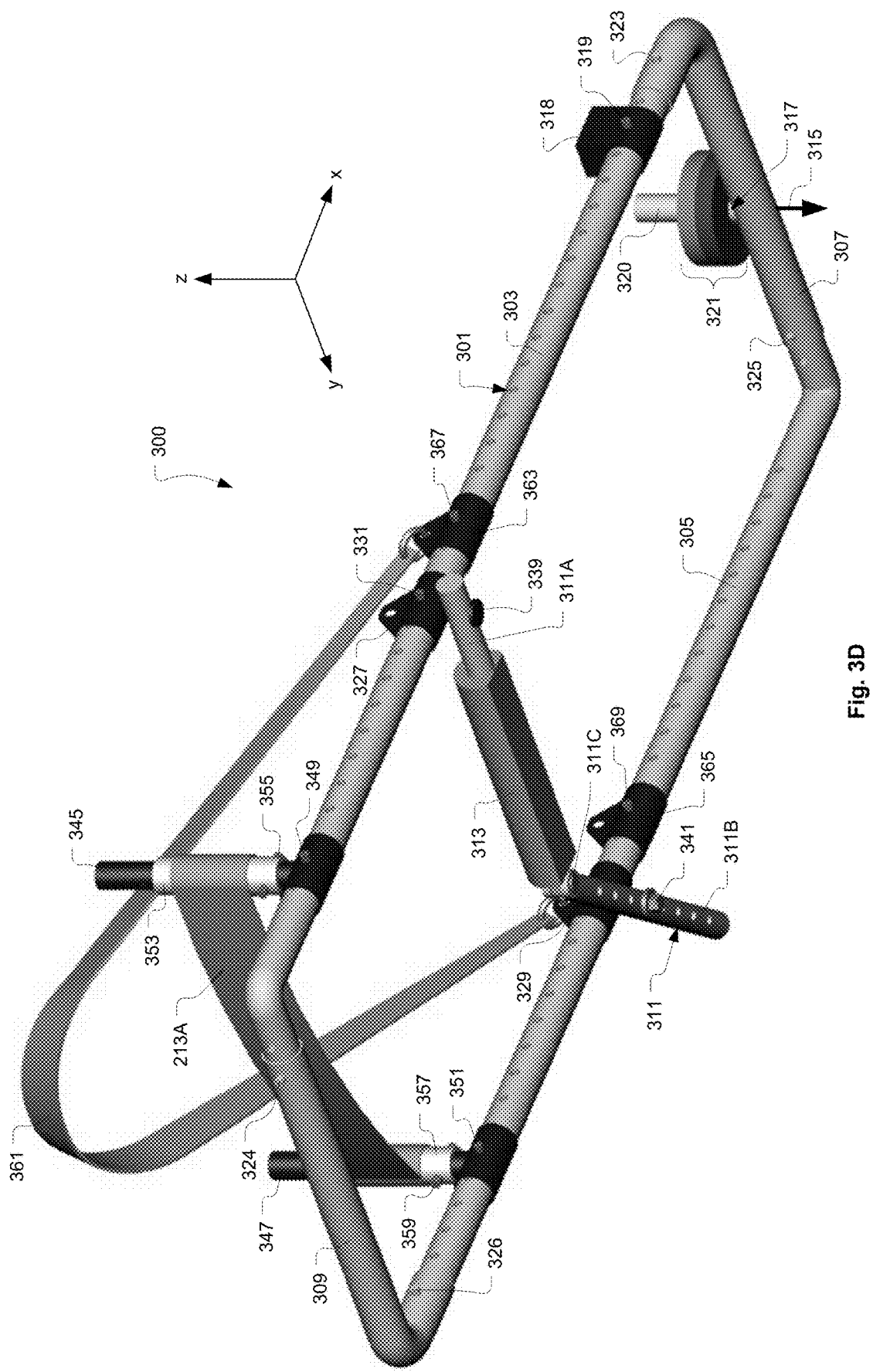
FIG. 3D shows an isometric view of the TLT apparatus from a viewpoint looking up toward the front-right corner of the TLT apparatus, in accordance with some embodiments of the present invention.
Figure 3E:
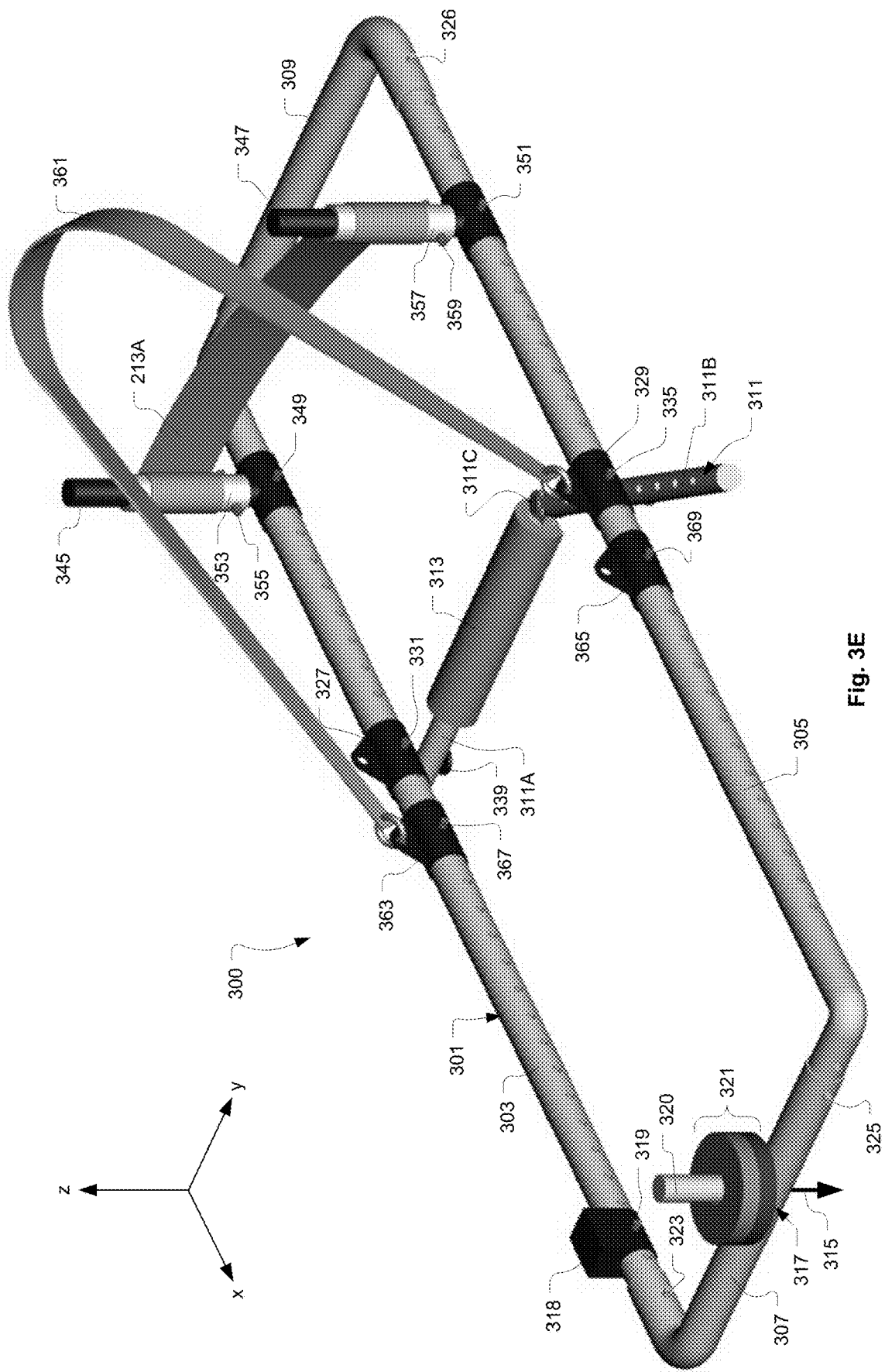
FIG. 3E shows an isometric view of an TLT apparatus from a viewpoint looking down toward a back-left corner of the TLT apparatus, in accordance with some embodiments of the present invention.
Figure 3F:
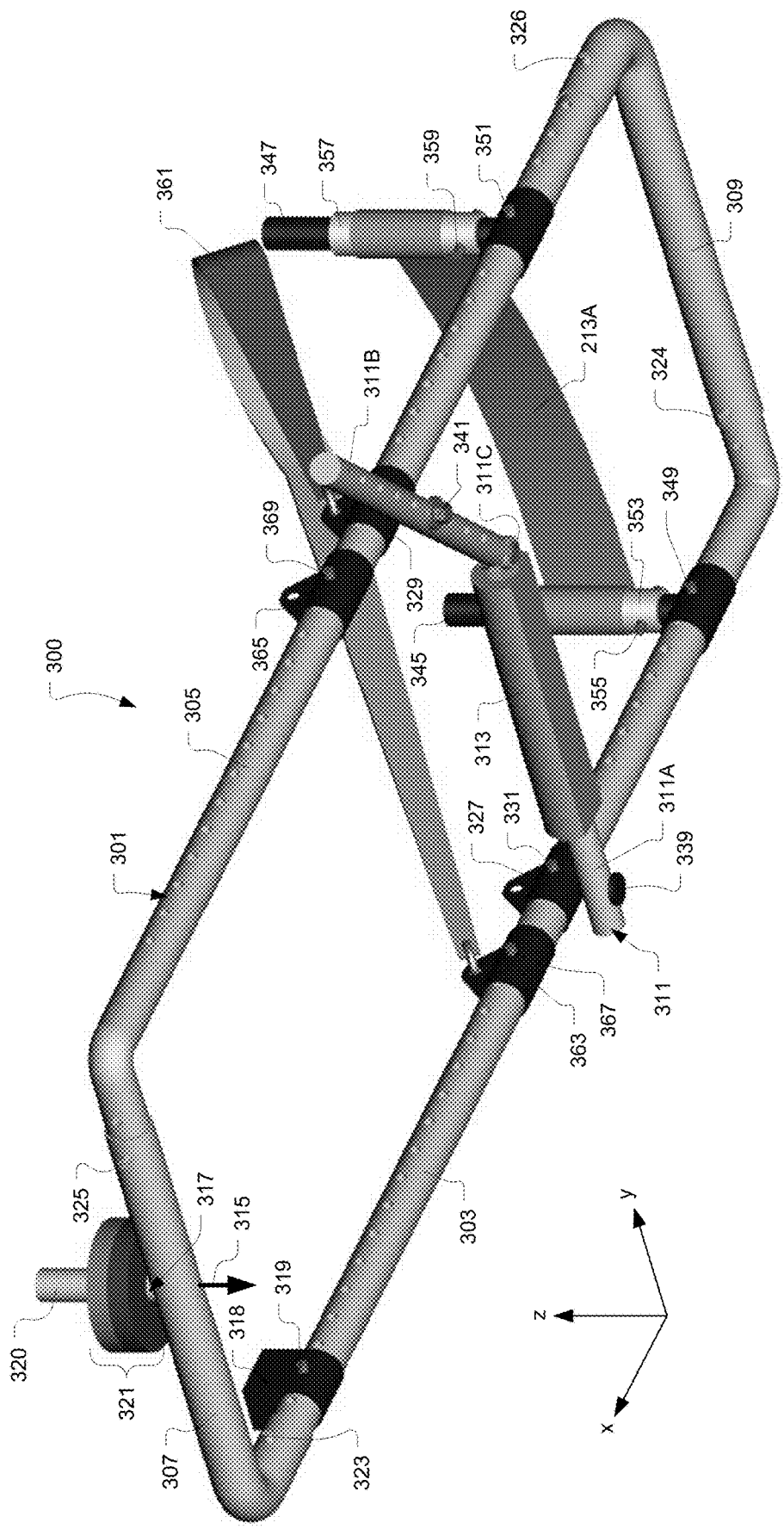
FIG. 3F shows an isometric view of the TLT apparatus from a viewpoint looking up toward the back-left corner of the apparatus, in accordance with some embodiments of the present invention.
Figure 3G:
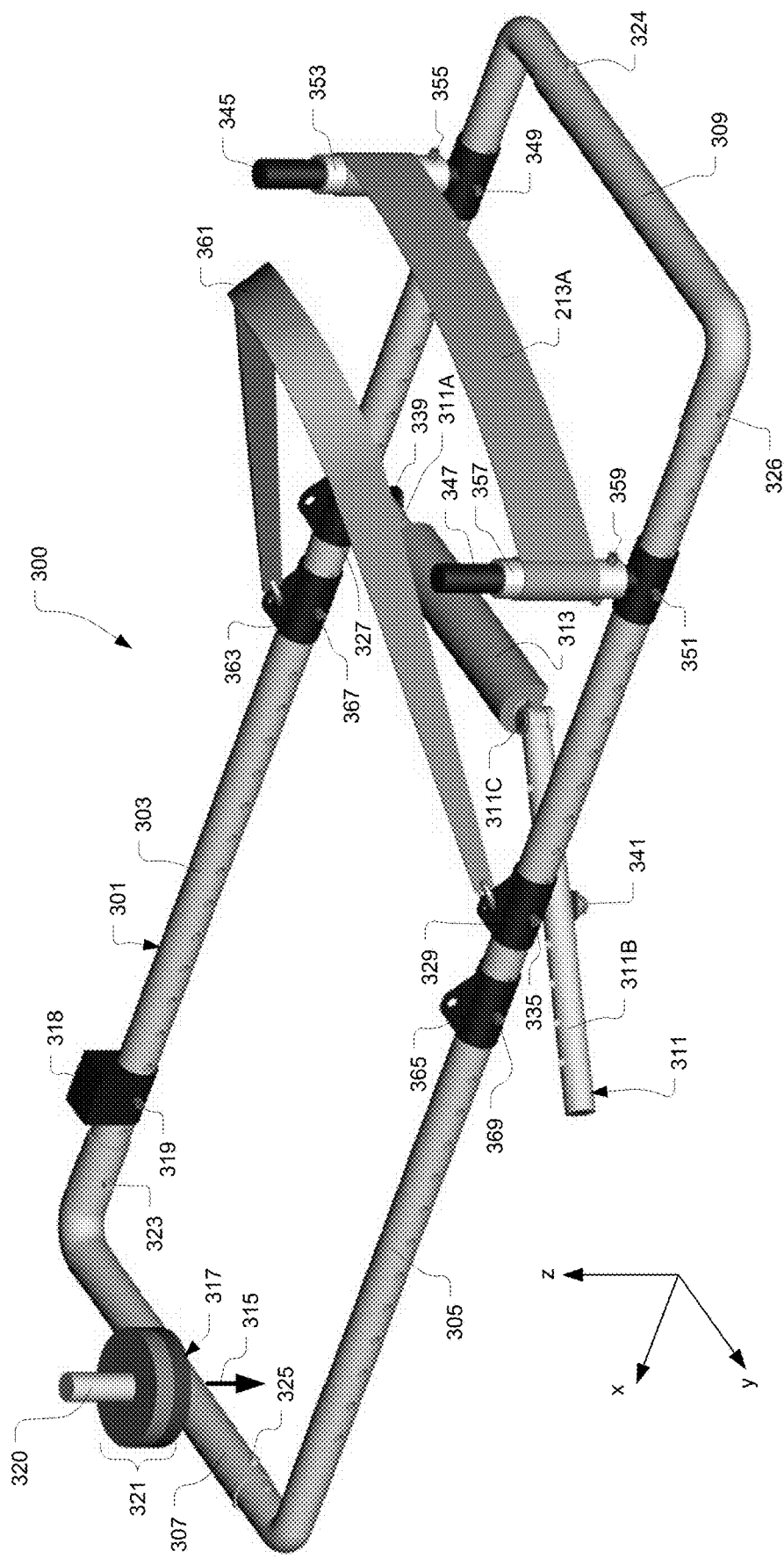
FIG. 3G shows an isometric view of the TLT apparatus from a viewpoint looking down toward the back-right corner of the TLT apparatus, in accordance with some embodiments of the present invention.
Figure 3H:
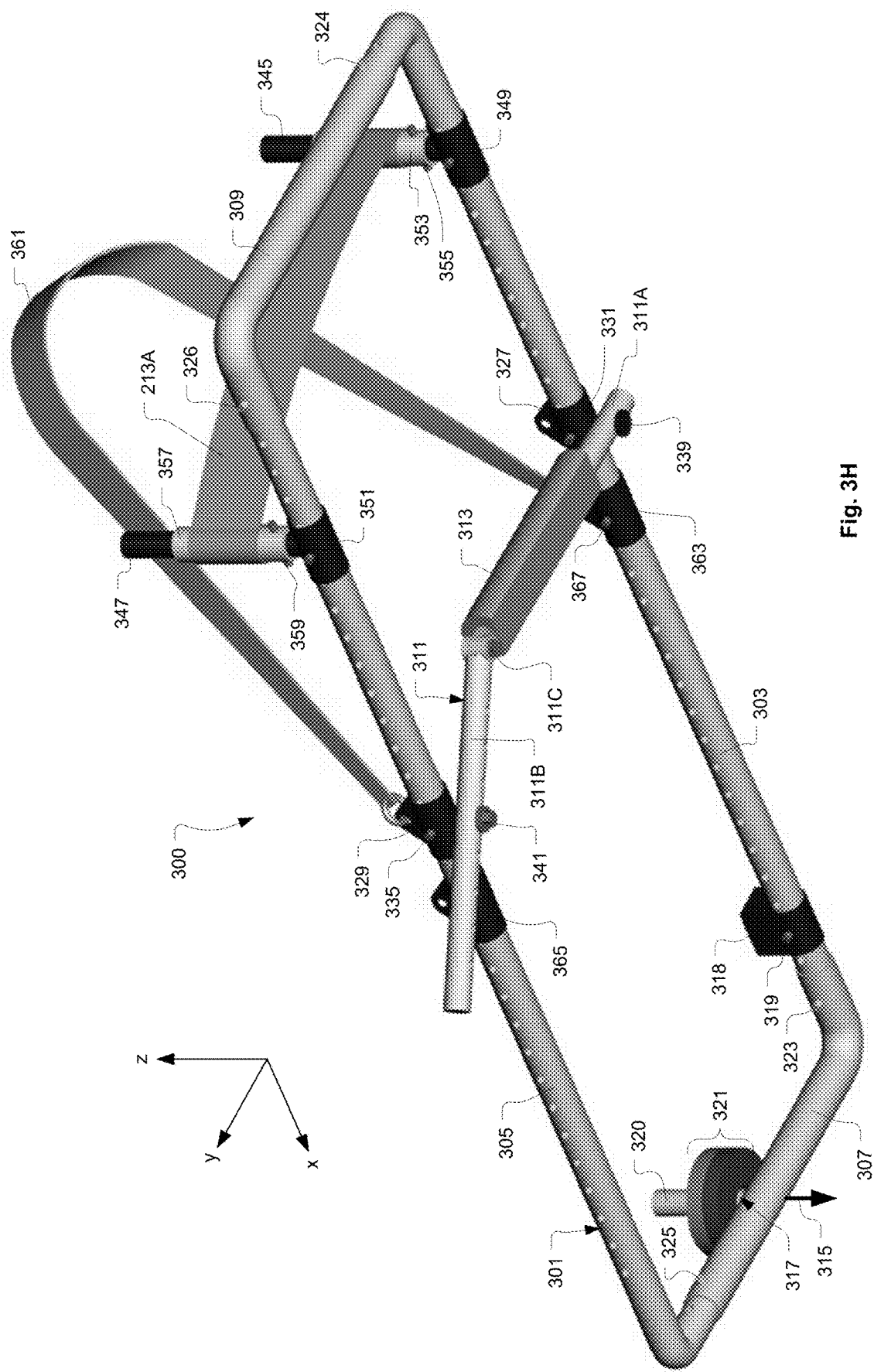
FIG. 3H shows an isometric view of the TLT apparatus from a viewpoint looking up toward the back-right corner of the apparatus, in accordance with some embodiments of the present invention.

FIG. 3A shows an isometric view of a TLT apparatus 300 for treatment of human scoliosis from a viewpoint looking down toward a front-left corner of the TLT apparatus 300, in accordance with some embodiments of the present invention. FIG. 3B shows an isometric view of the TLT apparatus 300 from a viewpoint looking up toward the front-left corner of the TLT apparatus 300, in accordance with some embodiments of the present invention. FIG. 3C shows an isometric view of the TLT apparatus 300 from a viewpoint looking down toward the front-right corner of the TLT apparatus 300, in accordance with some embodiments of the present invention. FIG. 3D shows an isometric view of the TLT apparatus 300 from a viewpoint looking up toward the front-right corner of the TLT apparatus 300, in accordance with some embodiments of the present invention. FIG. 3E shows an isometric view of an TLT apparatus 300 from a viewpoint looking down toward a back-left corner of the TLT apparatus 300, in accordance with some embodiments of the present invention. FIG. 3F shows an isometric view of the TLT apparatus 300 from a viewpoint looking up toward the back-left corner of the apparatus 300, in accordance with some embodiments of the present invention. FIG. 3G shows an isometric view of the TLT apparatus 300 from a viewpoint looking down toward the back-right corner of the TLT apparatus 300, in accordance with some embodiments of the present invention. FIG. 3H shows an isometric view of the TLT apparatus 300 from a viewpoint looking up toward the back-right corner of the apparatus 300, in accordance with some embodiments of the present invention.

Figure 3I:
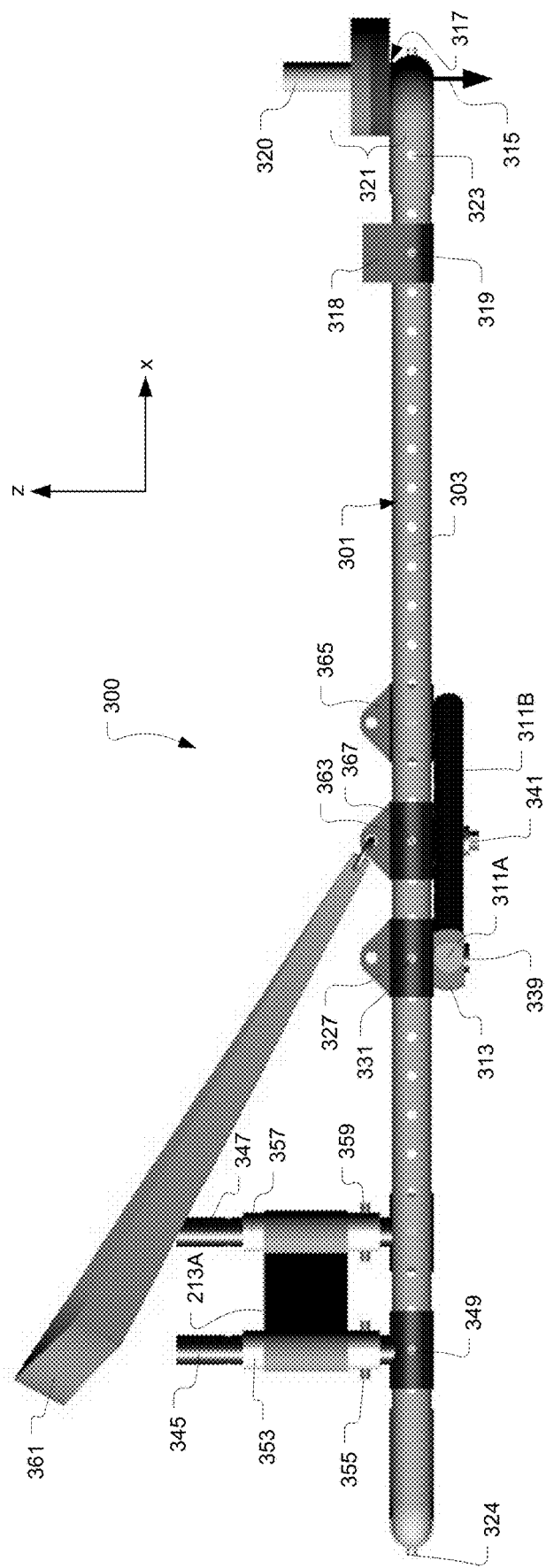
FIG. 3I shows a front view of the TLT apparatus, in accordance with some embodiments of the present invention.
Figure 3J:
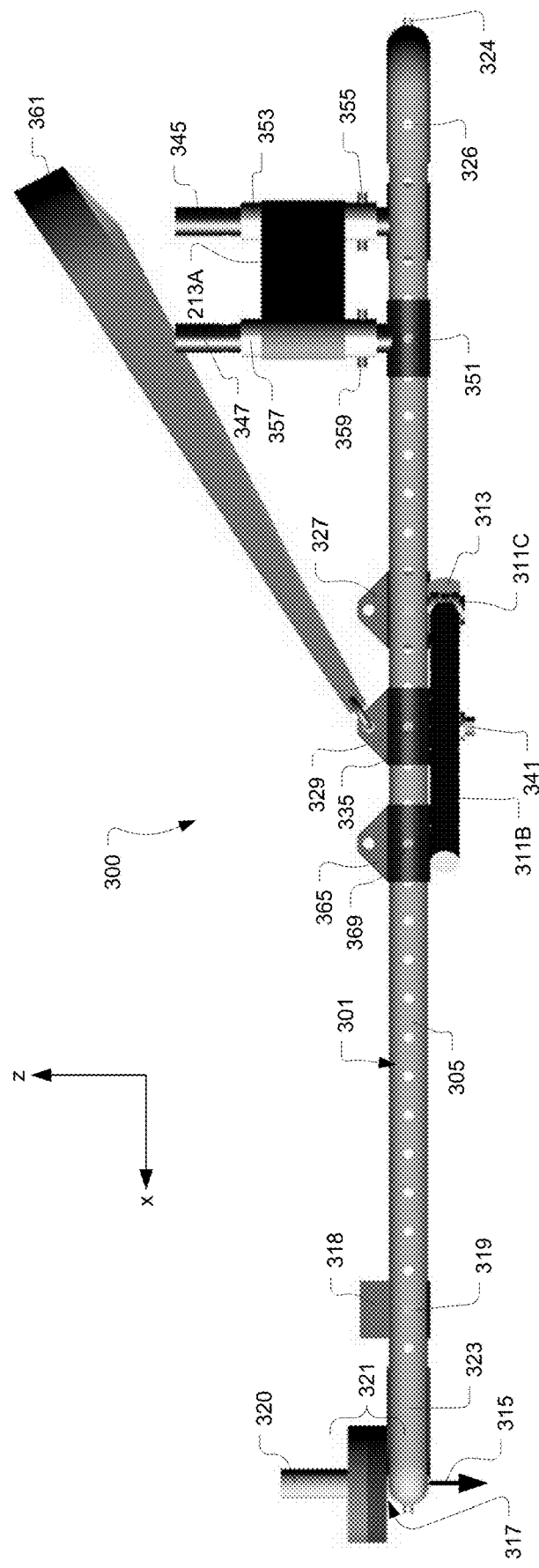
FIG. 3J shows a back view of the TLT apparatus, in accordance with some embodiments of the present invention.
Figure 3K:
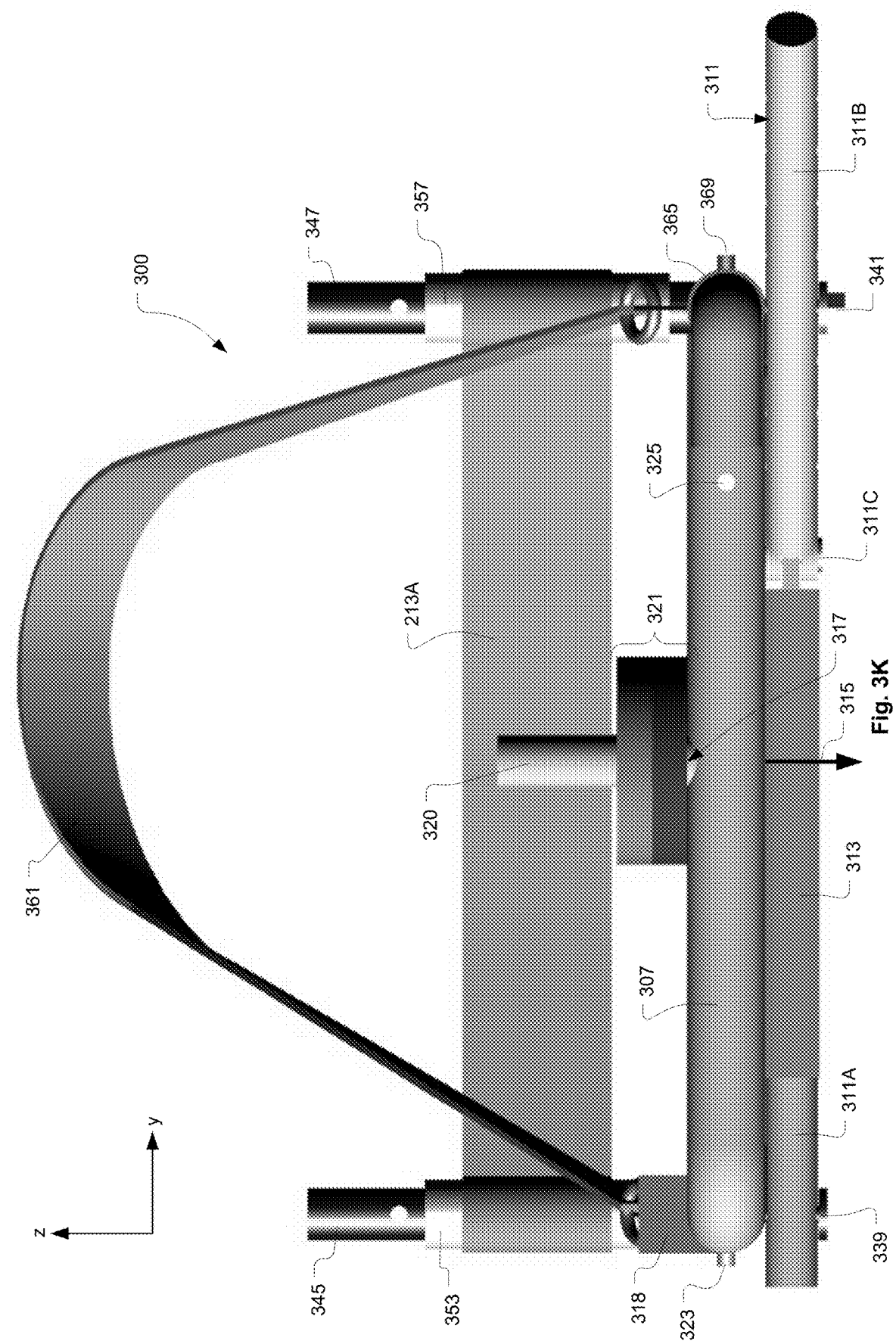
FIG. 3K shows a right side view of the TLT apparatus, in accordance with some embodiments of the present invention.
Figure 3L:
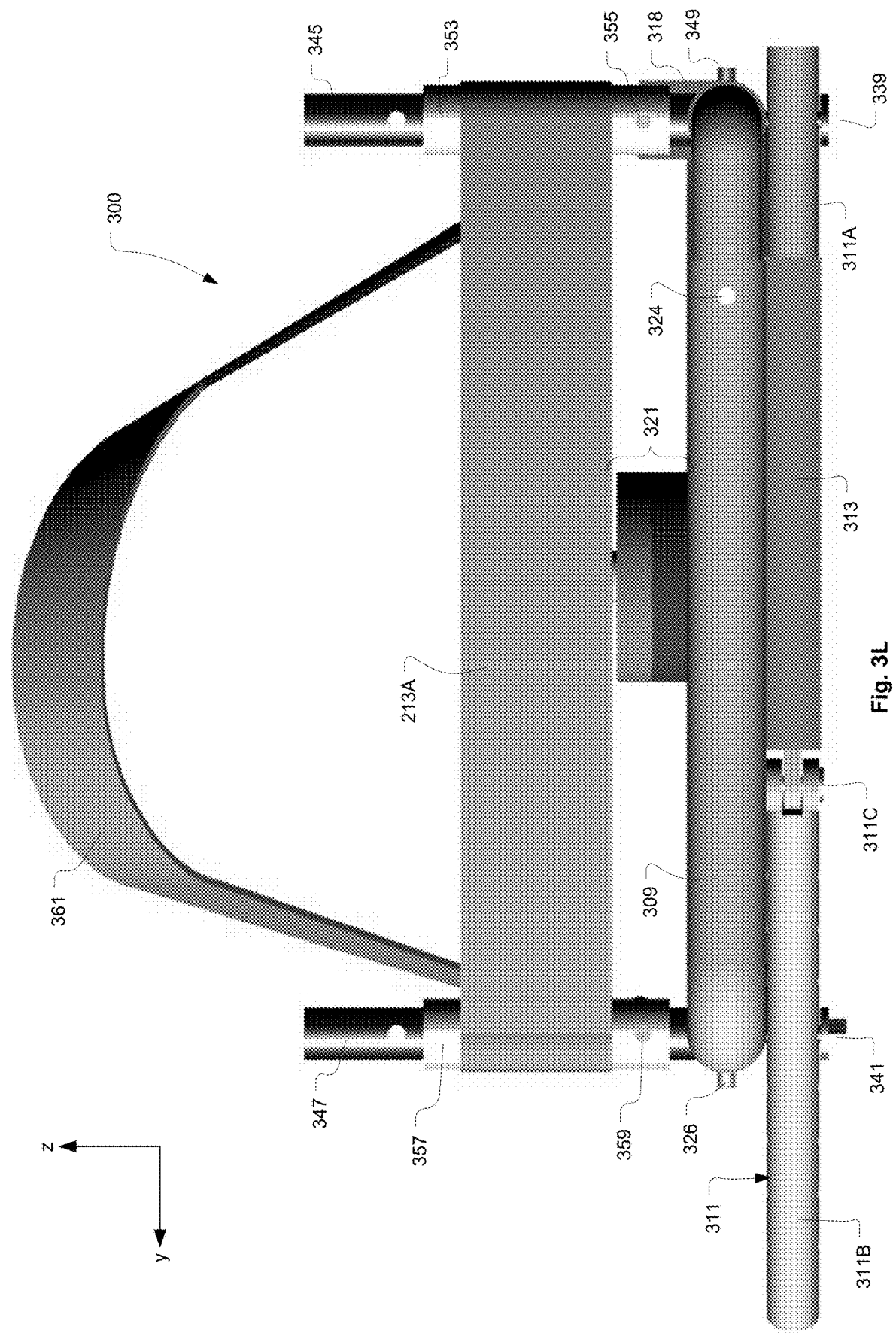
FIG. 3L shows a left side view of the TLT apparatus, in accordance with some embodiments of the present invention.
Figure 3M:
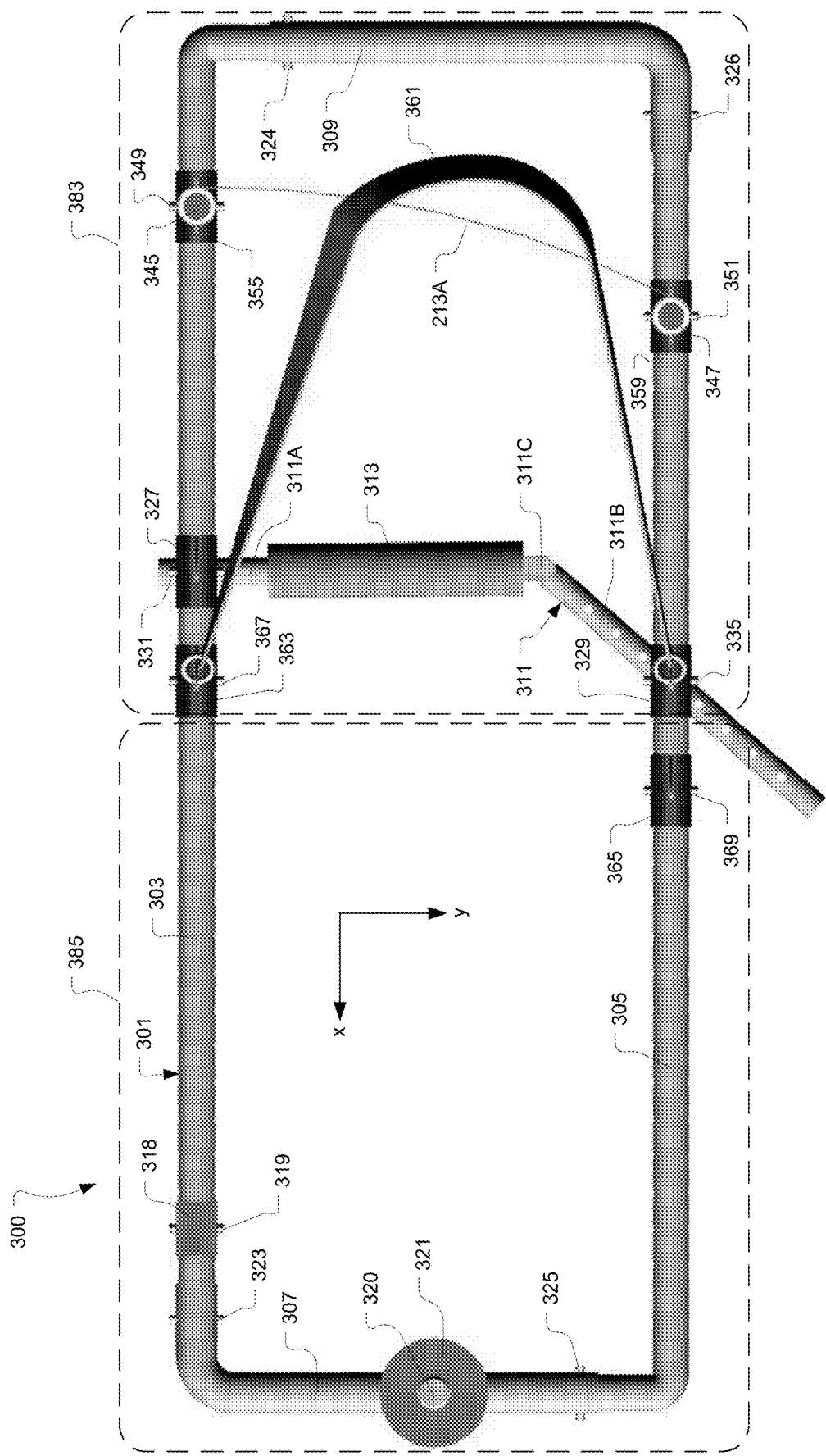
FIG. 3M shows a top view of the TLT apparatus, in accordance with some embodiments of the present invention.
Figure 3N:
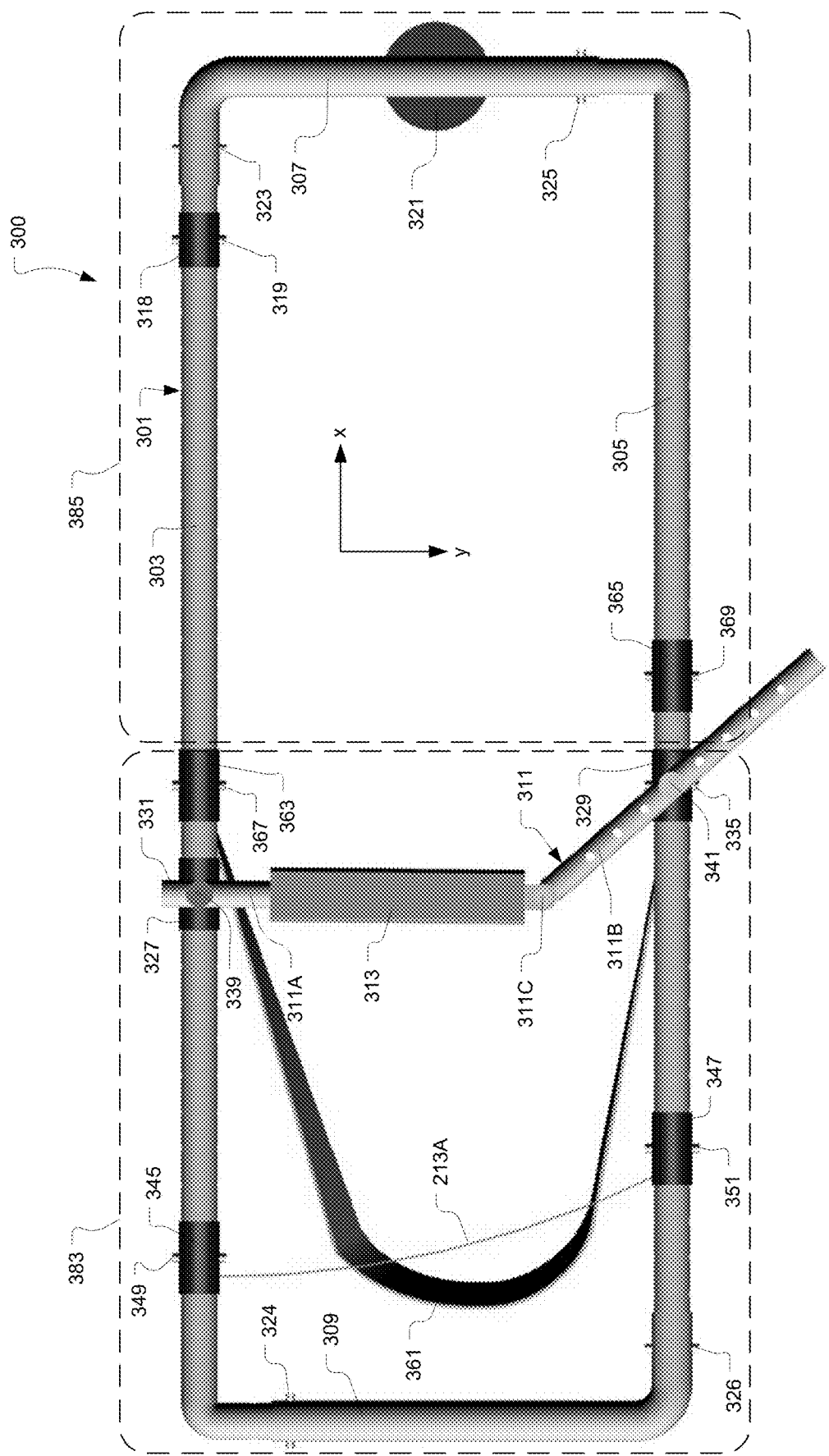
FIG. 3N shows a bottom view of the TLT apparatus, in accordance with some embodiments of the present invention.

FIG. 3I shows a front view of the TLT apparatus 300, in accordance with some embodiments of the present invention. FIG. 3J shows a back view of the TLT apparatus 300, in accordance with some embodiments of the present invention. FIG. 3K shows a right side view of the TLT apparatus 300, in accordance with some embodiments of the present invention. FIG. 3L shows a left side view of the TLT apparatus 300, in accordance with some embodiments of the present invention. FIG. 3M shows a top view of the TLT apparatus 300, in accordance with some embodiments of the present invention. FIG. 3N shows a bottom view of the TLT apparatus 300, in accordance with some embodiments of the present invention.

Figure 4A:
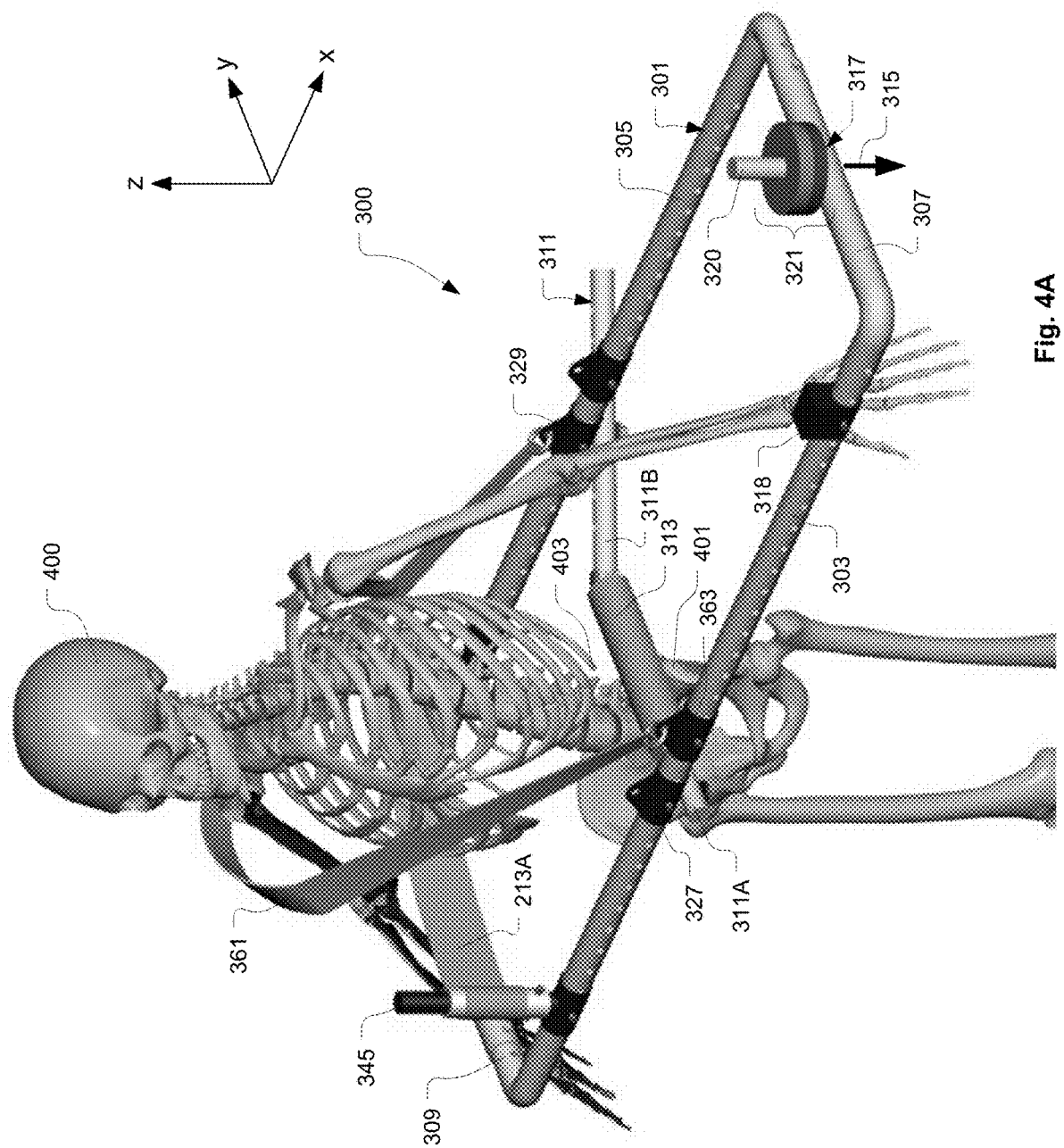
FIG. 4A shows the isometric view of the TLT apparatus of FIG. 3A with a human positioned within the TLT apparatus in a therapeutic position, in accordance with some embodiments of the present invention.
Figure 4B:
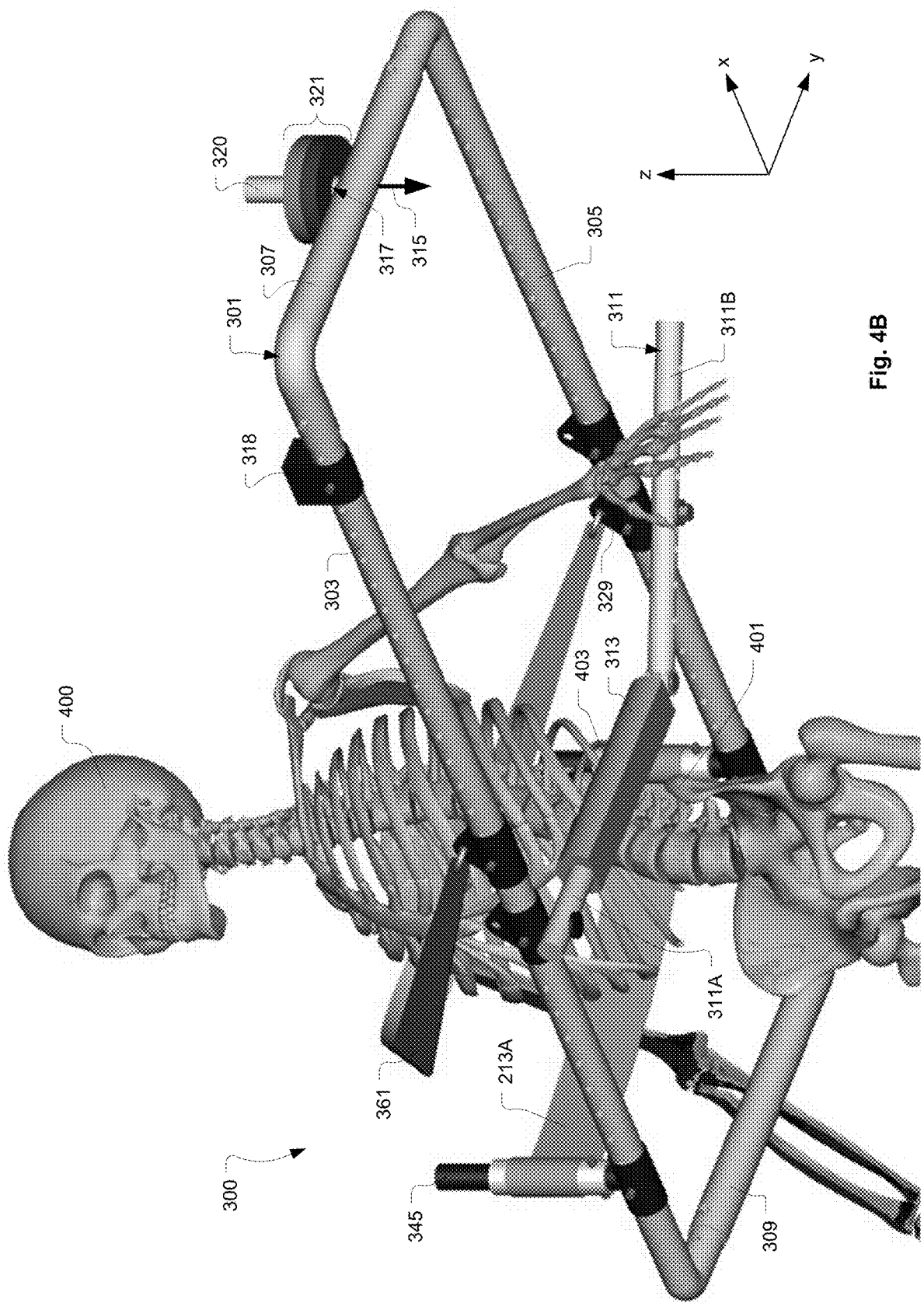
FIG. 4B shows the isometric view of the TLT apparatus of FIG. 3B with the human positioned within the TLT apparatus in the therapeutic position, in accordance with some embodiments of the present invention.
Figure 4D:
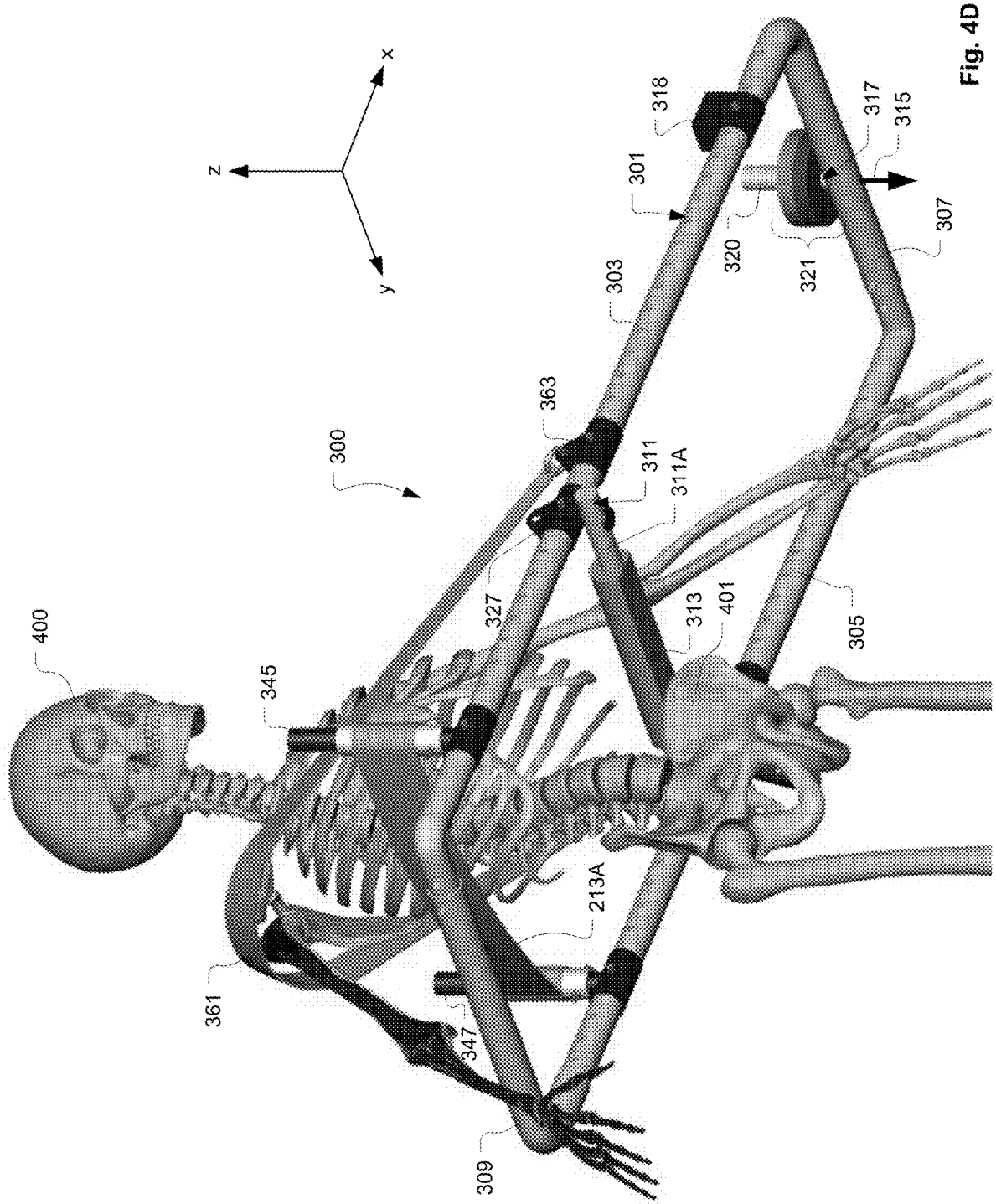
FIG. 4D shows the isometric view of the TLT apparatus of FIG. 3D with the human positioned within the TLT apparatus in the therapeutic position, in accordance with some embodiments of the present invention.
Figure 4E:
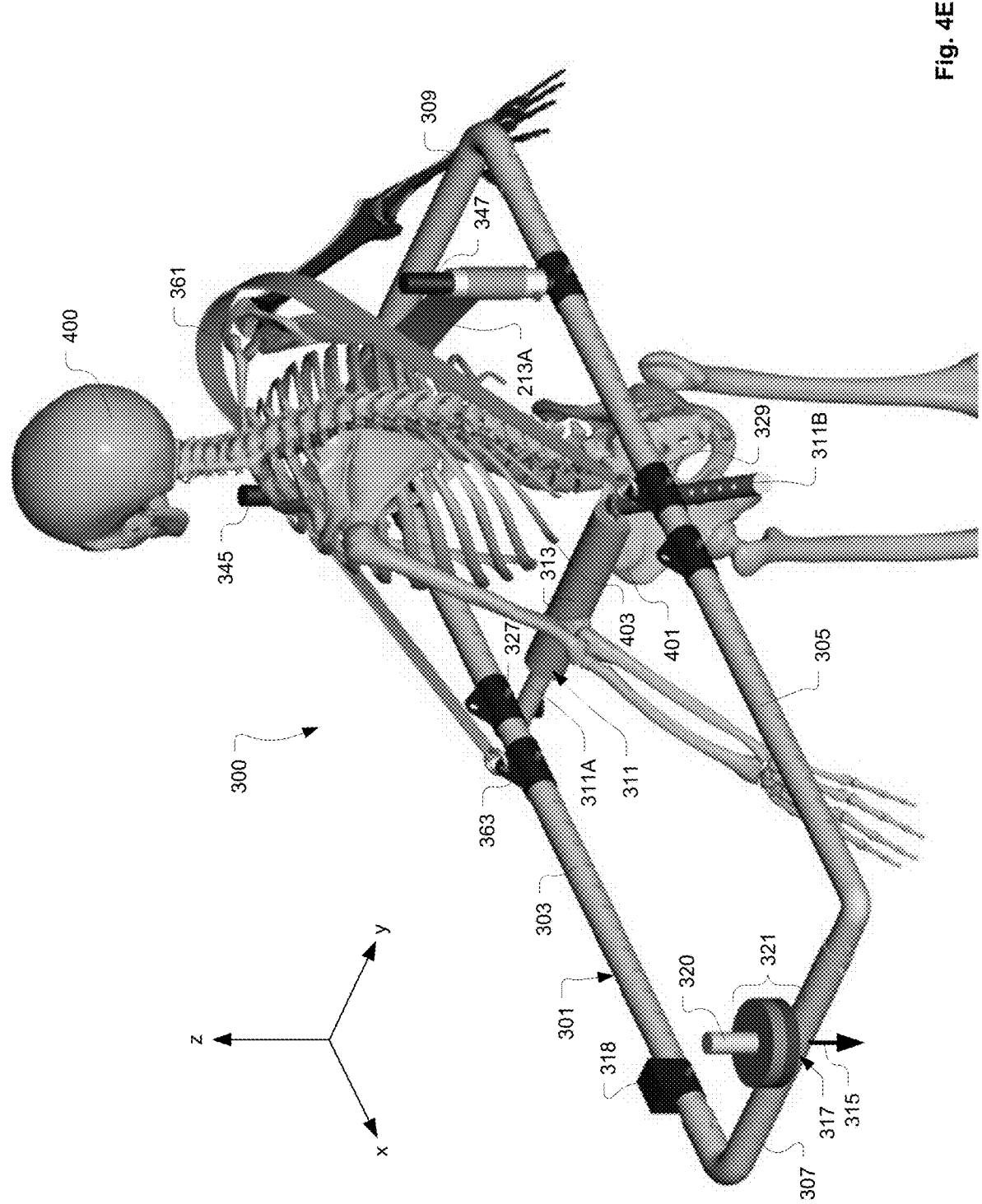
FIG. 4E shows the isometric view of the TLT apparatus of FIG. 3E with the human positioned within the TLT apparatus in the therapeutic position, in accordance with some embodiments of the present invention.
Figure 4F:
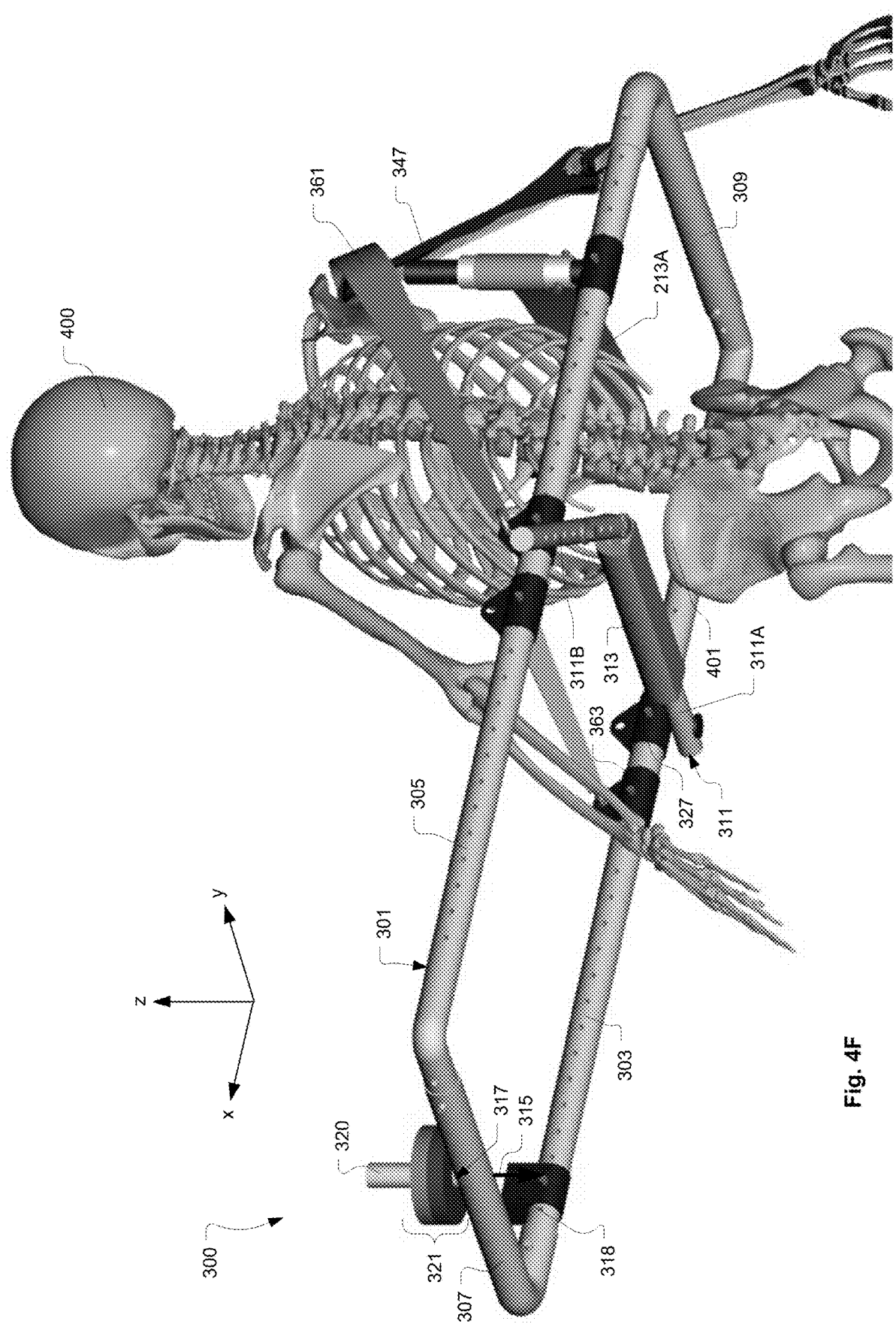
FIG. 4F shows the isometric view of the TLT apparatus of FIG. 3F with the human positioned within the TLT apparatus in the therapeutic position, in accordance with some embodiments of the present invention.
Figure 4G:
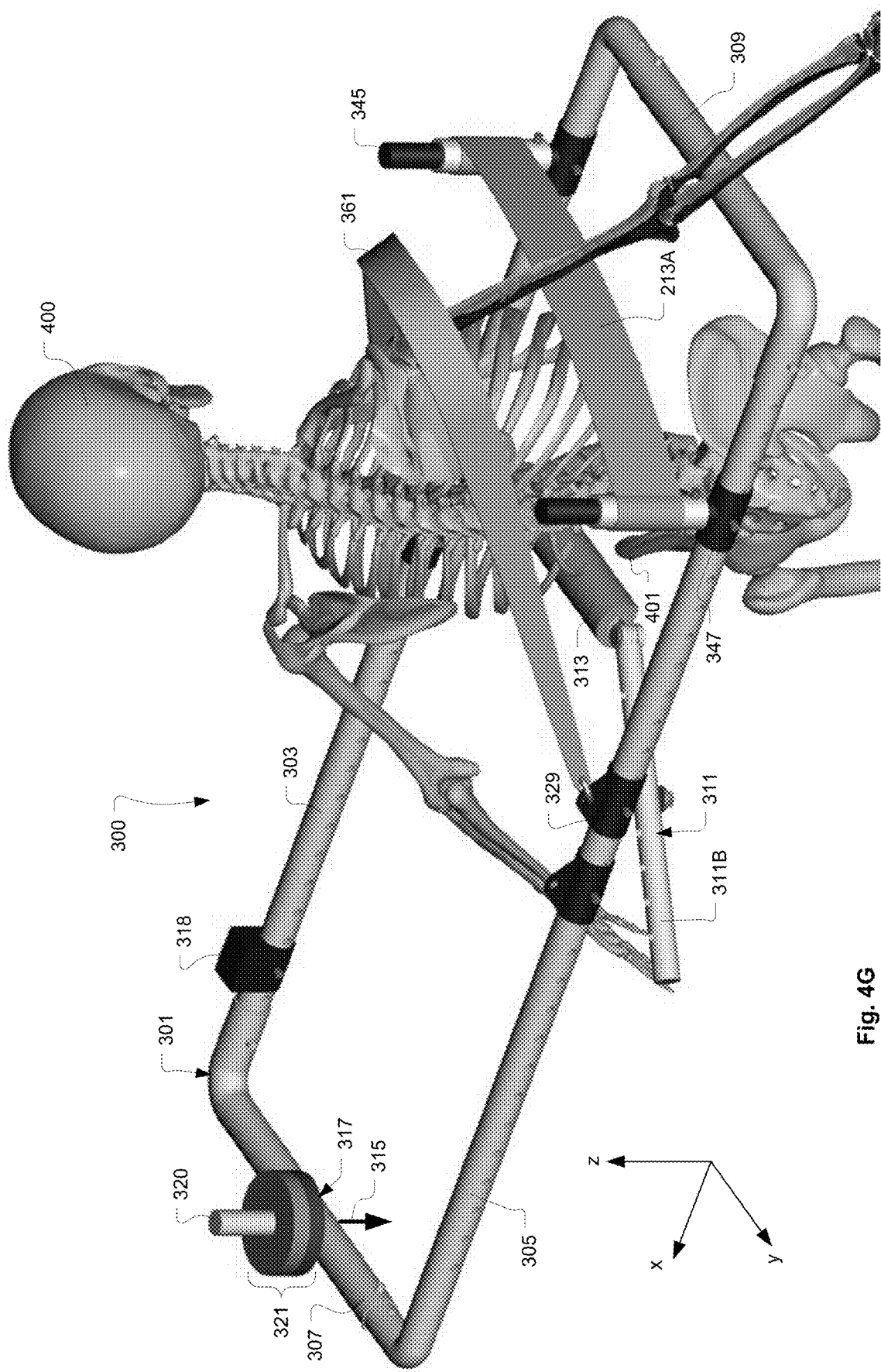
FIG. 4G shows the isometric view of the TLT apparatus of FIG. 3G with the human positioned within the TLT apparatus in the therapeutic position, in accordance with some embodiments of the present invention.
Figure 4H:
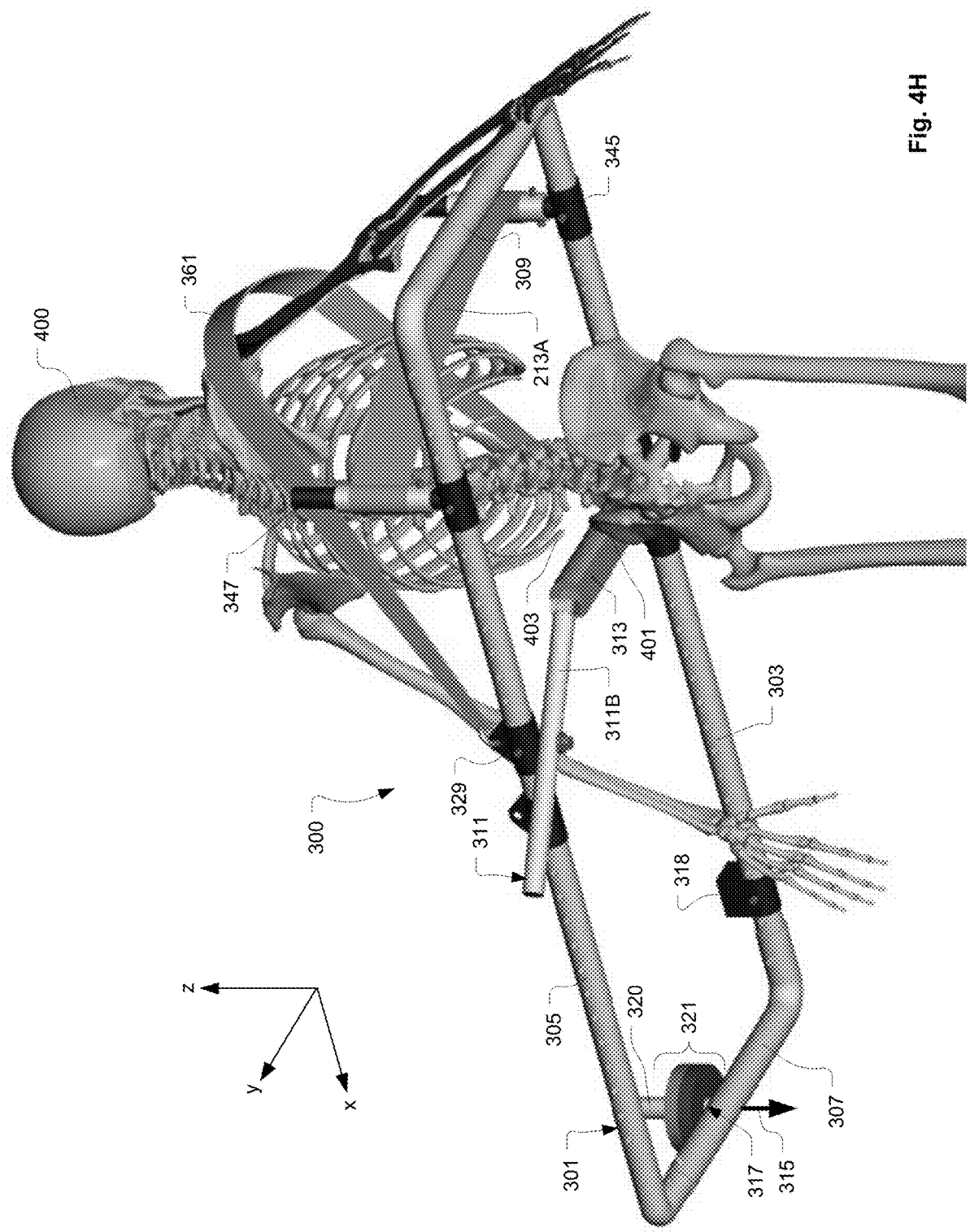
FIG. 4H shows the isometric view of the TLT apparatus of FIG. 3H with the human positioned within the TLT apparatus in the therapeutic position, in accordance with some embodiments of the present invention.

FIG. 4A shows the isometric view of the TLT apparatus 300 of FIG. 3A with a human 400 positioned within the TLT apparatus 300 in a therapeutic position, in accordance with some embodiments of the present invention. FIG. 4B shows the isometric view of the TLT apparatus 300 of FIG. 3B with the human 400 positioned within the TLT apparatus 300 in the therapeutic position, in accordance with some embodiments of the present invention. FIG. 4C shows the isometric view of the TLT apparatus 300 of FIG. 3C with the human 400 positioned within the TLT apparatus 300 in the therapeutic position, in accordance with some embodiments of the present invention. FIG. 4D shows the isometric view of the TLT apparatus 300 of FIG. 3D with the human 400 positioned within the TLT apparatus 300 in the therapeutic position, in accordance with some embodiments of the present invention. FIG. 4E shows the isometric view of the TLT apparatus 300 of FIG. 3E with the human 400 positioned within the TLT apparatus 300 in the therapeutic position, in accordance with some embodiments of the present invention. FIG. 4F shows the isometric view of the TLT apparatus 300 of FIG. 3F with the human 400 positioned within the TLT apparatus 300 in the therapeutic position, in accordance with some embodiments of the present invention. FIG. 4G shows the isometric view of the TLT apparatus 300 of FIG. 3G with the human 400 positioned within the TLT apparatus 300 in the therapeutic position, in accordance with some embodiments of the present invention. FIG. 4H shows the isometric view of the TLT apparatus 300 of FIG. 3H with the human 400 positioned within the TLT apparatus 300 in the therapeutic position, in accordance with some embodiments of the present invention.

Figure 4I:
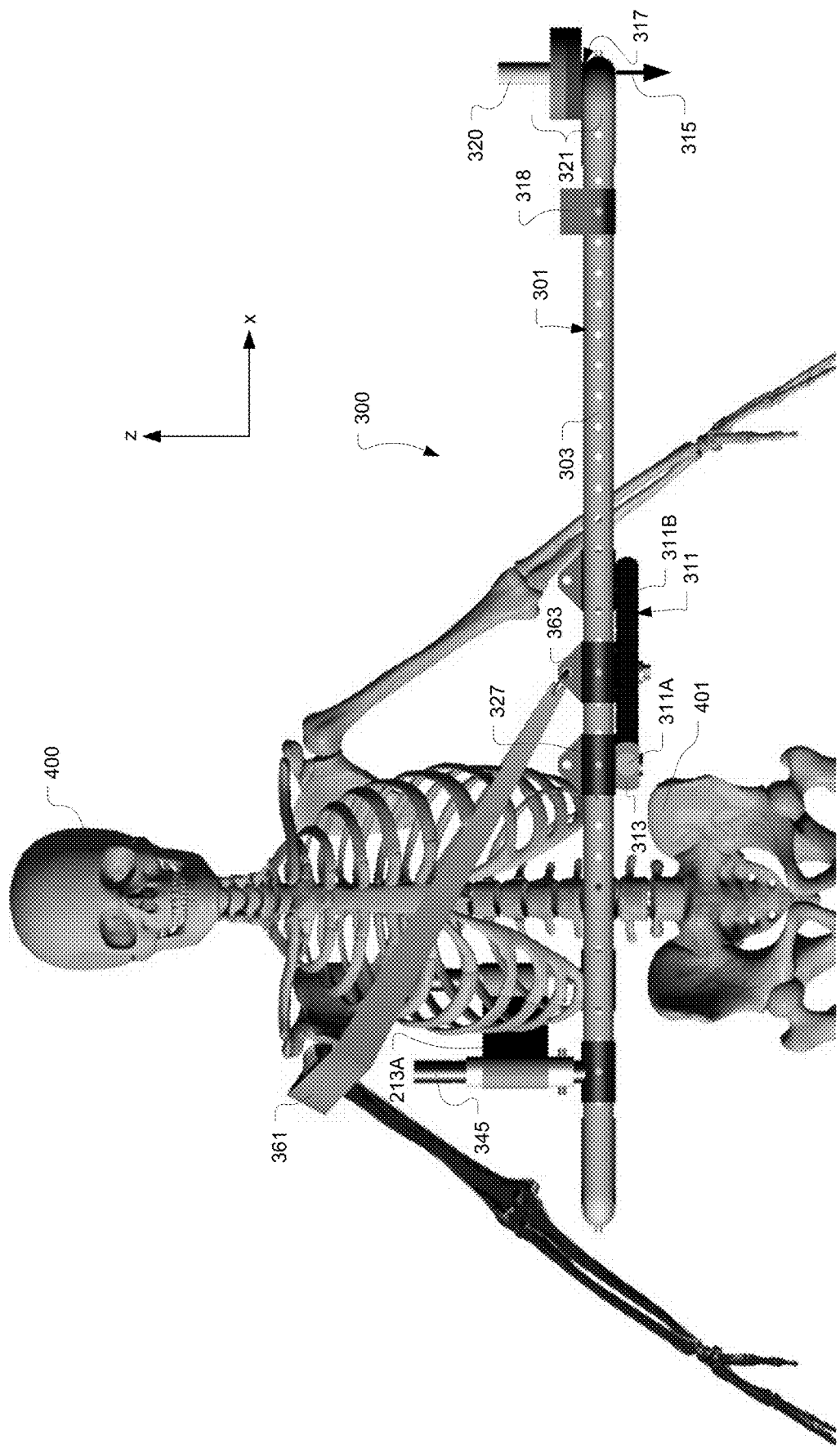
FIG. 4I shows the front view of the TLT apparatus with the human positioned within the TLT apparatus in the therapeutic position, in accordance with some embodiments of the present invention.
Figure 4J:
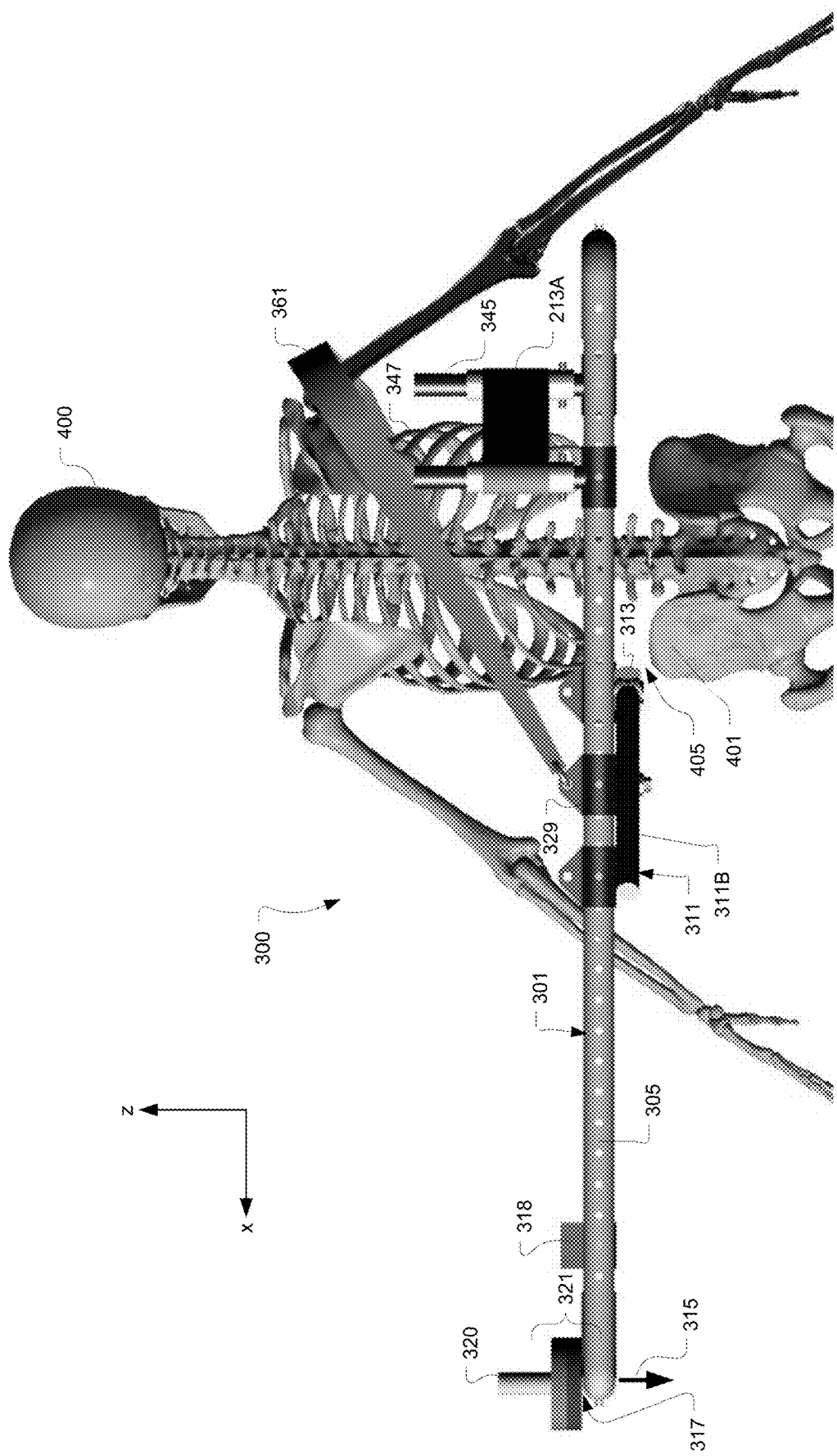
FIG. 4J shows the back view of the TLT apparatus with the human positioned within the TLT apparatus in the therapeutic position, in accordance with some embodiments of the present invention.
Figure 4K:
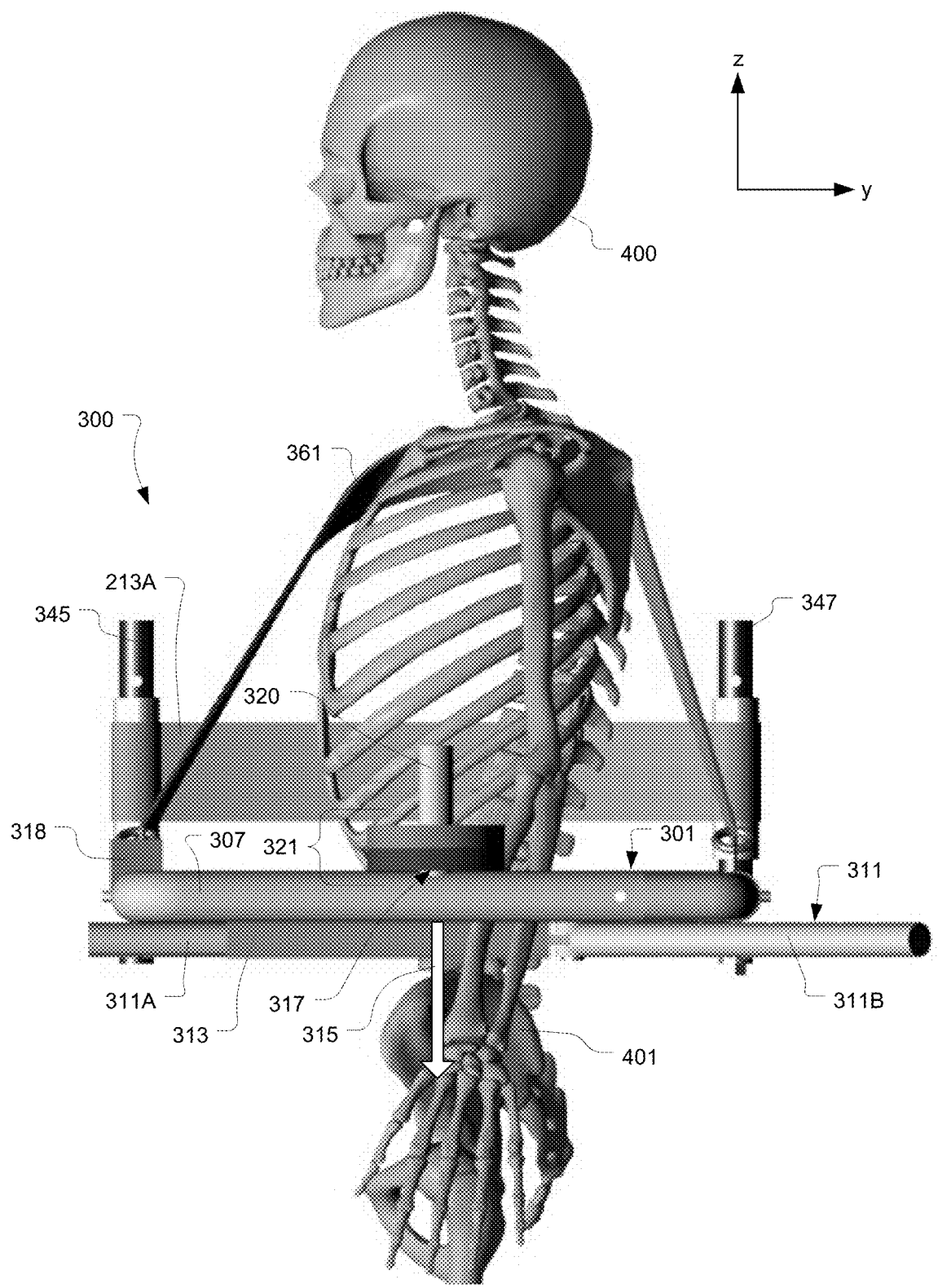
FIG. 4K shows the right side view of the TLT apparatus with the human positioned within the TLT apparatus in the therapeutic position, in accordance with some embodiments of the present invention.
Figure 4L:
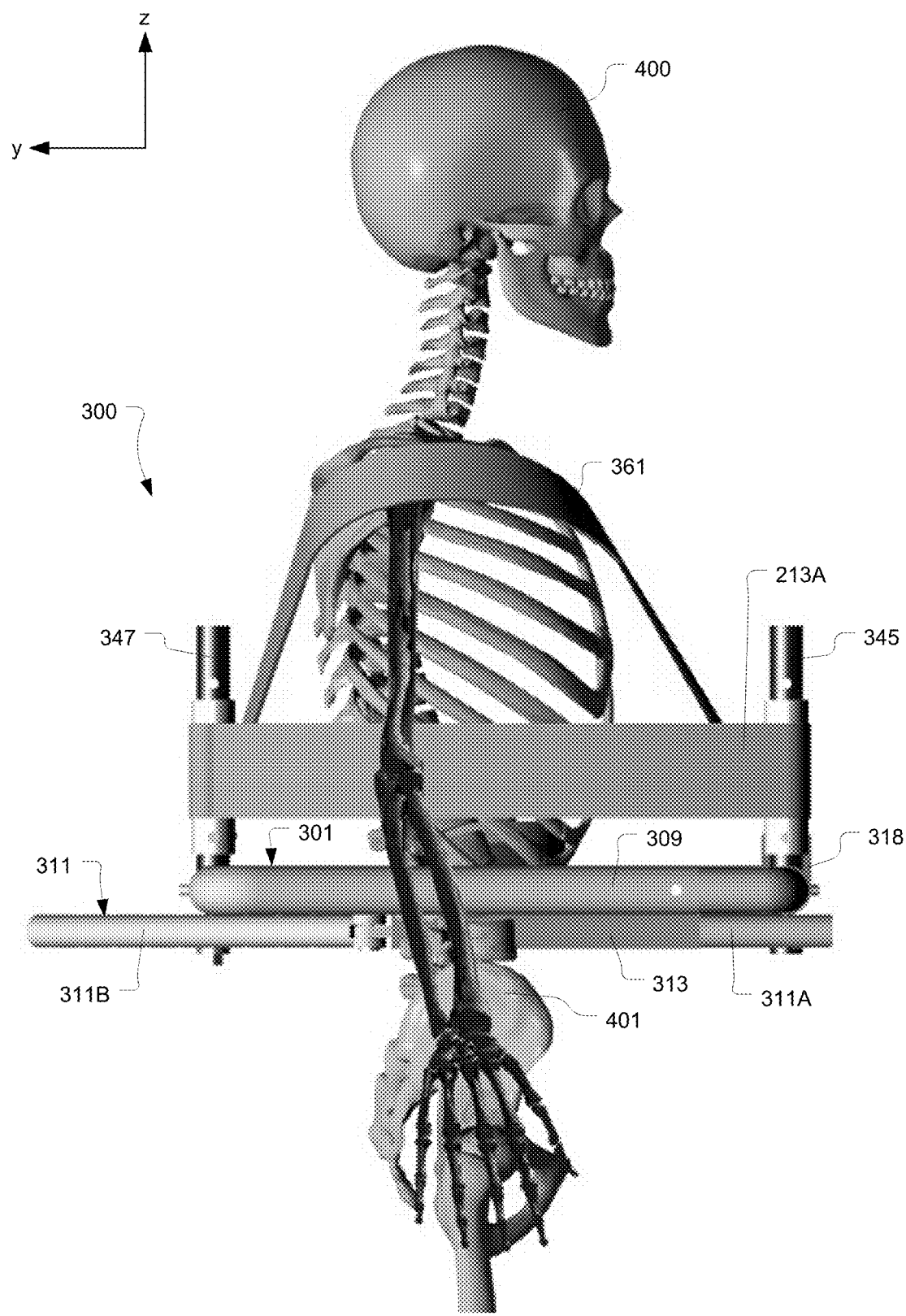
FIG. 4L shows the left side view of the TLT apparatus with the human positioned within the TLT apparatus in the therapeutic position, in accordance with some embodiments of the present invention.
Figure 4M:
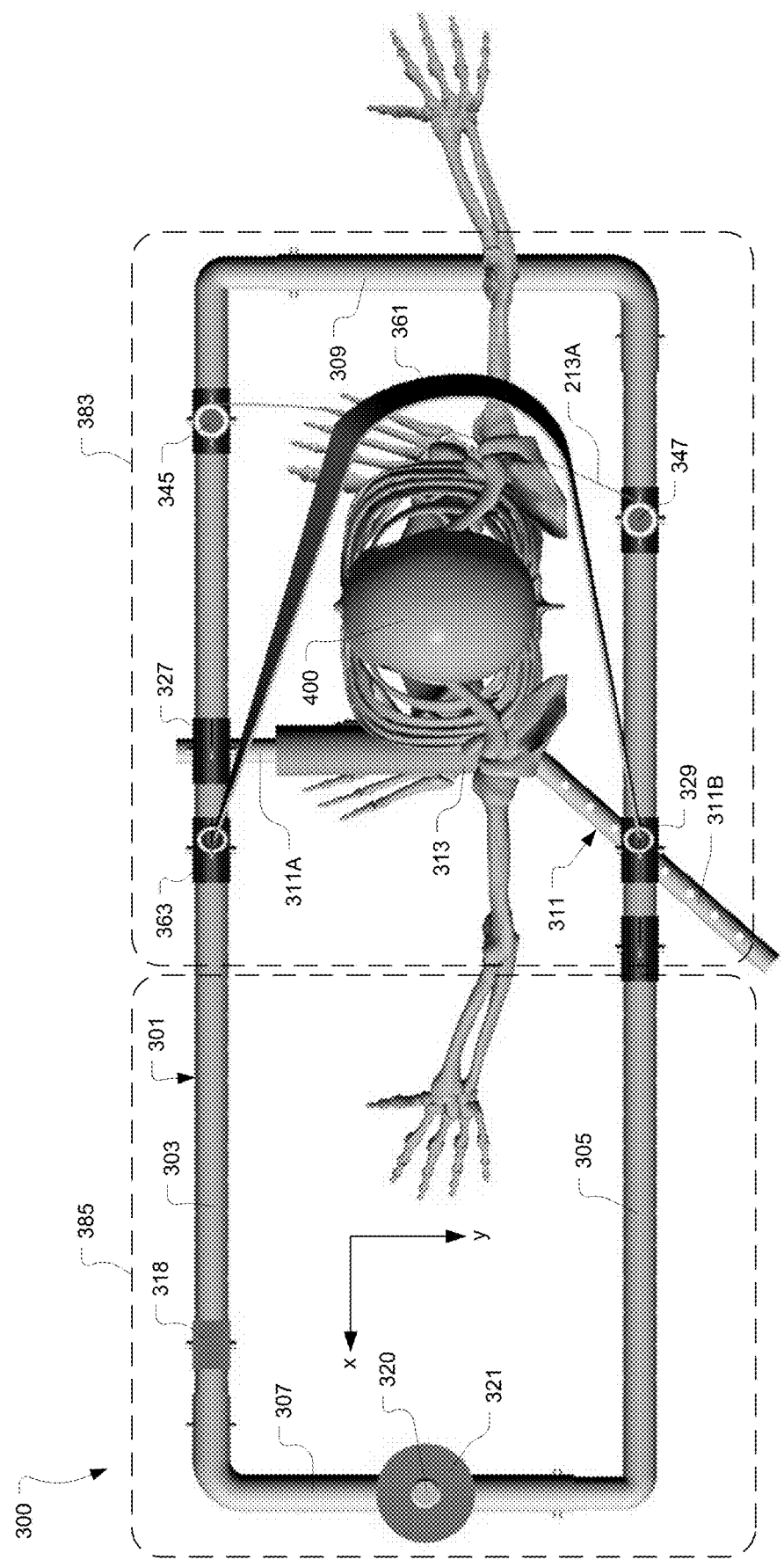
FIG. 4M shows the top view of the TLT apparatus with the human positioned within the TLT apparatus in the therapeutic position, in accordance with some embodiments of the present invention.
Figure 4N:
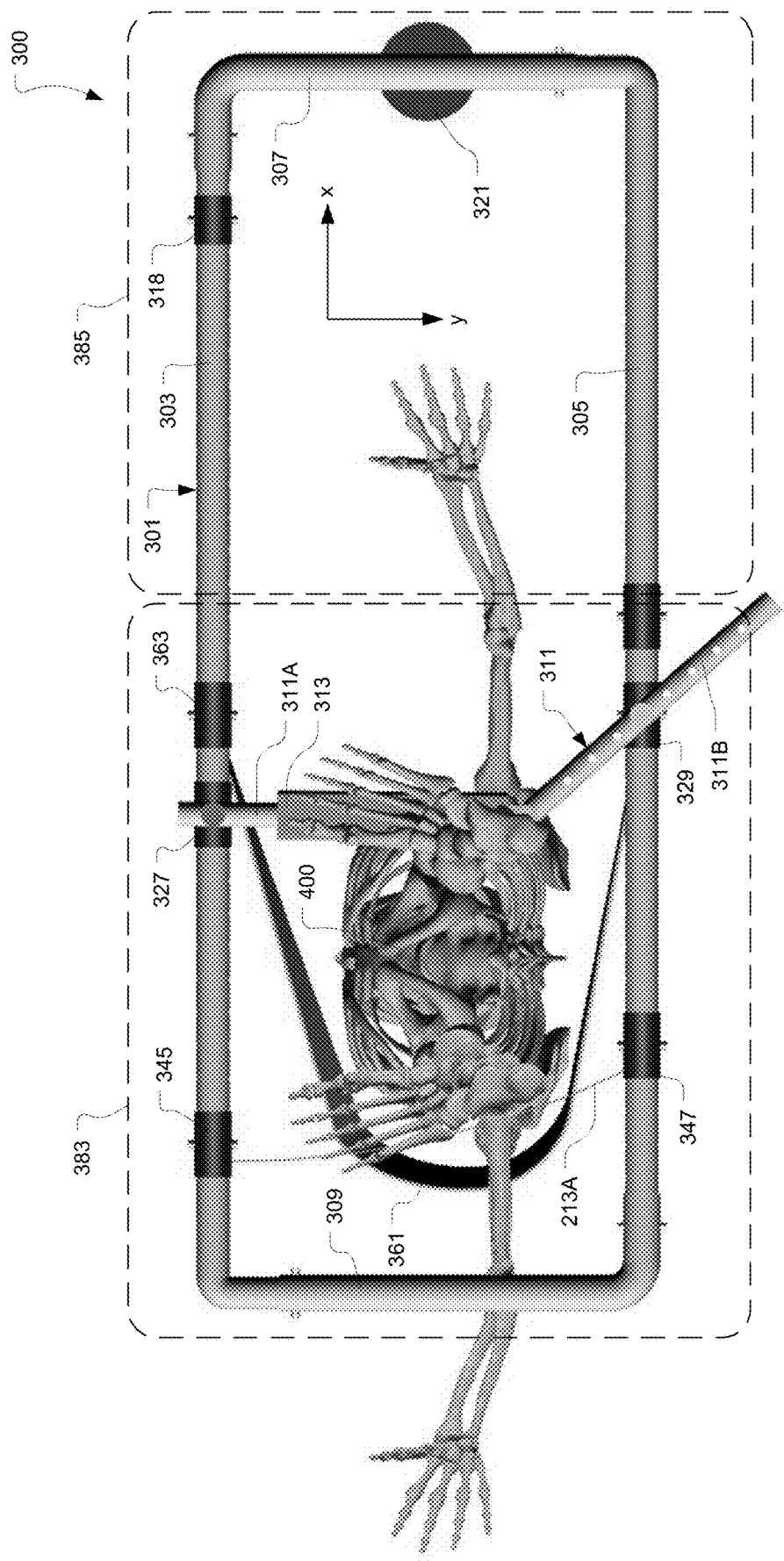
FIG. 4N shows the bottom view of the TLT apparatus with the human positioned within the TLT apparatus in the therapeutic position, in accordance with some embodiments of the present invention.
Figure 40:
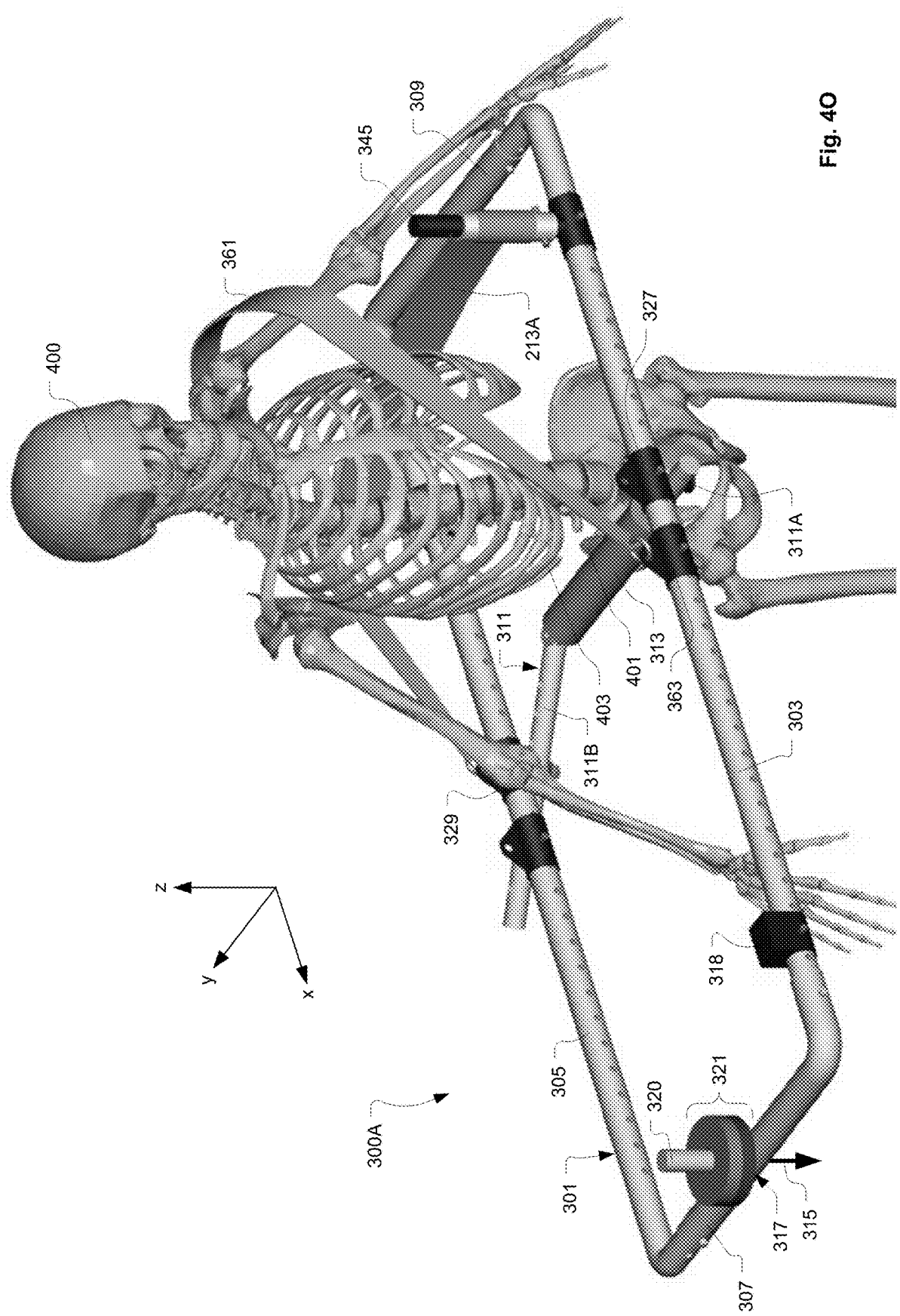

FIG. 4I shows the front view of the TLT apparatus 300 with the human 400 positioned within the TLT apparatus 300 in the therapeutic position, in accordance with some embodiments of the present invention. FIG. 4J shows the back view of the TLT apparatus 300 with the human 400 positioned within the TLT apparatus 300 in the therapeutic position, in accordance with some embodiments of the present invention. FIG. 4K shows the right side view of the TLT apparatus 300 with the human 400 positioned within the TLT apparatus 300 in the therapeutic position, in accordance with some embodiments of the present invention. FIG. 4L shows the left side view of the TLT apparatus 300 with the human 400 positioned within the TLT apparatus 300 in the therapeutic position, in accordance with some embodiments of the present invention. FIG. 4M shows the top view of the TLT apparatus 300 with the human 400 positioned within the TLT apparatus 300 in the therapeutic position, in accordance with some embodiments of the present invention. FIG. 4N shows the bottom view of the TLT apparatus 300 with the human 400 positioned within the TLT apparatus 300 in the therapeutic position, in accordance with some embodiments of the present invention.

The TLT apparatus 300 includes a frame assembly 301 that includes a front segment 303, a back segment 305, a left segment 307, and a right segment 309. The front segment 303 is configured to extend across an anterior side of the human 400 when the human 400 is present within the TLT apparatus 300. The back segment 305 is configured to extend across a posterior side of the human 400 when the human 400 is present within the TLT apparatus 300. The back segment 305 has a fixed spatial relationship with respect to the front segment 303. The left segment 307 extends between the front segment 303 and the back segment 305. The right segment 309 also extends between the front segment 303 and the back segment 305.

The TLT apparatus 300 also includes a clamp bar 311 configured to extend between the front segment 303 and the back segment 305. In some embodiments, a clamp pad 313 is positioned over a portion of the clamp bar 311. The clamp bar 311 is configured to extend across a first lateral side of the human 400 when the human 400 is present within the TLT apparatus 300. In the example TLT apparatus 300, the clamp bar 311 is configured and positioned to extend across the left lateral side of the human 400 when the human 400 is present within the TLT apparatus 300. The clamp bar 311 is configured to interface with the first lateral side of the human 400 at a location between a top surface of an ilium bone structure 401, i.e., hip bone, of the human 400 and a lowest rib 403 of a thoracic cage of the human 400 when the human 400 is present within the TLT apparatus 300, as shown in FIG. 4A. Additionally, the clamp bar 311 is configured to avoid resting on the ilium bone structure 401 of the human 400 when pressed firmly against the first lateral side of the human 400. For example, FIG. 4J shows the clamp bar 311 positioned to have a vertical gap 405 present between the clamp pad 313 and the top surface of the ilium bone structure 401 of the human 400. In this manner, the clamp bar 311 does not directly apply a downward force to the ilium bone structure 401 of the human 400. Also, in some embodiments, a lower portion/surface of the clamp pad 313 can be flattened to assist with establishing and maintaining the vertical gap 405 between the clamp pad 313 and the top surface of the ilium bone structure 401 of the human 400.

The TLT apparatus 300 also includes a lateral restraint band 213A positioned between the front segment 303 and the back segment 305. The lateral restraint band 213A is configured to interface with a second lateral side of the human 400 over an engagement area corresponding to a portion of the thoracic cage of the human 400 when the human 400 is present within the TLT apparatus 300. In the example TLT apparatus 300, the lateral restraint band 213A is configured to interface with a right lateral side of the human 400. For the example scoliotic spinal column 202A of FIG. 2, the engagement area to which the lateral restraint band 213A interfaces includes an exterior of the human 400 proximate to the ribs that connect to vertebrae (T9-T12) below the apex of the thoracic curve 205. However, it should be understood that the vertical position of the lateral restraint band 213A relative to the frame 301 can be adjusted to provide for positioning of the top of the lateral restraint band 213A to engage with the rib of the human that is connected to the vertebra just below the apex of the thoracic curve 205.

Figure 3O:
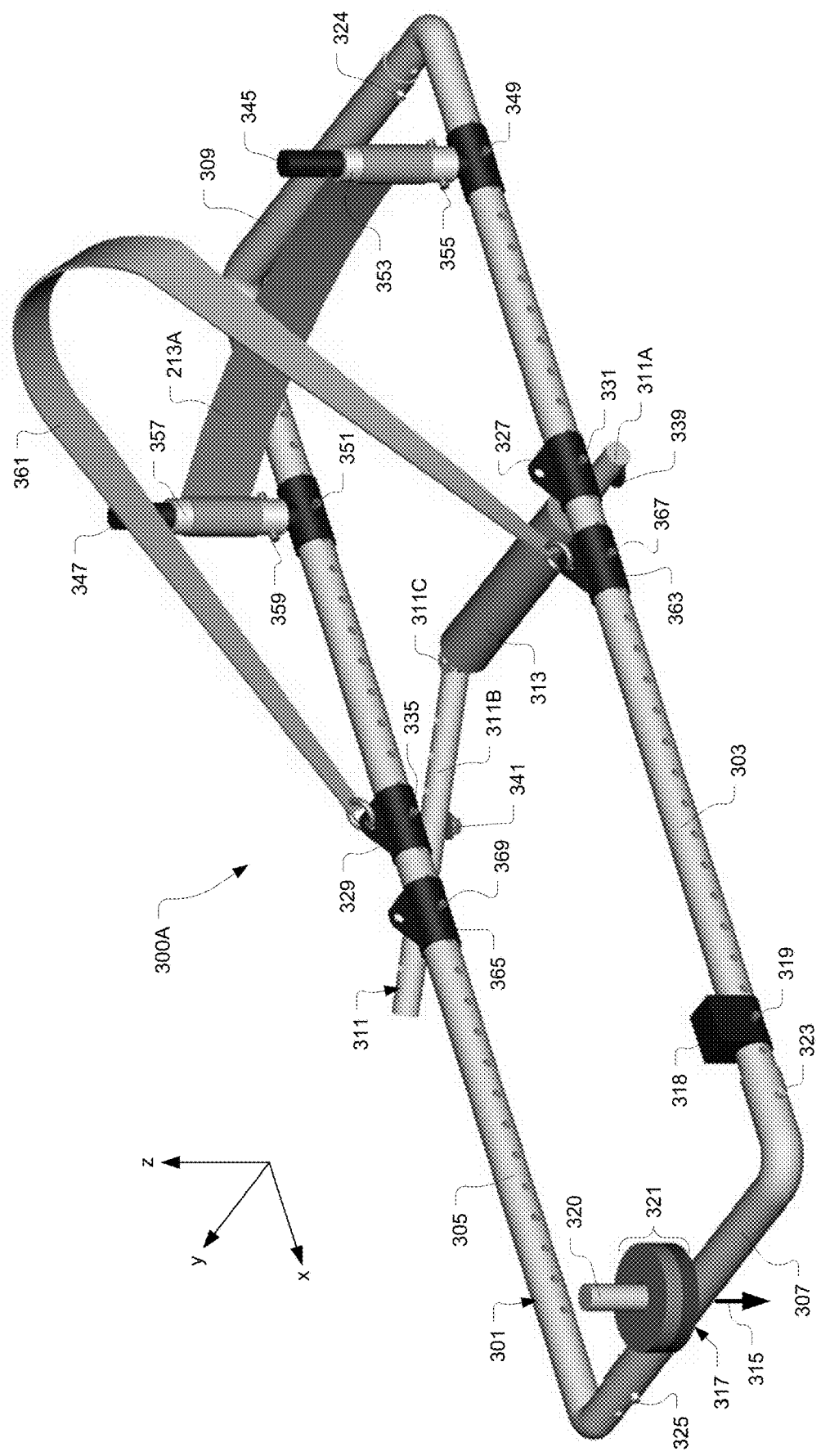
FIG. 3O shows a TLT apparatus configured for treatment of the human having the apex of the lumbar curve on the right side of the sacral vertical line and having the apex of the thoracic curve on the left side of the sacral vertical line, in accordance with some embodiments of the present invention.

With reference back to FIG. 2, it should be understood that the TLT apparatus 300 is configured for treatment of the human 400 having the apex of the lumbar curve 203 toward the left side of the sacral vertical line 206 and having the apex of the thoracic curve 205 toward the right side of the sacral vertical line 206. In other embodiments, the TLT apparatus 300 can be configured for treatment of the human 400 having the apex of the lumbar curve 203 toward the right side of the sacral vertical line 206 and having the apex of the thoracic curve 205 toward the left side of the sacral vertical line 206. In these other embodiments, the TLT apparatus 300 is configured in a reversed manner from left-to-right. FIG. 3O shows a TLT apparatus 300A configured for treatment of the human 400 having the apex of the lumbar curve 203 on the right side of the sacral vertical line 206 and having the apex of the thoracic curve 205 on the left side of the sacral vertical line 206, in accordance with some embodiments of the present invention. FIG. 4O shows the TLT apparatus 300A with the human 400 positioned therein for treatment, in accordance with some embodiments of the present invention. For ease of description, the TLT apparatus 300 is described herein for the human 400 having the apex of the lumbar curve 203 on the left side of the sacral vertical line 206 and having the apex of the thoracic curve 205 on the right side of the sacral vertical line 206. However, it should be understood that the disclosure of the TLT apparatus 300 provided herein is equally applicable to the TLT apparatus 300A having the reversed configuration, such as shown in FIG. 3O.

Figure 4P:
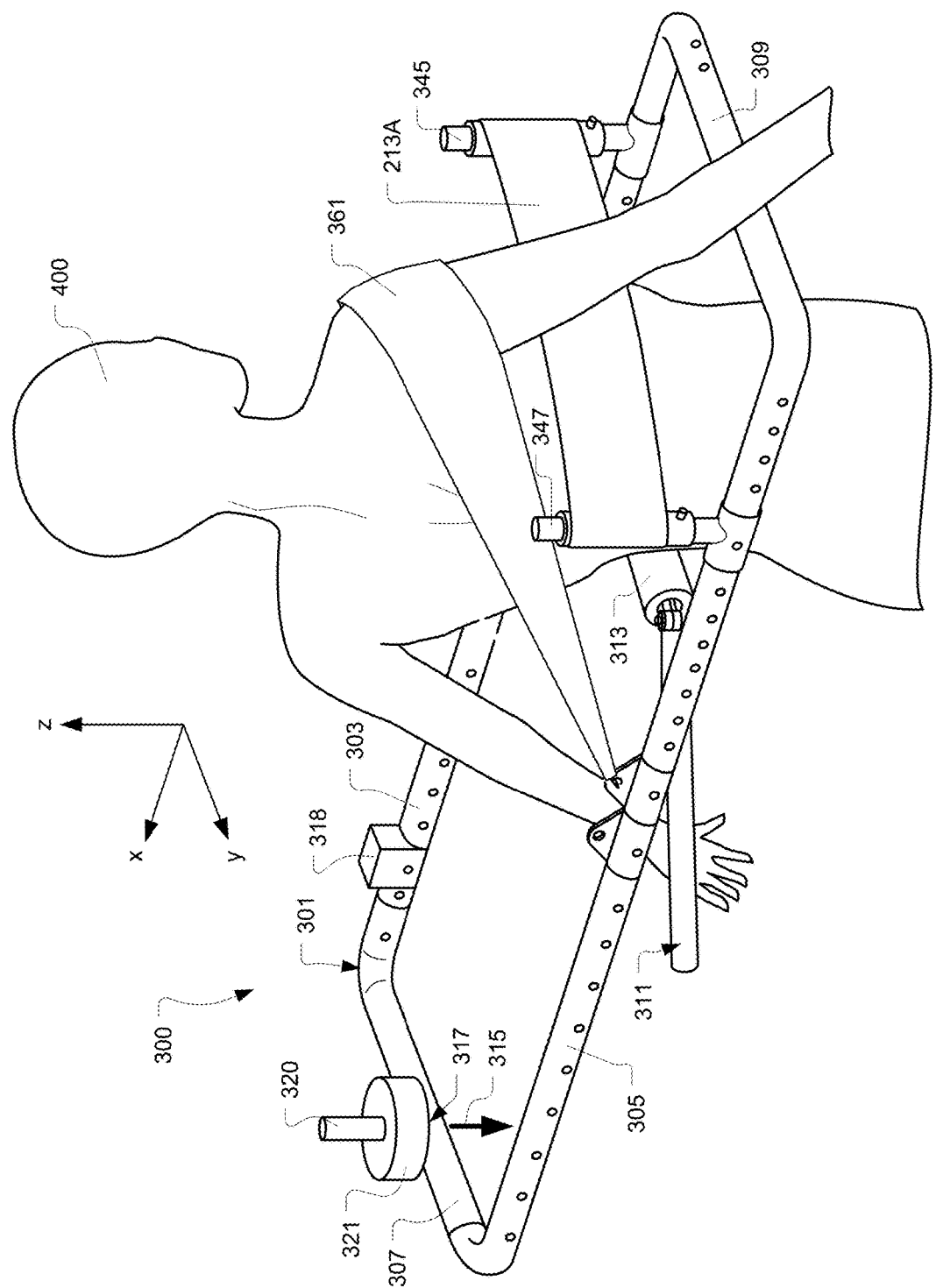
FIG. 4P shows an isometric view of the TLT apparatus 300 toward a posterior of the human 400, in accordance with some embodiments of the present invention.
Figure 4Q:
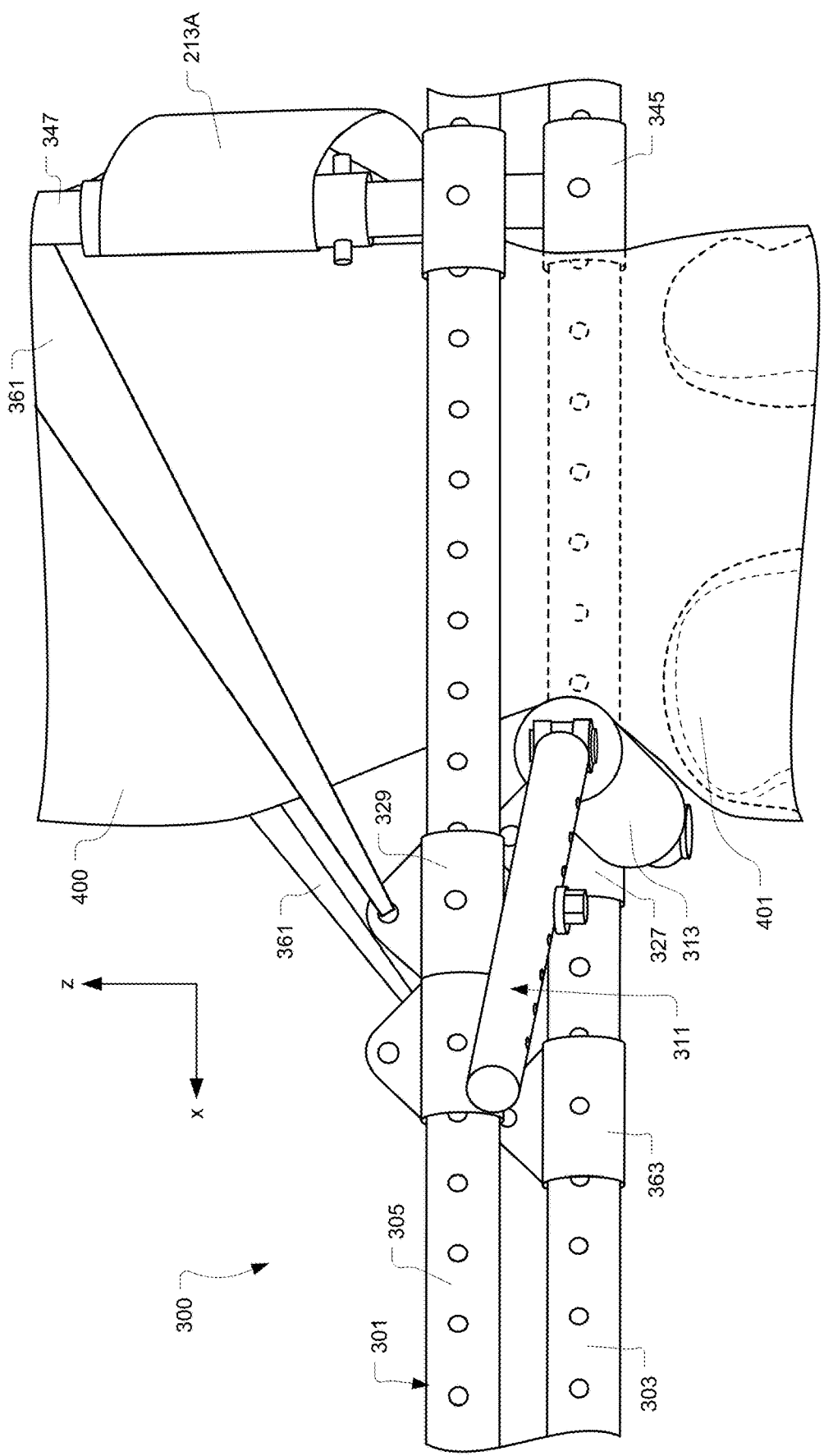
FIG. 4Q shows a view of the TLT apparatus 300 toward the posterior of the human 400 focused on the interface between the clamp pad 313 and the side of the human 400, in accordance with some embodiments of the present invention.

FIG. 4P shows an isometric view of the TLT apparatus 300 toward a posterior of the human 400, in accordance with some embodiments of the present invention. An exterior surface of the human 400 is depicted in FIG. 4P to illustrate an example fit of the shoulder strap 361 around the side of the human 400 where the lateral restraint band 213A is positioned. FIG. 4Q shows a view of the TLT apparatus 300 toward the posterior of the human 400 with focus on the interface between the clamp pad 313 and the side of the human 400, in accordance with some embodiments of the present invention. FIG. 4Q illustrates an example of how the clamp pad 313 interfaces with the side of the human 400 at the location above the ilium bone structure 401, i.e., hip bone, such that a space exists between the clamp pad 313 and the ilium bone structure 401. In this manner, the weight of the TLT apparatus 300 is substantially prevented from resting upon the ilium bone structure 401, i.e., hip bone.

During use of the TLT apparatus 300, the human 400 works to laterally translate the lower portion of their spinal column under their own neuro-muscular effort toward the lateral restraint band 213A, and the lateral restraint band 213A functions to provide a resisting force against the lateral translation by the human 400, thereby allowing the lumbar curve 203 to straighten. To enable the lateral restraint band 213A to provide the necessary resisting force, the lateral restraint band 213A is rigidly connected to the front segment 303 and the back segment 305 of the frame 301, and a downward treatment force 315 is applied to both the left segment 307 of the frame 301 at a treatment force location 317. The downward treatment force 315 generates a moment about the clamp bar 311 at the lateral restraint band 213A, which serves to resist the lateral translation by the human 400. During use of the TLT apparatus 300, the human 400 is required to laterally translate the lower portion of their spinal column toward the lateral restraint band 213A with sufficient force to maintain an attitude of the frame 301 within a prescribed range about level. Therefore, as the downward treatment force 315 is increased, the human 400 is required to laterally translate the lower portion of their spinal column toward the lateral restraint band 213A with increased force in order to maintain the attitude of the frame 301 within the prescribed range about level. In some embodiments, a treatment weight receiver 320 is positioned at the treatment force location 317, where the treatment weight receiver 320 is configured to receive and hold one or more weights 321 that apply the downward treatment force 315.

In some embodiments, the TLT apparatus 300 is equipped with a level sensor 318 to provide an indication of spatial orientation of the frame 301 with respect to level. In some embodiments, the level sensor 318 is configured to signal an alarm, either audibly, visually, haptically, etc., when an angle of the frame 301 relative to level is outside of the prescribed range about level. In various embodiments, the level sensor 318 is configured to allow setting of the prescribed range about level to allow either more or less tilt of the frame 301 relative to level during treatment. For example, when the human 400 initially begins treatment, the prescribed range about level may be larger, thus allowing the human 400 to more easily achieve and maintain an acceptable attitude of the frame 301 during treatment. Then, as treatment progresses, the level sensor 318 can be adjusted to tighten the prescribed range about level in order to challenge the human 400 in regard to achieving and maintaining an acceptable attitude of the frame 301 during treatment. In various embodiments, the prescribed range about level for the frame 301 during treatment is about +/−20 degrees, or +/−15 degrees, or +/−10 degrees, or +/−5 degrees, or +/−4 degrees, or +/−3 degrees, or +/−2 degrees, or +/−1 degree.

In various embodiments, the level sensor 318 can be affixed to either the front segment 303, the back segment 305, the left segment 307, or the right segment 309. In some embodiments, the level sensor 318 is configured to slide along the segment (303, 305, 307, 309) to which it is attached to a desired position. In some embodiments, the level sensor 318 is configured to be fixed in position relative to the segment (303, 305, 307, 309) to which it is attached by a connector pin 319. It should be understood, however, that in other embodiments the level sensor 318 can be fixed in position relative to the segment (303, 305, 307, 309) to which it is attached using essentially any connection mechanism, so long as the level sensor 318 is positioned and configured to provide an accurate indication of the spatial orientation of the frame 301 with respect to level. In some embodiments, the level sensor 318 is positioned near the treatment force location 317.

In some embodiments, an overall length of the front segment 303 and the back segment 305 of the frame 301 is adjustable in the x-direction. Also, in some embodiments, an overall length of the left segment 307 and the right segment 309 is adjustable in the y-direction. Additionally, in some embodiments, the overall length of the front segment 303 and the back segment 305 can be fixed in the x-direction, with the overall length of the left segment 307 and the right segment 309 being adjustable in the y-direction. And, in some embodiments, the overall length of the front segment 303 and the back segment 305 is adjustable in the x-direction, with the overall length of the left segment 307 and the right segment 309 being fixed in the y-direction. Also, in some embodiments, the overall length of the front segment 303 and the back segment 305 is fixed in the x-direction, and the overall length of the left segment 307 and the right segment 309 are fixed in the y-direction. In these embodiments, the TLT apparatus 300 can be configured in different sizes such as extra small, small, medium, large, extra large, among others, to enable effective use of the apparatus 200 with humans of different size.

In some embodiments, for an extra small version of the TLT apparatus 300, the overall length of each of the left segment 307 and the right segment 309 in the y-direction is within a range extending from about 10 inches to about 30 inches, and the overall length of each of the front segment 303 and the back segment 305 in the x-direction is within a range extending from about 10 inches to about 60 inches. In some embodiments, for a small version of the TLT apparatus 300, the overall length of each of the left segment 307 and the right segment 309 in the y-direction is within a range extending from about 10 inches to about 15 inches, and the overall length of each of the front segment 303 and the back segment 305 in the x-direction is within a range extending from about 10 inches to about 30 inches. In some embodiments, for a medium version of the TLT apparatus 300, the overall length of each of the left segment 307 and the right segment 309 in the y-direction is within a range extending from about 12 inches to about 20 inches, and the overall length of each of the front segment 303 and the back segment 305 in the x-direction is within a range extending from about 15 inches to about 30 inches. In some embodiments, for a large version of the TLT apparatus 300, the overall length of each of the left segment 307 and the right segment 309 in the y-direction is within a range extending from about 15 inches to about 25 inches, and the overall length of each of the front segment 303 and the back segment 305 in the x-direction is within a range extending from about 20 inches to about 50 inches. In some embodiments, for an extra large version of the TLT apparatus 300, the overall length of each of the left segment 307 and the right segment 309 in the y-direction is within a range extending from about 15 inches to about 30 inches, and the overall length of each of the front segment 303 and the back segment 305 in the x-direction is within a range extending from about 25 inches to about 60 inches.

In various embodiments, the front segment 303, the back segment 305, the left segment 307, and the right segment 309 can be connected together in a variety of ways to form the frame 301. In some embodiments, each of the front segment 303 and the back segment 305 is welded, soldered, glued, and/or otherwise rigidly adhered to each of the left segment 307 and the right segment 309 to form the frame 301. In some embodiments, each of the front segment 303 and the back segment 305 is rigidly connected to each of the left segment 307 and the right segment 309 using fasteners in order to form the frame 301. In some embodiments, each of the front segment 303 and the back segment 305 is rigidly connected to each of the left segment 307 and the right segment 309 using pressure/friction connections in order to form the frame 301. Also, in some embodiments, such as the example TLT apparatus 300, pinned connections are used to form the frame 301.

In the example TLT apparatus 300, the front segment 303 and the left segment 307 are secured together by a connector pin 323, and the front segment 303 and the right segment 309 are secured together by a connector pin 324, and the back segment 305 and the left segment 307 are secured together by a connector pin 325, and the back segment 305 and the right segment 309 are secured together by a connector pin 326. It should be understood that in other embodiments each of the front segment 303 and the back segment 305 can be rigidly connected to each of the left segment 307 and the right segment 309 using mechanisms and techniques other than those explicitly identified herein so long as the front segment 303, the back segment 305, the left segment 307, and the right segment 309 collectively form the frame 301 having a stable mechanical structure.

In the example TLT apparatus 300, the frame 301 is formed by four L-shaped structures. A first L-shaped structure forms the front segment 303 and an inner portion of the right segment 309. A second L-shaped structure forms the back segment 305 and an inner portion of the left segment 307. A third L-shaped structure forms an outer portion of the front segment 303 and an outer portion of the left segment 307. A fourth L-shaped structure forms an outer portion of the back segment 305 and an outer portion of the right segment 309. The inner portion of the left segment 307 can be moved in the y-direction relative to the outer portion of the left segment 307 to adjust the overall length of the left segment 307 in the y-direction. The inner portion of the right segment 309 can be moved in the y-direction relative to the outer portion of the right segment 309 to adjust the overall length of the right segment 309 in the y-direction.

Figure 5A:
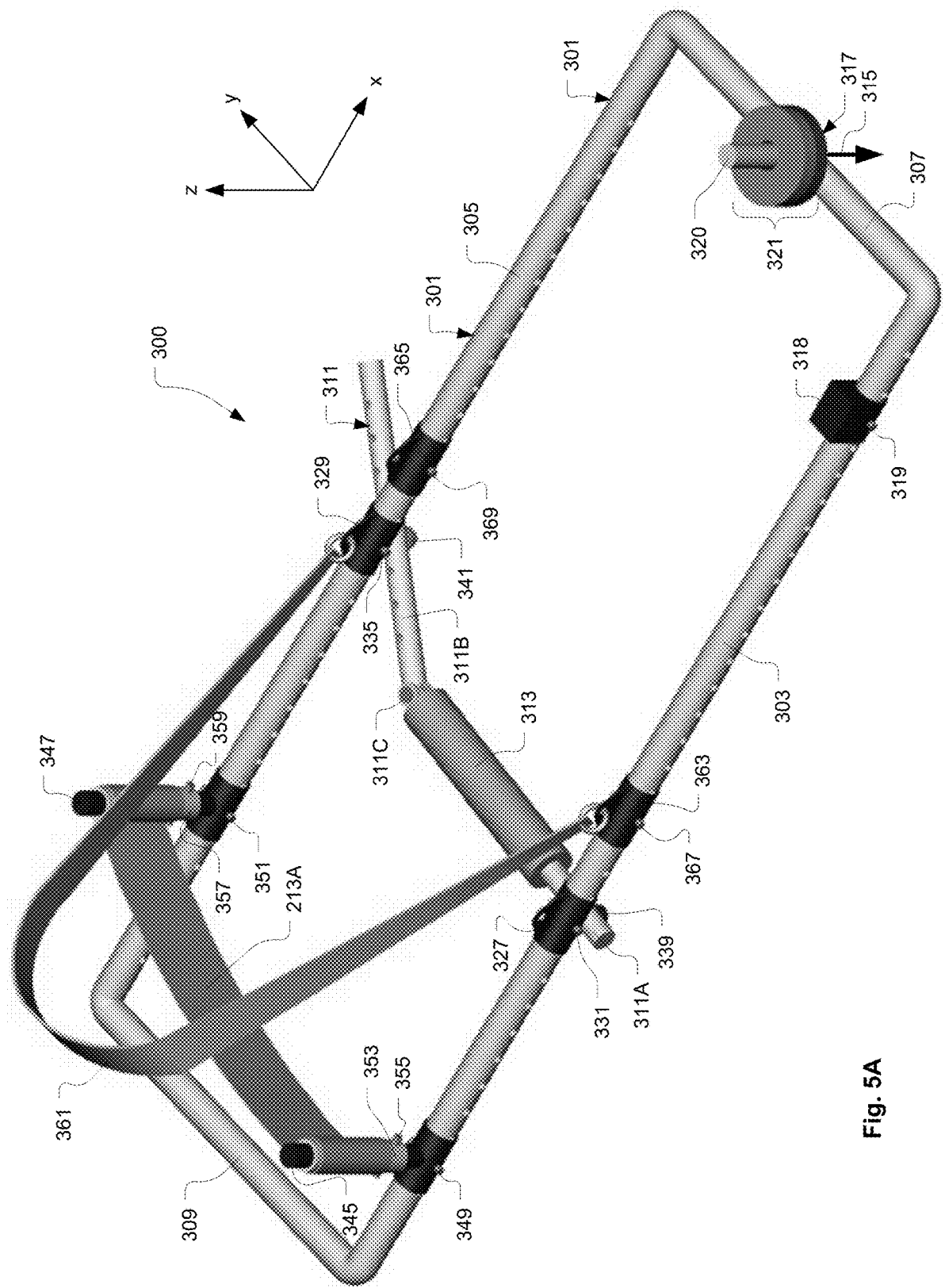
FIG. 5A shows an embodiment of the TLT apparatus in which the first segment is formed integrally with each of the left segment and the right segment, and in which the back segment is formed integrally with each of the left segment and the right segment, in accordance with some embodiments of the present invention.
Figure 5B:
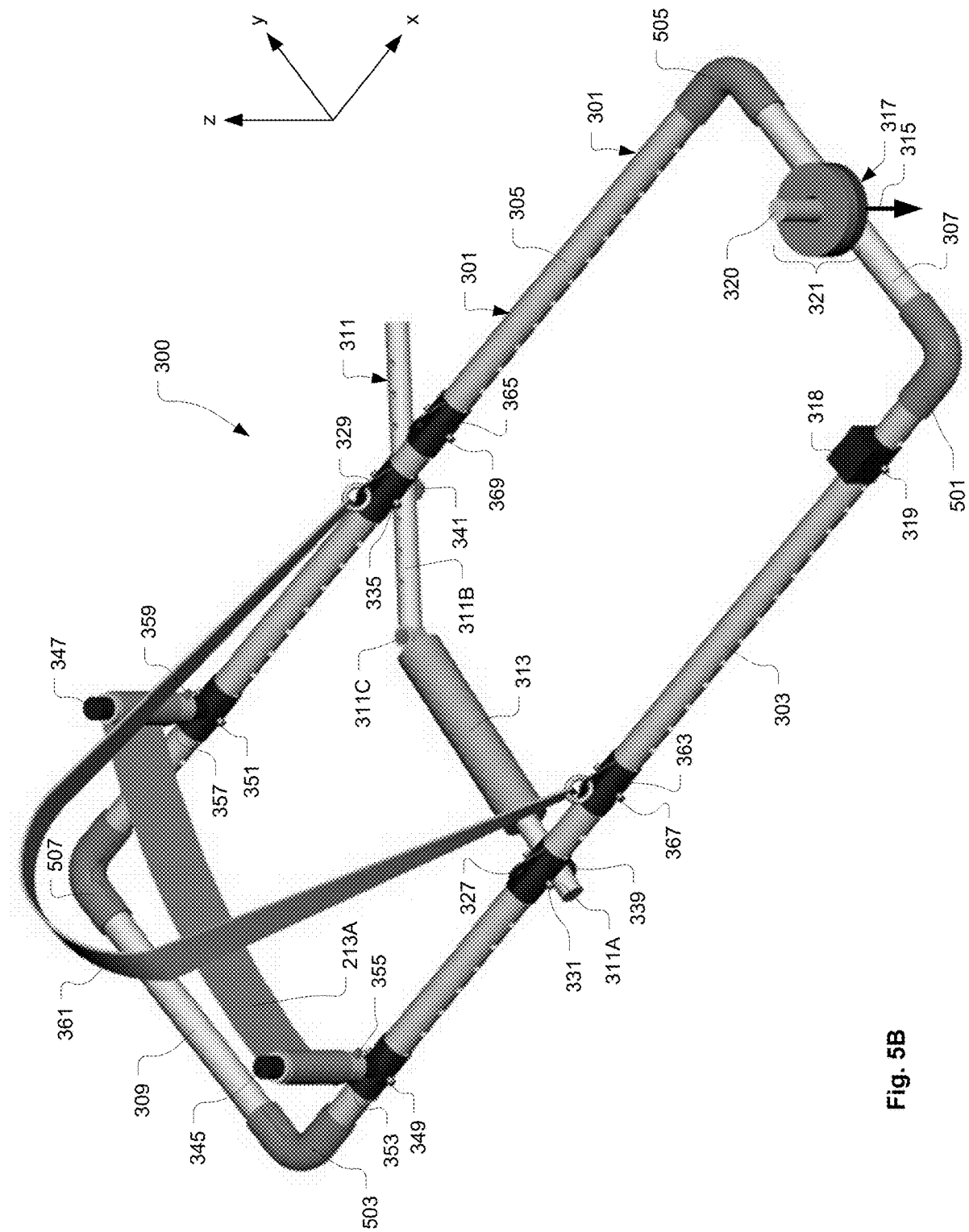
FIG. 5B shows another embodiment of the TLT apparatus in which the first segment is connected to the left segment by a fitting, and the first segment is connected to the right segment by a fitting, and the back segment is connected to the left segment by a fitting, and the back segment is connected to the right segment by a fitting, in accordance with some embodiments of the present invention.

It should be understood that the example TLT apparatus 300 represents one of many possible configurations of the TLT apparatus. In other embodiments, various components of the frame 301 can have different sizes, shapes, configurations, and/or connection mechanisms. For example, FIG. 5A shows an embodiment of the TLT apparatus 300 in which the first segment 303 is formed integrally with each of the left segment 307 and the right segment 309, and in which the back segment 305 is formed integrally with each of the left segment 307 and the right segment 309, in accordance with some embodiments of the present invention. FIG. 5B shows another embodiment of the TLT apparatus 300 in which the first segment 303 is connected to the left segment 307 by a fitting 501, and the first segment 303 is connected to the right segment 309 by a fitting 503, and the back segment 305 is connected to the left segment 307 by a fitting 505, and the back segment 305 is connected to the right segment 309 by a fitting 507, in accordance with some embodiments of the present invention.

Because an overall weight of the TLT apparatus 300 is supported by the human 400, a material used to form the frame 301 should provide an overall frame weight as low as possible while also providing sufficient rigidity and mechanical strength. In various embodiments, the frame 301 can be formed of one or more materials including, but not limited to, aluminum, carbon-fiber, fiberglass, plastic, and PVC, among others.

In the example TLT apparatus 300, each of the front segment 303, the back segment 305, the left segment 307, and the right segment 309 have a round vertical cross-section. However, it should be understood that in other embodiments, each of the front segment 303, the back segment 305, the left segment 307, and the right segment 309 can be formed to have another vertical cross-section shape, such as square, rectangular, triangular, oval, among others. Also, any one or more of the front segment 303, the back segment 305, the left segment 307, and the right segment 309 can be formed to have any number of channels and/or slots and/or grooves formed therein for various purposes. Additionally, the TLT apparatus 300 shows each of the front segment 303, the back segment 305, the left segment 307, and the right segment 309 have a substantially linear shape in the x-y plane. However, it should be understood that in other embodiments, any of the front segment 303, the back segment 305, the left segment 307, and the right segment 309 can be formed to have a non-linear shape in the x-y plane, such as a curved shape or an arcing shape, among other shapes. And, in some embodiments, a shape of the front segment 303 in the x-y plane can be different than a shape of the back segment 305 in the x-y plane, and/or a shape of the left segment 307 in the x-y plane can be different than a shape of the right segment 309 in the x-y plane.

Figure 6A:
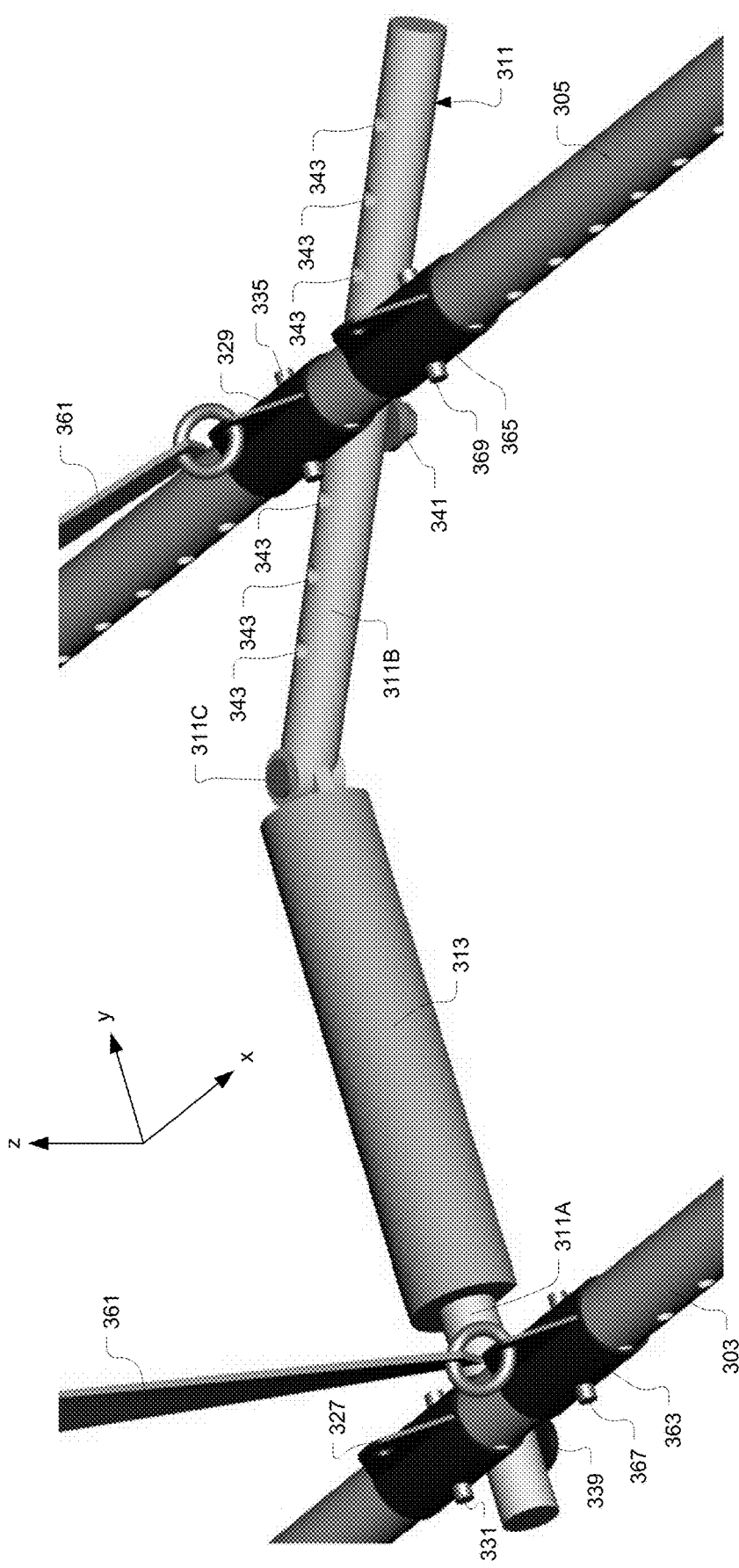
FIG. 6A shows a top isometric view of the clamp bar, in accordance with some embodiments of the present invention.
Figure 6B:
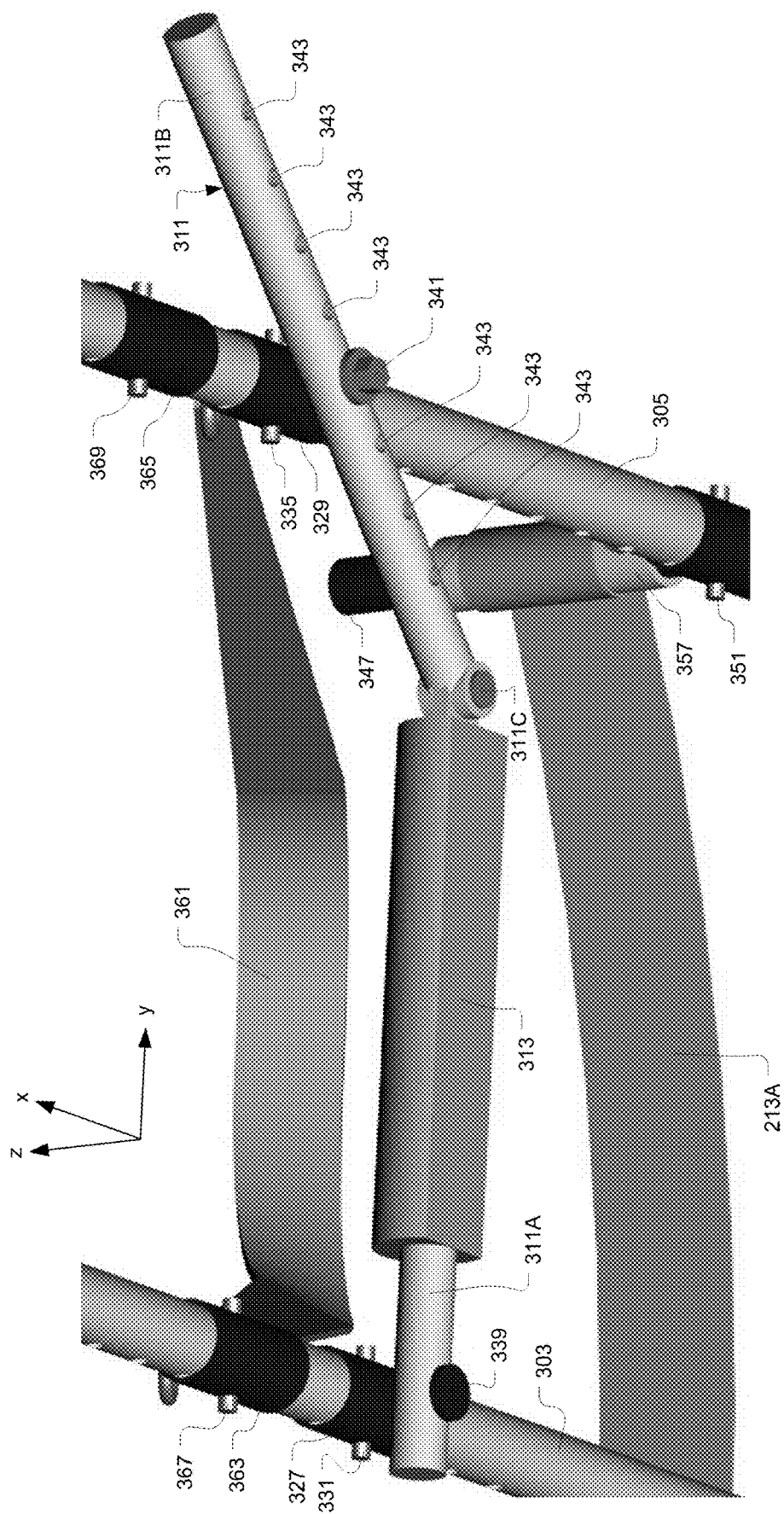
FIG. 6B shows a bottom isometric view of the clamp bar, in accordance with some embodiments of the present invention.

In the TLT apparatus 300, the clamp bar 311 includes a first segment 311A and a second segment 311B connected together by a pivot connection 311C. The clamp pad 313 is positioned over the first segment 311A. However, it should be understood that in various embodiments, the clamp pad 313 can be positioned over one or more of the first segment 311A, the pivot connection 311C, and the second segment 311B. FIG. 6A shows a top isometric view of the clamp bar 311, in accordance with some embodiments of the present invention. FIG. 6B shows a bottom isometric view of the clamp bar 311, in accordance with some embodiments of the present invention. The first segment 311A of the clamp bar 311 is connected to a first anchor member 327, and the second segment 311B of the clamp bar 311 is connected to a second anchor member 329. The first anchor member 327 is configured to slide along the front segment 303 to a desired position. And, the first anchor member 327 is configured to be fixed in position relative to the front segment 303 by a connector pin 331 that extends through both the first anchor member 327 and the front segment 303 at the desired position along the front segment 303. In some embodiments, the front segment 303 includes a number of holes 333 for receipt of various connector pins at different positions. Similarly, the second anchor member 329 is configured to slide along the back segment 305 to a desired position. And, the second anchor member 329 is configured to be fixed in position relative to the back segment 305 by a connector pin 335 that extends through both the second anchor member 329 and the back segment 305 at the desired position along the back segment 305. In some embodiments, the back segment 305 includes a number of holes 337 for receipt of various connector pins at different positions.

The first anchor member 327 includes a pivot structure 339 that passes through the first segment 311A of the clamp bar 311 and that secures the first segment 311A of the clamp bar 311 to the first anchor member 327. The pivot structure 339 is configured to provide for rotation of the first segment 311A of the clamp bar 311 within the x-y plane about the pivot structure 339. The second anchor member 329 includes a pivot structure 341 that passes through the second segment 311B of the clamp bar 311 and that secures the second segment 311B of the clamp bar 311 to the second anchor member 329. The pivot structure 341 is configured to be removable from the second anchor member 329 to provide for adjustable positioning of the second segment 311B of the clamp bar 311 relative to the second anchor member 329. More specifically, in some embodiments, the second segment 311B of the clamp bar 311 includes a number of holes 343 through which the pivot structure 341 can be inserted to provide for adjustable positioning of the second segment 311B of the clamp bar 311 relative to the second anchor member 329. In some embodiments, the pivot structure 341 is configured to fasten to the second anchor member 329 using a threaded connection. However, in other embodiments, the pivot structure 341 can be configured to fasten to the second anchor member 329 using a keyed connection, a clip connection, a cotter pin connection, or another type of connection.

It should be understood that through a combination of the position of the first anchor member 327 in the x-direction relative to the front segment 303 of the frame 301, and the position of the second anchor member 329 in the x-direction relative to the back segment 305 of the frame 301, and the position of the second segment 311B of the clamp bar 311 relative to the second anchor member 329, and by way of the pivot structure 311C, the second segment 311B of the clamp bar 311 can be set at a specified angle in the x-y plane relative to the y-axis direction. FIG. 7 shows a top view of the TLT apparatus 300 illustrating an angle 701 of the second segment 311A of the clamp bar 311 in the x-y plane relative to the y-axis, in accordance with some embodiments of the present invention. It should be appreciated that the angle 701 of the second segment 311B of the clamp bar 311 provides a space 703 within the boundary of the frame 301 that can be used to accommodate positioning of other equipment/devices to supplement treatment of the human 400 by the TLT apparatus 300.

The first segment 311A of the clamp bar 311 has a length large enough to extend past the first lateral side of the human 400 when the human 400 is present within the TLT apparatus 300. In some embodiments, the first segment 311A of the clamp bar 311 is positioned to extend in a substantially perpendicular direction, i.e., y-direction, between the front segment 303 and the second segment 305 of the frame 301. However, in some embodiments, the first segment 311A of the clamp bar 311 can be set at a specified angle 705 in the x-y plane relative to the y-axis direction to accommodate a body shape of the human 400 and/or to improve a comfort level of the human 400 and/or to achieve a desired therapeutic effect.

FIG. 8A shows the TLT apparatus 300 with a clamp bar 311-1 configured to have a substantially straight configuration, in accordance with some embodiments of the present invention. In this embodiment, relative to the clamp bar 311, the pivot connection 311C is removed and the first segment 311A and the second segment 311B are effectively joined together in an integral and linearly-aligned manner. The clamp bar 311-1 is adjustable in the x-direction along the length of the front segment 303 and the back segment 305 of the frame 301, by way of the first anchor member 327 and the second anchor member 329, respectively, in the same manner as described with regard to the clamp bar 311.

Figure 8B:
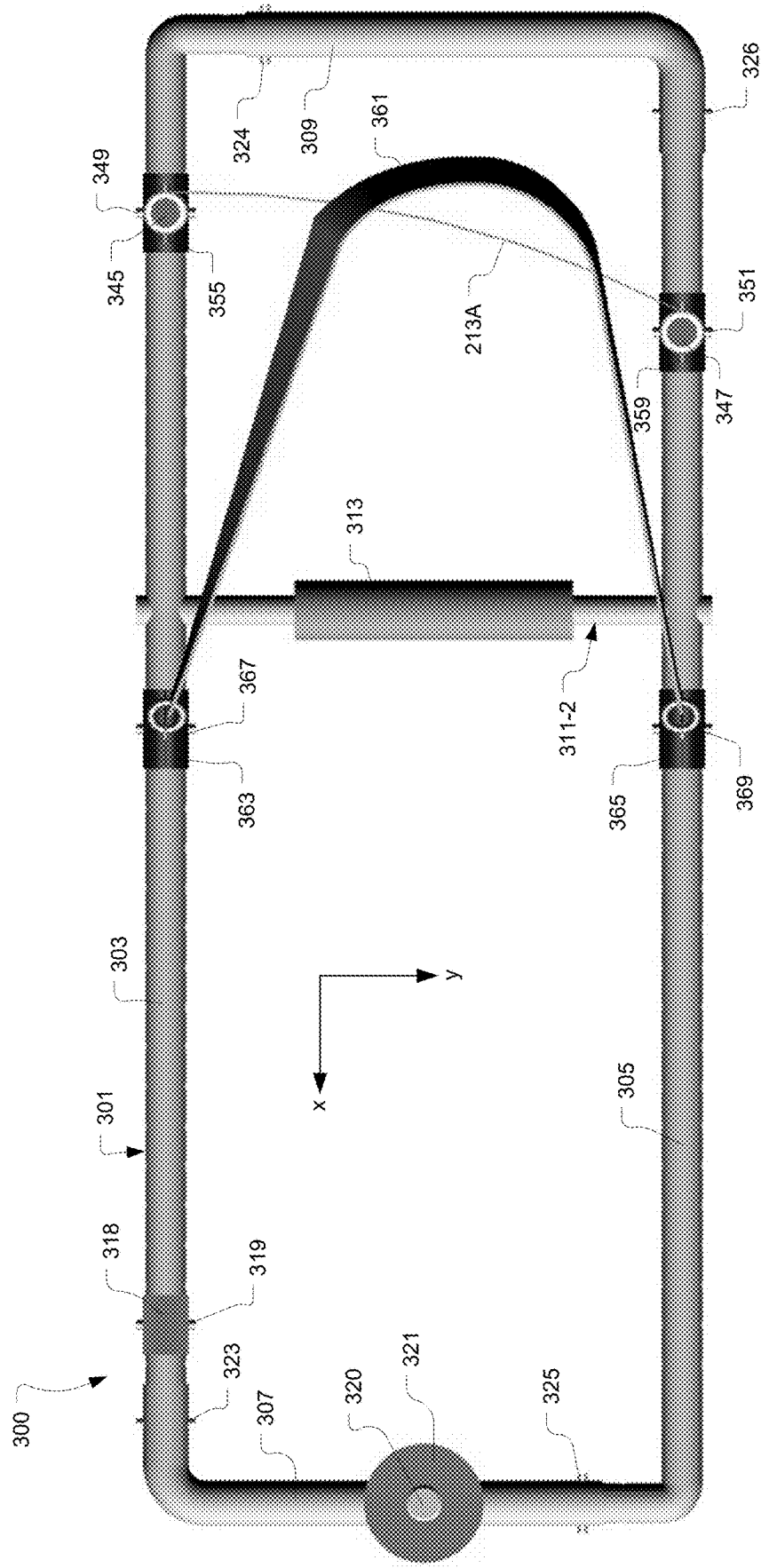
FIG. 8B shows the TLT apparatus with a clamp bar integrally connected to the frame and configured to have a substantially straight configuration, in accordance with some embodiments of the present invention.

FIG. 8B shows the TLT apparatus 300 with a clamp bar 311-2 integrally connected to the frame 301 and configured to have a substantially straight configuration, in accordance with some embodiments of the present invention. In this embodiment, a position of the clamp bar 311-2 is not adjustable in the x-direction along the length of the front segment 303 and the back segment 305 of the frame 301. This embodiment may be used when it is desirable to ensure that the human 400 cannot adjust a prescribed position of the clamp bar 311-2 in the x-direction along the length of the front segment 303 and the back segment 305 of the frame 301. In various embodiments, the clamp bar 311-2 can be affixed to the front segment 303 and the back segment 305 of the frame 301 in various ways, such as by welding, gluing, soldering, thermal fusing, among others. Also, in various embodiments, the clamp bar 311-2 can be affixed to the front segment 303 and the back segment 305 of the frame 301 using respective front and back fasteners, e.g., bolts, machine screws, among others. And, in some embodiments, one or both ends of the clamp bar 311-2 can have a threaded region configured to engage with a corresponding threaded region on one or both of the front segment 303 and the back segment 305 of the frame 301.

Figure 8C:
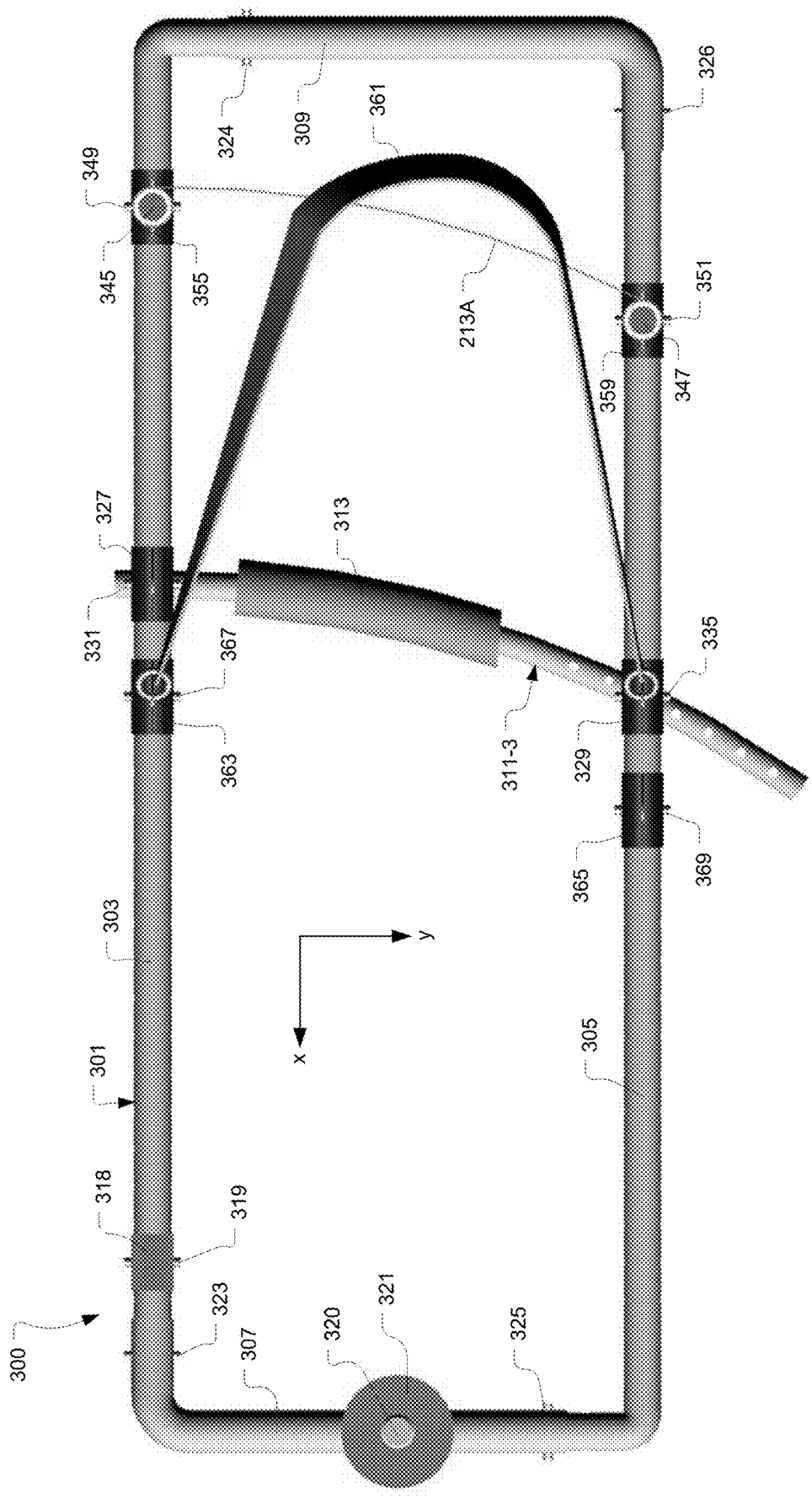
FIG. 8C shows the TLT apparatus with a clamp bar configured to have a curved configuration, in accordance with some embodiments of the present invention.

FIG. 8C shows the TLT apparatus 300 with a clamp bar 311-3 configured to have a curved configuration, in accordance with some embodiments of the present invention. The clamp bar 311-3 is essentially a curved version of the clamp bar 311-1, with the curve existing within the x-y plane. In various embodiments, the curve can have a different radius of curvature. In some embodiments, the radius of curvature of the clamp bar 311-3 is defined to ensure that the clamp bar 311-3 interfaces comfortably and firmly with the first lateral side of the human 400. The clamp bar 311-3 is adjustable in the x-direction along the length of the front segment 303 and the back segment 305 of the frame 301, by way of the first anchor member 327 and the second anchor member 329, respectively, in the same manner as described with regard to the clamp bar 311.

Figure 8D:
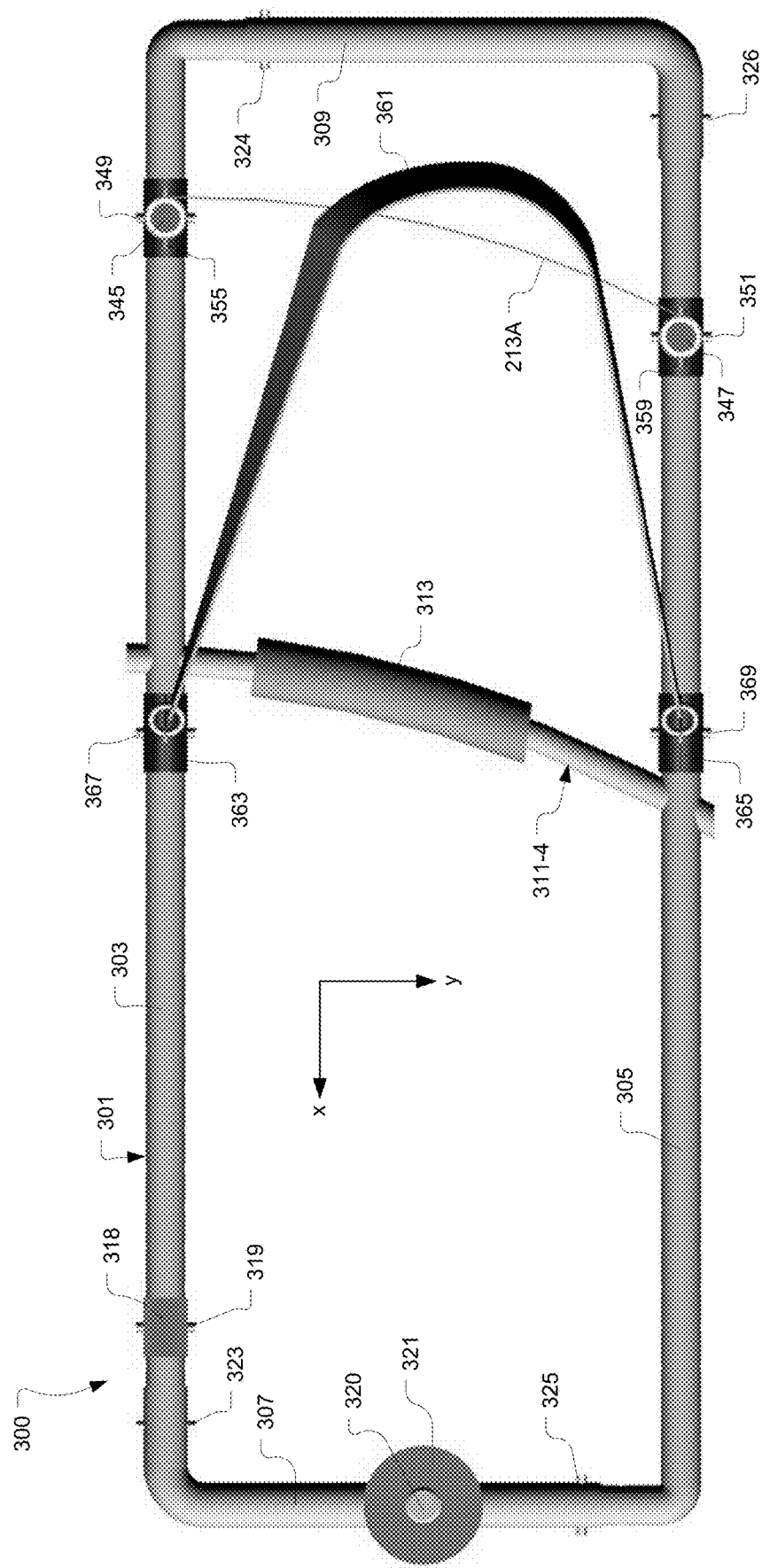
FIG. 8D shows the TLT apparatus with a clamp bar integrally connected to the frame and configured to have a curved configuration, in accordance with some embodiments of the present invention.

FIG. 8D shows the TLT apparatus 300 with a clamp bar 311-4 integrally connected to the frame 301 and configured to have a curved configuration, in accordance with some embodiments of the present invention. The clamp bar 311-4 is essentially a curved version of the clamp bar 311-2, with the curve existing within the x-y plane. In various embodiments, the curve can have a different radius of curvature. In some embodiments, the radius of curvature of the clamp bar 311-4 is defined to ensure that the clamp bar 311-4 interfaces comfortably and firmly with the first lateral side of the human 400. In this embodiment, a position of the clamp bar 311-4 is not adjustable in the x-direction along the length of the front segment 303 and the back segment 305 of the frame 301. This embodiment may be used when it is desirable to ensure that the human 400 cannot adjust a prescribed position of the clamp bar 311-4 in the x-direction along the length of the front segment 303 and the back segment 305 of the frame 301. In various embodiments, the clamp bar 311-4 can be affixed to the front segment 303 and the back segment 305 of the frame 301 in various ways, such as by welding, gluing, soldering, thermal fusing, among others. Also, in various embodiments, the clamp bar 311-4 can be affixed to the front segment 303 and the back segment 305 of the frame 301 using respective front and back fasteners, e.g., bolts, machine screws, among others. And, in some embodiments, one or both ends of the clamp bar 311-4 can have a threaded region configured to engage with a corresponding threaded region on one or both of the front segment 303 and the back segment 305 of the frame 301.

In the example TLT apparatus 300, the lateral restraint band 213A is configured as a strap that extends between the front segment 303 and the back segment 305 of the frame 301. In various embodiments, a vertical size of the lateral restraint band 213A is set based on the physical characteristics of the human 400 so as to effectively interface with the second lateral side of the human 400 over an engagement area corresponding to a target portion of the thoracic cage of the human 400, where the target portion of the thoracic cage extends vertically from a lowest rib (rib connected to T12 vertebra) to a higher rib that is connected to a vertebra just below the apex of the thoracic curve of the spinal column. In this manner, the vertical size of the lateral restraint band 213A is set to ensure that a top edge of the lateral restraint band 213A engages the second lateral side of the human 400 at a position that will apply a laterally resistance force from the lateral restraint band 213A through a portion of the thoracic cage of the human 400 that is connected to vertebrae below the apex of the thoracic curve of the human 400. It is of interest to have the lateral restraint band 213A vertically sized and positioned so that the human 400 can laterally rotate their spinal column over the top edge of the lateral restraint band 213A and about the apex of the thoracic curve so as to straighten out of the thoracic curve. Also, in some embodiments, the vertical size of the lateral restraint band 213A can be set to ensure that a lower edge of the lateral restraint band 213A is at or below the lowest rib, i.e., the rib connected to the T12 vertebra, on the second lateral side of the human 400 contacted by the lateral restraint band 213A. In some embodiments, the lateral restraint band 213A is configured to have a vertical size as measured in the z-direction within a range extending from about 2 inches to about 10 inches, or within a range extending from about 2 inches to about 6 inches, or within a range extending from about 2 inches to about 4 inches.

In various embodiments, the lateral restraint band 213A can be configured to have different shapes as needed to effectively interface with the engagement area corresponding to the target portion of the thoracic cage of the human 400. In some embodiments, the lateral restraint band 213A can be customized to fit the body shape of the human 400 present at the engagement area. Also, in some embodiments, the lateral restraint band 213A can be configured to provide increased comfort to the human 400. For example, in some embodiments, the lateral restraint band 213A can be formed of a single material, such as rubber, nylon, cotton, vinyl, polypropylene, hemp, among others. Also, in some embodiments, the lateral restraint band 213A can be formed to have multiple layers of material, with one or more layers of material closer to the human 400 having increased softness relative to one or more other layers of material farther away from the human 400. More specifically, in some embodiments, one or more layers of the lateral restraint band 213A that are positioned closer to the human 400 can be formed of material having a smaller modulus of elasticity, such as foam, rubber, gel, among others, whereas one or more layers of the lateral restraint band 213A that are positioned farther from the human 400 can be formed of material having a larger modulus of elasticity, such as nylon, cotton, vinyl, polypropylene, hemp, among others.

In the example TLT apparatus 300, the lateral restraint band 213A is secured to extend between a first lateral restraint support 345 and a second lateral restraint support 347. The first lateral restraint support 345 is configured to slide in the x-direction along the front segment 303 of the frame 301 to a desired position. And, the first lateral restraint support 345 is configured to be fixed in position relative to the front segment 303 of the frame 301 by a connector pin 349 that extends through both the first lateral restraint support 345 and the front segment 303. Similarly, the second lateral restraint support 347 is configured to slide in the x-direction along the back segment 305 of the frame 301 to a desired position. And, the second lateral restraint support 347 is configured to be fixed in position relative to the back segment 305 of the frame 301 by a connector pin 351 that extends through both the second lateral restraint support 347 and the back segment 305. It should be understood that independent adjustability in the x-direction of the first lateral restraint support 345 relative to the second lateral restraint support 347, and vice-versa, provides for adjustment of a primary angle 707 of the lateral restraint band 213A as measured in the x-y plane relative to the y-axis direction, as shown in FIG. 7.

In some embodiments, a first vertical adjustment member 353 is configured to slide along the first lateral restraint support 345 to a desired position in the z-direction. And, the first vertical adjustment member 353 is configured to be fixed in position relative to the first lateral restraint support 345 by a connector pin 355 that extends through both the first vertical adjustment member 353 and the first lateral restraint support 345 at the desired position in the z-direction along the first lateral restraint support 345. Similarly, a second vertical adjustment member 357 is configured to slide along the second lateral restraint support 347 to a desired position in the z-direction. And, the second vertical adjustment member 357 is configured to be fixed in position relative to the second lateral restraint support 347 by a connector pin 359 that extends through both the second vertical adjustment member 357 and the second lateral restraint support 347 at the desired position in the z-direction along the second lateral restraint support 347. It should be understood that the first vertical adjustment member 353 and the second vertical adjustment member 357 together provide for adjustment of the position of the lateral restraint band 213A in the vertical direction (z-direction) relative to the frame 301 which lies in the horizontal direction (in the x-y plane).

Also, independent adjustability of the first vertical adjustment member 353 relative to the second vertical adjustment member 357, and vice-versa, provides for adjustment of an angle of the lateral restraint band 213A as measured in the z-direction relative the frame 301, i.e., relative to the x-y plane. For example, FIG. 9A shows a view of the right end of the TLT apparatus 300 with the lateral restraint band 213A positioned at an angle 901 relative to the frame 301, in accordance with some embodiments of the invention. Also, FIG. 9B shows an isometric view of the TLT apparatus 300 as shown in FIG. 9A, in accordance with some embodiments of the invention. In the example of FIGS. 9A-9B, the first vertical adjustment member 345 and the second vertical adjustment member 347 are located at different vertical positions relative to the frame 301 to provide a non-zero value of the angle 901 of the lateral restraint band 213A relative to the frame 301. Also, as a further example, FIG. 3L shows the first vertical adjustment member 345 and the second vertical adjustment member 347 set at same vertical position relative to the frame 301 to provide a substantially zero value of the angle 901 of the lateral restraint band 213A relative to the frame 301.

In some embodiments, each of the first lateral restraint support 345 and the second lateral restraint support 347 is configured to extend in a substantially perpendicular direction to the frame 301. More specifically, the first lateral restraint support 345 is configured to extend in a substantially perpendicular direction upward, i.e., in the z-direction, from the front segment 303 of the frame 301. And, the second lateral restraint support 347 is configured to extend in a substantially perpendicular direction upward, i.e., in the z-direction, from the back segment 305 of the frame 301.

Figure 10:
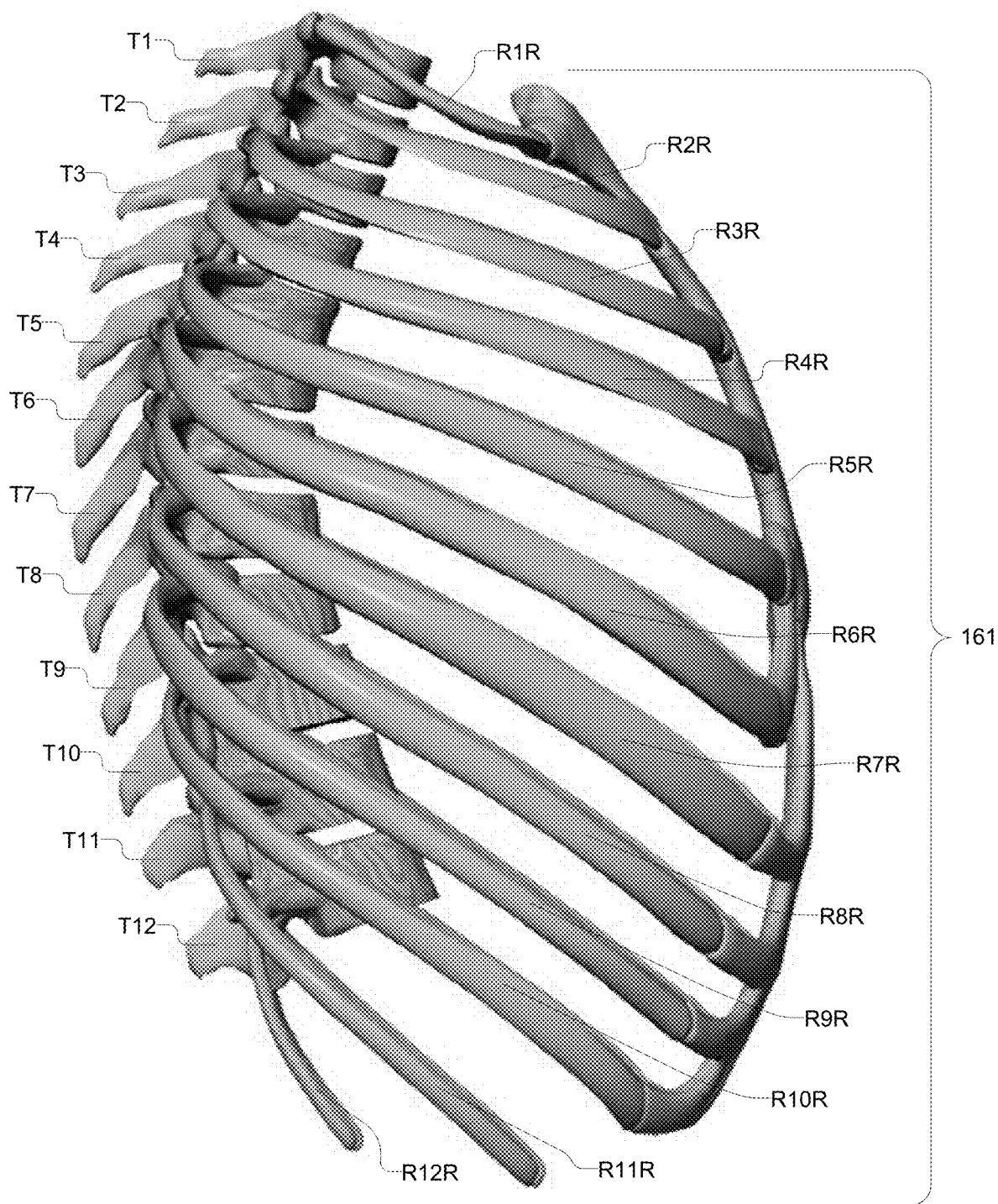
FIG. 10A shows a view toward the front of the TLT apparatus with an angular adjustable version of the first lateral restraint support connected to the front segment of the frame, in accordance with some embodiments of the invention.
FIG. 10B shows a view toward the back of the TLT apparatus with an angular adjustable version of the first lateral restraint support connected to the back segment of the frame, in accordance with some embodiments of the invention.
Figure 10B:
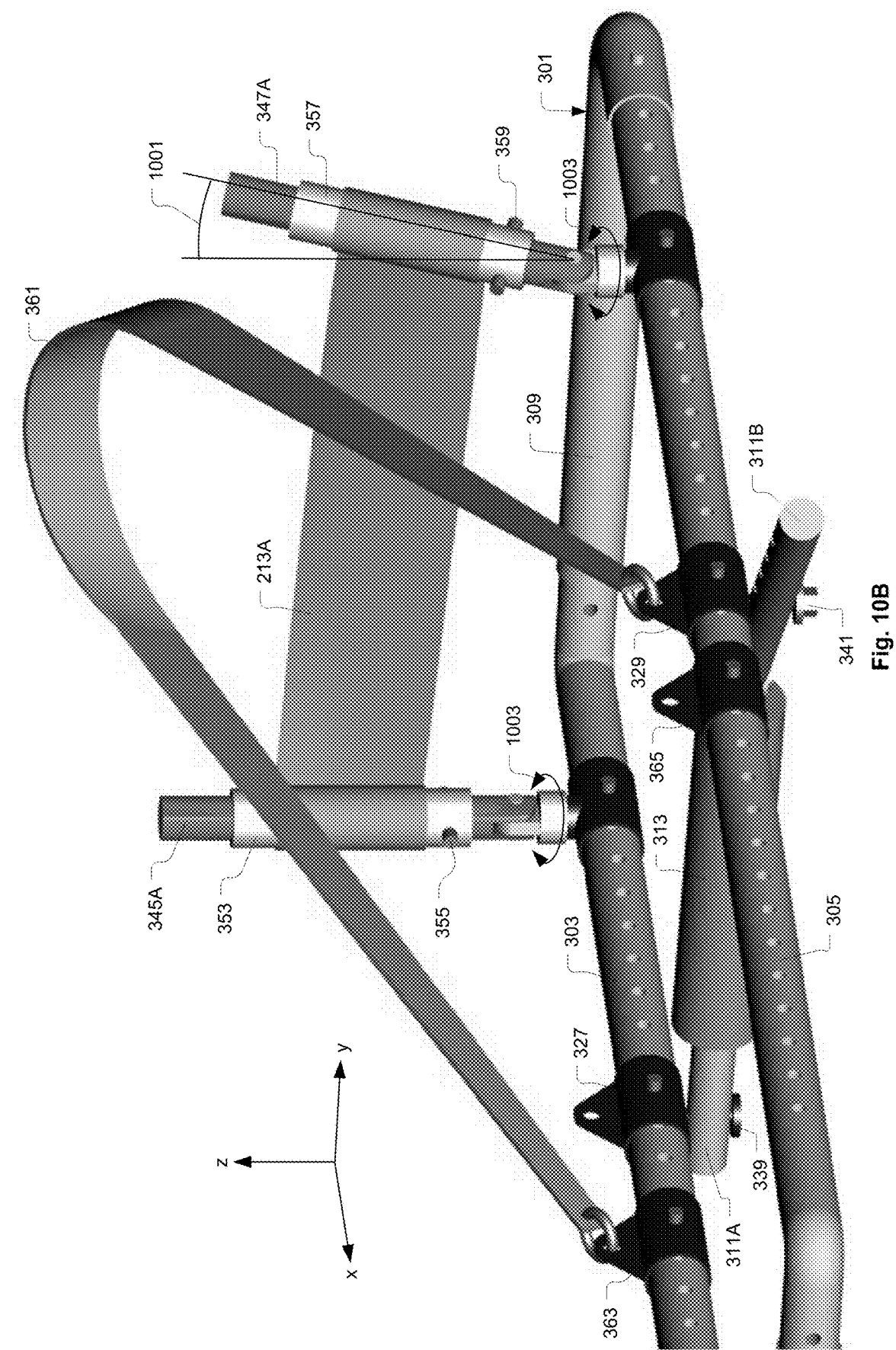

In some embodiments, one or both of the first lateral restraint support 345 and the second lateral restraint support 347 can be configured to be adjustable in angle relative to the frame 301, i.e., relative to the x-y plane. FIG. 10A shows a view toward the front of the TLT apparatus 300 with an angular adjustable version of the first lateral restraint support 345A connected to the front segment 303 of the frame 301, in accordance with some embodiments of the invention. FIG. 10B shows a view toward the back of the TLT apparatus 300 with an angular adjustable version of the first lateral restraint support 347A connected to the back segment 305 of the frame 301, in accordance with some embodiments of the invention. Each of the angular adjustable version of the first lateral restraint support 345A and the angular adjustable version of the second lateral restraint support 347A can be positioned and held at an angle with respect to the z-direction, such as illustrated by the angle 1001 shown in FIGS. 10A-10B. Also, each of the angular adjustable version of the first lateral restraint support 345A and the angular adjustable version of the second lateral restraint support 347A can be rotated and held at an azimuthal angle about the z-direction, such as illustrated by the arrows 1003 in FIGS. 10A-10B. Given the vertical adjustability relative to the frame 301 in conjunction with the angular adjustability relative to the z-direction and azimuthally about the z-direction of each of the angular adjustable version of the first lateral restraint support 345A and the angular adjustable version of the second lateral restraint support 347A, it should be understood that the lateral restraint band 213A can be positioned and held in essentially any fixed three-dimensional configuration between the front segment 303 and the back segment 305 of the frame 301.

Figure 11A:
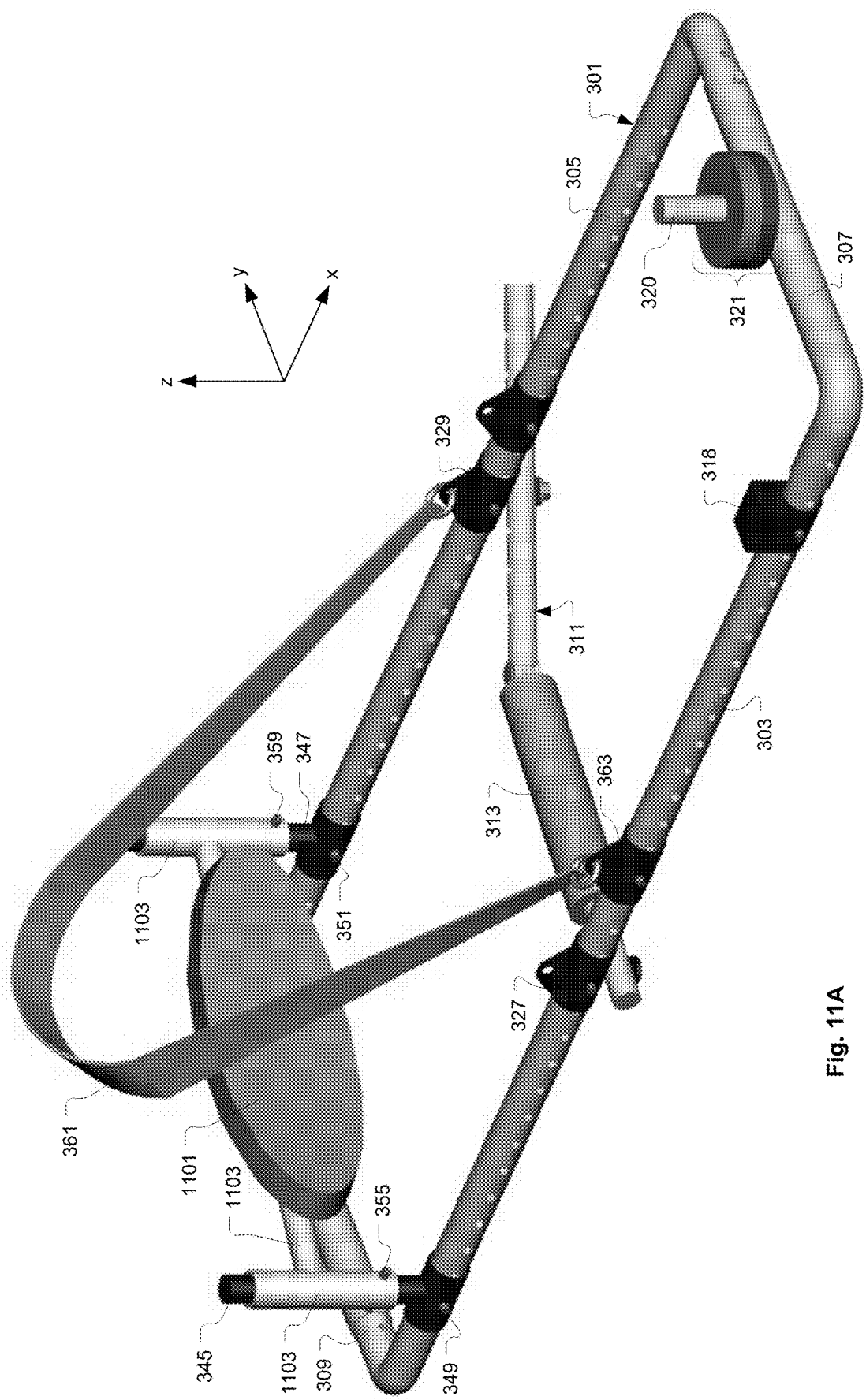
FIG. 11A shows the TLT apparatus in which the lateral restraint is configured as a lateral restraint pad connected to a lateral restraint support extending between the first lateral restraint support and the second lateral restraint support, in accordance with some embodiments of the invention.
Figure 11B:
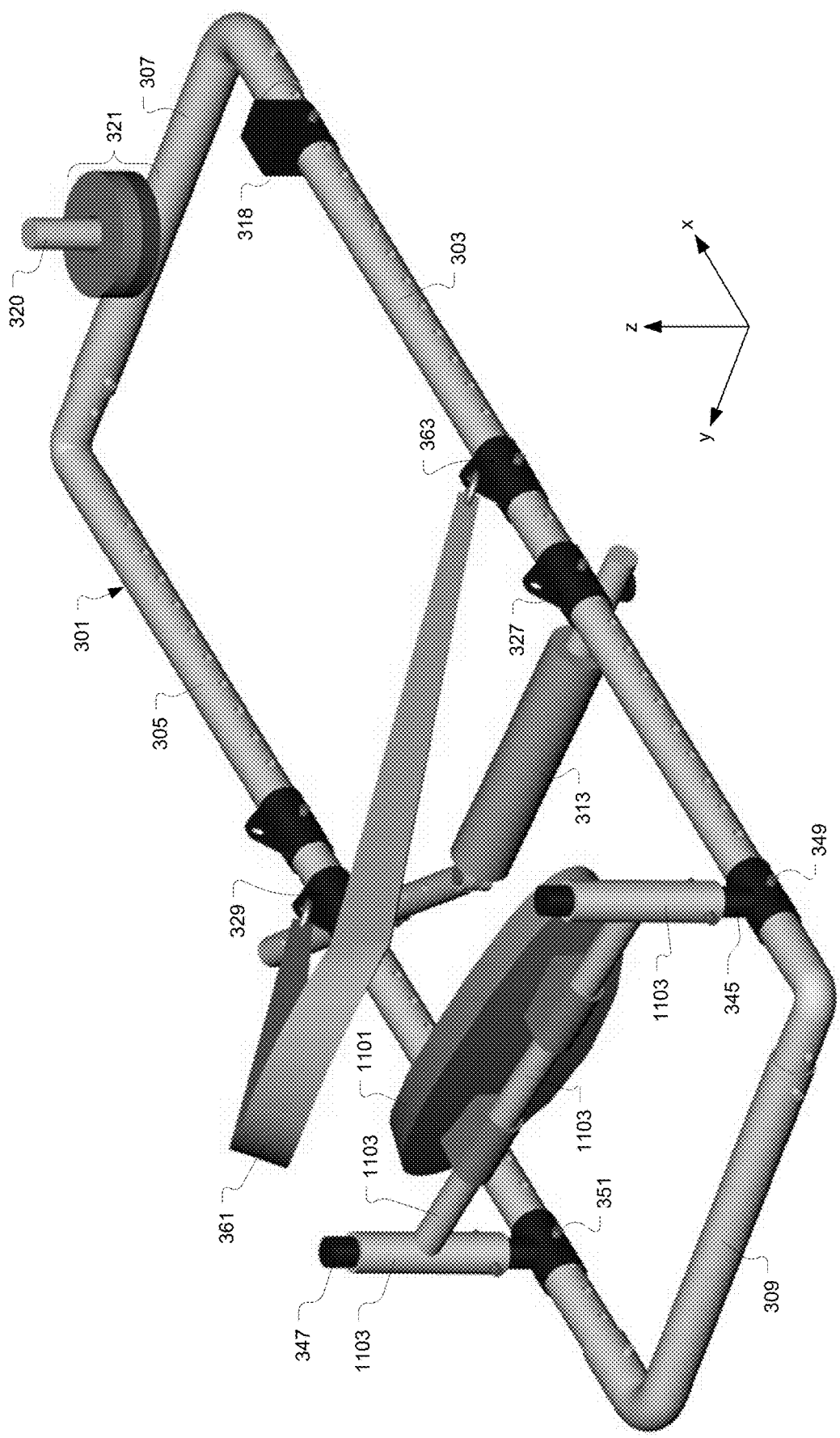
FIG. 11B shows a backside view of the lateral restraint pad connected to the lateral restraint support, in accordance with some embodiments of the invention.
Figure 11D:
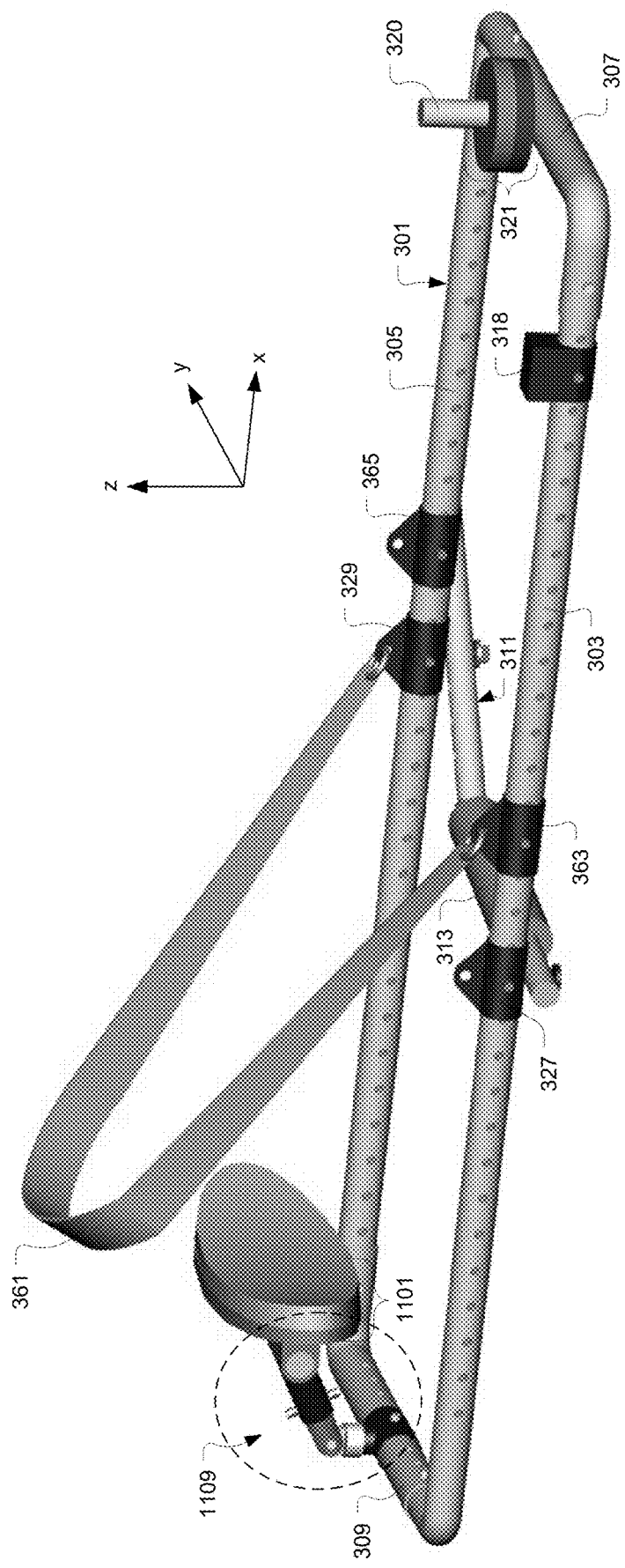
FIGS. 11D, 11E, 11F, and 11G show the TLT apparatus equipped with an end-mount lateral restraint support assembly, in accordance with some embodiments of the present invention.
Figure 11E:
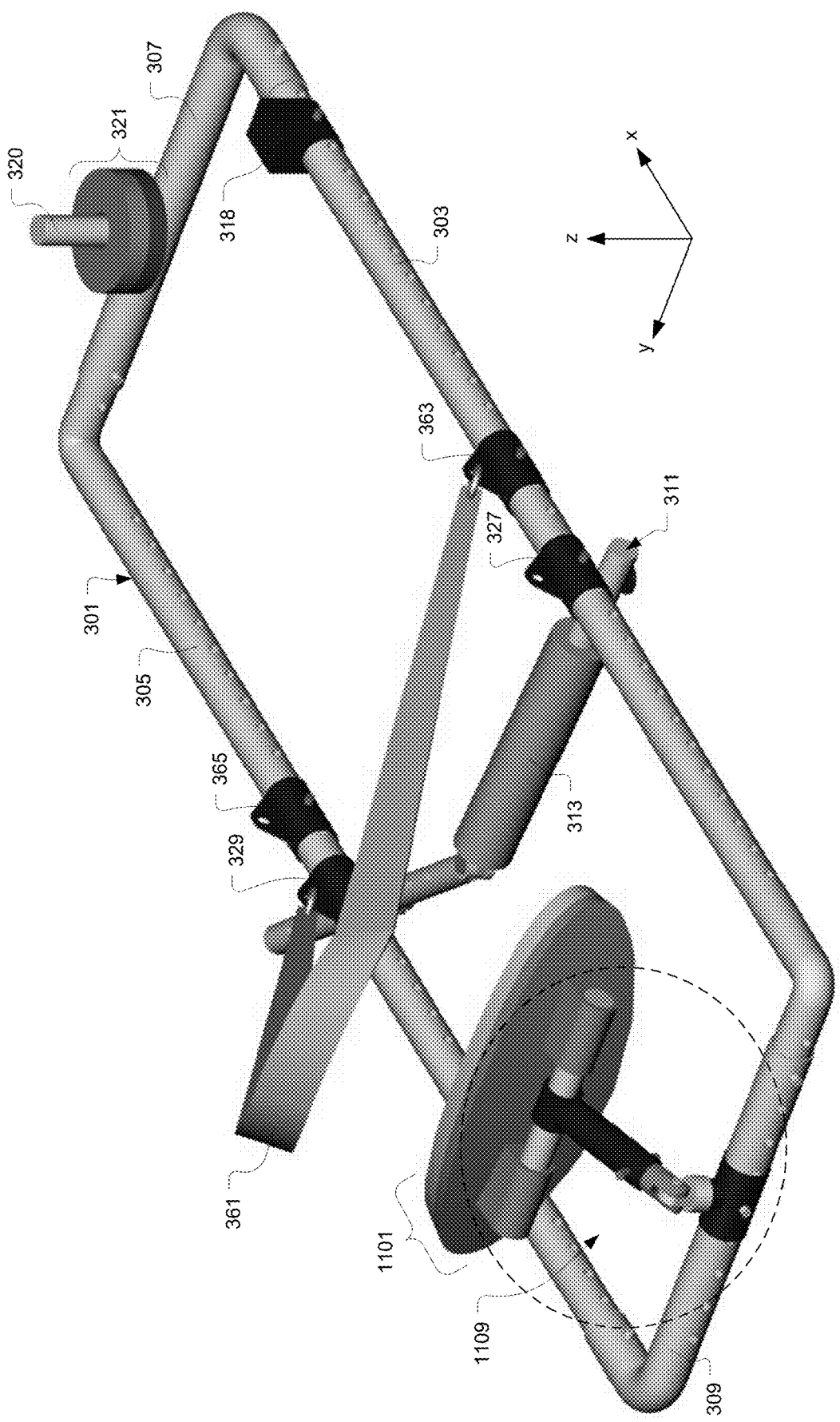
Figure 11F:
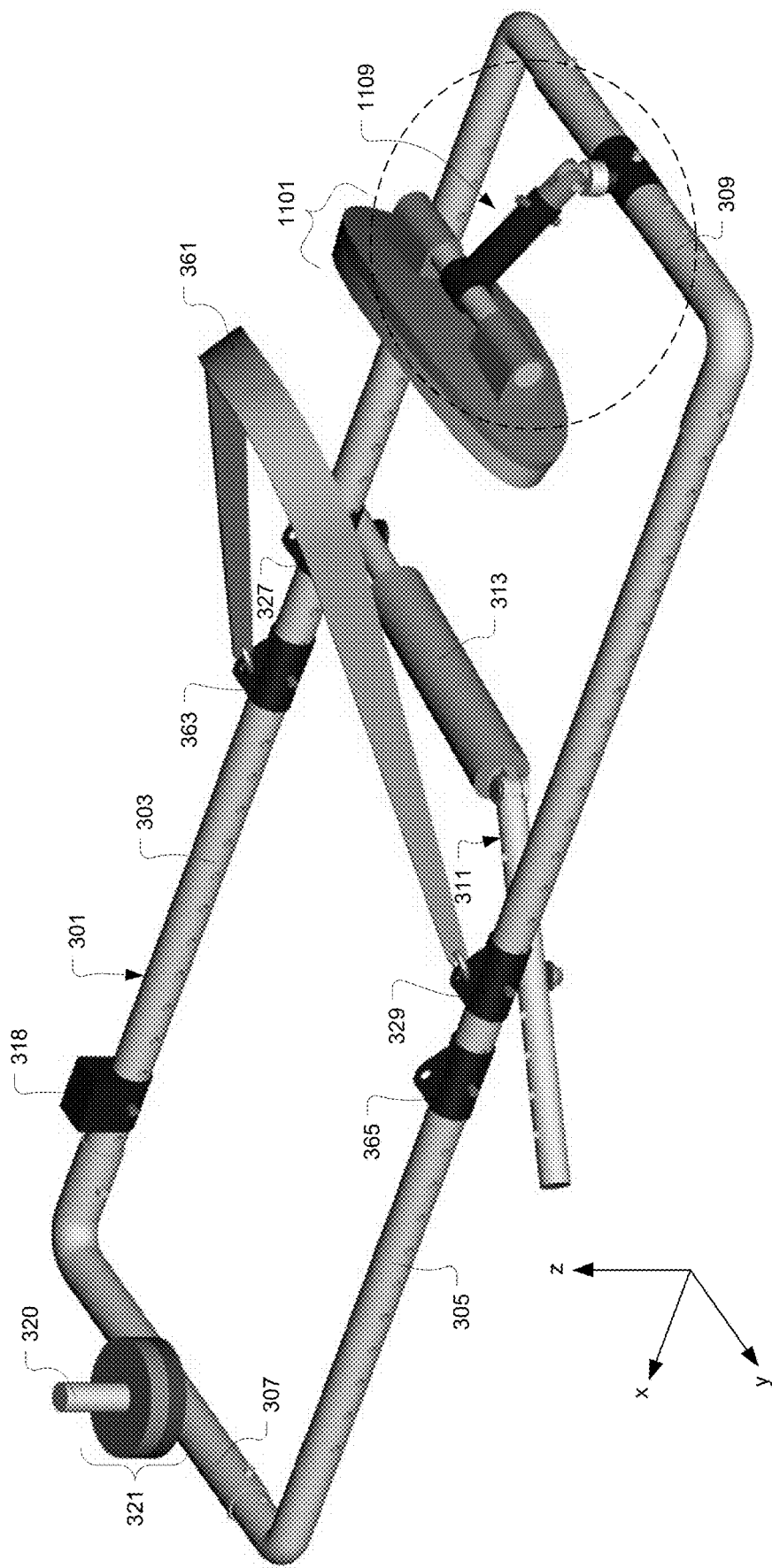
Figure 11G:
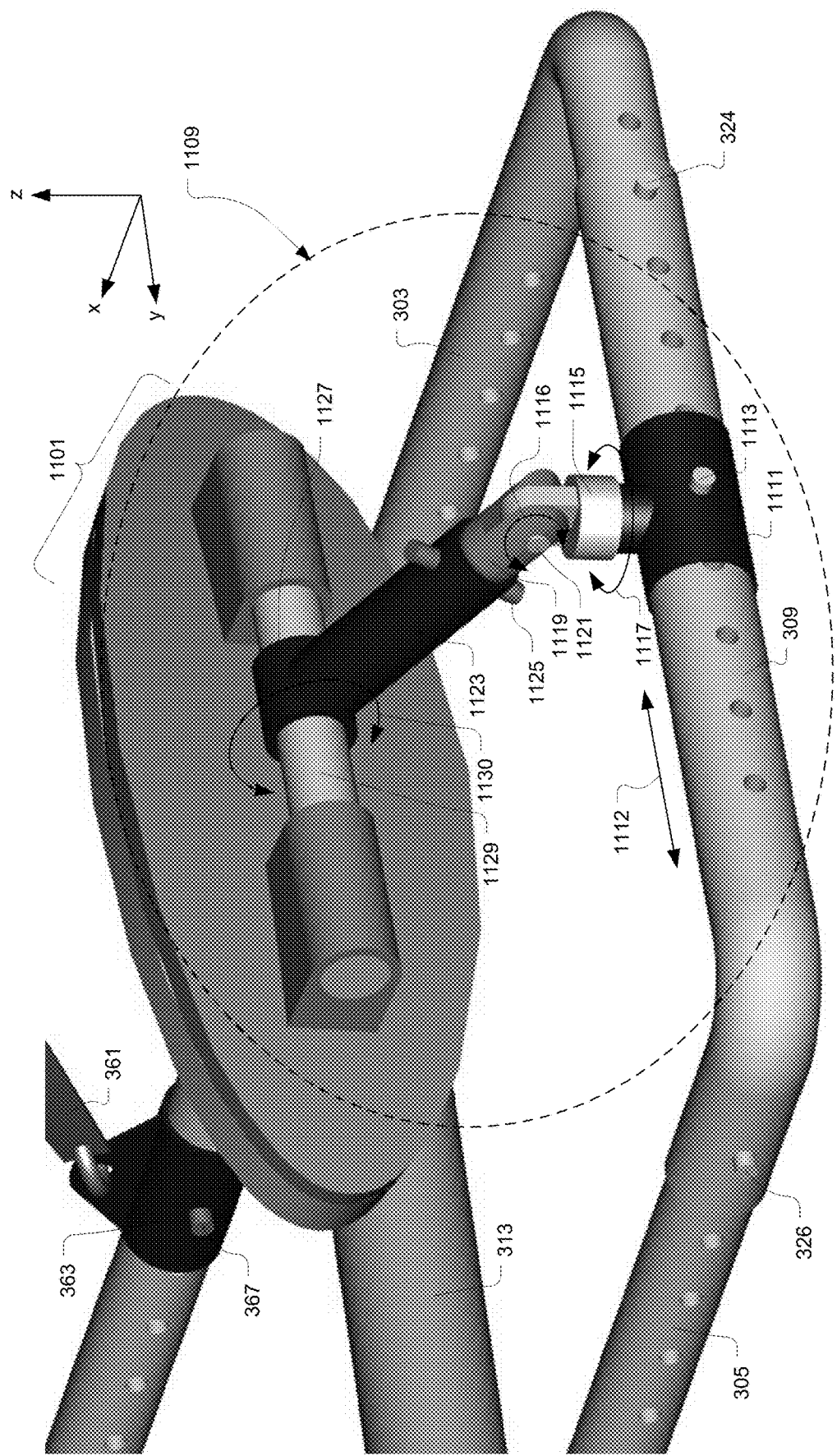

In some embodiments the lateral restraint 213 can be configured in a manner other than as the lateral restraint band 213A. For example, FIG. 11A shows the TLT apparatus 300 in which the lateral restraint 213 is configured as a lateral restraint pad 1101 connected to a lateral restraint support 1103 extending between the first lateral restraint support 345/345A and the second lateral restraint support 347/347A, in accordance with some embodiments of the invention. FIG. 11B shows a backside view of the lateral restraint pad 1101 connected to the lateral restraint support 1103, in accordance with some embodiments of the invention. In this example, the lateral restraint support 1103 is connected to the front segment 303 and the back segment 305 of the frame 301. It should be understood that in various embodiments, an orientation of the lateral restraint pad 1101 can be adjusted in essentially any manner required to properly interface with the engagement area on the human 400. For example, in some embodiments, the lateral restraint support 1103 can be positioned at an angle as measured in the x-y plane relative to the y-axis direction, similar to the angle 707 shown in FIG. 7. Also, in some embodiments, the lateral restraint support 1103 is configured to provide for adjustment of the angle of the lateral restraint pad 1101 relative to the z-direction, such as shown in FIG. 11A. Also, a vertical position of the lateral restraint support 1103 and lateral restraint pad 1101 connected thereto relative to the frame 301 can be adjusted by positioning the lateral restraint support 1103 at a desired vertical position along each of the first lateral restraint support 345/345A and the second lateral restraint support 347/347A, either in tandem or independently.

In various embodiments, the lateral restraint pad 1101 can be configured to have different shapes and/or surface contours as needed to effectively interface with the second lateral side of the human 400 over the engagement area that is to be pressed upon by the lateral restraint pad 1101. In some embodiments, the lateral restraint pad 1101 can be customized to fit the body shape of the human 400 present at the engagement area. Also, in some embodiments, the lateral restraint pad 1101 can be configured to provide various levels of comfort to the human 400. For example, in some embodiments, the lateral restraint pad 1101 can be formed of a single material, such as rubber, nylon, plastic, foam, among others. Also, in some embodiments, the lateral restraint pad 1101 can be formed to have multiple layers of material, with one or more layers of material closer to the engagement area with the human 400 having increased softness relative to one or more other layers of material farther from the engagement area with the human 400. More specifically, in some embodiments, one or more layers of the lateral restraint pad 1101 that are positioned closer to the human 400 can be formed of material having a smaller modulus of elasticity, such as rubber, gel, among others, whereas one or more layers of the lateral restraint pad 1101 that are positioned farther from the human 400 can be formed of stiffer material having a larger modulus of elasticity, such as nylon, acrylic, plastic, aluminum, among others.

FIG. 11C shows an example of the lateral restraint pad 1101 formed by multiple layers of material, in accordance with some embodiments of the present invention. A first layer of material 1105 is formed to interface with the engagement area on the human 400. A second layer of material 1107 is formed to provide structural support for the first layer of material 1105. In some embodiments, the first layer of material 1105 is softer than that the second layer of material 1107. For example, in some embodiments, the first layer of material 1105 is formed of rubber, foam, gel, or similar type of soft material, and the second layer of material 1107 is formed of plastic, acrylic, nylon, or similar type of harder and more rigid material. Also, in some embodiments, the first layer of material 1105 can be removable from the second layer of material 1107. Therefore, in these embodiments, the first layer of material 1105 can be customized in shape, size, softness, etc. for a particular human 400, while being simultaneously configured to fit on and secure to a universal version of the second layer of material 1107 which remains unchanged in shape, size, softness, etc. Thus, the first layer of material 1105 can be replaceable and/or consumable and/or washable, independent from the second layer of material 1107.

FIGS. 11D, 11E, 11F, and 11G show the TLT apparatus 300 equipped with an end-mount lateral restraint support assembly 1109, in accordance with some embodiments of the present invention. The end-mount lateral restraint support assembly 1109 includes a frame connection member 1111 configured to connect to the right segment 309 of the frame 301. The frame connection member 1111 is configured to slide along the right segment 309 to a desired position, as indicated by the arrow 1112. The frame connection member 1111 is also configured to be fixed in position relative to the right segment 309 by a connector pin 1113 that extends through both the frame connection member 1111 and the right segment 309. The end-mount lateral restraint support assembly 1109 also includes a position adjustment member 1115 connected to the frame connection member 1111. The position adjustment member 1115 is configured to rotate azimuthally about the z-direction, as indicated by arrow 1117, to a desired azimuthal position at which the position adjustment member 1115 can be rigidly held. An inner extension member 1119 is configured to connect to the position adjustment member 1115, and rotate in the vertical direction about a rotational pin 1121 affixed to the position adjustment member 1115, as indicated by arrow 1116, to a desired vertical position at which the inner extension member 1119 can be rigidly held. An outer extension member 1123 is configured to slide over the inner extension member 1119 to a desired position along the inner extension member 1119, as indicted by arrow 1124. A connection pin 1125 can be inserted through the outer extension member 1123 and the inner extension member 1119 to hold the outer extension member 1123 at a desired position along the inner extension member 1119. A support coupling 1127 is provided at the end of the outer extension member 1123 closest to the lateral restraint pad 1101. A support bar 1129 extends through the support coupling 1127 and is connected to a backside of the lateral restraint pad 1101. The support bar 1129 can rotate within the support coupling 1127 about the axis of the support bar 1129, as indicated by arrow 1130, to a desired rotational position at which the support bar 1129 can be rigidly held relative to the support coupling 1127, thereby providing for angular positioning of the lateral restraint pad 1101 about the axis of the support bar 1129. It should be understood that the configuration of the end-mount lateral restraint support assembly 1109 provides for positioning of the lateral restraint pad 1101 in essentially any three-dimensional orientation with respect to the physical exterior of the human 400.

The TLT apparatus 300 also includes a shoulder strap 361 connected to the frame 301. The shoulder strap 361 is configured to extend over a shoulder region of the human 400 on a same side of the human 400 where the lateral restraint 213 is located. In some embodiments, the shoulder strap 361 has a first end connected to the front segment 303 and a second end connected to the back segment 305. More specifically, the first end of the shoulder strap 361 can be connected to either the first anchor member 327 or to a first shoulder strap anchor member 363. And, the second end of the shoulder strap 361 can be connected to either the second anchor member 329 or to a second shoulder strap anchor member 365. The first shoulder strap anchor member 363 is configured to slide along the front segment 303 of the frame 301 to a desired position. And, the first shoulder strap anchor member 363 is configured to be fixed in position relative to the front segment 303 of the frame 301 by a connector pin 367 that extends through both the first shoulder strap anchor member 363 and the front segment 303. Similarly, the second shoulder strap anchor member 365 is configured to slide along the back segment 305 of the frame 301 to a desired position. And, the second shoulder strap anchor member 365 is configured to be fixed in position relative to the back segment 305 of the frame 301 by a connector pin 369 that extends through both the second shoulder strap anchor member 365 and the back segment 305. In some embodiments, each of the first anchor member 327, the second anchor member 329, the first shoulder strap anchor member 363, and the second shoulder strap anchor member 365 includes a hole through which the shoulder strap 361 can be connected. In some embodiments, the shoulder strap 361 includes clips, such as carabiner clips by way of example, for connection to and release from the first anchor member 327, the second anchor member 329, the first shoulder strap anchor member 363, and the second shoulder strap anchor member 365.

In some embodiments, the shoulder strap 361 can be flexible to conform to a body shape of the human 400 or can be customized to fit the body shape of the human 400 at the shoulder region that is contacted by the shoulder strap 361. In various embodiments, the shoulder strap 361 can be formed of one or more material(s) that is/are either non-elastic or semi-elastic. Also, in some embodiments, the shoulder strap 361 can be configured to provide various levels of comfort to the human 400. For example, in some embodiments, the shoulder strap 361 can be formed of a single material, such as rubber, nylon, cotton, vinyl, polypropylene, hemp, among others. Also, in some embodiments, the shoulder strap 361 can be formed to have multiple layers of material, with one or more layers of material closer to the shoulder region of the human 400 having increased softness relative to one or more other layers of material farther from to the shoulder region of the human 400. More specifically, in some embodiments, one or more layers of the shoulder strap 361 that contact the human 400 can be formed of material having a smaller modulus of elasticity, such as foam, rubber, gel, among others, whereas one or more layers of the shoulder strap 361 that are positioned farther from the human 400 can be formed of material having a larger modulus of elasticity, such as nylon, cotton, vinyl, polypropylene, hemp, among others.

In some embodiments, the shoulder strap 361 is configured to fit over a lateral (side) portion of the shoulder region. Also, in some embodiments, the shoulder strap 361 is configured to wrap over the downward turn of the shoulder region. The shoulder strap 361 should be positioned on the shoulder region of the human 400 so as to avoid causing vertical compression of the spinal column of the human 400 by a downward force component applied by the shoulder strap 361 to the human 400. In some embodiments, the shoulder strap 361 is positioned to wrap around a side of an arm of the person at a location just below a top surface of the shoulder region. In this configuration, the shoulder strap 361 assists with maintaining a snug compression of the camp bar 311 into the first lateral side of the human 400 at the location between the top surface of an ilium bone structure 401 of the human 400 and the lowest rib 403 of the thoracic cage of the human 400. Also, in this configuration, the shoulder strap 361 serves to balance the TLT apparatus 300 in the anterior-to-posterior direction, i.e., in the y-direction, relative to the human 400. Also, in some embodiments, the shoulder strap 361 is connected to the frame 301 of the TLT apparatus 300 at locations along the front segment 303 and the back segment 305 of the frame 301 so that a lateral force applied by the human 400 to the should strap 361 will assist with maintaining the frame 301 is a substantially level orientation as allowed by the setting of the level sensor 318. In this manner, the presence of the shoulder strap 361 encourages the human 400 to rotate/translate out of the thoracic curve at a vertical location over the top of the lateral restraint 213 in an effort to resist the downward treatment force 315 and maintain an acceptable (near-level) orientation of the frame 301.

With the shoulder strap 361 connected to the front segment 303 and back segment 305 of the frame 301 at respective locations closer to the human 400 and farther from the downward treatment force location 317, the human 400 is required to apply more lateral force to the shoulder strap 361 to resist a given amount of the downward treatment force 317 as compared to having the shoulder strap 361 connected to the front segment 303 and back segment 305 of the frame 301 at respective locations farther from the human 400 and closer to the downward treatment force location 317. In this manner, the connection locations of the shoulder strap 361 to the front segment 303 and the back segment 305 of the frame 301 can be adjusted to tune an effectiveness of the shoulder strap 361 in resisting the downward treatment force 315 and maintaining an acceptable (near-level) orientation of the frame 301. Additionally, because lateral translation of the human 400 into both the lateral restraint 213 and the shoulder strap 361 combine to resist the downward treatment force 315 in order to maintain the acceptable (near-level) orientation of the frame 301, it should be understood that when the shoulder strap 361 is connected to the front segment 303 and back segment 305 of the frame 301 at respective locations farther from the human 400 and closer to the downward treatment force location 317, lateral translation force applied by the human 400 into the shoulder strap 361 balances more of the downward treatment force 315, thereby reducing the amount of lateral translation force that the human 400 has to apply into the lateral restraint 213 to fully balance the downward treatment force 315. Similarly, when the shoulder strap 361 is connected to the front segment 303 and back segment 305 of the frame 301 at respective locations closer to the human 400 and farther from the downward treatment force location 317, lateral translation force applied by the human 400 into the shoulder strap 361 balances less of the downward treatment force 315, thereby increasing the amount of lateral translation force that the human 400 has to apply into the lateral restraint 213 to fully balance the downward treatment force 315. Therefore, the connection locations of the shoulder strap 361 to the front segment 303 and the back segment 305 of the frame 301 can be adjusted to control respective amounts of lateral force applied by the human 400 into the lateral restraint 213 and the shoulder strap 361, with the amount of force applied by the human 400 into the lateral restraint 213 being correlated to straightening of the lumbar curve 203, and with the amount of force applied by the human 400 into the shoulder strap 361 being correlated to straightening of the thoracic curve 205.

In the TLT apparatus 300, a downward lever arm portion of the frame 301 includes the left segment 307, and a portion of the front segment 303 extending between the clamp bar 311 and the left segment 307, and a portion of the back segment 305 extending between the clamp bar 311 and the left segment 307. And, an upward lever arm portion of the frame 301 includes the right segment 309, and a portion of the front segment 303 extending between the clamp bar 311 and the right segment 309, and a portion of the back segment 305 extending between the clamp bar 311 and the right segment 309. The lateral restraint 213 is attached to the upward lever arm portion of the frame 301. Also, in some embodiments, the lateral restraint 213 is positioned at a vertical location above the frame 301. The treatment weight receiver 219 is attached to the downward lever arm portion of the frame 301 at the treatment force location 217.

Figure 12A:
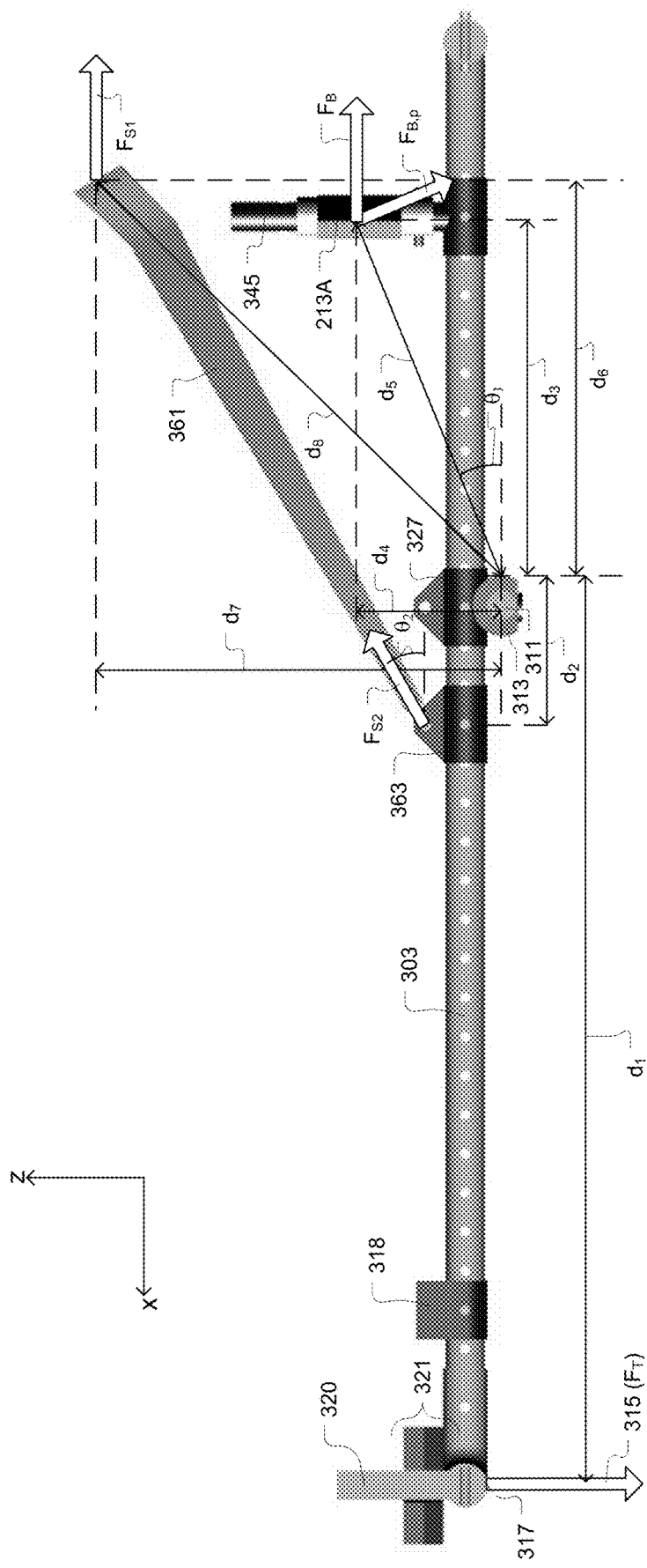
FIG. 12A shows a vertical cross-section through the TLT apparatus including identification of certain forces applied during treatment of the human, in accordance with some embodiments of the present invention.
Figure 12B:
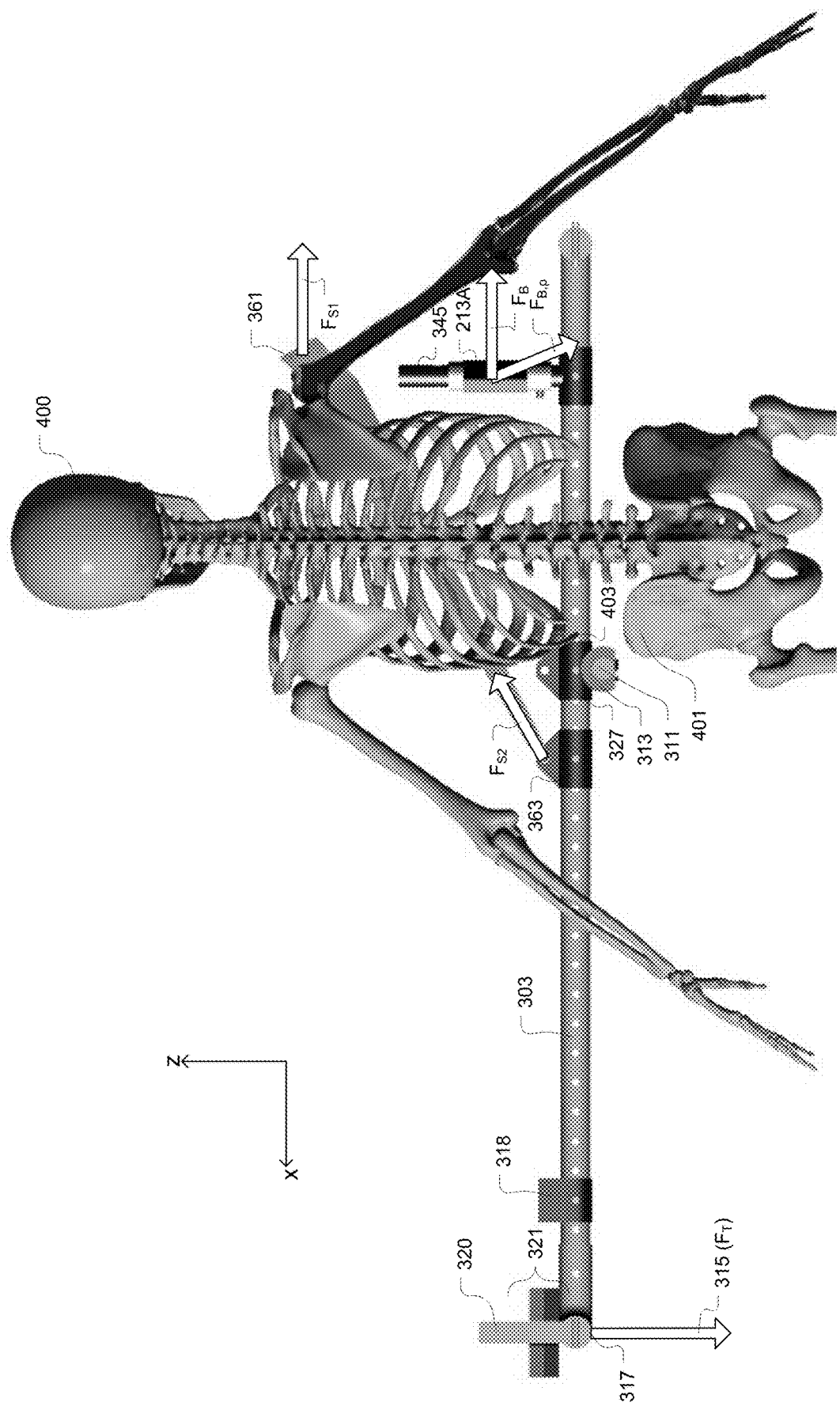
FIG. 12B shows the same vertical cross-section through the TLT apparatus with the human positioned within the TLT apparatus, in accordance with some embodiments of the present invention.

FIG. 12A shows a vertical cross-section through the TLT apparatus 300 including identification of certain forces applied during treatment of the human 400, in accordance with some embodiments of the present invention. For clarity, the human 400 is not shown in FIG. 12A. FIG. 12B shows the same vertical cross-section through the TLT apparatus 300 with the human 400 positioned within the TLT apparatus 300, in accordance with some embodiments of the present invention. During treatment, the downward treatment force 315 ($F_T$) is applied at the treatment force location 317 located a distance ($d_1$) away from the location at which the clamp bar 311 (or clamp pad 313 if present) interfaces with the human 400. Also, during treatment, in order to maintain the frame 301 in the near-level orientation, the human 400 works to laterally translate their lumbar spinal column region toward the lateral restraint 213, which results in application of a force ($F_B$) against the lateral restraint 213. Also, during treatment, in order to maintain the frame 301 in the near-level orientation, the human 400 works to laterally translate their thoracic spinal column region toward the shoulder strap 361, which results in application of a force ($F_{S1}$) against the shoulder strap 361. With the human 400 having laterally translated their lumbar spinal column region and their thoracic spinal column region to maintain the frame 301 in the near-level orientation in the presence of the downward treatment force 315 ($F_T$), the human 400 will have a substantially straightened spinal column and the forces applied against the lateral restraint 213 and the shoulder strap 361 will be substantially directed in the horizontal direction, i.e., x-direction, parallel to the frame 301. In this manner, the human 400 will be using their own neuro-muscular effort to simultaneously straighten both the lumbar curve 203 and the thoracic curve 205, which serves to train and the strengthen the nerves and muscles of the human 400 to resist the proclivity of their spinal column to assume the scoliotic curvatures, thereby increasing the natural ability of the human 400 to achieve and maintain a non-scoliotic spinal column configuration outside of the TLT apparatus 300.

In order to analyze the forces $F_T$, $F_B$, and $F_{S1}$ associated with the TLT apparatus 300, it is possible to make a few simplifying assumptions that do not significantly impact the results of the analysis. First, by proper positioning of the shoulder strap 361 on the side of the shoulder region of the human 400, e.g., over an upper most outer arm portion of the human 400, it is possible to neglect any vertical forces applied against the shoulder strap 361 with regard to balancing the downward treatment force 315 ($F_T$). Second, it is assumed that a co-planar (parallel to the x-z plane) relationship exists between the treatment force location 317, a centroid of the contact area between the clamp bar 311 and the human 400, a centroid of the engagement area of the lateral restraint 213 with the human 400, and a centroid of the engagement area of the shoulder strap 361 with the human 400. Third, it is assumed that any other external forces applied to the TLT apparatus 300 are negligible. With these simplifying assumptions, it is considered that the downward treatment force 315 ($F_T$) is applied at the treatment force location 317 that is the distance ($d_1$) from the centroid of the contact area between the clamp bar 311 and the human 400.

It is also considered that the human 400 applies the force ($F_B$) against the lateral restraint 213 along a vector located at the centroid of the engagement area of the lateral restraint 213 with the human 400, which is located a distance ($d_3$) as measured in the x-direction from the centroid of the contact area between the clamp bar 311 and the human 400. It should be understood, however, that the force ($F_B$) is distributed over the engagement area of the lateral restraint 213 with the human 400. Also, the centroid of the engagement area of the lateral restraint 213 with the human 400 is located a distance ($d_4$) as measured in the z-direction from the centroid of the contact area between the clamp bar 311 and the human 400. Geometrically, the centroid of the engagement area of the lateral restraint 213 with the human 400 is located a distance ($d_5$) from the centroid of the contact area between the clamp bar 311 and the human 400.

It is also considered that the human 400 applies the force ($F_{S1}$) against the shoulder strap 361 along a vector located at the centroid of the engagement area of the shoulder strap 361 with the human 400, which is located a distance ($d_6$) as measured in the x-direction from the centroid of the contact area between the clamp bar 311 and the human 400. It should be understood, however, that the force ($F_{S1}$) is distributed over the engagement area of the shoulder strap 361 with the human 400. Also, the shoulder strap 361 is connected to the frame 301 (to the front segment 303 and the back segment 305) at a distance ($d_2$) as measured in the x-direction from the centroid of the contact area between the clamp bar 311 and the human 400. Also, the centroid of the engagement area of the shoulder strap 361 with the human 400 is located a distance ($d_7$) as measured in the z-direction from the centroid of the contact area between the clamp bar 311 and the human 400. Geometrically, the centroid of the engagement area of the shoulder strap 361 with the human 400 is located a distance ($d_8$) from the centroid of the contact area between the clamp bar 311 and the human 400.

A first moment ($M_1$) relative to the centroid of the contact area between the clamp bar 311 and the human 400 is generated by the downward treatment force 315 ($F_T$). Also, a second moment ($M_2$) relative to the centroid of the contact area between the clamp bar 311 and the human 400 is generated by the force ($F_B$) applied by the human 400 to the lateral restraint 213. Also, a third moment ($M_3$) relative to the centroid of the contact area between the clamp bar 311 and the human 400 is generated by the force ($F_{S1}$) applied by the human 400 to the shoulder strap 361. With the human 400 positioned in the TLT apparatus 300 and working to laterally translate both their lumbar spinal column region and their thoracic spinal column region so as to maintain the frame 301 in the near-level orientation, the TLT apparatus 300 is maintained a state of static equilibrium with the first moment ($M_1$) balanced by a combination of the second moment ($M_2$) and the third moment ($M_3$).

Equation 1 shows the first moment ($M_1$) equal to the product of the downward treatment force 315 ($F_T$) and the distance ($d_1$). Equation 2 shows the second moment ($M_2$) equal to the product of a force ($F_{S2,z}$) and the distance ($d_2$), where the force ($F_{S2,z}$) is the z-direction component of the force ($F_{S2}$). Equation 3 shows the force ($F_{S2,z}$) equal to the product of the force ($F_{S2}$) and the sine of the angle ($\theta_2$) as measured parallel to the x-z plane between a vector of the force ($F_{S2}$) and the x-direction. Equation 4 shows the force ($F_{S1}$) as the product of the force ($F_{S2}$) and the cosine of the angle ($\theta_2$). Equation 5 shows the force ($F_{S2,z}$) expressed as a function of the force ($F_{S1}$) and the angle ($\theta_2$), using Equations 3 and 4. Equation 6 shows the second moment ($M_2$) equal to the product of the force ($F_{S1}$), the tangent of the angle ($\theta_2$), and the distance ($d_2$).

Equation 7 shows the third moment ($M_3$) equal to the product of a force ($F_{B,p}$) and the distance ($d_5$), where the force ($F_{B,p}$) is a component of the force ($F_B$) that is directed perpendicular to the direction extending between the centroid of the contact area between the clamp bar 311 and the human 400 and the centroid of the engagement area of the lateral restraint 213 with the human 400, i.e., perpendicular to the direction along which the distance ($d_5$) is measured. Equation 8 shows the force ($F_{B,p}$) equal to the force ($F_B$) divided by the cosine of the angle $[(\pi/2)-\theta_1]$, wherein the angle ($\theta_1$) is measured parallel to the x-z plane between the direction along which the distance ($d_5$) is measured and the x-direction. Equation 9 shows the third moment ($M_3$) equal to the product of the force ($F_B$) and the distance ($d_5$) divided by the cosine of the angle $[(\pi/2)-\theta_1]$.

When the TLT apparatus 300 is maintained the state of static equilibrium, the sum of the first moment ($M_1$), the second moment ($M_2$), and the third moment ($M_3$) is equal to zero, as shown in Equation 10. Using Equations 1, 6, and 9, the sum of the first moment ($M_1$), the second moment ($M_2$), and the third moment ($M_3$) can be expressed as shown in Equation 11. Also, Equation 12 shows Equation 11 rewritten to express the tangent of the angle ($\theta_2$) as a function of the distances ($d_2$), ($d_6$), and ($d_7$), and to express the cosine of the angle ($\theta_1$) as a function of the distances ($d_3$) and ($d_4$). Considering that the force ($F_T$) is negative in relation to the forces ($F_{S1}$) and ($F_B$), Equation 12 can be rewritten as shown in Equation 13 to demonstrate the balance between the first moment ($M_1$) and the sum of the second moment ($M_2$) and third moment ($M_3$). The first moment ($M_1$) given by left-side term of Equation 13 represents a treatment weight operational component of the TLT apparatus 300 when in use. The second moment ($M_2$) given by the first term on the right-side of Equation 13 represents a thoracic straightening operational component of the TLT apparatus 300 when in use. The third moment ($M_3$) given by the second term on the right-side of Equation 13 represents a lumbar straightening operational component of the TLT apparatus 300 when in use.

$$M_1 = F_T d_1. \qquad \text{Equation 1}$$

$$M_2 = F_{S2,z} d_2. \qquad \text{Equation 2}$$

$$F_{S2,z} = F_{S2}\sin(\theta_2). \qquad \text{Equation 3}$$

$$F_{S2} = \frac{F_{S1}}{\cos(\theta_2)}. \qquad \text{Equation 4}$$

$$F_{S2,z} = F_{S1}\frac{\sin(\theta_2)}{\cos(\theta_2)} = F_{S1}\tan(\theta_2). \qquad \text{Equation 5}$$

$$M_2 = F_{S1}\tan(\theta_2) d_2. \qquad \text{Equation 6}$$

$$M_3 = f_{B,p} d_5. \qquad \text{Equation 7}$$

$$F_{B,p} = \frac{F_B}{\cos\left(\frac{\pi}{2} - \theta_1\right)}. \qquad \text{Equation 8}$$

$$M_3 = F_B \frac{d_5}{\cos\left(\frac{\pi}{5} - \theta_1\right)}. \qquad \text{Equation 9}$$

$$M_1 + M_2 + M_3 = 0. \qquad \text{Equation 10}$$

$$F_T d_1 + F_{S1}\tan(\theta_2) + F_B \frac{d_5}{\cos\left(\frac{\pi}{2} - \theta_1\right)} = 0. \qquad \text{Equation 11}$$

$$F_T d_1 + F_{S1}\frac{d_7 d_2}{(d_6 + d_2)} + F_B \frac{(d_3^2 + d_4^2)}{d_4} = 0. \qquad \text{Equation 12}$$

$$F_{S1}\frac{d_7 d_2}{(d_6 + d_2)} + F_B \frac{(d_3^2 + d_4^2)}{d_4} = F_T d_1. \qquad \text{Equation 13}$$

With reference to Equation 13, the distances ($d_3$), ($d_4$), ($d_6$), and ($d_7$) are fixed based on the physical size of the human 400. The force ($F_T$) and the distances ($d_1$) and ($d_2$) are adjustable to achieve various treatment results using the TLT apparatus 300. The forces ($F_{S1}$) and ($F_B$) are reactive forces generated by the human 400 during treatment. Although the forces ($F_{S1}$) and ($F_B$) can be applied in a separate and independent manner by the human 400, the prescription to maintain the frame 301 of the TLT apparatus 300 in the substantially level orientation during treatment generates a relationship between the forces ($F_{S1}$) and ($F_B$). For example, if the human 400 works to apply more lateral translation force against the lateral restraint 213, the force ($F_B$) will increase, which allows for a decrease in the force ($F_{S1}$) applied by the human 400 to the shoulder strap 361 while still maintaining the frame 301 of the TLT apparatus 300 in the substantially level orientation during treatment. Similarly, if the human 400 works to apply more lateral translation force against the shoulder strap 361, the force ($F_{S1}$) will increase, which allows for a decrease in the force ($F_B$) applied by the human 400 to the lateral restraint 213 while still maintaining the frame 301 of the TLT apparatus 300 in the substantially level orientation during treatment. Also, the second moment ($M_2$) corresponding to the thoracic straightening operational component of the TLT apparatus 300 is given by the force ($F_{S1}$) multiplied by an adjustable weighting factor equal to the distance ($d_7$) times the adjustable distance ($d_2$) divided by the sum of the distance ($d_6$) and the adjustable distance ($d_2$). Therefore, as the distance ($d_2$) is increased, a smaller amount of change in the force ($F_{S1}$) is needed to provide a same amount of thoracic straightening operational component of the TLT apparatus 300 during treatment. And, as the distance ($d_2$) is decreased, a larger amount of change in the force ($F_{S1}$) is needed to provide a same amount of thoracic straightening operational component of the TLT apparatus 300 during treatment. Therefore, the distance ($d_2$) can be increased to effectively amplify the force ($F_{S1}$) relative to the force ($F_B$), which allows the human 400 to decrease their lumbar lateral translation effort relative to their thoracic translation effort while still maintaining the frame 301 of the TLT apparatus 300 in the substantially level orientation during treatment. And, in a complementary manner, the distance ($d_2$) can be decreased to effectively suppress the force ($F_{S1}$) relative to the force ($F_B$), which requires the human 400 to increase their lumbar lateral translation effort relative to their thoracic translation effort in order to maintain the frame 301 of the TLT apparatus 300 in the substantially level orientation during treatment.

Figure 13A:
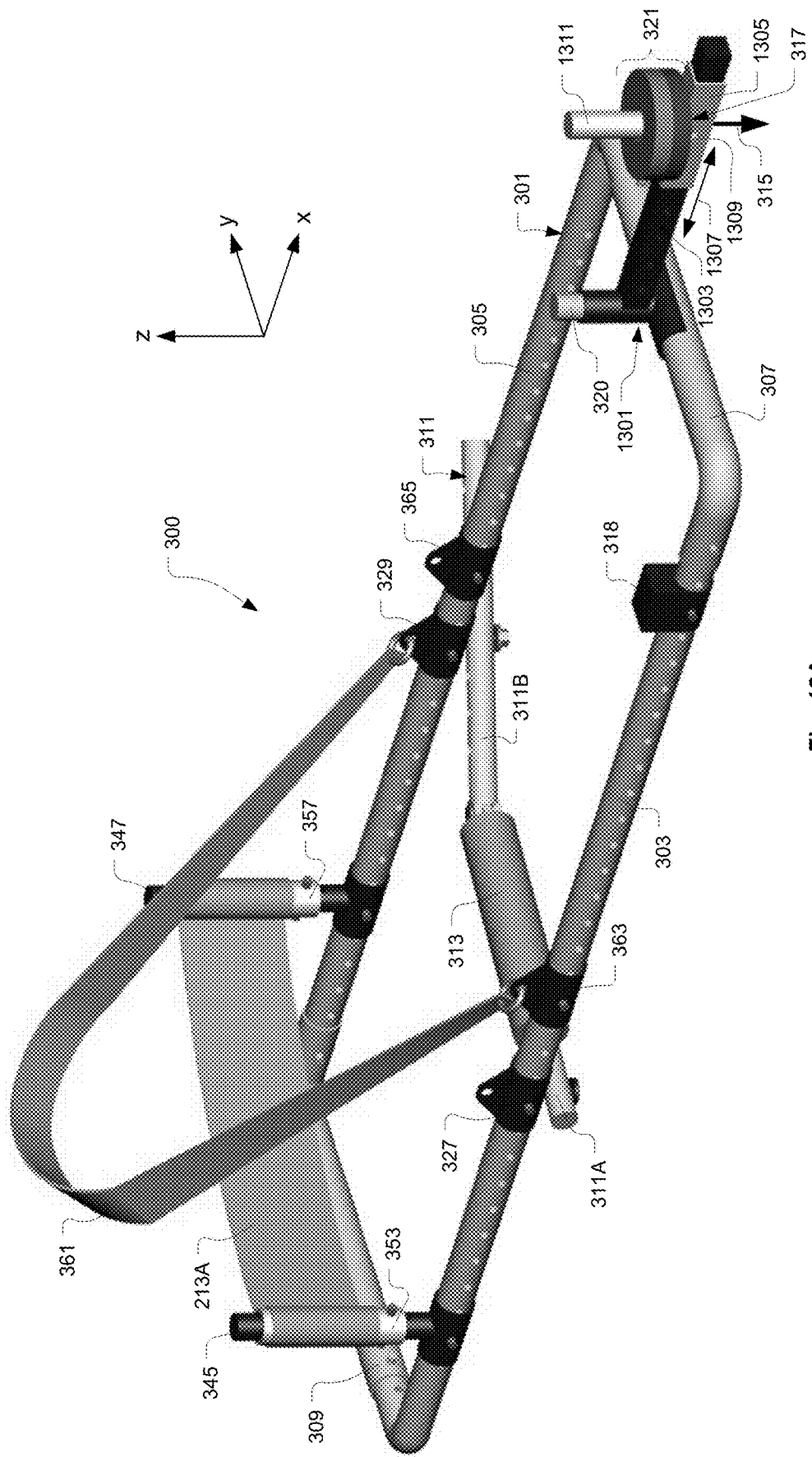
FIG. 13A shows the TLT apparatus with an extendable treatment weight receiver assembly installed on the treatment weight receiver, in accordance with some embodiments of the present invention.
Figure 13B:
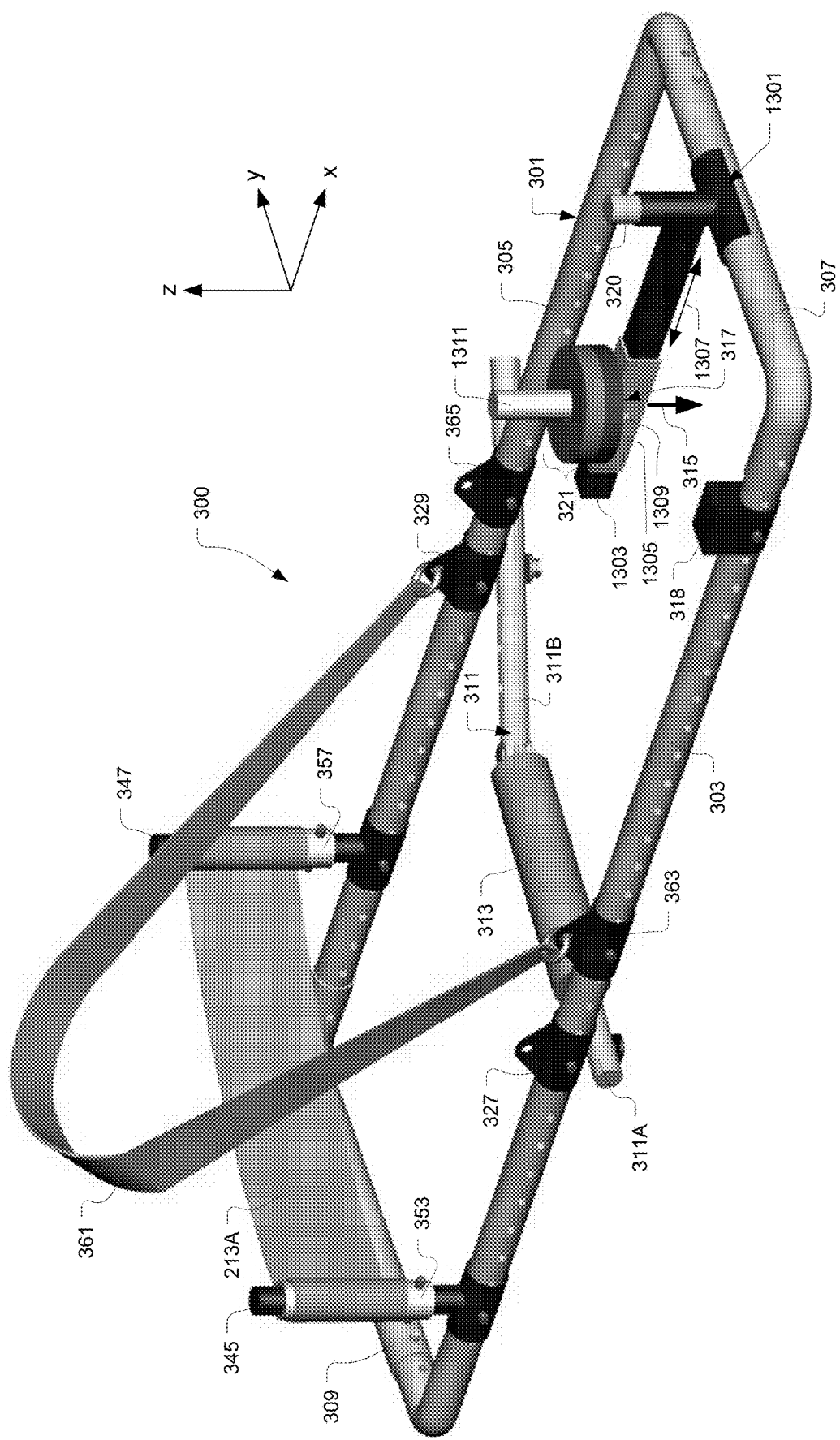
FIG. 13B shows the extendable treatment weight receiver assembly positioned on the treatment weight receiver to extend toward from the clamp bar, in accordance with some embodiments of the present invention.

As shown in Equation 13, the treatment weight operational component of the TLT apparatus 300 (first moment $M_1$) is a function of the distance ($d_1$) between the treatment force location 317 and the location at which the clamp bar 311 (or clamp pad 313 if present) interfaces with the human 400. FIG. 13A shows the TLT apparatus 300 with an extendable treatment weight receiver assembly 1301 installed on the treatment weight receiver 320, in accordance with some embodiments of the present invention. The treatment weight receiver assembly 1301 is configured to provide for adjustment of the distance ($d_1$). The treatment weight receiver assembly 1301 includes a horizontal support member 1303 configured to connect to the treatment weight receiver 320. The treatment weight receiver assembly 1301 also includes a horizontal adjustment member 1305 configured to slide along the horizontal support member 1303 to a desired position, as indicated by arrow 1307. The horizontal adjustment member 1305 is configured to be fixed in position relative to the horizontal support member 1303 by a connector pin 1309 that extends through both the horizontal adjustment member 1305 and the horizontal support member 1303. The horizontal adjustment member 1305 includes a treatment weight receiver 1311 configured to receive and hold one or more weights 321 that apply the downward treatment force 315. Also, in some embodiments, the extendable treatment weight receiver assembly 1301 can be positioned on the treatment weight receiver 320 to extend away from the clamp bar 311 to increase the distance ($d_1$), such as shown in FIG. 13A. However, in other embodiments, the extendable treatment weight receiver assembly 1301 can be positioned on the treatment weight receiver 320 to extend toward from the clamp bar 311 to decrease the distance ($d_1$). FIG. 13B shows the extendable treatment weight receiver assembly 1301 positioned on the treatment weight receiver 320 to extend toward from the clamp bar 311, in accordance with some embodiments of the present invention.

Figure 14A:
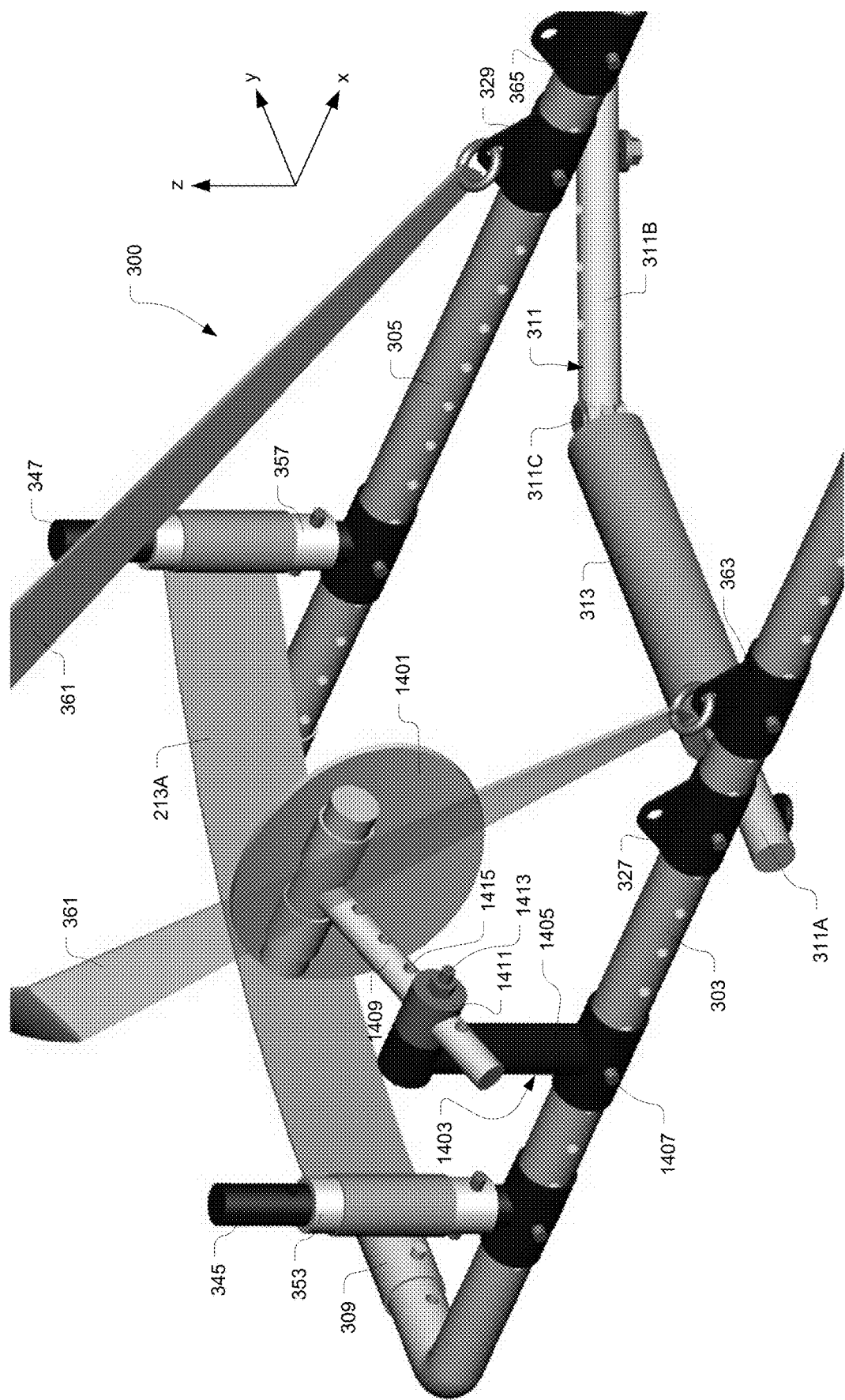
FIG. 14A shows the TLT apparatus with the anterior pad support assembly connected to the frame to support the anterior pad, in accordance with some embodiments of the present invention.
Figure 14B:
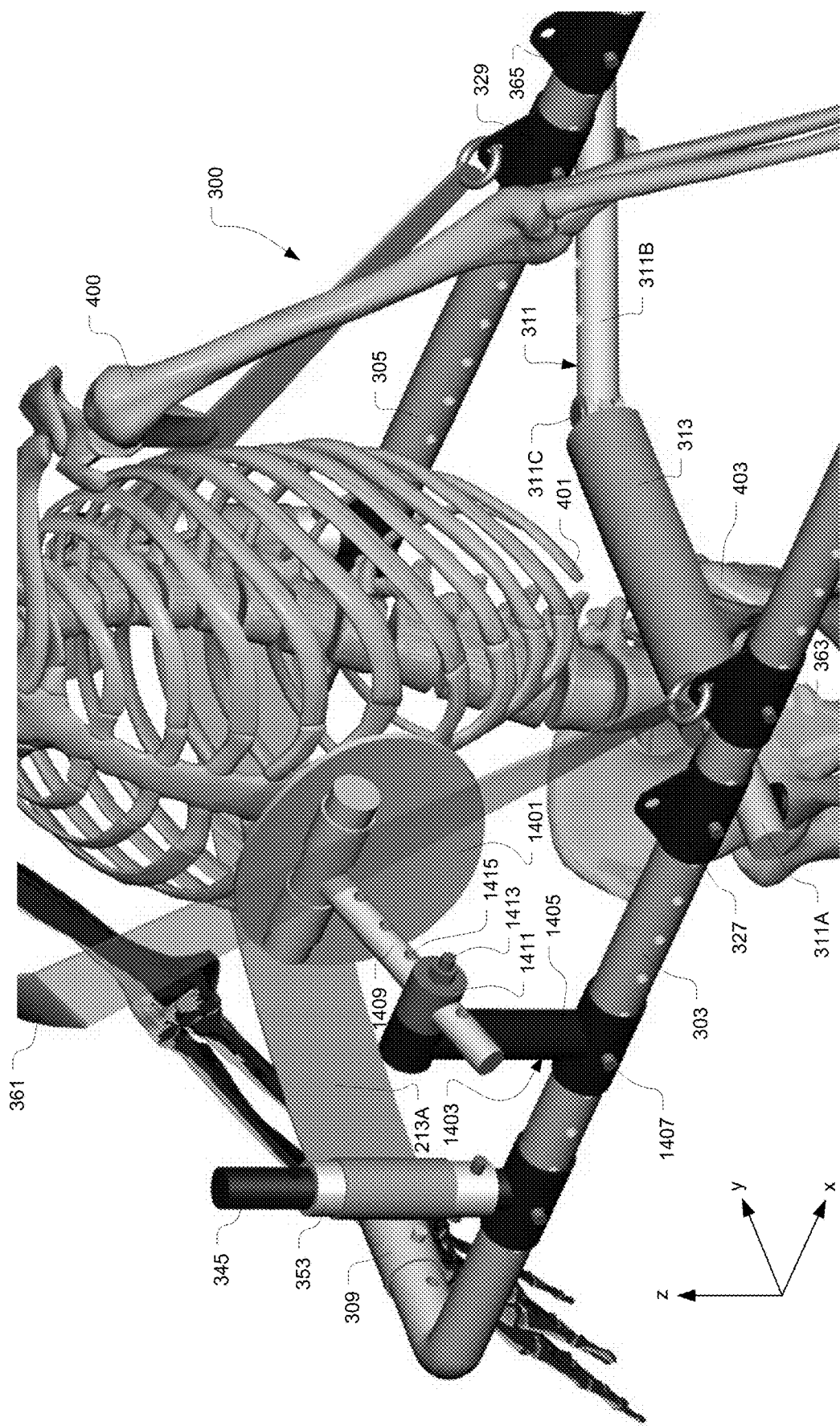
FIG. 14B shows an example spatial relationship between the anterior pad and the human when present within the TLT apparatus, in accordance with some embodiments of the present invention.

In some embodiments, the example TLT apparatus 300 can optionally include an anterior pad 1401 supported by an anterior pad support assembly 1403. FIG. 14A shows the TLT apparatus 300 with the anterior pad support assembly 1403 connected to the frame 301 to support the anterior pad 1401, in accordance with some embodiments of the present invention. FIG. 14B shows an example spatial relationship between the anterior pad 1401 and the human 400 when present within the TLT apparatus 300, in accordance with some embodiments of the present invention. The anterior pad 1401 can be positioned proximate to an anterior of the human 400 at a position between the clamp bar 311 and the lateral restraint 213. In some embodiments, the anterior pad 1401 can be positioned to physically contact the anterior of the human 400. More specifically, in some embodiments, the anterior pad 1401 is positioned to apply pressure to a lower anterior portion of the thoracic cage on a side of the human 400 next to the clamp bar 311. In this manner, with the lateral restraint 213 positioned at an angle to encourage de-rotation of the spinal column in the lumbar region, the anterior pad 1401 can further assist with de-rotation of the spinal column in the lumbar region as the human 400 laterally translates their lumbar spinal column region toward the lateral restraint 213.

The anterior pad support assembly 1403 includes an anchor structure 1405 configured to slide along the front segment 303 of the frame 301 to a desired position. The anchor structure 1405 is configured to be fixed in position along the front segment 303 of the frame 301 by a connector pin 1407 that extends through both the anchor structure 1405 and the front segment 303. The anterior pad support assembly 1403 also includes a support bar 1409 configured to support the anterior pad 1401. The support bar 1409 is configured to slide through a hole formed within an adjustment coupling 1411 to position the anterior pad 1401 at a desired distance from the adjustment coupling 1411. The adjustment coupling 1411 is configured to attach to the anchor structure 1405. A fastener 1413 is positioned to extend through the anchor structure 1405, through the adjustment coupling 1411, and through the support bar 1409 present within the adjustment coupling 1411, so as to rigidly secure the adjustment coupling 1411 and support bar 1409 in a fixed position relative to the anchor structure 1405. In some embodiments, the fastener 1413 is a bolt and nut combination. However, it should be understood that in other embodiments essentially any type of fastener 1413 can be used, so long as the fastener 1413 is configured to rigidly secure the adjustment coupling 1411 and support bar 1409 in a fixed position relative to the anchor structure 1405. In some embodiments, the support bar 1409 includes a number of holes 1415 through which the fastener 1413 can be inserted to provided for positional adjustment of the support bar 1415, and the anterior pad 1401 connected thereto, relative to the anchor structure 1405, thereby providing for adjustment in a position of the anterior pad 1401 relative to the anterior surface of the human 400. In various embodiments, the components of the anterior pad support assembly 1403 can be formed of essentially any material(s) capable of providing sufficient mechanical strength and rigidity, while preferably being light weight, such as aluminum, carbonfiber, fiberglass, plastic, and PVC, metal, among others.

In some embodiments, the anterior pad 1401 is configured to rotate about a portion of the support bar 1409 to which it is affixed to enable conformation of the anterior pad 1401 to the shape of the anterior surface of the human 400. Also, it should be understood that by setting a rotational position of the adjustment coupling 1411 relative to the anchor structure 1405, it is possible to adjust a vertical position (in the z-direction) of the anterior pad 1401 relative to the frame 301. Also, if the anterior pad 1401 is attached to the support bar 1409 in a fixed spatial relationship, setting of the rotational position of the adjustment coupling 1411 relative to the anchor structure 1405 can be done to set a desired angle of the anterior pad 1401 relative to the anterior surface of the human 400.

Also, in various embodiments, the anterior pad 1401 can be configured to have different shapes as needed to accommodate a body shape of the human 400. Also, in some embodiments, the anterior pad 1401 can be configured to provide various levels of comfort to the human 400. For example, in some embodiments, the anterior pad 1401 can be formed of a single material, such as rubber, nylon, plastic, foam, among others. Also, in some embodiments, the anterior pad 1401 can be formed to have multiple layers of material, with one or more layers of material closer to the human 400 having increased softness relative to one or more other layers of material farther away from the human 400. More specifically, in some embodiments, one or more layers of the anterior pad 1401 that are positioned closer to the human 400 can be formed of material having a smaller modulus of elasticity, such as rubber, gel, among others, whereas one or more layers of the anterior pad 1401 that are positioned farther from the human 400 can be formed of material having a larger modulus of elasticity, such as nylon, acrylic, plastic, aluminum, among others. Also, in some embodiments where the anterior pad 1401 is intended to press into the human 400, the anterior pad 1401 can be formed of a material having a sufficiently large coefficient of friction to substantially prevent sliding of the anterior pad 1401 on the surface of the human 400.

Figure 14C:
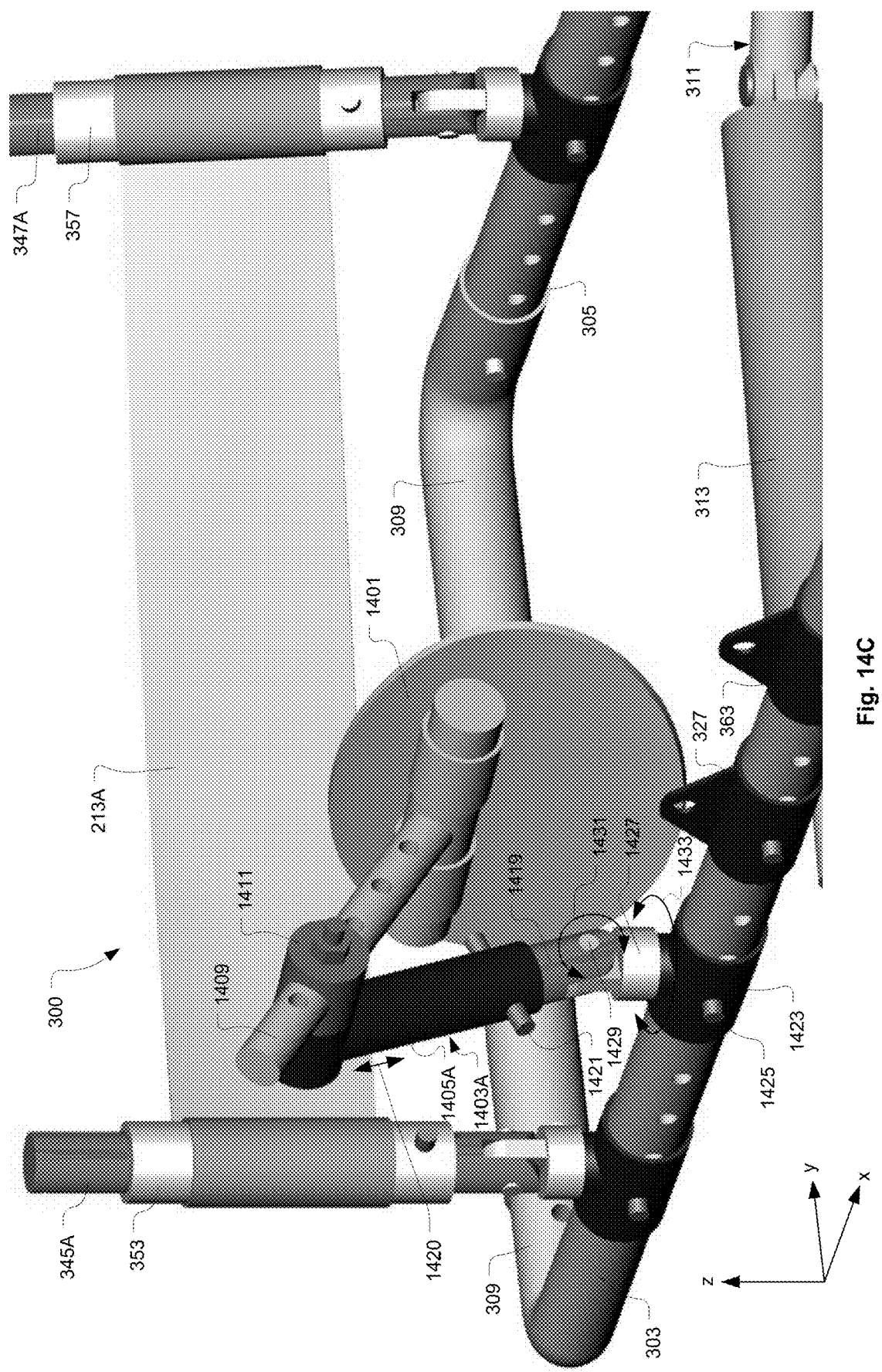
FIG. 14C shows an angular adjustable anterior pad support assembly, in accordance with some embodiments of the present invention.

FIG. 14C shows an angular adjustable anterior pad support assembly 1403A, in accordance with some embodiments of the present invention. The angular adjustable anterior pad support assembly 1403A is a modification of the anterior pad support assembly 1403 in which the anchor structure 1405 is replaced by a vertically adjustable anchor structure 1405A that is configured to slide over a vertical support structure 1419, as indicated by arrow 1420, with a connection pin 1421 used to rigidly maintain a position of the vertically adjustable anchor structure 1405A along the vertical support structure 1419. The angular adjustable anterior pad support assembly 1403A includes a position adjustment member 1427 to which the vertical support structure 1419 is connected. The vertical support structure 1419 is configured to rotate in the vertical direction about a rotational pin 1429 affixed to the position adjustment member 1427, as indicated by arrow 1431, to a desired position at which the vertical support structure 1419 can be rigidly held. The position adjustment member 1427 is connected to a frame connection member 1423 and is configured to rotate azimuthally about the z-direction relative to the frame connection member 1423, as indicated by arrow 1433, to a desired azimuthal position at which the position adjustment member 1427 can be rigidly held. The frame connection member 1423 is configured to connect to the front segment 303 of the frame 301. The frame connection member 1423 is configured to slide along the front segment 303 to a desired position, and is configured to be fixed in position relative to the front segment 303 by a connector pin 1425 that extends through both the frame connection member 1423 and the front segment 303.

Figure 15A:
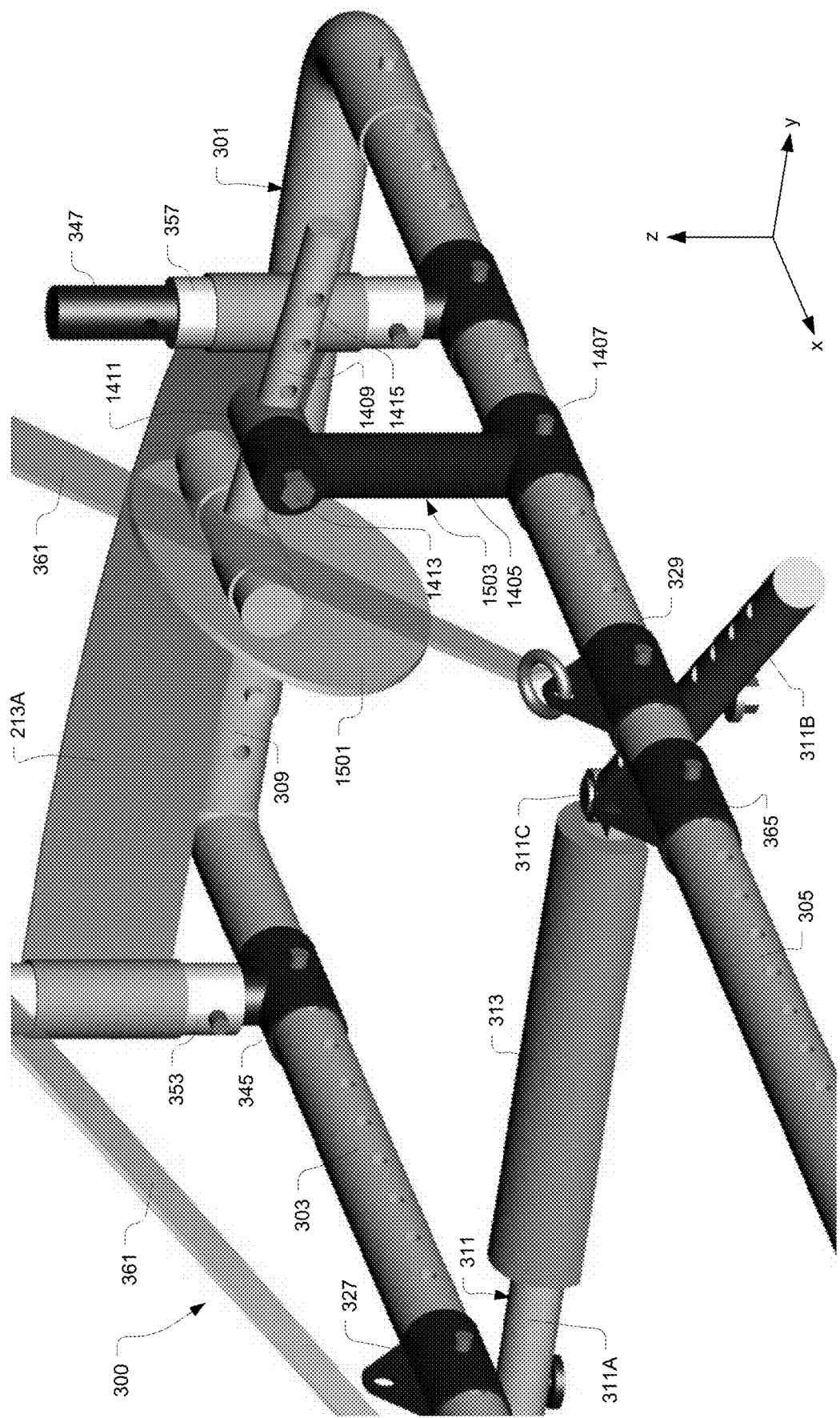
FIG. 15A shows the TLT apparatus with the posterior pad support assembly connected to the frame to support the posterior pad, in accordance with some embodiments of the present invention.
Figure 15B:
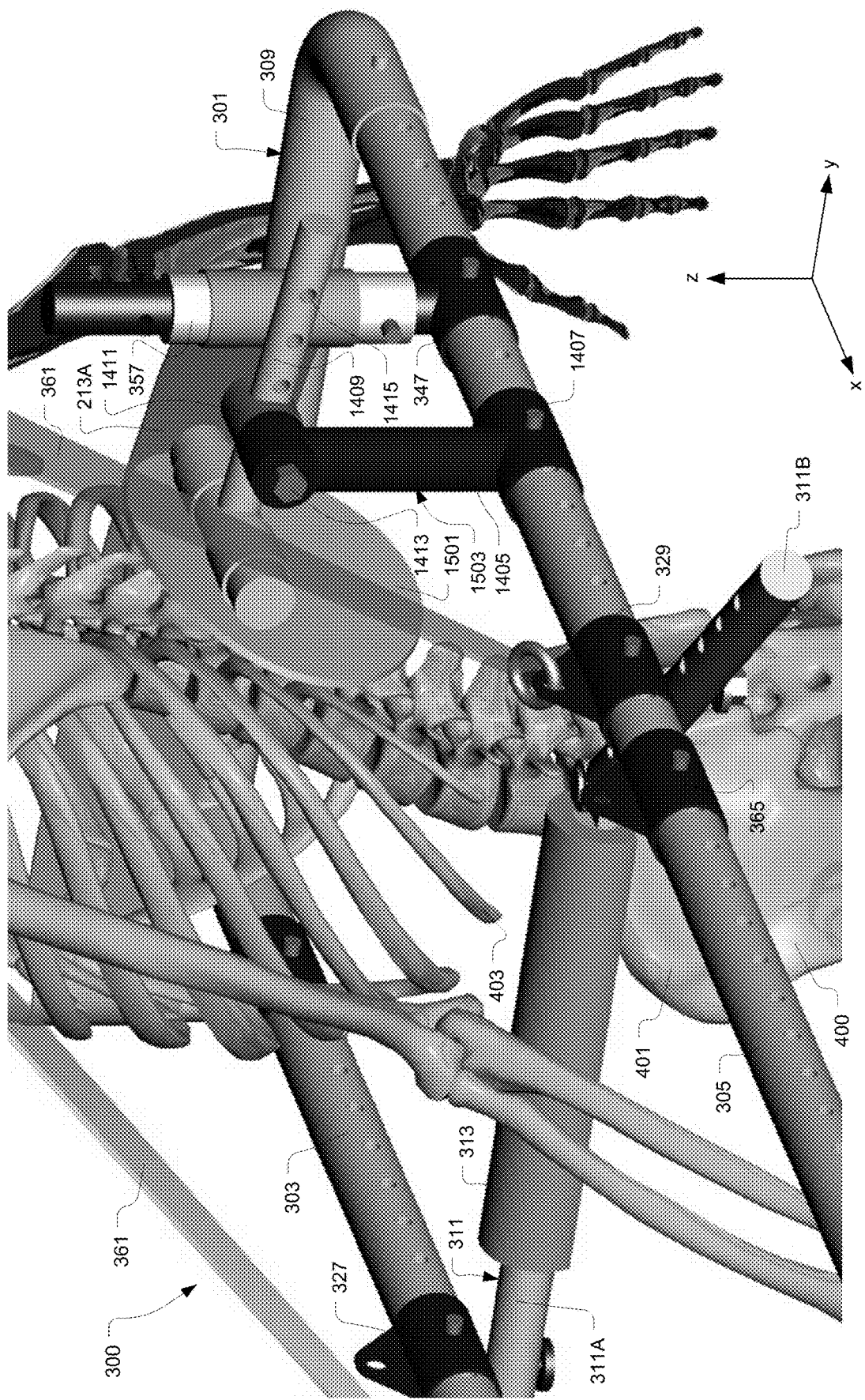
FIG. 15B shows an example spatial relationship between the posterior pad and the human when present within the TLT apparatus, in accordance with some embodiments of the present invention.

In some embodiments, the example TLT apparatus 300 can optionally include an posterior pad 1501 supported by a posterior pad support assembly 1503. FIG. 15A shows the TLT apparatus 300 with the posterior pad support assembly 1503 connected to the frame 301 to support the posterior pad 1501, in accordance with some embodiments of the present invention. FIG. 15B shows an example spatial relationship between the posterior pad 1501 and the human 400 when present within the TLT apparatus 300, in accordance with some embodiments of the present invention. In some embodiments, the posterior pad support assembly 1503 can be configured in the same manner as the anterior pad support assembly 1403, as shown in FIGS. 15A and 15B. Also, in some embodiments, the posterior pad support assembly 1503 can be configured in the same manner as the angular adjustable anterior pad support assembly 1403A. The posterior pad 1501 can be positioned to contact the posterior surface of the human 400 at essentially any prescribed spatial orientation. In some embodiments, the posterior pad

1501 can be utilized to support and/or encourage de-rotation of the spinal column during treatment using the TLT apparatus 300. Also, in some embodiments, the posterior pad 1501 can be utilized to prevent further adverse rotation of the spinal column during treatment using the TLT apparatus 300. And, in some embodiments, the posterior pad 1501 can be utilized to enhance anterior-to-posterior balance of the TLT apparatus 300.

As with the anterior pad 1401, in various embodiments, the posterior pad 1501 can be configured to have different shapes as needed to accommodate a body shape of the human 400. Also, in some embodiments, the posterior pad 1501 can be configured to provide various levels of comfort to the human 400. For example, in some embodiments, the posterior pad 1501 can be formed of a single material, such as rubber, nylon, plastic, foam, among others. Also, in some embodiments, the posterior pad 1501 can be formed to have multiple layers of material, with one or more layers of material closer to the human 400 having increased softness relative to one or more other layers of material farther away from the human 400. More specifically, in some embodiments, one or more layers of the posterior pad 1501 that are positioned closer to the human 400 can be formed of material having a smaller modulus of elasticity, such as rubber, gel, among others, whereas one or more layers of the posterior pad 1501 that are positioned farther from the human 400 can be formed of material having a larger modulus of elasticity, such as nylon, acrylic, plastic, aluminum, among others. Also, in some embodiments where the posterior pad 1501 is intended to press into the human 400, the posterior pad 1501 can be formed of a material having a sufficiently large coefficient of friction to substantially prevent sliding of the anterior pad 1501 on the surface of the human 400.

Figure 16:
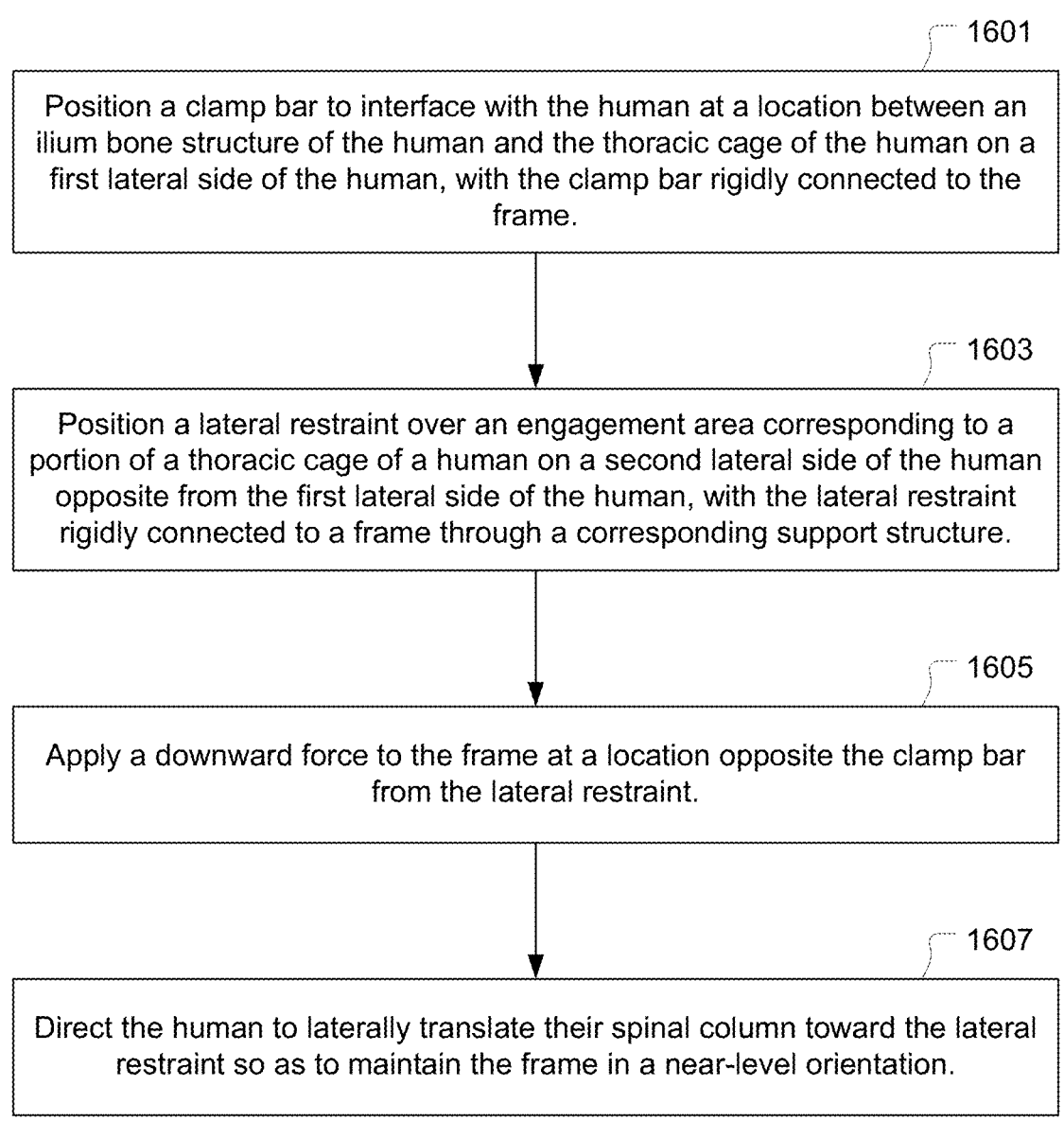
FIG. 16 shows a flowchart of a method for treatment of human scoliosis, in accordance with some embodiments of the present invention.

FIG. 16 shows a flowchart of a method for treatment of human scoliosis, in accordance with some embodiments of the present invention. The method includes an operation 1601 for positioning a clamp bar (311) to interface with the human at a location between an ilium bone structure of the human and the thoracic cage of the human on a first lateral side of the human. The clamp bar (311) is rigidly connected to the frame (301). In some embodiments, the method can include positioning the clamp bar (311) to extend in a direction substantially parallel to a sagittal plane of the human. In some embodiments, the method can include positioning the clamp bar (311) at an angle relative to the sagittal plane of the human. The method can also include an operation for covering a portion of the clamp bar (311) that interfaces with the human with a clamp pad (313). Also, the method can include an operation for flattening a bottom surface of the clamp pad (313) to assist with maintaining a space between the clamp pad (313) an the ilium bone structure of the human.

The method also includes an operation 1603 for positioning a lateral restraint (213) over an engagement area corresponding to a portion of a thoracic cage of a human on a second lateral side of the human opposite from the first lateral side of the human. The lateral restraint (213) is rigidly connected to a frame (301) through a corresponding support structure. In some embodiments, the portion of the thoracic cage corresponding to the engagement area includes one or more ribs connected to one or more vertebrae positioned below an apex of a scoliotic curve to be straightened by the human working to laterally translate their spinal column toward the lateral restraint (213) so as to maintain the frame (301) in the near-level orientation. In some embodiments, the method includes operating a level sensor to provide an indication of spatial orientation of the frame with respect to level. Also, in some embodiments, the lateral restraint conforms to a physical shape of the engagement area. In some embodiments, the method can include positioning the lateral restraint (213) at an angle relative to the second lateral side of the human to cause de-rotation of vertebrae along the scoliotic curve to be straightened by the human as the human works to laterally translate their spinal column toward the lateral restraint (213) so as to maintain the frame (301) in the near-level orientation. For example, FIG. 7 illustrates positioning of the lateral restraint band 213A at the angle 707, which can be effective in causing de-rotation of vertebrae along the scoliotic curve to be straightened by the human as the human works to laterally translate their spinal column toward the lateral restraint (213A) so as to maintain the frame (301) in the near-level orientation. Also, the method can include positioning the lateral restraint (213) at an angle in the vertical direction to facilitate proper interfacing with the engagement area. For example, FIG. 9A illustrates positioning of the lateral restraint band (213A) at the angle 901 in the vertical direction.

The method also includes an operation 1605 for applying a downward force to the frame (301) at a location (317) opposite the clamp bar (311) from the lateral restraint (213). The method also includes an operation 1607 for directing the human to laterally translate their spinal column toward the lateral restraint (213) so as to maintain the frame (301) in a near-level orientation. In some embodiments, the downward force is applied to the frame (301) by placing a number of weights on the frame (301) at the location (317). In some embodiments, the method includes adjusting the location (317) of the downward force to be closer to the clamp bar (311). And, in some embodiments, the method includes adjusting the location (317) of the downward force to be farther from the clamp bar (313). The method can also include adjusting an amount of the downward force in a scheduled manner during a course of treatment and/or during a given treatment session.

In some embodiments, the method includes connecting a shoulder strap (361) to the frame (301) at locations opposite the clamp bar (311) from the lateral restraint (213). The method can also include positioning the shoulder strap (361) around a shoulder of the human on the second lateral side of the human. The method can also include directing the human to laterally translate their spinal column toward the shoulder strap (361) so as to maintain the frame (301) in the near-level orientation. Also, in some embodiments, the method can include adjusting the locations at which the shoulder strap (361) is connected to the frame (301) to be farther from the clamp bar (311) and closer to the location (317) at which the downward force is applied to the frame (301). And, in some embodiments, the method can include adjusting the locations at which the shoulder strap (361) is connected to the frame (301) to be closer to the clamp bar (311) and farther from to the location (317) at which the downward force is applied to the frame (301). The method can also include adjusting the locations at which the shoulder strap (361) is connected to the frame (301) in a scheduled manner during a course of treatment and/or during a given treatment session.

Additionally, in some embodiments, the method can include positioning an anterior pad (1401) between the clamp bar (311) and the lateral restraint (213) to interface with an anterior surface of the human, with the anterior pad (1401) rigidly connected to the frame (301) through a corresponding support structure (1403/1403A). Also, the method can include positioning a posterior pad (1501)

between the clamp bar (311) and the lateral restraint (213) to interface with a posterior surface of the human, with the posterior pad (1501) rigidly connected to the frame (301) through a corresponding support structure (1503). Also, in some embodiments, the method can include directing the human to stand upon a semi-unstable surface while working to laterally translate their spinal column toward the lateral restraint (213) and shoulder strap (361) so as to maintain the frame (301) in the near-level orientation. In these embodiments, the neuro-muscular systems of the human are required to work more intensely to maintain a balance of the human as they are being trained and strengthened to resist the proclivity of the spinal column to assume the scoliotic curvature. In some embodiments, the semi-unstable surface is provided by an inflatable disc upon which the human stands while positioned within the TLT apparatus 300 during treatment. In other embodiments, the semi-unstable surface can be a flat tilting surface configured to tilt in any three-dimensional direction about a central location underneath the flat tilting surface and substantially centered upon the human. Also, it should be understood that in other embodiments the semi-unstable surface can have configurations other than the inflatable disc and flat tilting surface.

In view of the foregoing, it should be understood and appreciated that the TLT apparatus 300, in its various embodiments, is an apparatus for treatment of human scoliosis. The TLT apparatus 300 includes the front segment 303 of the frame 301 configured to extend across the anterior side of the human 400 when the human 400 is present within the TLT apparatus 300. The TLT apparatus 300 also includes the back segment 305 of the frame 301 configured to extend across the posterior side of the human 400 when the human 400 is present within the TLT apparatus 300, with the back segment 305 having a fixed spatial relationship with respect to the front segment 303. In some embodiments, the front segment 303 is a bar having a substantially straight configuration, and the back segment 305 is a bar having a substantially straight configuration. In some embodiments, the front segment 303 and the back segment 305 are positioned in a substantially parallel orientation.

The TLT apparatus 300 also includes the clamp bar 311 configured to extend between the front segment 303 and the back segment 305. The clamp bar 311 is configured to extend across the first lateral side of the human 400 when the human 400 is present within the TLT apparatus 300. The clamp bar 311 is also configured to interface with the first lateral side of the human 400 at a location between the ilium bone structure 401 of the human 400 and the thoracic cage of the human 400 when the human 400 is present within the TLT apparatus 300. In some embodiments, the clamp bar 311 is positioned in a substantially perpendicular orientation to both the front segment 303 and the back segment 305. In some embodiments, the clamp bar 311 is positioned non-perpendicular to each of the front segment 303 and the back segment 305. In some embodiments, the clamp bar 311 includes the pivot connection 311C at the location between the front segment 303 and the back segment 305. In some embodiments, the pivot connection 311C is set such that an angle between the clamp bar 311 and the front segment 303 is different than an angle between the clamp bar 311 and the back segment 305. In some embodiments, the clamp bar 311 includes the clamp pad 313 positioned to interface with the first lateral side of the human 400 when the human 400 is present within the TLT apparatus 300. In some embodiments, the bottom surface of the clamp pad 313 is flattened to maintain a spacing between the clamp pad 313 and the ilium bone structure 401 of the human 400 when the human 400 is present within the TLT apparatus 300.

The TLT apparatus 300 also includes the lateral restraint 213 positioned between the front segment 303 and the back segment 305 and rigidly connected to both the front segment 303 and the back segment 305. The lateral restraint 213 is configured to interface with the second lateral side of the human 400 over an engagement area corresponding to a portion of the thoracic cage of the human 400 when the human 400 is present within the TLT apparatus 300. In some embodiments, the lateral restraint 213 is a band 213A extending between the first lateral restraint support 345 and the second lateral restraint support 347. The first lateral restraint support 345 is connected to the front segment 303, and the second lateral restraint support 347 is connected to the back segment 305. In some embodiments, the band 213A has a width within a range extending from about 2 inches to about 10 inches. In some embodiments, the lateral restraint 213 is the lateral restraint pad 1101 affixed to the lateral restraint support 1103, i.e., pad support structure, wherein the lateral restraint support 1103 is connected to both the front segment 303 and the back segment 305.

The TLT apparatus 300 also includes the weight receiver 320 connected to apply the downward treatment force 315 to both the front segment 303 and the back segment 305 at a position opposite the clamp bar 311 from the lateral restraint 213. The lateral restraint 213 is configured to receive a lateral translation force generated by the human 400 to maintain a near-level orientation of the front segment 303 and the back segment 305 when the downward treatment force 315 is applied from the weight receiver 320. In some embodiments, the level sensor 318 is affixed to the frame 301. The level sensor 318 is configured to provide an indication of spatial orientation of the front segment 303 and the back segment 305 with respect to level.

The TLT apparatus 300 also includes a first side segment, e.g., left segment 307, of the frame 301 extending between the front segment 303 and the back segment 305, with the weight receiver 320 affixed to the first side segment. The TLT apparatus 300 also includes a second side segment, e.g., the right segment 309, of the frame 301 extending between the front segment 303 and the back segment 305, with the lateral restraint 213 positioned between the second side segment and the clamp bar 311. In some embodiments, the first side segment and the second side segment are adjustable in length to control a separation distance between the front segment 303 and the back segment 305. In some embodiments, the lateral restraint 213 is the lateral restraint pad 1101 affixed to a pad support structure configured as the end-mount lateral restraint support assembly 1109, with the end-mount lateral restraint support assembly 1109 connected to the second side segment which is rigidly connected to both the front segment 303 and the back segment 305.

The TLT apparatus 300 also includes the shoulder strap 361 having the first end connected to the front segment 303 and the second end connected to the back segment 305. The shoulder strap 361 is configured to extend around a shoulder region of the human 400 when the human 400 is present within the TLT apparatus 300. The shoulder strap 361 is configured to extend around the shoulder region of the human 400 on the second lateral side of the human 400 when the human 400 is present within the TLT apparatus 300. In some embodiments, the connection location between the first end of the shoulder strap 361 and the front segment 303 is adjustable along the front segment 303, and the connection location between the second end of the shoulder strap 361 and the back segment 305 is adjustable along the back segment 305.

In some embodiments, the TLT apparatus 300 includes the anterior pad 1401 affixed to the anterior pad support structure 1403/1403A. The anterior pad support structure 1403/1403A is connected to the front segment 303 at a location between the lateral restraint 213 and the clamp bar 311. The anterior pad 1401 is configured to interface with the anterior surface of the human 400 when the human 400 is present within the TLT apparatus 300. In some embodiments, the TLT apparatus 300 includes the posterior pad 1501 affixed to the posterior pad support structure 1503. The posterior pad support structure 1503 is connected to the back segment 305 at a location between the lateral restraint 213 and the clamp bar 311. The posterior pad 1501 is configured to interface with the posterior surface of the human 400 when the human 400 is present within the TLT apparatus 300.

In some embodiments, the TLT apparatus 300 can be characterized as an apparatus for treatment of human scoliosis that includes the frame 301, the clamp bar 311, the lateral restraint 213, and the treatment weight receiver 320. The frame 301 includes the front segment 303, the back segment 305, a first side segment (e.g., the left segment 307), and a second side segment (e.g., the right segment 309). Each of the first side segment and the second side segment extend between and rigidly connected to the front segment 303 and the back segment 305. The clamp bar 311 extends between and connects to the front segment 303 and the back segment 305. A downward lever arm portion of the frame 301 includes the first side segment (e.g., the left segment 307), and a portion of the front segment 303 extending between the clamp bar 311 and the first side segment, and a portion of the back segment 305 extending between the clamp bar 311 and the first side segment. An upward lever arm portion of the frame 301 includes the second side segment (e.g., the right segment 309), and a portion of the front segment 303 extending between the clamp bar 311 and the second side segment, and a portion of the back segment 305 extending between the clamp bar 311 and the second side segment. The lateral restraint 213 is attached to the upward lever arm portion of the frame 301. The lateral restraint 213 is also positioned at a vertical location above the frame 301. In some embodiments, the lateral restraint 213 includes the band 213A positioned between the front segment 303 and the back segment 305. In some embodiments, the lateral restraint 213 includes the pad 1101 is positioned between the front segment 303 and the back segment 305. The treatment weight receiver 320 is attached to the downward lever arm portion of the frame 301. A region between the clamp bar 311 and the lateral restraint 213 and between the front segment 303 and the back segment 305 is configured for occupancy by the human 400. The clamp bar 311 is configured to interface with the first lateral side of the human 400 at the location between the ilium bone structure 401 of the human 400 and the thoracic cage of the human 400 when the human 400 is present within the region. The lateral restraint 213 is configured to interface with the second lateral side of the human over the engagement area corresponding to the portion of the thoracic cage of the human 400 when the human 400 is present within the region.

In some embodiments, the TLT apparatus 300 can be characterized a treatment apparatus for scoliosis that includes the frame 301, an attachment section 383 of the frame 301, an extension section 385 of the frame 301, and the weight receiver 320. The attachment section 383 and the extension section 385 is shown in FIG. 3M. The attachment section 383 of the frame 301 is for coupling the TLT apparatus 300 to the human 400. The extension section 385 of the frame 301 is a lateral continuation of the frame 301 to a side of the attachment section 383. The weight receiver 320 is coupled to an outer end of the extension section 385 that is away from the attachment section 383. The attachment section 383 includes a clamp attachment, such as the clamp bar 311, for a first lateral side of the human 400, when the human 400 is fitted with the TLT apparatus 300. The attachment section 383 also includes a lateral attachment, such as the lateral restraint 213, for a second lateral side of the human 400, when the human 400 is fitted with the TLT apparatus 300. The clamp attachment includes a first surface to be interfaced with the first lateral side of the human 400. In various embodiments, the first surface of the clamp attachment is one of a band, or a pad, or a brace. The lateral attachment includes a second surface to be interfaced with the second lateral side of the human 400. In various embodiments, the second surface of the lateral attachment is one of a pad, or a roll, or a foam, or a brace, or a band.

The frame 301 has a length and a width, where the length has the front segment 303 and the back segment 305, and where the width has the first-side segment and a second-side segment. In various embodiments, the frame 301 is defined from one or more sections of a material arranged, formed or connected to define the length and width of the front segment 303, the back segment 305, the first-side segment, and the second-side segment. In various embodiments, the material is one or more of a pipe material, a tube material, a plastic material, a carbon fiber material, a steel material, an aluminum material, a metallic material, a cloth material, and a hybrid material. The first-side segment is part of the attachment section 383. The second-side segment is part of the extension section 385. The human 400, when present, is disposed between the front segment 303, the back segment 305, and the first-side segment of the frame 301 in a region of the attachment section 383. The front segment 303 and back segment 305 extend to the second-side segment that is in a region of the extension section 385. The weight receiver 320 is configured hold one or more weights 321 that cause the downward treatment force 315 at the second-side segment when the TLT apparatus 300 is fitted to the human 400.

The clamp attachment is connected between the front segment 303 of the frame 301 and the back segment 305 of the frame 301. The TLT apparatus 300 further includes the shoulder strap 361 having the first end, the second end, and a side-shoulder contact surface. The first end of the shoulder strap 361 is connected to a first anchor member that is coupled to the front segment 303 of the frame 301. The second end of the shoulder strap 361 is connected to a second anchor member that is coupled to the back segment 305 of the frame 301. The human 400, when fitted with the TLT apparatus 300, faces toward the front segment 303 of the frame 301, such that the extension section 385 is positioned to extend away from the first lateral side of the human 400 and the side-shoulder contact surface of the shoulder strap 361 is interfaced to a side shoulder of the second lateral side of the human 400, such that the side-shoulder contact surface of the shoulder strap 361 and the extension section 385 are on opposite sides of the human 400 when the human 400 faces the front segment 303 of the frame 301.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

Although the foregoing invention has been described in some detail for purposes of clarity of understanding, it will be apparent that certain changes and modifications can be practiced within the scope of the appended claims. Accordingly, the present embodiments are to be considered as illustrative and not restrictive, and the invention is not to be limited to the details given herein, but may be modified within the scope and equivalents of the described embodiments.

What is claimed is:

1. An apparatus for treatment of human scoliosis, comprising:
    a front segment of a frame configured to extend across an anterior side of a human when the human is present within the apparatus, the front segment extending linearly and parallel to a reference x-direction;
    a back segment of the frame configured to extend across a posterior side of the human when the human is present within the apparatus, the back segment extending linearly and parallel to the reference x-direction, the back segment having a fixed spatial relationship with respect to the front segment;
    a first side segment of the frame extending between the front segment and the back segment at a first end of the frame, the first side segment extending linearly and parallel to a reference y-direction;
    a second side segment of the frame extending between the front segment and the back segment at a second end of the frame, the second side segment extending linearly and parallel to the reference y-direction, wherein an area bounded by the front segment, the back segment, the first side segment, and the second side segment collectively defines an x-y reference plane;
    a clamp bar connected to both the front segment and the back segment at a location between the first side segment and the second side segment, the clamp bar extending within the x-y reference plane between the front segment and the back segment, the clamp bar configured to extend across a first lateral side of the human when the human is present within the apparatus;
    a lateral restraint supported by a connection to the frame, the lateral restraint positioned between the front segment and the back segment at a location between the second side segment and the clamp bar and above the x-y reference plane, the lateral restraint separated from the clamp bar by a distance that accommodates positioning of the human between the lateral restraint and the clamp bar, the lateral restraint positioned to interface with a second lateral side of the human over an engagement area corresponding to a portion of a thoracic cage of the human when the clamp bar is positioned to interface with the first lateral side of the human at a location between an ilium bone structure of the human and the thoracic cage of the human when the human is present within the apparatus; and
    a weight receiver connected to apply a downward treatment force to both the front segment and the back segment at a position on the frame opposite the clamp bar from the lateral restraint, wherein the lateral restraint is configured to receive a lateral translation force generated by the human to maintain a near-level orientation of the front segment and the back segment when the downward treatment force is applied from the weight receiver.

2. The apparatus for treatment of human scoliosis as recited in claim 1, wherein the front segment is a bar having a substantially straight configuration, and wherein the back segment is a bar having a substantially straight configuration.

3. The apparatus for treatment of human scoliosis as recited in claim 2, wherein the front segment and the back segment are positioned in a substantially parallel orientation.

4. The apparatus for treatment of human scoliosis as recited in claim 3, wherein the clamp bar is positioned in a substantially perpendicular orientation to both the front segment and the back segment.

5. The apparatus for treatment of human scoliosis as recited in claim 3, wherein the clamp bar is positioned non-perpendicular to each of the front segment and the back segment.

6. The apparatus for treatment of human scoliosis as recited in claim 1, wherein the clamp bar includes a pivot connection at a location between the front segment and the back segment.

7. The apparatus for treatment of human scoliosis as recited in claim 6, wherein the pivot connection is set such that an angle between the clamp bar and the front segment is different than an angle between the clamp bar and the back segment.

8. The apparatus for treatment of human scoliosis as recited in claim 1, wherein the clamp bar includes a clamp pad positioned to interface with the first lateral side of the human when the human is present within the apparatus.

9. The apparatus for treatment of human scoliosis as recited in claim 8, wherein a bottom surface of the clamp pad is flattened to maintain a spacing between the clamp pad and the ilium bone structure of the human when the human is present within the apparatus.

10. The apparatus for treatment of human scoliosis as recited in claim 1, wherein the lateral restraint is a band extending between a first lateral restraint support and a second lateral restraint support, the first lateral restraint support connected to the front segment, the second lateral restraint support connected to the back segment, the first lateral restraint support and the second lateral restraint support forming part of the connection to the frame.

11. The apparatus for treatment of human scoliosis as recited in claim 10, wherein the band has a width within a range extending from about 2 inches to about 10 inches.

12. The apparatus for treatment of human scoliosis as recited in claim 1, wherein the lateral restraint is a pad affixed to a pad support structure, wherein the pad support structure is connected to both the front segment and the back segment, the pad support structure forming part of the connection to the frame.

13. The apparatus for treatment of human scoliosis as recited in claim 1,
    wherein the weight receiver is affixed to the first side segment.

14. The apparatus for treatment of human scoliosis as recited in claim 1, wherein the first side segment and the second side segment are adjustable in length to control a separation distance between the front segment and the back segment.

15. The apparatus for treatment of human scoliosis as recited in claim 1, wherein the lateral restraint is a pad affixed to a pad support structure, wherein the pad support structure is connected to the second side segment, the pad support structure forming part of the connection to the frame.

16. The apparatus for treatment of human scoliosis as recited in claim 1, further comprising:
a shoulder strap having a first end connected to the front segment and a second end connected to the back segment, the shoulder strap configured to extend around a shoulder region of the human when the human is present within the apparatus.

17. The apparatus for treatment of human scoliosis as recited in claim 16, wherein the shoulder strap is configured to extend around the shoulder region of the human on the second lateral side of the human when the human is present within the apparatus.

18. The apparatus for treatment of human scoliosis as recited in claim 16, wherein a connection location between the first end of the shoulder strap and the front segment is adjustable along the front segment, and wherein a connection location between the second end of the shoulder strap and the back segment is adjustable along the back segment.

19. The apparatus for treatment of human scoliosis as recited in claim 1, further comprising:
an anterior pad affixed to an anterior pad support structure, wherein the anterior pad support structure is connected to the front segment at a location between the lateral restraint and the clamp bar, the anterior pad configured to interface with the anterior surface of the human when the human is present within the apparatus.

20. The apparatus for treatment of human scoliosis as recited in claim 1, further comprising:
a posterior pad affixed to a posterior pad support structure, wherein the posterior pad support structure is connected to the back segment at a location between the lateral restraint and the clamp bar, the posterior pad configured to interface with the posterior surface of the human when the human is present within the apparatus.

21. The apparatus for treatment of human scoliosis as recited in claim 1, further comprising:
a level sensor affixed to the frame, the level sensor configured to provide an indication of spatial orientation of the front segment and the back segment with respect to level.

22. The apparatus for treatment of human scoliosis as recited in claim 16, wherein the first end of the shoulder strap is connected to the front segment at a location between the first side segment and the clamp bar, and wherein the second end of the shoulder strap is connected to the back segment at a location between the first side segment and the clamp bar.

* * * * *